US010927383B2

(12) United States Patent
Aneja et al.

(10) Patent No.: US 10,927,383 B2
(45) Date of Patent: Feb. 23, 2021

(54) CAS9 MRNAS

(71) Applicant: ethris GmbH, Planegg (DE)

(72) Inventors: Manish Kumar Aneja, Munich (DE); Rebekka Kubisch-Dohmen, Munich (DE); Christian Plank, Wessling (DE); Carsten Rudolph, Krailling (DE)

(73) Assignee: ethris GmbH, Planegg (DE)

( * ) Notice: Subject to any disclaimer, the term of this patent is extended or adjusted under 35 U.S.C. 154(b) by 591 days.

(21) Appl. No.: 15/639,069

(22) Filed: Jun. 30, 2017

(65) Prior Publication Data

US 2018/0163213 A1 Jun. 14, 2018

Related U.S. Application Data

(60) Provisional application No. 62/357,106, filed on Jun. 30, 2016.

(51) Int. Cl.
*C12N 15/52* (2006.01)
*C12N 9/22* (2006.01)

(52) U.S. Cl.
CPC ............... *C12N 15/52* (2013.01); *C12N 9/22* (2013.01); *C12N 2310/20* (2017.05)

(58) Field of Classification Search
CPC ........ C12N 9/22; C12N 15/111; C12N 15/115
See application file for complete search history.

(56) References Cited

U.S. PATENT DOCUMENTS

| | | | |
|---|---|---|---|
| 5,965,434 | A | 10/1999 | Wolff et al. |
| 6,077,835 | A | 6/2000 | Hanson et al. |
| 6,734,171 | B1 | 5/2004 | Saravolac et al. |
| 2011/0311583 | A1 | 12/2011 | Manoharan et al. |
| 2014/0010861 | A1* | 1/2014 | Bancel ............... C07K 14/4713 424/450 |
| 2016/0367702 | A1* | 12/2016 | Hoge .................... C12N 15/111 |

FOREIGN PATENT DOCUMENTS

| | | |
|---|---|---|
| WO | WO 1990/011092 | 10/1990 |
| WO | WO 2005/120152 | 12/2005 |
| WO | WO 2007/024708 | 3/2007 |
| WO | WO 2011/068810 | 6/2011 |
| WO | WO 2013/182683 | 12/2013 |

OTHER PUBLICATIONS

Wang et al.; CRISPR-Cas9 Targeting of PCSK9 in Human Hepatocytes In Vivo—Brief Report; Arteriosclerosis, Thrombosis, and Vascular Biology; vol. 36, Issue 5, pp. 783-786, published online Mar. 3, 2016 (Year: 2016).*

Su, Xingfang, et al. "In vitro and in vivo mRNA delivery using lipid-enveloped pH-responsive polymer nanoparticles." *Molecular pharmaceutics* 8.3 (2011): 774-787.

Kormann, Michael SD, et al. "Expression of therapeutic proteins after delivery of chemically modified mRNA in mice." *Nature biotechnology* 29.2 (2011): 154.

Rudolph, Carsten, et al. "In vivo gene delivery to the lung using polyethylenimine and fractured polyamidoamine dendrimers," *The journal of gene medicine* 2.4 (2000): 269-278.

* cited by examiner

*Primary Examiner* — Antonio Galisteo Gonzalez
(74) *Attorney, Agent, or Firm* — Morse, Barnes-Brown & Pendleton, P.C.; Lisa M. Warren, Esq.

(57) ABSTRACT

In certain aspects, the disclosure relates to compositions comprising modified Cas9 polyribonucleotides and methods of use, as well as Cas9 polynucleotides and polyribonucleotides.

10 Claims, 8 Drawing Sheets

Specification includes a Sequence Listing.

ETH015T05: modification 3, Cong sequence no particular UTR

Indel-analysis (1) sgRNA1 + Cas9 mRNA 24h
(2) sgRNA1 + Cas9 mRNA 48h
(3) sgRNA3 + Cas9 mRNA 24h
(4) sgRNA3 + Cas9 mRNA 48h
(5) sgRNA1 Cas9 mRNA only 24h
(6) sgRNA1 Cas9 mRNA only 48h
(7) sgRNA3 Cas9 mRNA only 24h
(8) sgRNA3 Cas9 mRNAonly 48h

| | Band % |
|---|---|
| Lane 1 | 83,1 |
| | 16,9 |
| Lane 2 | 80,8 |
| | 19,2 |
| Lane 3 | 69,5 |
| | 30,5 |
| Lane 4 | 64,1 |
| | 35,9 |
| Lane 5 | 100,0 |
| Lane 6 | 100,0 |
| Lane 7 | 100,0 |
| Lane 8 | 100,0 |

eGFP gRNA #4 strongly reduces eGFP signal in eGFP expressing HepG2 cells
A.

eGFP signal intensity [percent of control]
150
100
50
0
gRNA1
gRNA2
gRNA3
gRNA4
gRNA5
gRNA-eGFP
Cas9
Cas9D10
B.

SEQUENCE LISTING

```
<160> NUMBER OF SEQ ID NOS: 84

<210> SEQ ID NO 1
<211> LENGTH: 4203
<212> TYPE: RNA
<213> ORGANISM: Artificial
<220> FEATURE:
<223> OTHER INFORMATION: wildtype Cas9

<400> SEQUENCE: 1

auggccccaa agaagaagcg gaaggucggu auccacggag ucccagcagc cgacaagaag     60
```

-continued

```
uacagcaucg gccuggacau cggcaccaac ucugugggcu gggccgugau caccgacgag    120
uacaaggugc ccagcaagaa auucaaggug cugggcaaca ccgaccggca cagcaucaag    180
aagaaccuga ucggagcccu gcuguucgac agcggcgaaa cagccgaggc cacccggcug    240
aagagaaccg ccagaagaag auacaccaga cggaagaacc ggaucugcua ucugcaagag    300
aucuucagca acgagauggc caagguggac gacagcuucu uccacagacu ggaagagucc    360
uuccuggugg aagaggauaa gaagcacgag cggcacccca ucuucggcaa caucguggac    420
gagguggccu accacgagaa guaccccacc aucuaccacc ugagaaagaa acugguggac    480
agcaccgaca aggccgaccu gcggcugauc uaucuggccc uggcccacau gaucaaguuc    540
cggggccacu uccugaucga gggcgaccug aaccccgaca acagcgacgu ggacaagcug    600
uucauccagc uggugcagac cuacaaccag cuguucgagg aaaaccccau caacgccagc    660
ggcguggacg ccaaggccau ccugucugcc agacugagca agagcagacg gcuggaaaau    720
cugaucgccc agcugcccgg cgagaagaag aauggccugu ucggaaaccu gauugcccug    780
agccugggcc ugacccccaa cuucaagagc aacuucgacc uggccgagga ugccaaacug    840
cagcugagca aggacaccua cgacgacgac cuggacaacc ugcuggccca gaucggcgac    900
caguacgccg accuguuucu ggccgccaag aaccuguccg acgccauccu gcugagcgac    960
auccugagag ugaacaccga gaucaccaag gccccccuga gcgccucuau gaucaagaga   1020
uacgacgagc accaccagga ccugacccug cugaaagcuc ucgugcggca gcagcugccu   1080
gagaaguaca aagagauuuu cuucgaccag agcaagaacg gcuacgccgg cuacauugac   1140
ggcggagcca gccaggaaga guucuacaag uucaucaagc ccauccugga aaagauggac   1200
ggcaccgagg aacugcucgu gaagcugaac agagaggacc ugcugcggaa gcagcggacc   1260
uucgacaacg gcagcauccc ccaccagauc caccugggag agcugcacgc cauucugcgg   1320
cggcaggaag auuuuuaccc auuccugaag gacaaccggg aaaagaucga gaagauccug   1380
accuuccgca uccccuacua cgugggcccu cuggccaggg gaaacagcag auucgccugg   1440
augaccagaa agagcgagga aaccaucacc cccuggaacu ucgaggaagu gguggacaag   1500
ggcgcuuccg cccagagcuu caucgagcgg augaccaacu ucgauaagaa ccugcccaac   1560
gagaaggugc ugcccaagca cagccugcug uacgaguacu ucaccgugua uaacgagcug   1620
accaaaguga aauacgugac cgagggaaug agaaagcccg ccuuccugag cggcgagcag   1680
aaaaaggcca ucguggaccu gcuguucaag accaaccgga aagugaccgu gaagcagcug   1740
aaagaggacu acuucaagaa aaucgagugc uucgacuccg uggaaaucuc cggcguggaa   1800
gaucgguuca acgccucccu gggcacauac cacgaucugc ugaaaauuau caaggacaag   1860
gacuuccugg acaaugagga aaacgaggac auucuggaag auaucgugcu gacccugaca   1920
cuguuugagg acagagagau gaucgaggaa cggcugaaaa ccuaugccca ccuguucgac   1980
gacaaaguga ugaagcagcu gaagcggcgg agauacaccg gcuggggcag gcugagccgg   2040
aagcugauca acggcauccg ggacaagcag uccggcaaga caauccugga uuuccugaag   2100
uccgacggcu ucgccaacag aaacuucaug cagcugaucc acgacgacag ccugaccuuu   2160
aaagaggaca uccagaaagc ccaggugucc ggccagggcg auagccugca cgagcacauu   2220
gccaaucugg ccggcagccc cgccauuaag aagggcaucc ugcagacagu gaagguggug   2280
gacgagcucg ugaaagugau gggccggcac aagcccgaga acaucgugau cgaaauggcc   2340
agagagaacc agaccaccca gaagggacag aagaacagcc gcgagagaau gaagcggauc   2400
gaagagggca ucaaagagcu gggcagccag auccugaaag aacaccccgu ggaaaacacc   2460
```

```
cagcugcaga acgagaagcu guaccuguac uaccugcaga augggcggga uauguacgug   2520

gaccaggaac uggacaucaa ccggcugucc gacuacgaug uggaccauau cgugccucag   2580

agcuuucuga aggacgacuc caucgacaac aaggugcuga ccagaagcga caagaaccgg   2640

ggcaagagcg acaacgugcc cuccgaagag gucgugaaga agaugaagaa cuacuggcgg   2700

cagcugcuga acgccaagcu gauuacccag agaaaguucg acaaucugac caaggccgag   2760

agaggcggcc ugagcgaacu ggauaaggcc ggcuucauca agagacagcu gguggaaacc   2820

cggcagauca caaagcacgu ggcacagauc cuggacuccc ggaugaacac uaaguacgac   2880

gagaaugaca agcugauccg ggaagugaaa gugaucaccc ugaaguccaa gcuggugucc   2940

gauuuccgga aggauuucca guuuuacaaa gugcgcgaga ucaacaacua ccaccacgcc   3000

cacgacgccu accugaacgc cgucguggga accgcccuga ucaaaaagua cccuaagcug   3060

gaaagcgagu ucguguacgg cgacuacaag guguacgacg ugcggaagau gaucgccaag   3120

agcgagcagg aaaucggcaa ggcuaccgcc aaguacuucu ucuacagcaa caucaugaac   3180

uuuuucaaga ccgagauuac ccuggccaac ggcgagaucc ggaagcggcc ucugaucgag   3240

acaaacggcg aaaccgggga gaucgugugg gauaagggcc gggauuuugc caccgugcgg   3300

aaagugcuga gcaugcccca agugaauauc gugaaaaaga ccgaggugca gacaggcggc   3360

uucagcaaag agucuauccu gcccaagagg aacagcgaua agcugaucgc cagaaagaag   3420

gacugggacc cuaagaagua cggcggcuuc gacagcccca ccguggccua uucugugcug   3480

gugguggcca aaguggaaaa gggcaagucc aagaaacuga agagugugaa agagcugcug   3540

gggaucacca ucauggaaag aagcagcuuc gagaagaauc ccaucgacuu ucuggaagcc   3600

aagggcuaca aagaagugaa aaaggaccug aucaucaagc ugccuaagua cucccuguuc   3660

gagcuggaaa acggccggaa gagaaugcug gccucugccg gcgaacugca gaagggaaac   3720

gaacuggccc ugcccuccaa auaugugaac uuccuguacc uggccagcca cuaugagaag   3780

cugaagggcu cccccgagga uaaugagcag aaacagcugu uuguggaaca gcacaagcac   3840

uaccuggacg agaucaucga gcagaucagc gaguucucca agagagugau ccuggccgac   3900

gcuaaucugg acaaagugcu guccgccuac aacaagcacc gggauaagcc caucagagag   3960

caggccgaga auaucaucca ccuguuuacc cugaccaauc ugggagcccc ugccgccuuc   4020

aaguacuuug acaccaccau cgaccggaag agguacacca gcaccaaaga ggugcuggac   4080

gccacccuga uccaccagag caucaccggc cuguacgaga cacggaucga ccugucucag   4140

cugggaggcg acaaaaggcc ggcggccacg aaaaaggccg gccaggcaaa aaagaaaaag   4200

uaa                                                                 4203
```

```
<210> SEQ ID NO 2
<211> LENGTH: 4203
<212> TYPE: RNA
<213> ORGANISM: Artificial
<220> FEATURE:
<223> OTHER INFORMATION: D10A Cas9

<400> SEQUENCE: 2

auggccccaa agaagaagcg gaaggucggu auccacggag ucccagcagc cgacaagaag     60

uacagcaucg gccuggccau cggcaccaac ucugugggcu gggccgugau caccgacgag    120

uacaaggugc ccagcaagaa auucaaggug cugggcaaca ccgaccggca cagcaucaag    180

aagaaccuga ucggagcccu gcuguucgac agcggcgaaa cagccgaggc cacccggcug    240
```

-continued

```
aagagaaccg ccagaagaag auacaccaga cggaagaacc ggaucugcua ucugcaagag    300
aucuucagca acgagauggc caagguggac gacagcuucu uccacagacu ggaagagucc    360
uuccuggugg aagaggauaa gaagcacgag cggcacccca ucuucggcaa caucguggac    420
gagguggccu accacgagaa guaccccacc aucuaccacc ugagaaagaa acugguggac    480
agcaccgaca aggccgaccu gcggcugauc uaucuggccc uggcccacau gaucaaguuc    540
cggggccacu uccugaucga gggcgaccug aaccccgaca acagcgacgu ggacaagcug    600
uucauccagc uggugcagac cuacaaccag cuguucgagg aaaaccccau caacgccagc    660
ggcguggacg ccaaggccau ccugucugcc agacugagca agagcagacg gcuggaaaau    720
cugaucgccc agcugcccgg cgagaagaag aauggccugu ucggaaaccu gauugcccug    780
agccugggcc ugacccccaa cuucaagagc aacuucgacc uggccgagga ugccaaacug    840
cagcugagca aggacaccua cgacgacgac cuggacaacc ugcuggccca gaucggcgac    900
caguacgccg accuguuucu ggccgccaag aaccuguccg acgccauccu gcugagcgac    960
auccugagag ugaacaccga gaucaccaag gccccccuga gcgccucuau gaucaagaga   1020
uacgacgagc accaccagga ccugacccug cugaaagcuc ucgugcggca gcagcugccu   1080
gagaaguaca aagagauuuu cuucgaccag agcaagaacg gcuacgccgg cuacauugac   1140
ggcggagcca gccaggaaga guucuacaag uucaucaagc ccauccugga aaagauggac   1200
ggcaccgagg aacugcucgu gaagcugaac agagaggacc ugcugcggaa gcagcggacc   1260
uucgacaacg gcagcauccc ccaccagauc caccugggag agcugcacgc cauucugcgg   1320
cggcaggaag auuuuuaccc auuccugaag gacaaccggg aaaagaucga gaagauccug   1380
accuuccgca uccccuacua cgugggcccu cuggccaggg gaaacagcag auucgccugg   1440
augaccagaa agagcgagga aaccaucacc cccuggaacu ucgaggaagu gguggacaag   1500
ggcgcuuccg cccagagcuu caucgagcgg augaccaacu ucgauaagaa ccugcccaac   1560
gagaaggugc ugcccaagca cagccugcug uacgaguacu ucaccgugua uaacgagcug   1620
accaaaguga aauacgugac cgagggaaug agaaagcccg ccuuccugag cggcgagcag   1680
aaaaaggcca ucguggaccu gcuguucaag accaaccgga aagugaccgu gaagcagcug   1740
aaagaggacu acuucaagaa aaucgagugc uucgacuccg uggaaaucuc cggcguggaa   1800
gaucgguuca acgccucccu gggcacauac cacgaucugc ugaaaauuau caaggacaag   1860
gacuuccugg acaaugagga aaacgaggac auucuggaag auaucgugcu gacccugaca   1920
cuguuugagg acagagagau gaucgaggaa cggcugaaaa ccuaugccca ccuguucgac   1980
gacaaaguga ugaagcagcu gaagcggcgg agauacaccg gcuggggcag gcugagccgg   2040
aagcugauca acggcauccg ggacaagcag uccggcaaga caauccugga uuuccugaag   2100
uccgacggcu ucgccaacag aaacuucaug cagcugaucc acgacgacag ccugaccuuu   2160
aaagaggaca uccagaaagc ccaggugucc ggccagggcg auagccugca cgagcacauu   2220
gccaaucugg ccggcagccc cgccauuaag aagggcaucc ugcagacagu gaagguggug   2280
gacgagcucg ugaaagugau gggccggcac aagcccgaga acaucgugau cgaaauggcc   2340
agagagaacc agaccaccca gaagggacag aagaacagcc gcgagagaau gaagcggauc   2400
gaagagggca ucaaagagcu gggcagccag auccugaaag aacacccccgu ggaaaacacc   2460
cagcugcaga acgagaagcu guaccuguac uaccugcaga augggcggga uauguacgug   2520
gaccaggaac uggacaucaa ccggcugucc gacuacgaug uggaccauau cgugccucag   2580
agcuuucuga aggacgacuc caucgacaac aaggugcuga ccagaagcga caagaaccgg   2640
```

```
ggcaagagcg acaacgugcc cuccgaagag gucgugaaga agaugaagaa cuacuggcgg   2700

cagcugcuga acgccaagcu gauuacccag agaaaguucg acaaucugac caaggccgag   2760

agaggcggcc ugagcgaacu ggauaaggcc ggcuucauca agagacagcu gguggaaacc   2820

cggcagauca caaagcacgu ggcacagauc cuggacuccc ggaugaacac uaaguacgac   2880

gagaaugaca agcugauccg ggaagugaaa gugaucaccc ugaaguccaa gcugguguccc   2940

gauuuccgga aggauuucca guuuuacaaa gugcgcgaga ucaacaacua ccaccacgcc   3000

cacgacgccu accugaacgc cgucguggga accgcccuga ucaaaaagua cccuaagcug   3060

gaaagcgagu ucguguacgg cgacuacaag guguacgacg ugcggaagau gaucgccaag   3120

agcgagcagg aaaucggcaa ggcuaccgcc aaguacuucu ucuacagcaa caucaugaac   3180

uuuuucaaga ccgagauuac ccuggccaac ggcgagaucc ggaagcggcc ucugaucgag   3240

acaaacggcg aaaccgggga gaucgugugg gauaagggcc gggauuuugc caccgugcgg   3300

aaagugcuga gcaugcccca agugaauauc gugaaaaaga ccgaggugca gacaggcggc   3360

uucagcaaag agucuauccu gcccaagagg aacagcgaua agcugaucgc cagaaagaag   3420

gacugggacc cuaagaagua cggcggcuuc gacagcccca ccguggccua uucugugcug   3480

gugguggcca aaguggaaaa gggcaagucc aagaaacuga agagugugaa agagcugcug   3540

gggaucacca ucauggaaag aagcagcuuc gagaagaauc ccaucgacuu ucuggaagcc   3600

aagggcuaca aagaagugaa aaaggaccug aucaucaagc ugccuaagua cucccuguuc   3660

gagcuggaaa acggccggaa gagaaugcug gccucugccg gcgaacugca gaagggaaac   3720

gaacuggccc ugcccuccaa auaugugaac uuccuguacc uggccagcca cuaugagaag   3780

cugaagggcu cccccgagga uaaugagcag aaacagcugu uuguggaaca gcacaagcac   3840

uaccuggacg agaucaucga gcagaucagc gaguucucca agagagugau ccuggccgac   3900

gcuaaucugg acaaagugcu guccgccuac aacaagcacc gggauaagcc caucagagag   3960

caggccgaga auaucaucca ccuguuuacc cugaccaauc ugggagcccc ugccgccuuc   4020

aaguacuuug acaccaccau cgaccggaag agguacacca gcaccaaaga ggugcuggac   4080

gccacccuga uccaccagag caucaccggc cuguacgaga cacggaucga ccugucucag   4140

cugggaggcg acaaaaggcc ggcggccacg aaaaaggccg gccaggcaaa aaagaaaaag   4200

uaa                                                                 4203
```

<210> SEQ ID NO 3
<211> LENGTH: 18
<212> TYPE: RNA
<213> ORGANISM: Artificial
<220> FEATURE:
<223> OTHER INFORMATION: T7 promoter

<400> SEQUENCE: 3

```
uaauacgacu cacuauag                                                   18
```

<210> SEQ ID NO 4
<211> LENGTH: 18
<212> TYPE: RNA
<213> ORGANISM: Artificial
<220> FEATURE:
<223> OTHER INFORMATION: T3 promoter

<400> SEQUENCE: 4

```
aauuaacccu cacuaaag                                                   18
```

<210> SEQ ID NO 5
<211> LENGTH: 18
<212> TYPE: RNA
<213> ORGANISM: Artificial
<220> FEATURE:
<223> OTHER INFORMATION: SP6 promoter

<400> SEQUENCE: 5
auuuagguga cacuauag 18

<210> SEQ ID NO 6
<211> LENGTH: 21
<212> TYPE: RNA
<213> ORGANISM: Artificial
<220> FEATURE:
<223> OTHER INFORMATION: K11 promoter

<400> SEQUENCE: 6
aauuagggca cacuauaggg a 21

<210> SEQ ID NO 7
<211> LENGTH: 13
<212> TYPE: RNA
<213> ORGANISM: Artificial
<220> FEATURE:
<223> OTHER INFORMATION: minimal 5' UTR

<400> SEQUENCE: 7
gggagacgcc acc 13

<210> SEQ ID NO 8
<211> LENGTH: 43
<212> TYPE: RNA
<213> ORGANISM: Artificial
<220> FEATURE:
<223> OTHER INFORMATION: alpha-GLOBIN 5' UTR (hAg)

<400> SEQUENCE: 8
gggagacucu ucuggucccc acagacucag agagaacgcc acc 43

<210> SEQ ID NO 9
<211> LENGTH: 13
<212> TYPE: RNA
<213> ORGANISM: Artificial
<220> FEATURE:
<223> OTHER INFORMATION: TISU 5' UTR

<400> SEQUENCE: 9
gggagacgcc aag 13

<210> SEQ ID NO 10
<211> LENGTH: 14
<212> TYPE: RNA
<213> ORGANISM: Artificial
<220> FEATURE:
<223> OTHER INFORMATION: TISU+T 5' UTR

<400> SEQUENCE: 10
gggagacugc caag 14

<210> SEQ ID NO 11
<211> LENGTH: 4484
<212> TYPE: RNA
<213> ORGANISM: Artificial
<220> FEATURE:
<223> OTHER INFORMATION: polynucleotide sequence

<400> SEQUENCE: 11
gggagaccca agcuggcuag cguuuaaacu uaagcuugcc accauggacu auaaggacca 60
cgacggagac uacaaggauc augauauuga uuacaaagac gaugacgaua agauggcccc 120
aaagaagaag cggaaggucg guauccacgg agucccagca gccgacaaga aguacagcau 180
cggccuggac aucggcacca acucuguggg cugggccgug aucaccgacg aguacaaggu 240
gcccagcaag aaauucaagg ugcugggcaa caccgaccgg cacagcauca agaagaaccu 300
gaucggagcc cugcuguucg acagcggcga aacagccgag gccacccggc ugaagagaac 360
cgccagaaga agauacacca gacggaagaa ccggaucugc uaucugcaag agaucuucag 420
caacgagaug gccaaggugg acgacagcuu cuuccacaga cuggaagagu ccuuccuggu 480
ggaagaggau aagaagcacg agcggcaccc caucuucggc aacaucgugg acgagguggc 540
cuaccacgag aaguacccca ccaucuacca ccugagaaag aaacuggugg acagcaccga 600
caaggccgac cugcggcuga ucuaucuggc ccuggcccac augaucaagu uccggggcca 660
cuuccugauc gagggcgacc ugaaccccga caacagcgac guggacaagc uguucaucca 720
gcuggugcag accuacaacc agcuguucga ggaaaacccc aucaacgcca gcggcgugga 780
cgccaaggcc auccugucug ccagacugag caagagcaga cggcuggaaa aucugaucgc 840
ccagcugccc ggcgagaaga agaauggccu guucggaaac cugauugccc ugagccuggg 900
ccugaccccc aacuucaaga gcaacuucga ccuggccgag gaugccaaac ugcagcugag 960
caaggacacc uacgacgacg accuggacaa ccugcuggcc cagaucggcg accaguacgc 1020
cgaccuguuu cuggccgcca agaaccuguc cgacgccauc cugcugagcg acauccugag 1080
agugaacacc gagaucacca aggccccccu gagcgccucu augaucaaga gauacgacga 1140
gcaccaccag gaccugaccc ugcugaaagc ucucgugcgg cagcagcugc cugagaagua 1200
caaagagauu uucuucgacc agagcaagaa cggcuacgcc ggcuacauug acggcggagc 1260
cagccaggaa gaguucuaca aguucaucaa gcccauccug gaaaagaugg acggcaccga 1320
ggaacugcuc gugaagcuga acagagagga ccugcugcgg aagcagcgga ccuucgacaa 1380
cggcagcauc ccccaccaga uccaccuggg agagcugcac gccauucugc ggcggcagga 1440
agauuuuuac ccauuccuga aggacaaccg ggaaaagauc gagaagaucc ugaccuuccg 1500
cauccccuac uacgugggcc cucuggccag gggaaacagc agauucgccu ggaugaccag 1560
aaagagcgag gaaaccauca ccccccuggaa cuucgaggaa gugguggaca agggcgcuuc 1620
cgcccagagc uucaucgagc ggaugaccaa cuucgauaag aaccugccca acgagaaggu 1680
gcugcccaag cacagccugc uguacgagua cuucaccgug uauaacgagc ugaccaaagu 1740
gaaauacgug accgagggaa ugagaaagcc cgccuuccug agcggcgagc agaaaaaggc 1800
caucguggac cugcuguuca agaccaaccg gaaagugacc gugaagcagc ugaaagagga 1860
cuacuucaag aaaaucgagu gcuucgacuc cguggaaauc uccggcgugg aagaucgguu 1920
caacgccucc cugggcacau accacgaucu gcugaaaauu aucaaggaca aggacuuccu 1980
ggacaaugag gaaaacgagg acauucugga agauaucgug cugacccuga cacuguuuga 2040
ggacagagag augaucgagg aacggcugaa aaccuaugcc caccuguucg acgacaaagu 2100
gaugaagcag cugaagcggc ggagauacac cggcuggggc aggcugagcc ggaagcugau 2160
caacggcauc cgggacaagc aguccggcaa gacaauccug gauuuccuga aguccgacgg 2220
cuucgccaac agaaacuuca ugcagcugau ccacgacgac agccugaccu uuaaagagga 2280

-continued

```
cauccagaaa gcccaggugu ccggccaggg cgauagccug cacgagcaca uugccaaucu   2340
ggccggcagc cccgccauua agaagggcau ccugcagaca gugaaggugg uggacgagcu   2400
cgugaaagug augggccggc acaagcccga gaacaucgug aucgaaaugg ccagagagaa   2460
ccagaccacc cagaagggac agaagaacag ccgcgagaga augaagcgga ucgaagaggg   2520
caucaaagag cugggcagcc agauccugaa agaacacccc guggaaaaca cccagcugca   2580
gaacgagaag cuguaccugu acuaccugca gaaugggcgg gauauguacg uggaccagga   2640
acuggacauc aaccggcugu ccgacuacga uguggaccau aucgugccuc agagcuuucu   2700
gaaggacgac uccaucgaca acaaggugcu gaccagaagc gacaagaacc ggggcaagag   2760
cgacaacgug cccuccgaag aggucgugaa gaagaugaag aacuacuggc ggcagcugcu   2820
gaacgccaag cugauuaccc agagaaaguu cgacaaucug accaaggccg agagaggcgg   2880
ccugagcgaa cuggauaagg ccggcuucau caagagacag cugguggaaa cccggcagau   2940
cacaaagcac guggcacaga uccuggacuc ccggaugaac acuaaguacg acgagaauga   3000
caagcugauc cgggaaguga aagugaucac ccugaagucc aagcuggugu ccgauuuccg   3060
gaaggauuuc caguuuuaca aagugcgcga gaucaacaac uaccaccacg cccacgacgc   3120
cuaccugaac gccgucgugg gaaccgcccu gaucaaaaag uacccuaagc uggaaagcga   3180
guucguguac ggcgacuaca agguguacga cgugcggaag augaucgcca agagcgagca   3240
ggaaaucggc aaggcuaccg ccaaguacuu cuucuacagc aacaucauga acuuuuucaa   3300
gaccgagauu acccuggcca acggcgagau ccggaagcgg ccucugaucg agacaaacgg   3360
cgaaaccggg gagaucgugu gggauaaggg ccgggauuuu gccaccgugc ggaaagugcu   3420
gagcaugccc caagugaaua ucgugaaaaa gaccgaggug cagacaggcg gcuucagcaa   3480
agagucuauc cugcccaaga ggaacagcga uaagcugauc gccagaaaga aggacuggga   3540
cccuaagaag uacggcggcu ucgacagccc caccguggcc uauucugugc ugguggugc    3600
caaaguggaa aagggcaagu ccaagaaacu gaagagugug aaagagcugc uggggaucac   3660
caucauggaa agaagcagcu ucgagaagaa ucccaucgac uuucuggaag ccaagggcua   3720
caaagaagug aaaaaggacc ugaucaucaa gcugccuaag uacucccugu ucgagcugga   3780
aaacggccgg aagagaaugc uggccucugc cggcgaacug cagaagggaa acgaacuggc   3840
ccugcccucc aaauauguga acuuccugua ccuggccagc cacuaugaga agcugaaggg   3900
cucccccgag gauaaugagc agaaacagcu guuuguggaa cagcacaagc acuaccugga   3960
cgagaucauc gagcagauca gcgaguucuc caagagagug auccuggccg acgcuaaucu   4020
ggacaaagug cuguccgccu acaacaagca ccgggauaag cccaucagag agcaggccga   4080
gaauaucauc caccuguuua cccugaccaa ucugggagcc ccugccgccu ucaaguacuu   4140
ugacaccacc aucgaccgga agagguacac cagcaccaaa gaggugcugg acgccacccu   4200
gauccaccag agcaucaccg gccuguacga gacacggauc gaccugucuc agcugggagg   4260
cgacaaaagg ccggcggcca cgaaaaaggc cggccaggca aaaaagaaaa aguaagaauu   4320
ccuaggaucc acuaguccag ugugguggaa uucugcagaa aaaaaaaaaa aaaaaaaaaa   4380
aaaaaaaaaa aaaaaaaaaa aaaaaaaaaa aaaaaaaaaa aaaaaaaaaa aaaaaaaaaa   4440
aaaaaaaaaa aaaaaaaaaa aaaaaaaaaa aaaaaaaagc ggcc                    4484
```

<210> SEQ ID NO 12
<211> LENGTH: 4221
<212> TYPE: RNA
<213> ORGANISM: Artificial
<220> FEATURE:
<223> OTHER INFORMATION: polynucleotide sequence

<400> SEQUENCE: 12
gggagacgcc accauggccc caaagaagaa gcggaagguc gguauccacg gagucccagc 60
agccgacaag aaguacagca ucggccugga caucggcacc aacucugugg gcugggccgu 120
gaucaccgac gaguacaagg ugcccagcaa gaaauucaag gugcugggca acaccgaccg 180
gcacagcauc aagaagaacc ugaucggagc ccugcuguuc gacagcggcg aaacagccga 240
ggccacccgg cugaagagaa ccgccagaag aagauacacc agacggaaga accggaucug 300
cuaucugcaa gagaucuuca gcaacgagau ggccaaggug gacgacagcu ucuuccacag 360
acuggaagag uccuuccugg uggaagagga uaagaagcac gagcggcacc ccaucuucgg 420
caacaucgug gacgaggugg ccuaccacga gaaguacccc accaucuacc accugagaaa 480
gaaacuggug gacagcaccg acaaggccga ccugcggcug aucuaucugg cccuggccca 540
caugaucaag uuccggggcc acuuccugau cgagggcgac cugaaccccg acaacagcga 600
cguggacaag cuguucaucc agcuggugca gaccuacaac cagcuguucg aggaaaaccc 660
caucaacgcc agcggcgugg acgccaaggc cauccugucu gccagacuga gcaagagcag 720
acggcuggaa aaucugaucg cccagcugcc cggcgagaag aagaauggcc uguucggaaa 780
ccugauugcc cugagccugg gccugacccc caacuucaag agcaacuucg accuggccga 840
ggaugccaaa cugcagcuga gcaaggacac cuacgacgac gaccuggaca accugcuggc 900
ccagaucggc gaccaguacg ccgaccuguu ucuggccgcc aagaaccugu ccgacgccau 960
ccugcugagc gacauccuga gagugaacac cgagaucacc aaggcccccc ugagcgccuc 1020
uaugaucaag agauacgacg agcaccacca ggaccugacc cugcugaaag cucucgugcg 1080
gcagcagcug ccugagaagu acaaagagau uuucuucgac cagagcaaga acggcuacgc 1140
cggcuacauu gacggcggag ccagccagga agaguucuac aaguucauca agcccauccu 1200
ggaaaagaug gacggcaccg aggaacugcu cgugaagcug aacagagagg accugcugcg 1260
gaagcagcgg accuucgaca acggcagcau cccccaccag auccaccugg gagagcugca 1320
cgccauucug cggcggcagg aagauuuuua cccauuccug aaggacaacc gggaaaagau 1380
cgagaagauc cugaccuucc gcauccccua cuacgugggc ccucuggcca ggggaaacag 1440
cagauucgcc uggaugacca gaaagagcga ggaaaccauc acccccugga acuucgagga 1500 aguggguggac aagggcgcuu ccgcccagag cuucaucgag cggaugacca acuucgauaa 1560
gaaccugccc aacgagaagg ugcugcccaa gcacagccug cuguacgagu acuucaccgu 1620
guauaacgag cugaccaaag ugaaauacgu gaccgaggga augagaaagc ccgccuuccu 1680
gagcggcgag cagaaaaagg ccaucgugga ccugcuguuc aagaccaacc ggaaagugac 1740
cgugaagcag cugaaagagg acuacuucaa gaaaaucgag ugcuucgacu ccguggaaau 1800
cuccggcgug gaagaucggu ucaacgccuc ccugggcaca uaccacgauc ugcugaaaau 1860
uaucaaggac aaggacuucc uggacaauga ggaaaacgag gacauucugg aagauaucgu 1920
gcugacccug acacuguuug aggacagaga gaugaucgag gaacggcuga aaaccuaugc 1980
ccaccuguuc gacgacaaag ugaugaagca gcugaagcgg cggagauaca ccggcugggg 2040
caggcugagc cggaagcuga ucaacggcau ccgggacaag caguccggca agacaauccu 2100
ggauuuccug aaguccgacg gcuucgccaa cagaaacuuc augcagcuga uccacgacga 2160
cagccugacc uuuaaagagg acauccagaa agcccaggug uccggccagg gcgauagccu 2220
gcacgagcac auugccaauc uggccggcag ccccgccauu aagaagggca uccugcagac 2280
agugaaggug guggacgagc ucgugaaagu gaugggccgg cacaagcccg agaacaucgu 2340
gaucgaaaug gccagagaga accagaccac ccagaaggga cagaagaaca gccgcgagag 2400
aaugaagcgg aucgaagagg gcaucaaaga gcugggcagc cagauccuga aagaacaccc 2460
cguggaaaac acccagcugc agaacgagaa gcuguaccug uacuaccugc agaaugggcg 2520
ggauauguac guggaccagg aacuggacau caaccggcug uccgacuacg auguggacca 2580
uaucgugccu cagagcuuuc ugaaggacga cuccaucgac aacaaggugc ugaccagaag 2640
cgacaagaac cggggcaaga gcgacaacgu gcccuccgaa gaggucguga agaagaugaa 2700
gaacuacugg cggcagcugc ugaacgccaa gcugauuacc cagagaaagu ucgacaaucu 2760
gaccaaggcc gagagaggcg gccugagcga acuggauaag gccggcuuca ucaagagaca 2820
gcugguggaa acccggcaga ucacaaagca cguggcacag auccuggacu cccggaugaa 2880
cacuaaguac gacgagaaug acaagcugau ccgggaagug aaagugauca cccugaaguc 2940
caagcuggug uccgauuucc ggaaggauuu ccaguuuuac aaagugcgcg agaucaacaa 3000
cuaccaccac gcccacgacg ccuaccugaa cgccgucgug ggaaccgccc ugaucaaaaa 3060
guacccuaag cuggaaagcg aguucgugua cggcgacuac aagguguacg acgugcggaa 3120
gaugaucgcc aagagcgagc aggaaaucgg caaggcuacc gccaaguacu ucuucuacag 3180
caacaucaug aacuuuuuca agaccgagau uacccuggcc aacggcgaga uccggaagcg 3240
gccucugauc gagacaaacg gcgaaaccgg ggagaucgug ugggauaagg gccgggauuu 3300
ugccaccgug cggaaagugc ugagcaugcc ccaagugaau aucgugaaaa agaccgaggu 3360
gcagacaggc ggcuucagca aagagucuau ccugcccaag aggaacagcg auaagcugau 3420
cgccagaaag aaggacuggg acccuaagaa guacggcggc uucgacagcc ccaccguggc 3480
cuauucugug cugguggugg ccaaagugga aaagggcaag uccaagaaac ugaagagugu 3540
gaaagagcug cuggggauca ccaucaugga aagaagcagc uucgagaaga aucccaucga 3600
cuuucuggaa gccaagggcu acaaagaagu gaaaaaggac cugaucauca agcugccuaa 3660
guacucccug uucgagcugg aaaacggccg gaagagaaug cuggccucug ccggcgaacu 3720
gcagaaggga aacgaacugg cccugcccuc caaauaugug aacuuccugu accuggccag 3780
ccacuaugag aagcugaagg gcucccccga ggauaaugag cagaaacagc uguuugugga 3840
acagcacaag cacuaccugg acgagaucau cgagcagauc agcgaguucu ccaagagagu 3900
gauccuggcc gacgcuaauc uggacaaagu gcuguccgcc uacaacaagc accgggauaa 3960
gcccaucaga gagcaggccg agaauaucau ccaccuguuu acccugacca aucugggagc 4020
cccugccgcc uucaaguacu uugacaccac caucgaccgg aagagguaca ccagcaccaa 4080
agaggugcug gacgccaccc ugauccacca gagcaucacc ggccuguacg agacacggau 4140
cgaccugucu cagcugggag gcgacaaaag gccggcggcc acgaaaaagg ccggccaggc 4200
aaaaaagaaa aaguaagaau u 4221

<210> SEQ ID NO 13
<211> LENGTH: 4251
<212> TYPE: RNA
<213> ORGANISM: Artificial
<220> FEATURE:
<223> OTHER INFORMATION: polynucleotide sequence

<400> SEQUENCE: 13
gggagacucu ucuggucccc acagacucag agagaacgcc accauggccc caaagaagaa 60

-continued

```
gcggaagguc gguauccacg gagucccagc agccgacaag aaguacagca ucggccugga    120
caucggcacc aacucugugg gcugggccgu gaucaccgac gaguacaagg ugcccagcaa    180
gaaauucaag gugcugggca acaccgaccg gcacagcauc aagaagaacc ugaucggagc    240
ccugcuguuc gacagcggcg aaacagccga ggccacccgg cugaagagaa ccgccagaag    300
aagauacacc agacggaaga accggaucug cuaucugcaa gagaucuuca gcaacgagau    360
ggccaaggug gacgacagcu ucuuccacag acuggaagag uccuuccugg uggaagagga    420
uaagaagcac gagcggcacc ccaucuucgg caacaucgug gacgaggugg ccuaccacga    480
gaaguacccc accaucuacc accugagaaa gaaacuggug gacagcaccg acaaggccga    540
ccugcggcug aucuaucugg cccuggccca caugaucaag uuccggggcc acuuccugau    600
cgagggcgac cugaaccccg acaacagcga cguggacaag cuguucaucc agcuggugca    660
gaccuacaac cagcuguucg aggaaaaccc caucaacgcc agcggcgugg acgccaaggc    720
cauccugucu gccagacuga gcaagagcag acggcuggaa aaucugaucg cccagcugcc    780
cggcgagaag aagaauggcc uguucggaaa ccugauugcc cugagccugg gccugacccc    840
caacuucaag agcaacuucg accuggccga ggaugccaaa cugcagcuga gcaaggacac    900
cuacgacgac gaccuggaca accugcuggc ccagaucggc gaccaguacg ccgaccuguu    960
ucuggccgcc aagaaccugu ccgacgccau ccugcugagc gacauccuga gagugaacac   1020
cgagaucacc aaggcccccc ugagcgccuc uaugaucaag agauacgacg agcaccacca   1080
ggaccugacc cugcugaaag cucucgugcg gcagcagcug ccugagaagu acaaagagau   1140
uuucuucgac cagagcaaga acggcuacgc cggcuacauu gacggcggag ccagccagga   1200
agaguucuac aaguucauca agcccauccu ggaaaagaug gacggcaccg aggaacugcu   1260
cgugaagcug aacagagagg accugcugcg gaagcagcgg accuucgaca acggcagcau   1320
cccccaccag auccaccugg gagagcugca cgccauucug cggcggcagg aagauuuuua   1380
cccauuccug aaggacaacc gggaaaagau cgagaagauc cugaccuucc gcauccccua   1440
cuacgugggc ccucuggcca ggggaaacag cagauucgcc uggaugacca gaaagagcga   1500
ggaaaccauc acccccugga acuucgagga agugguggac aagggcgcuu ccgcccagag   1560
cuucaucgag cggaugacca acuucgauaa gaaccugccc aacgagaagg ugcugcccaa   1620
gcacagccug cuguacgagu acuucaccgu guauaacgag cugaccaaag ugaaauacgu   1680
gaccgaggga augagaaagc ccgccuuccu gagcggcgag cagaaaaagg ccaucgugga   1740
ccugcuguuc aagaccaacc ggaaagugac cgugaagcag cugaaagagg acuacuucaa   1800
gaaaaucgag ugcuucgacu ccguggaaau cuccggcgug gaagaucggu ucaacgccuc   1860
ccugggcaca uaccacgauc ugcugaaaau uaucaaggac aaggacuucc uggacaauga   1920
ggaaaacgag gacauucugg aagauaucgu gcugacccug acacuguuug aggacagaga   1980
gaugaucgag gaacggcuga aaaccuaugc ccaccuguuc gacgacaaag ugaugaagca   2040
gcugaagcgg cggagauaca ccggcugggg caggcugagc cggaagcuga ucaacggcau   2100
ccgggacaag caguccggca agacaauccu ggauuuccug aaguccgacg gcuucgccaa   2160
cagaaacuuc augcagcuga uccacgacga cagccugacc uuuaaagagg acauccagaa   2220
agcccaggug uccggccagg gcgauagccu gcacgagcac auugccaauc uggccggcag   2280
ccccgccauu aagaagggca uccugcagac agugaaggug guggacgagc ucgugaaagu   2340
gaugggccgg cacaagcccg agaacaucgu gaucgaaaug gccagagaga accagaccac   2400
```

-continued ccagaaggga cagaagaaca gccgcgagag aaugaagcgg aucgaagagg gcaucaaaga 2460
gcugggcagc cagauccuga aagaacaccc cguggaaaac acccagcugc agaacgagaa 2520
gcuguaccug uacuaccugc agaaugggcg ggauauguac guggaccagg aacuggacau 2580
caaccggcug uccgacuacg auguggacca uaucgugccu cagagcuuuc ugaaggacga 2640
cuccaucgac aacaaggugc ugaccagaag cgacaagaac cggggcaaga gcgacaacgu 2700
gcccuccgaa gaggucguga agaagaugaa gaacuacugg cggcagcugc ugaacgccaa 2760
gcugauuacc cagagaaagu ucgacaaucu gaccaaggcc gagagaggcg gccugagcga 2820
acuggauaag gccggcuuca ucaagagaca gcugguggaa acccggcaga ucacaaagca 2880
cguggcacag auccuggacu cccggaugaa cacuaaguac gacgagaaug acaagcugau 2940
ccgggaagug aaagugauca cccugaaguc caagcuggug uccgauuucc ggaaggauuu 3000
ccaguuuuac aaagugcgcg agaucaacaa cuaccaccac gcccacgacg ccuaccugaa 3060
cgccgucgug ggaaccgccc ugaucaaaaa guacccuaag cuggaaagcg aguucgugua 3120
cggcgacuac aagguguacg acgugcggaa gaugaucgcc aagagcgagc aggaaaucgg 3180
caaggcuacc gccaaguacu ucuucuacag caacaucaug aacuuuuuca agaccgagau 3240
uacccuggcc aacggcgaga uccggaagcg gccucugauc gagacaaacg gcgaaaccgg 3300
ggagaucgug ugggauaagg gccgggauuu ugccaccgug cggaaagugc ugagcaugcc 3360
ccaagugaau aucgugaaaa agaccgaggu gcagacaggc ggcuucagca aagagucuau 3420
ccugcccaag aggaacagcg auaagcugau cgccagaaag aaggacuggg acccuaagaa 3480
guacggcggc uucgacagcc ccaccguggc cuauucugug cugguggugg ccaaagugga 3540
aaagggcaag uccaagaaac ugaagagugu gaaagagcug cuggggauca ccaucaugga 3600
aagaagcagc uucgagaaga aucccaucga cuuucuggaa gccaagggcu acaaagaagu 3660
gaaaaaggac cugaucauca agcugccuaa guacucccug uucgagcugg aaaacggccg 3720
gaagagaaug cuggccucug ccggcgaacu gcagaaggga aacgaacugg cccugcccuc 3780
caaauaugug aacuuccugu accuggccag ccacuaugag aagcugaagg gcucccccga 3840
ggauaaugag cagaaacagc uguuugugga acagcacaag cacuaccugg acgagaucau 3900
cgagcagauc agcgaguucu ccaagagagu gauccuggcc gacgcuaauc uggacaaagu 3960
gcuguccgcc uacaacaagc accgggauaa gcccaucaga gagcaggccg agaauaucau 4020
ccaccuguuu acccugacca aucugggagc cccugccgcc uucaaguacu uugacaccac 4080
caucgaccgg aagagguaca ccagcaccaa agaggugcug gacgccaccc ugauccacca 4140
gagcaucacc ggccuguacg agacacggau cgaccugucu cagcugggag gcgacaaaag 4200
gccggcggcc acgaaaaagg ccggccaggc aaaaaagaaa aaguaagaau u 4251

<210> SEQ ID NO 14
<211> LENGTH: 4222
<212> TYPE: RNA
<213> ORGANISM: Artificial
<220> FEATURE:
<223> OTHER INFORMATION: polynucleotide sequence

<400> SEQUENCE: 14
gggagacugc caagauggcc ccaaagaaga agcggaaggu cgguauccac ggagucccag 60
cagccgacaa gaaguacagc aucggccugg acaucggcac caacucugug ggcugggccg 120
ugaucaccga cgaguacaag gugcccagca agaaauucaa ggugcugggc aacaccgacc 180
ggcacagcau caagaagaac cugaucggag cccugcuguu cgacagcggc gaaacagccg 240

-continued

```
aggccacccg gcugaagaga accgccagaa gaagauacac cagacggaag aaccggaucu    300
gcuaucugca agagaucuuc agcaacgaga uggccaaggu ggacgacagc uucuuccaca    360
gacuggaaga guccuuccug guggaagagg auaagaagca cgagcggcac cccaucuucg    420
gcaacaucgu ggacgaggug gccuaccacg agaaguaccc caccaucuac caccugagaa    480
agaaacuggu ggacagcacc gacaaggccg accugcggcu gaucuaucug gcccuggccc    540
acaugaucaa guuccggggc cacuuccuga ucgagggcga ccugaacccc gacaacagcg    600
acguggacaa gcuguucauc cagcuggugc agaccuacaa ccagcuguuc gaggaaaacc    660
ccaucaacgc cagcggcgug gacgccaagg ccauccuguc ugccagacug agcaagagca    720
gacggcugga aaaucugauc gcccagcugc ccggcgagaa gaagaauggc cuguucggaa    780
accugauugc ccugagccug ggccugaccc ccaacuucaa gagcaacuuc gaccuggccg    840
aggaugccaa acugcagcug agcaaggaca ccuacgacga cgaccuggac aaccugcugg    900
cccagaucgg cgaccaguac gccgaccugu uucuggccgc caagaaccug uccgacgcca    960
uccugcugag cgacauccug agagugaaca ccgagaucac caaggccccc cugagcgccu   1020
cuaugaucaa gagauacgac gagcaccacc aggaccugac ccugcugaaa gcucucgugc   1080
ggcagcagcu gccugagaag uacaaagaga uuuucuucga ccagagcaag aacggcuacg   1140
ccggcuacau ugacggcgga gccagccagg aagaguucua caaguucauc aagcccaucc   1200
uggaaaagau ggacggcacc gaggaacugc ucgugaagcu gaacagagag gaccugcugc   1260
ggaagcagcg gaccuucgac aacggcagca ucccccacca gauccaccug ggagagcugc   1320
acgccauucu gcggcggcag gaagauuuuu acccauuccu gaaggacaac cgggaaaaga   1380
ucgagaagau ccugaccuuc cgcauccccu acuacguggg cccucuggcc aggggaaaca   1440
gcagauucgc cuggaugacc agaaagagcg aggaaaccau caccccccugg aacuucgagg  1500
aaguggugga caagggcgcu uccgcccaga gcuucaucga gcggaugacc aacuucgaua   1560
agaaccugcc caacgagaag gugcugccca agcacagccu gcuguacgag uacuucaccg   1620
uguauaacga gcugaccaaa gugaaauacg ugaccgaggg aaugagaaag cccgccuucc   1680
ugagcggcga gcagaaaaag gccaucgugg accugcuguu caagaccaac cggaaaguga   1740
ccgugaagca gcugaaagag gacuacuuca agaaaaucga gugcuucgac uccguggaaa   1800
ucuccggcgu ggaagaucgg uucaacgccu cccugggcac auaccacgau cugcugaaaa   1860
uuaucaagga caaggacuuc cuggacaaug aggaaaacga ggacauucug gaagauaucg   1920
ugcugacccu gacacuguuu gaggacagag agaugaucga ggaacggcug aaaaccuaug   1980
cccaccuguu cgacgacaaa gugaugaagc agcugaagcg gcggagauac accggcuggg   2040
gcaggcugag ccggaagcug aucaacggca uccgggacaa gcaguccggc aagacaaucc   2100
uggauuuccu gaaguccgac ggcuucgcca acagaaacuu caugcagcug auccacgacg   2160
acagccugac cuuuaaagag gacauccaga aagcccaggu guccggccag ggcgauagcc   2220
ugcacgagca cauugccaau cuggccggca gccccgccau uaagaagggc auccugcaga   2280
cagugaaggu gguggacgag cucgugaaag ugaugggccg gcacaagccc gagaacaucg   2340
ugaucgaaau ggccagagag aaccagacca cccagaaggg acagaagaac agccgcgaga   2400
gaaugaagcg gaucgaagag ggcaucaaag agcugggcag ccagauccug aaagaacacc   2460
ccguggaaaa cacccagcug cagaacgaga agcuguaccu guacuaccug cagaaugggc   2520
gggauaugua cguggaccag gaacuggaca ucaaccggcu guccgacuac gauguggacc   2580
```

auaucgugcc ucagagcuuu cugaaggacg acuccaucga caacaaggug cugaccagaa 2640
gcgacaagaa ccggggcaag agcgacaacg ugcccuccga agaggucgug aagaagauga 2700
agaacuacug gcggcagcug cugaacgcca agcugauuac ccagagaaag uucgacaauc 2760
ugaccaaggc cgagagaggc ggccugagcg aacuggauaa ggccggcuuc aucaagagac 2820
agcugguggu aacccggcag aucacaaagc acguggcaca gauccuggac ucccggauga 2880
acacuaagua cgacgagaau gacaagcuga uccgggaagu gaaagugauc acccugaagu 2940
ccaagcuggu guccgauuuc cggaaggauu uccaguuuua caaagugcgc gagaucaaca 3000
acuaccacca cgcccacgac gccuaccuga acgccgucgu gggaaccgcc cugaucaaaa 3060
aguacccuaa gcuggaaagc gaguucgugu acggcgacua caagguguac gacgugcgga 3120
agaugaucgc caagagcgag caggaaaucg gcaaggcuac cgccaaguac uucuucuaca 3180
gcaacaucau gaacuuuuuc aagaccgaga uuacccuggc caacggcgag auccggaagc 3240
ggccucugau cgagacaaac ggcgaaaccg gggagaucgu gugggauaag ggccgggauu 3300
uugccaccgu gcggaaagug cugagcaugc cccaagugaa uaucgugaaa aagaccgagg 3360
ugcagacagg cggcuucagc aaagagucua uccugcccaa gaggaacagc gauaagcuga 3420
ucgccagaaa gaaggacugg gacccuaaga aguacggcgg cuucgacagc cccaccgugg 3480
ccuauucugu gcugguggug gccaaagugg aaaagggcaa guccaagaaa cugaagagug 3540
ugaaagagcu gcuggggauc accaucaugg aaagaagcag cuucgagaag aaucccaucg 3600
acuuucugga agccaagggc uacaaagaag ugaaaaagga ccugaucauc aagcugccua 3660
aguacucccu guucgagcug gaaaacggcc ggaagagaau gcuggccucu gccggcgaac 3720
ugcagaaggg aaacgaacug gcccugcccu ccaaauaugu gaacuuccug uaccuggcca 3780
gccacuauga gaagcugaag ggcucccccg aggauaauga gcagaaacag cuguuugugg 3840
aacagcacaa gcacuaccug gacgagauca ucgagcagau cagcgaguuc uccaagagag 3900
ugauccuggc cgacgcuaau cuggacaaag ugcuguccgc cuacaacaag caccgggaua 3960
agcccaucag agagcaggcc gagaauauca uccaccuguu uacccugacc aaucugggag 4020
ccccugccgc cuucaaguac uuugacacca ccaucgaccg gaagagguac accagcacca 4080
aagaggugcu ggacgccacc cugauccacc agagcaucac cggccuguac gagacacgga 4140
ucgaccuguc ucagcuggga ggcgacaaaa ggccggcggc cacgaaaaag gccggccagg 4200
caaaaaagaa aaaguaagaa uu 4222

<210> SEQ ID NO 15
<211> LENGTH: 4445
<212> TYPE: RNA
<213> ORGANISM: Artificial
<220> FEATURE:
<223> OTHER INFORMATION: polynucleotide sequence

<400> SEQUENCE: 15
gggagaccca agcuggcuag cguuuaaacu uaagcuugcc accauguacc cauacgaugu 60
uccagauuac gcuauggccc caaagaagaa gcggaagguc gguauccacg gagucccagc 120
agccgacaag aaguacagca ucggccuggc caucggcacc aacucugugg gcugggccgu 180
gaucaccgac gaguacaagg ugcccagcaa gaaauucaag gugcugggca acaccgaccg 240
gcacagcauc aagaagaacc ugaucggagc ccugcuguuc gacagcggcg aaacagccga 300
ggccacccgg cugaagagaa ccgccagaag aagauacacc agacggaaga accggaucug 360
cuaucugcaa gagaucuuca gcaacgagau ggccaaggug gacgacagcu ucuuccacag 420

-continued

```
acuggaagag uccuuccugg uggaagagga uaagaagcac gagcggcacc ccaucuucgg    480
caacaucgug gacgaggugg ccuaccacga gaaguacccc accaucuacc accugagaaa    540
gaaacuggug gacagcaccg acaaggccga ccugcggcug aucuaucugg cccuggccca    600
caugaucaag uuccggggcc acuuccugau cgagggcgac cugaaccccg acaacagcga    660
cguggacaag cuguucaucc agcuggugca gaccuacaac cagcuguucg aggaaaaccc    720
caucaacgcc agcggcgugg acgccaaggc cauccugucu gccagacuga gcaagagcag    780
acggcuggaa aaucugaucg cccagcugcc cggcgagaag aagaauggcc uguucggaaa    840
ccugauugcc cugagccugg gccugacccc caacuucaag agcaacuucg accuggccga    900
ggaugccaaa cugcagcuga gcaaggacac cuacgacgac gaccuggaca accugcuggc    960
ccagaucggc gaccaguacg ccgaccuguu ucuggccgcc aagaaccugu ccgacgccau   1020
ccugcugagc gacauccuga gagugaacac cgagaucacc aaggcccccc ugagcgccuc   1080
uaugaucaag agauacgacg agcaccacca ggaccugacc cugcugaaag cucucgugcg   1140
gcagcagcug ccugagaagu acaaagagau uuucuucgac cagagcaaga acggcuacgc   1200
cggcuacauu gacggcggag ccagccagga agaguucuac aaguucauca agcccauccu   1260
ggaaaagaug gacggcaccg aggaacugcu cgugaagcug aacagagagg accugcugcg   1320
gaagcagcgg accuucgaca acggcagcau cccccaccag auccaccugg gagagcugca   1380
cgccauucug cggcggcagg aagauuuuua cccauuccug aaggacaacc gggaaaagau   1440
cgagaagauc cugaccuucc gcauccccua cuacgugggc ccucuggcca ggggaaacag   1500
cagauucgcc uggaugacca gaaagagcga ggaaaccauc acccccugga acuucgagga   1560
agugguggac aagggcgcuu ccgcccagag cuucaucgag cggaugacca acuucgauaa   1620
gaaccugccc aacgagaagg ugcugcccaa gcacagccug cuguacgagu acuucaccgu   1680
guauaacgag cugaccaaag ugaaauacgu gaccgaggga augagaaagc ccgccuuccu   1740
gagcggcgag cagaaaaagg ccaucgugga ccugcuguuc aagaccaacc ggaaagugac   1800
cgugaagcag cugaaagagg acuacuucaa gaaaaucgag ugcuucgacu ccguggaaau   1860
cuccggcgug gaagaucggu ucaacgccuc ccugggcaca uaccacgauc ugcugaaaau   1920
uaucaaggac aaggacuucc uggacaauga ggaaaacgag gacauucugg aagauaucgu   1980
gcugacccug acacuguuug aggacagaga gaugaucgag gaacggcuga aaaccuaugc   2040
ccaccuguuc gacgacaaag ugaugaagca gcugaagcgg cggagauaca ccggcugggg   2100
caggcugagc cggaagcuga ucaacggcau ccgggacaag caguccggca agacaauccu   2160
ggauuuccug aaguccgacg gcuucgccaa cagaaacuuc augcagcuga uccacgacga   2220
cagccugacc uuuaaagagg acauccagaa agcccaggug uccggccagg gcgauagccu   2280
gcacgagcac auugccaauc uggccggcag ccccgccauu aagaagggca uccugcagac   2340
agugaaggug guggacgagc ucgugaaagu gaugggccgg cacaagcccg agaacaucgu   2400
gaucgaaaug gccagagaga accagaccac ccagaaggga cagaagaaca gccgcgagag   2460
aaugaagcgg aucgaagagg gcaucaaaga gcugggcagc cagauccuga aagaacaccc   2520
cguggaaaac acccagcugc agaacgagaa gcuguaccug uacuaccugc agaaugggcg   2580
ggauauguac guggaccagg aacuggacau caaccggcug uccgacuacg auguggacca   2640
uaucgugccu cagagcuuuc ugaaggacga cuccaucgac aacaaggugc ugaccagaag   2700
cgacaagaac cggggcaaga gcgacaacgu gcccuccgaa gaggucguga agaagaugaa   2760
```

gaacuacugg cggcagcugc ugaacgccaa gcugauuacc cagagaaagu ucgacaaucu 2820
gaccaaggcc gagagaggcg gccugagcga acuggauaag gccggcuuca ucaagagaca 2880
gcugguggaa acccggcaga ucacaaagca cguggcacag auccuggacu cccggaugaa 2940
cacuaaguac gacgagaaug acaagcugau ccgggaagug aaagugauca cccugaaguc 3000
caagcuggug uccgauuucc ggaaggauuu ccaguuuuac aaagugcgcg agaucaacaa 3060
cuaccaccac gcccacgacg ccuaccugaa cgccgucgug ggaaccgccc ugaucaaaaa 3120
guacccuaag cuggaaagcg aguucgugua cggcgacuac aagguguacg acgugcggaa 3180
gaugaucgcc aagagcgagc aggaaaucgg caaggcuacc gccaaguacu ucuucuacag 3240
caacaucaug aacuuuuuca agaccgagau uacccuggcc aacggcgaga uccggaagcg 3300
gccucugauc gagacaaacg gcgaaaccgg ggagaucgug ugggauaagg gccgggauuu 3360
ugccaccgug cggaaagugc ugagcaugcc ccaagugaau aucgugaaaa agaccgaggu 3420
gcagacaggc ggcuucagca aagagucuau ccugcccaag aggaacagcg auaagcugau 3480
cgccagaaag aaggacuggg acccuaagaa guacggcggc uucgacagcc ccaccguggc 3540
cuauucugug cugguggugg ccaaagugga aaagggcaag uccaagaaac ugaagagugu 3600
gaaagagcug cuggggauca ccaucaugga aagaagcagc uucgagaaga aucccaucga 3660
cuuucuggaa gccaagggcu acaaagaagu gaaaaaggac cugaucauca agcugccuaa 3720
guacucccug uucgagcugg aaaacggccg gaagagaaug cuggccucug ccggcgaacu 3780
gcagaaggga aacgaacugg cccugcccuc caaauaugug aacuuccugu accuggccag 3840
ccacuaugag aagcugaagg gcucccccga ggauaaugag cagaaacagc uguuugugga 3900
acagcacaag cacuaccugg acgagaucau cgagcagauc agcgaguucu ccaagagagu 3960
gauccuggcc gacgcuaauc uggacaaagu gcuguccgcc uacaacaagc accgggauaa 4020
gcccaucaga gagcaggccg agaauaucau ccaccuguuu acccugacca aucugggagc 4080
cccugccgcc uucaaguacu uugacaccac caucgaccgg aagagguaca ccagcaccaa 4140
agaggugcug gacgccaccc ugauccacca gagcaucacc ggccuguacg agacacggau 4200
cgaccugucu cagcugggag gcgacaaaag gccggcggcc acgaaaaagg ccggccaggc 4260
aaaaaagaaa aaguaagaau uccuaggauc cacuagucca guguggugga auucugcaga 4320
aaaaaaaaaa aaaaaaaaaa aaaaaaaaaa aaaaaaaaaa aaaaaaaaaa aaaaaaaaaa 4380
aaaaaaaaaa aaaaaaaaaa aaaaaaaaaa aaaaaaaaaa aaaaaaaaaa aaaaaaaaag 4440
cggcc 4445

<210> SEQ ID NO 16
<211> LENGTH: 4221
<212> TYPE: RNA
<213> ORGANISM: Artificial
<220> FEATURE:
<223> OTHER INFORMATION: polynucleotide sequence

<400> SEQUENCE: 16
gggagacgcc accauggccc caaagaagaa gcggaagguc gguauccacg gagucccagc 60
agccgacaag aaguacagca ucggccuggc caucggcacc aacucugugg gcugggccgu 120
gaucaccgac gaguacaagg ugcccagcaa gaaauucaag gugcugggca acaccgaccg 180
gcacagcauc aagaagaacc ugaucggagc ccugcuguuc gacagcggcg aaacagccga 240
ggccacccgg cugaagagaa ccgccagaag aagauacacc agacggaaga accggaucug 300
cuaucugcaa gagaucuuca gcaacgagau ggccaaggug gacgacagcu ucuuccacag 360
acuggaagag uccuuccugg uggaagagga uaagaagcac gagcggcacc ccaucuucgg 420
caacaucgug gacgaggugg ccuaccacga gaaguacccc accaucuacc accugagaaa 480
gaaacuggug gacagcaccg acaaggccga ccugcggcug aucuaucugg cccuggccca 540
caugaucaag uuccggggcc acuuccugau cgagggcgac cugaaccccg acaacagcga 600
cguggacaag cuguucaucc agcuggugca gaccuacaac cagcuguucg aggaaaaccc 660
caucaacgcc agcggcgugg acgccaaggc cauccugucu gccagacuga gcaagagcag 720
acggcuggaa aaucugaucg cccagcugcc cggcgagaag aagaauggcc uguucggaaa 780
ccugauugcc cugagccugg gccugacccc caacuucaag agcaacuucg accuggccga 840
ggaugccaaa cugcagcuga gcaaggacac cuacgacgac gaccuggaca accugcuggc 900
ccagaucggc gaccaguacg ccgaccuguu ucuggccgcc aagaaccugu ccgacgccau 960
ccugcugagc gacauccuga gagugaacac cgagaucacc aaggcccccc ugagcgccuc 1020
uaugaucaag agauacgacg agcaccacca ggaccugacc cugcugaaag cucucgugcg 1080
gcagcagcug ccugagaagu acaaagagau uuucuucgac cagagcaaga acggcuacgc 1140
cggcuacauu gacggcggag ccagccagga agaguucuac aaguucauca agcccauccu 1200
ggaaaagaug gacggcaccg aggaacugcu cgugaagcug aacagagagg accugcugcg 1260
gaagcagcgg accuucgaca acggcagcau cccccaccag auccaccugg gagagcugca 1320
cgccauucug cggcggcagg aagauuuuua cccauuccug aaggacaacc gggaaaagau 1380
cgagaagauc cugaccuucc gcauccccua cuacgugggc ccucuggcca ggggaaacag 1440
cagauucgcc uggaugacca gaaagagcga ggaaaccauc acccccugga acuucgagga 1500
agugguggac aagggcgcuu ccgcccagag cuucaucgag cggaugacca acuucgauaa 1560
gaaccugccc aacgagaagg ugcugcccaa gcacagccug cuguacgagu acuucaccgu 1620
guauaacgag cugaccaaag ugaaauacgu gaccgaggga augagaaagc ccgccuuccu 1680
gagcggcgag cagaaaaagg ccaucgugga ccugcuguuc aagaccaacc ggaaagugac 1740
cgugaagcag cugaaagagg acuacuucaa gaaaaucgag ugcuucgacu ccguggaaau 1800
cuccggcgug gaagaucggu ucaacgccuc ccugggcaca uaccacgauc ugcugaaaau 1860
uaucaaggac aaggacuucc uggacaauga ggaaaacgag gacauucugg aagauaucgu 1920
gcugacccug acacuguuug aggacagaga gaugaucgag gaacggcuga aaaccuaugc 1980
ccaccuguuc gacgacaaag ugaugaagca gcugaagcgg cggagauaca ccggcugggg 2040
caggcugagc cggaagcuga ucaacggcau ccgggacaag caguccggca agacaauccu 2100
ggauuuccug aaguccgacg gcuucgccaa cagaaacuuc augcagcuga uccacgacga 2160
cagccugacc uuuaaagagg acauccagaa agcccaggug uccggccagg gcgauagccu 2220
gcacgagcac auugccaauc uggccggcag ccccgccauu aagaagggca uccugcagac 2280
agugaaggug guggacgagc ucgugaaagu gaugggccgg cacaagcccg agaacaucgu 2340
gaucgaaaug gccagagaga accagaccac ccagaaggga cagaagaaca gccgcgagag 2400
aaugaagcgg aucgaagagg gcaucaaaga gcugggcagc cagauccuga aagaacaccc 2460
cguggaaaac acccagcugc agaacgagaa gcuguaccug uacuaccugc agaaugggcg 2520
ggauauguac guggaccagg aacuggacau caaccggcug uccgacuacg auguggacca 2580
uaucgugccu cagagcuuuc ugaaggacga cuccaucgac aacaaggugc ugaccagaag 2640
cgacaagaac cggggcaaga gcgacaacgu gcccuccgaa gaggucguga agaagaugaa 2700

```
gaacuacugg cggcagcugc ugaacgccaa gcugauuacc cagagaaagu ucgacaaucu   2760

gaccaaggcc gagagaggcg gccugagcga acuggauaag gccggcuuca ucaagagaca   2820

gcugguggaa acccggcaga ucacaaagca cguggcacag auccuggacu cccggaugaa   2880

cacuaaguac gacgagaaug acaagcugau ccgggaagug aaagugauca cccugaaguc   2940

caagcuggug uccgauuucc ggaaggauuu ccaguuuuac aaagugcgcg agaucaacaa   3000

cuaccaccac gcccacgacg ccuaccugaa cgccgucgug ggaaccgccc ugaucaaaaa   3060

guacccuaag cuggaaagcg aguucgugua cggcgacuac aagguguacg acgugcggaa   3120

gaugaucgcc aagagcgagc aggaaaucgg caaggcuacc gccaaguacu ucuucuacag   3180

caacaucaug aacuuuuuca agaccgagau uacccuggcc aacggcgaga uccggaagcg   3240

gccucugauc gagacaaacg gcgaaaccgg ggagaucgug ugggauaagg gccgggauuu   3300

ugccaccgug cggaaagugc ugagcaugcc ccaagugaau aucgugaaaa agaccgaggu   3360

gcagacaggc ggcuucagca aagagucuau ccugcccaag aggaacagcg auaagcugau   3420

cgccagaaag aaggacuggg acccuaagaa guacggcggc uucgacagcc ccaccguggc   3480

cuauucugug cugguggugg ccaaagugga aaagggcaag uccaagaaac ugaagagugu   3540

gaaagagcug cuggggauca ccaucaugga aagaagcagc uucgagaaga aucccaucga   3600

cuuucuggaa gccaagggcu acaaagaagu gaaaaaggac cugaucauca agcugccuaa   3660

guacucccug uucgagcugg aaaacggccg gaagagaaug cuggccucug ccggcgaacu   3720

gcagaaggga aacgaacugg cccugcccuc caaauaugug aacuuccugu accuggccag   3780

ccacuaugag aagcugaagg gcucccccga ggauaaugag cagaaacagc uguuugugga   3840

acagcacaag cacuaccugg acgagaucau cgagcagauc agcgaguucu ccaagagagu   3900

gauccuggcc gacgcuaauc uggacaaagu gcuguccgcc uacaacaagc accgggauaa   3960

gcccaucaga gagcaggccg agaauaucau ccaccuguuu acccugacca aucugggagc   4020

cccugccgcc uucaaguacu uugacaccac caucgaccgg aagagguaca ccagcaccaa   4080

agaggugcug gacgccaccc ugauccacca gagcaucacc ggccuguacg agacacggau   4140

cgaccugucu cagcugggag gcgacaaaag gccggcggcc acgaaaaagg ccggccaggc   4200

aaaaaagaaa aaguaagaau u                                             4221
```

<210> SEQ ID NO 17
<211> LENGTH: 4251
<212> TYPE: RNA
<213> ORGANISM: Artificial
<220> FEATURE:
<223> OTHER INFORMATION: polynucleotide sequence

<400> SEQUENCE: 17

```
gggagacucu ucuggucccc acagacucag agagaacgcc accauggccc caaagaagaa     60

gcggaagguc gguauccacg gagucccagc agccgacaag aaguacagca ucggccuggc    120

caucggcacc aacucugugg gcugggccgu gaucaccgac gaguacaagg ugcccagcaa    180

gaaauucaag gugcugggca acaccgaccg gcacagcauc aagaagaacc ugaucggagc    240

ccugcuguuc gacagcggcg aaacagccga ggccacccgg cugaagagaa ccgccagaag    300

aagauacacc agacggaaga accggaucug cuaucugcaa gagaucuuca gcaacgagau    360

ggccaaggug gacgacagcu ucuuccacag acuggaagag uccuuccugg uggaagagga    420

uaagaagcac gagcggcacc ccaucuucgg caacaucgug gacgaggugg ccuaccacga    480

gaaguacccc accaucuacc accugagaaa gaaacuggug gacagcaccg acaaggccga    540
```

-continued

```
ccugcggcug aucuaucugg cccuggccca caugaucaag uuccggggcc acuuccugau    600
cgagggcgac cugaaccccg acaacagcga cguggacaag cuguucaucc agcuggugca    660
gaccuacaac cagcuguucg aggaaaaccc caucaacgcc agcggcgugg acgccaaggc    720
cauccugucu gccagacuga gcaagagcag acggcuggaa aaucugaucg cccagcugcc    780
cggcgagaag aagaauggcc uguucggaaa ccugauugcc cugagccugg gccugacccc    840
caacuucaag agcaacuucg accuggccga ggaugccaaa cugcagcuga gcaaggacac    900
cuacgacgac gaccuggaca accugcuggc ccagaucggc gaccaguacg ccgaccuguu    960
ucuggccgcc aagaaccugu ccgacgccau ccugcugagc gacauccuga gagugaacac   1020
cgagaucacc aaggcccccc ugagcgccuc uaugaucaag agauacgacg agcaccacca   1080
ggaccugacc cugcugaaag cucucgugcg gcagcagcug ccugagaagu acaaagagau   1140
uuucuucgac cagagcaaga acggcuacgc cggcuacauu gacggcggag ccagccagga   1200
agaguucuac aaguucauca agcccauccu ggaaaagaug gacggcaccg aggaacugcu   1260
cgugaagcug aacagagagg accugcugcg gaagcagcgg accuucgaca acggcagcau   1320
cccccaccag auccaccugg gagagcugca cgccauucug cggcggcagg aagauuuuua   1380
cccauuccug aaggacaacc gggaaaagau cgagaagauc cugaccuucc gcauccccua   1440
cuacgugggc ccucuggcca ggggaaacag cagauucgcc uggaugacca gaaagagcga   1500
ggaaaccauc acccccugga acuucgagga agugguggac aagggcgcuu ccgcccagag   1560
cuucaucgag cggaugacca acuucgauaa gaaccugccc aacgagaagg ugcugcccaa   1620
gcacagccug cuguacgagu acuucaccgu guauaacgag cugaccaaag ugaaauacgu   1680
gaccgaggga augagaaagc ccgccuuccu gagcggcgag cagaaaaagg ccaucgugga   1740
ccugcuguuc aagaccaacc ggaaagugac cgugaagcag cugaaagagg acuacuucaa   1800
gaaaaucgag ugcuucgacu ccguggaaau cuccggcgug gaagaucggu ucaacgccuc   1860
ccugggcaca uaccacgauc ugcugaaaau uaucaaggac aaggacuucc uggacaauga   1920
ggaaaacgag gacauucugg aagauaucgu gcugacccug acacuguuug aggacagaga   1980
gaugaucgag gaacggcuga aaaccuaugc ccaccuguuc gacgacaaag ugaugaagca   2040
gcugaagcgg cggagauaca ccggcugggg caggcugagc cggaagcuga ucaacggcau   2100
ccgggacaag caguccggca agacaauccu ggauuuccug aaguccgacg gcuucgccaa   2160
cagaaacuuc augcagcuga uccacgacga cagccugacc uuuaaagagg acauccagaa   2220
agcccaggug uccggccagg gcgauagccu gcacgagcac auugccaauc uggccggcag   2280
ccccgccauu aagaagggca uccugcagac agugaaggug guggacgagc ucgugaaagu   2340
gaugggccgg cacaagcccg agaacaucgu gaucgaaaug gccagagaga accagaccac   2400
ccagaaggga cagaagaaca gccgcgagag aaugaagcgg aucgaagagg gcaucaaaga   2460
gcugggcagc cagauccuga aagaacaccc cguggaaaac acccagcugc agaacgagaa   2520
gcuguaccug uacuaccugc agaaugggcg ggauauguac guggaccagg aacuggacau   2580
caaccggcug uccgacuacg auguggacca uaucgugccu cagagcuuuc ugaaggacga   2640
cuccaucgac aacaaggugc ugaccagaag cgacaagaac cggggcaaga gcgacaacgu   2700
gcccuccgaa gaggucguga agaagaugaa gaacuacugg cggcagcugc ugaacgccaa   2760
gcugauuacc cagagaaagu ucgacaaucu gaccaaggcc gagagaggcg gccugagcga   2820
acuggauaag gccggcuuca ucaagagaca gcugguggaa acccggcaga ucacaaagca   2880
```

cgucggcacag auccuggacu cccggaugaa cacuaaguac gacgagaaug acaagcugau 2940
ccgggaagug aaagugauca cccugaaguc caagcuggug uccgauuucc ggaaggauuu 3000
ccaguuuuac aaagugcgcg agaucaacaa cuaccaccac gcccacgacg ccuaccugaa 3060
cgccgucgug ggaaccgccc ugaucaaaaa guacccuaag cuggaaagcg aguucgugua 3120
cggcgacuac aagguguacg acgugcggaa gaugaucgcc aagagcgagc aggaaaucgg 3180
caaggcuacc gccaaguacu ucuucuacag caacaucaug aacuuuuuca agaccgagau 3240
uacccuggcc aacggcgaga uccggaagcg gccucugauc gagacaaacg gcgaaaccgg 3300
ggagaucgug ugggauaagg gccgggauuu ugccaccgug cggaaagugc ugagcaugcc 3360
ccaagugaau aucgugaaaa agaccgaggu gcagacaggc ggcuucagca aagagucuau 3420
ccugcccaag aggaacagcg auaagcugau cgccagaaag aaggacuggg acccuaagaa 3480
guacggcggc uucgacagcc ccaccguggc cuauucugug cugguggugg ccaaagugga 3540
aaagggcaag uccaagaaac ugaagagugu gaaagagcug cuggggauca ccaucaugga 3600
aagaagcagc uucgagaaga aucccaucga cuuucuggaa gccaagggcu acaaagaagu 3660
gaaaaaggac cugaucauca agcugccuaa guacucccug uucgagcugg aaaacggccg 3720
gaagagaaug cuggccucug ccggcgaacu gcagaaggga aacgaacugg cccugcccuc 3780
caaauaugug aacuuccugu accuggccag ccacuaugag aagcugaagg gcuccccga 3840 ggauaaugag cagaaacagc uguuugugga acagcacaag cacuaccugg acgagaucau 3900
cgagcagauc agcgaguucu ccaagagagu gauccuggcc gacgcuaauc uggacaaagu 3960
gcuguccgcc uacaacaagc accgggauaa gcccaucaga gagcaggccg agaauaucau 4020
ccaccuguuu acccugacca aucugggagc cccugccgcc uucaaguacu uugacaccac 4080
caucgaccgg aagagguaca ccagcaccaa agaggugcug gacgccaccc ugauccacca 4140
gagcaucacc ggccuguacg agacacggau cgaccugucu cagcugggag gcgacaaaag 4200
gccggcggcc acgaaaaagg ccggccaggc aaaaaagaaa aaguaagaau u 4251

<210> SEQ ID NO 18
<211> LENGTH: 4222
<212> TYPE: RNA
<213> ORGANISM: Artificial
<220> FEATURE:
<223> OTHER INFORMATION: polynucleotide sequence

<400> SEQUENCE: 18
gggagacugc caagauggcc ccaaagaaga agcggaaggu cgguauccac ggagucccag 60
cagccgacaa gaaguacagc aucggccugg ccaucggcac caacucugug ggcugggccg 120
ugaucaccga cgaguacaag gugcccagca agaaauucaa ggugcugggc aacaccgacc 180
ggcacagcau caagaagaac cugaucggag cccugcuguu cgacagcggc gaaacagccg 240
aggccacccg gcugaagaga accgccagaa gaagauacac cagacggaag aaccggaucu 300
gcuaucugca agagaucuuc agcaacgaga uggccaaggu ggacgacagc uucuuccaca 360
gacuggaaga guccuuccug guggaagagg auaagaagca cgagcggcac cccaucuucg 420
gcaacaucgu ggacgaggug gccuaccacg agaaguaccc caccaucuac caccugagaa 480
agaaacuggu ggacagcacc gacaaggccg accugcggcu gaucuaucug gcccuggccc 540
acaugaucaa guuccggggc cacuuccuga ucgagggcga ccugaacccc gacaacagcg 600
acguggacaa gcuguucauc cagcuggugc agaccuacaa ccagcuguuc gaggaaaacc 660
ccaucaacgc cagcggcgug gacgccaagg ccauccuguc ugccagacug agcaagagca 720

```
gacggcugga aaaucugauc gcccagcugc ccggcgagaa gaagaauggc cuguucggaa    780
accugauugc ccugagccug ggccugaccc ccaacuucaa gagcaacuuc gaccuggccg    840
aggaugccaa acugcagcug agcaaggaca ccuacgacga cgaccuggac aaccugcugg    900
cccagaucgg cgaccaguac gccgaccugu uucuggccgc caagaaccug uccgacgcca    960
uccugcugag cgacauccug agagugaaca ccgagaucac caaggccccc cugagcgccu   1020
cuaugaucaa gagauacgac gagcaccacc aggaccugac ccugcugaaa gcucucgugc   1080
ggcagcagcu gccugagaag uacaaagaga uuuucuucga ccagagcaag aacggcuacg   1140
ccggcuacau ugacggcgga gccagccagg aagaguucua caaguucauc aagcccaucc   1200
uggaaaagau ggacggcacc gaggaacugc ucgugaagcu gaacagagag gaccugcugc   1260
ggaagcagcg gaccuucgac aacggcagca ucccccacca gauccaccug ggagagcugc   1320
acgccauucu gcggcggcag gaagauuuuu acccauuccu gaaggacaac cgggaaaaga   1380
ucgagaagau ccugaccuuc cgcauccccu acuacguggg cccucuggcc aggggaaaca   1440
gcagauucgc cuggaugacc agaaagagcg aggaaaccau caccccccugg aacuucgagg   1500
aaguggugga caagggcgcu uccgcccaga gcuucaucga gcggaugacc aacuucgaua   1560
agaaccugcc caacgagaag gugcugccca agcacagccu gcuguacgag uacuucaccg   1620
uguauaacga gcugaccaaa gugaaauacg ugaccgaggg aaugagaaag cccgccuucc   1680
ugagcggcga gcagaaaaag gccaucgugg accugcuguu caagaccaac cggaaaguga   1740
ccgugaagca gcugaaagag gacuacuuca agaaaaucga gugcuucgac uccguggaaa   1800
ucuccggcgu ggaagaucgg uucaacgccu cccugggcac auaccacgau cugcugaaaa   1860
uuaucaagga caaggacuuc cuggacaaug aggaaaacga ggacauucug gaagauaucg   1920
ugcugacccu gacacuguuu gaggacagag agaugaucga ggaacggcug aaaaccuaug   1980
cccaccuguu cgacgacaaa gugaugaagc agcugaagcg gcggagauac accggcuggg   2040
gcaggcugag ccggaagcug aucaacggca uccgggacaa gcaguccggc aagacaaucc   2100
uggauuuccu gaaguccgac ggcuucgcca acagaaacuu caugcagcug auccacgacg   2160
acagccugac cuuuaaagag gacauccaga aagcccaggu guccggccag ggcgauagcc   2220
ugcacgagca cauugccaau cuggccggca gccccgccau uaagaagggc auccugcaga   2280
cagugaaggu gguggacgag cucgugaaag ugaugggccg gcacaagccc gagaacaucg   2340
ugaucgaaau ggccagagag aaccagacca cccagaaggg acagaagaac agccgcgaga   2400
gaaugaagcg gaucgaagag ggcaucaaag agcugggcag ccagauccug aaagaacacc   2460
ccguggaaaa cacccagcug cagaacgaga agcuguaccu guacuaccug cagaaugggc   2520
gggauaugua cguggaccag gaacuggaca ucaaccggcu guccgacuac gauguggacc   2580
auaucgugcc ucagagcuuu cugaaggacg acuccaucga caacaaggug cugaccagaa   2640
gcgacaagaa ccggggcaag agcgacaacg ugcccuccga agaggucgug aagaagauga   2700
agaacuacug gcggcagcug cugaacgcca agcugauuac ccagagaaag uucgacaauc   2760
ugaccaaggc cgagagaggc ggccugagcg aacuggauaa ggccggcuuc aucaagagac   2820
agcuggugga aacccggcag aucacaaagc acguggcaca gauccuggac ucccggauga   2880
acacuaagua cgacgagaau gacaagcuga uccgggaagu gaaagugauc acccugaagu   2940
ccaagcuggu guccgauuuc cggaaggauu uccaguuuua caaagugcgc gagaucaaca   3000
acuaccacca cgcccacgac gccuaccuga acgccgucgu gggaaccgcc cugaucaaaa   3060
```

-continued

```
aguacccuaa gcuggaaagc gaguucgugu acggcgacua caaggugaac gacgugcgga   3120

agaugaucgc caagagcgag caggaaaucg gcaaggcuac cgccaaguac uucuucuaca   3180

gcaacaucau gaacuuuuuc aagaccgaga uuacccuggc caacggcgag auccggaagc   3240

ggccucugau cgagacaaac ggcgaaaccg gggagaucgu gugggauaag ggccgggauu   3300

uugccaccgu gcggaaagug cugagcaugc cccaagugaa uaucgugaaa aagaccgagg   3360

ugcagacagg cggcuucagc aaagagucua uccugcccaa gaggaacagc gauaagcuga   3420

ucgccagaaa gaaggacugg gacccuaaga aguacggcgg cuucgacagc cccaccgugg   3480

ccuauucugu gcugguggug gccaaagugg aaaagggcaa guccaagaaa cugaagagug   3540

ugaaagagcu gcuggggauc accaucaugg aaagaagcag cuucgagaag aaucccaucg   3600

acuuucugga agccaagggc uacaaagaag ugaaaaagga ccugaucauc aagcugccua   3660

aguacucccu guucgagcug gaaaacggcc ggaagagaau gcuggccucu gccggcgaac   3720

ugcagaaggg aaacgaacug gcccugcccu ccaaauaugu gaacuuccug uaccuggcca   3780

gccacuauga gaagcugaag ggcucccccg aggauaauga gcagaaacag cuguuugugg   3840

aacagcacaa gcacuaccug gacgagauca ucgagcagau cagcgaguuc uccaagagag   3900

ugauccuggc cgacgcuaau cuggacaaag ugcuguccgc cuacaacaag caccgggaua   3960

agcccaucag agagcaggcc gagaauauca uccaccuguu uacccugacc aaucugggag   4020

ccccugccgc cuucaaguac uuugacacca ccaucgaccg gaagagguac accagcacca   4080

aagaggugcu ggacgccacc cugauccacc agagcaucac cggccuguac gagacacgga   4140

ucgaccuguc ucagcuggga ggcgacaaaa ggccggcggc cacgaaaaag gccggccagg   4200

caaaaaagaa aaaguaagaa uu                                            4222
```

```
<210> SEQ ID NO 19
<211> LENGTH: 1399
<212> TYPE: PRT
<213> ORGANISM: Artificial
<220> FEATURE:
<223> OTHER INFORMATION: wildtype Cas9

<400> SEQUENCE: 19

Met Ala Pro Lys Lys Lys Arg Lys Val Gly Ile His Gly Val Pro Ala
1               5                   10                  15

Ala Asp Lys Lys Tyr Ser Ile Gly Leu Asp Ile Gly Thr Asn Ser Val
            20                  25                  30

Gly Trp Ala Val Ile Thr Asp Glu Tyr Lys Val Pro Ser Lys Lys Phe
        35                  40                  45

Lys Val Leu Gly Asn Thr Asp Arg His Ser Ile Lys Lys Asn Leu Ile
    50                  55                  60

Gly Ala Leu Leu Phe Asp Ser Gly Glu Thr Ala Glu Ala Thr Arg Leu
65                  70                  75                  80

Lys Arg Thr Ala Arg Arg Arg Tyr Thr Arg Arg Lys Asn Arg Ile Cys
                85                  90                  95

Tyr Leu Gln Glu Ile Phe Ser Asn Glu Met Ala Lys Val Asp Asp Ser
            100                 105                 110

Phe Phe His Arg Leu Glu Glu Ser Phe Leu Val Glu Glu Asp Lys Lys
        115                 120                 125

His Glu Arg His Pro Ile Phe Gly Asn Ile Val Asp Glu Val Ala Tyr
    130                 135                 140

His Glu Lys Tyr Pro Thr Ile Tyr His Leu Arg Lys Lys Leu Val Asp
145                 150                 155                 160
```

-continued

```
Ser Thr Asp Lys Ala Asp Leu Arg Leu Ile Tyr Leu Ala Leu Ala His
                165                 170                 175

Met Ile Lys Phe Arg Gly His Phe Leu Ile Glu Gly Asp Leu Asn Pro
            180                 185                 190

Asp Asn Ser Asp Val Asp Lys Leu Phe Ile Gln Leu Val Gln Thr Tyr
        195                 200                 205

Asn Gln Leu Phe Glu Glu Asn Pro Ile Asn Ala Ser Gly Val Asp Ala
    210                 215                 220

Lys Ala Ile Leu Ser Ala Arg Leu Ser Lys Ser Arg Arg Leu Glu Asn
225                 230                 235                 240

Leu Ile Ala Gln Leu Pro Gly Glu Lys Lys Asn Gly Leu Phe Gly Asn
                245                 250                 255

Leu Ile Ala Leu Ser Leu Gly Leu Thr Pro Asn Phe Lys Ser Asn Phe
            260                 265                 270

Asp Leu Ala Glu Asp Ala Lys Leu Gln Leu Ser Lys Asp Thr Tyr Asp
        275                 280                 285

Asp Asp Leu Asp Asn Leu Leu Ala Gln Ile Gly Asp Gln Tyr Ala Asp
    290                 295                 300

Leu Phe Leu Ala Ala Lys Asn Leu Ser Asp Ala Ile Leu Leu Ser Asp
305                 310                 315                 320

Ile Leu Arg Val Asn Thr Glu Ile Thr Lys Ala Pro Leu Ser Ala Ser
                325                 330                 335

Met Ile Lys Arg Tyr Asp Glu His His Gln Asp Leu Thr Leu Leu Lys
            340                 345                 350

Ala Leu Val Arg Gln Gln Leu Pro Glu Lys Tyr Lys Glu Ile Phe Phe
        355                 360                 365

Asp Gln Ser Lys Asn Gly Tyr Ala Gly Tyr Ile Asp Gly Gly Ala Ser
    370                 375                 380

Gln Glu Glu Phe Tyr Lys Phe Ile Lys Pro Ile Leu Glu Lys Met Asp
385                 390                 395                 400

Gly Thr Glu Glu Leu Leu Val Lys Leu Asn Arg Glu Asp Leu Leu Arg
                405                 410                 415

Lys Gln Arg Thr Phe Asp Asn Gly Ser Ile Pro His Gln Ile His Leu
            420                 425                 430

Gly Glu Leu His Ala Ile Leu Arg Arg Gln Glu Asp Phe Tyr Pro Phe
        435                 440                 445

Leu Lys Asp Asn Arg Glu Lys Ile Glu Lys Ile Leu Thr Phe Arg Ile
    450                 455                 460

Pro Tyr Tyr Val Gly Pro Leu Ala Arg Gly Asn Ser Arg Phe Ala Trp
465                 470                 475                 480

Met Thr Arg Lys Ser Glu Glu Thr Ile Thr Pro Trp Asn Phe Glu Glu
                485                 490                 495

Val Val Asp Lys Gly Ala Ser Ala Gln Ser Phe Ile Glu Arg Met Thr
            500                 505                 510

Asn Phe Asp Lys Asn Leu Pro Asn Glu Lys Val Leu Pro Lys His Ser
        515                 520                 525

Leu Leu Tyr Glu Tyr Phe Thr Val Tyr Asn Glu Leu Thr Lys Val Lys
    530                 535                 540

Tyr Val Thr Glu Gly Met Arg Lys Pro Ala Phe Leu Ser Gly Glu Gln
545                 550                 555                 560

Lys Lys Ala Ile Val Asp Leu Leu Phe Lys Thr Asn Arg Lys Val Thr
                565                 570                 575
```

```
Val Lys Gln Leu Lys Glu Asp Tyr Phe Lys Lys Ile Glu Cys Phe Asp
            580                 585                 590

Ser Val Glu Ile Ser Gly Val Glu Asp Arg Phe Asn Ala Ser Leu Gly
        595                 600                 605

Thr Tyr His Asp Leu Leu Lys Ile Ile Lys Asp Lys Asp Phe Leu Asp
    610                 615                 620

Asn Glu Glu Asn Glu Asp Ile Leu Glu Asp Ile Val Leu Thr Leu Thr
625                 630                 635                 640

Leu Phe Glu Asp Arg Glu Met Ile Glu Glu Arg Leu Lys Thr Tyr Ala
                645                 650                 655

His Leu Phe Asp Asp Lys Val Met Lys Gln Leu Lys Arg Arg Arg Tyr
            660                 665                 670

Thr Gly Trp Gly Arg Leu Ser Arg Lys Leu Ile Asn Gly Ile Arg Asp
        675                 680                 685

Lys Gln Ser Gly Lys Thr Ile Leu Asp Phe Leu Lys Ser Asp Gly Phe
    690                 695                 700

Ala Asn Arg Asn Phe Met Gln Leu Ile His Asp Asp Ser Leu Thr Phe
705                 710                 715                 720

Lys Glu Asp Ile Gln Lys Ala Gln Val Ser Gly Gln Gly Asp Ser Leu
                725                 730                 735

His Glu His Ile Ala Asn Leu Ala Gly Ser Pro Ala Ile Lys Lys Gly
            740                 745                 750

Ile Leu Gln Thr Val Lys Val Val Asp Glu Leu Val Lys Val Met Gly
        755                 760                 765

Arg His Lys Pro Glu Asn Ile Val Ile Glu Met Ala Arg Glu Asn Gln
    770                 775                 780

Thr Thr Gln Lys Gly Gln Lys Asn Ser Arg Glu Arg Met Lys Arg Ile
785                 790                 795                 800

Glu Glu Gly Ile Lys Glu Leu Gly Ser Gln Ile Leu Lys Glu His Pro
                805                 810                 815

Val Glu Asn Thr Gln Leu Gln Asn Glu Lys Leu Tyr Leu Tyr Tyr Leu
            820                 825                 830

Gln Asn Gly Arg Asp Met Tyr Val Asp Gln Glu Leu Asp Ile Asn Arg
        835                 840                 845

Leu Ser Asp Tyr Asp Val Asp His Ile Val Pro Gln Ser Phe Leu Lys
    850                 855                 860

Asp Asp Ser Ile Asp Asn Lys Val Leu Thr Arg Ser Asp Lys Asn Arg
865                 870                 875                 880

Gly Lys Ser Asp Asn Val Pro Ser Glu Glu Val Val Lys Lys Met Lys
                885                 890                 895

Asn Tyr Trp Arg Gln Leu Leu Asn Ala Lys Leu Ile Thr Gln Arg Lys
            900                 905                 910

Phe Asp Asn Leu Thr Lys Ala Glu Arg Gly Gly Leu Ser Glu Leu Asp
        915                 920                 925

Lys Ala Gly Phe Ile Lys Arg Gln Leu Val Glu Thr Arg Gln Ile Thr
    930                 935                 940

Lys His Val Ala Gln Ile Leu Asp Ser Arg Met Asn Thr Lys Tyr Asp
945                 950                 955                 960

Glu Asn Asp Lys Leu Ile Arg Glu Val Lys Val Ile Thr Leu Lys Ser
                965                 970                 975

Lys Leu Val Ser Asp Phe Arg Lys Asp Phe Gln Phe Tyr Lys Val Arg
            980                 985                 990

Glu Ile Asn Asn Tyr His His Ala  His Asp Ala Tyr Leu  Asn Ala Val
```

```
        995                 1000                1005

Val Gly  Thr Ala Leu Ile Lys  Lys Tyr Pro Lys Leu  Glu Ser Glu
    1010                 1015                 1020

Phe Val  Tyr Gly Asp Tyr Lys  Val Tyr Asp Val Arg  Lys Met Ile
    1025                 1030                 1035

Ala Lys  Ser Glu Gln Glu Ile  Gly Lys Ala Thr Ala  Lys Tyr Phe
    1040                 1045                 1050

Phe Tyr  Ser Asn Ile Met Asn  Phe Phe Lys Thr Glu  Ile Thr Leu
    1055                 1060                 1065

Ala Asn  Gly Glu Ile Arg Lys  Arg Pro Leu Ile Glu  Thr Asn Gly
    1070                 1075                 1080

Glu Thr  Gly Glu Ile Val Trp  Asp Lys Gly Arg Asp  Phe Ala Thr
    1085                 1090                 1095

Val Arg  Lys Val Leu Ser Met  Pro Gln Val Asn Ile  Val Lys Lys
    1100                 1105                 1110

Thr Glu  Val Gln Thr Gly Gly  Phe Ser Lys Glu Ser  Ile Leu Pro
    1115                 1120                 1125

Lys Arg  Asn Ser Asp Lys Leu  Ile Ala Arg Lys Lys  Asp Trp Asp
    1130                 1135                 1140

Pro Lys  Lys Tyr Gly Gly Phe  Asp Ser Pro Thr Val  Ala Tyr Ser
    1145                 1150                 1155

Val Leu  Val Val Ala Lys Val  Glu Lys Gly Lys Ser  Lys Lys Leu
    1160                 1165                 1170

Lys Val  Lys Glu Leu Leu Gly  Ile Thr Ile Met Glu  Arg Ser Ser
    1175                 1180                 1185

Phe Glu  Lys Asn Pro Ile Asp  Phe Leu Glu Ala Lys  Gly Tyr Lys
    1190                 1195                 1200

Glu Val  Lys Lys Asp Leu Ile  Ile Lys Leu Pro Lys  Tyr Ser Leu
    1205                 1210                 1215

Phe Glu  Leu Glu Asn Gly Arg  Lys Arg Met Leu Ala  Ser Ala Gly
    1220                 1225                 1230

Glu Leu  Gln Lys Gly Asn Glu  Leu Ala Leu Pro Ser  Lys Tyr Val
    1235                 1240                 1245

Asn Phe  Leu Tyr Leu Ala Ser  His Tyr Glu Lys Leu  Lys Gly Ser
    1250                 1255                 1260

Pro Glu  Asp Asn Glu Gln Lys  Gln Leu Phe Val Glu  Gln His Lys
    1265                 1270                 1275

His Tyr  Leu Asp Glu Ile Ile  Glu Gln Ile Ser Glu  Phe Ser Lys
    1280                 1285                 1290

Arg Val  Ile Leu Ala Asp Ala  Asn Leu Asp Lys Val  Leu Ser Ala
    1295                 1300                 1305

Tyr Asn  Lys His Arg Asp Lys  Pro Ile Arg Glu Gln  Ala Glu Asn
    1310                 1315                 1320

Ile Ile  His Leu Phe Thr Leu  Thr Asn Leu Gly Ala  Pro Ala Ala
    1325                 1330                 1335

Phe Lys  Tyr Phe Asp Thr Thr  Ile Asp Arg Lys Arg  Tyr Thr Ser
    1340                 1345                 1350

Thr Lys  Glu Val Leu Asp Ala  Thr Leu Ile His Gln  Ser Ile Thr
    1355                 1360                 1365

Gly Leu  Tyr Glu Thr Arg Ile  Asp Leu Ser Gln Leu  Gly Gly Asp
    1370                 1375                 1380

Lys Arg  Pro Ala Ala Thr Lys  Lys Ala Gly Gln Ala  Lys Lys Lys
    1385                 1390                 1395
```

Lys

<210> SEQ ID NO 20
<211> LENGTH: 1399
<212> TYPE: PRT
<213> ORGANISM: Artificial
<220> FEATURE:
<223> OTHER INFORMATION: D10A Cas9

<400> SEQUENCE: 20

Met Ala Pro Lys Lys Lys Arg Lys Val Gly Ile His Gly Val Pro Ala
1 5 10 15

Ala Asp Lys Lys Tyr Ser Ile Gly Leu Ala Ile Gly Thr Asn Ser Val
20 25 30

Gly Trp Ala Val Ile Thr Asp Glu Tyr Lys Val Pro Ser Lys Lys Phe
35 40 45

Lys Val Leu Gly Asn Thr Asp Arg His Ser Ile Lys Lys Asn Leu Ile
50 55 60

Gly Ala Leu Leu Phe Asp Ser Gly Glu Thr Ala Glu Ala Thr Arg Leu
65 70 75 80

Lys Arg Thr Ala Arg Arg Arg Tyr Thr Arg Arg Lys Asn Arg Ile Cys
85 90 95

Tyr Leu Gln Glu Ile Phe Ser Asn Glu Met Ala Lys Val Asp Asp Ser
100 105 110

Phe Phe His Arg Leu Glu Glu Ser Phe Leu Val Glu Glu Asp Lys Lys
115 120 125

His Glu Arg His Pro Ile Phe Gly Asn Ile Val Asp Glu Val Ala Tyr
130 135 140

His Glu Lys Tyr Pro Thr Ile Tyr His Leu Arg Lys Lys Leu Val Asp
145 150 155 160

Ser Thr Asp Lys Ala Asp Leu Arg Leu Ile Tyr Leu Ala Leu Ala His
165 170 175

Met Ile Lys Phe Arg Gly His Phe Leu Ile Glu Gly Asp Leu Asn Pro
180 185 190

Asp Asn Ser Asp Val Asp Lys Leu Phe Ile Gln Leu Val Gln Thr Tyr
195 200 205

Asn Gln Leu Phe Glu Glu Asn Pro Ile Asn Ala Ser Gly Val Asp Ala
210 215 220

Lys Ala Ile Leu Ser Ala Arg Leu Ser Lys Ser Arg Arg Leu Glu Asn
225 230 235 240

Leu Ile Ala Gln Leu Pro Gly Glu Lys Lys Asn Gly Leu Phe Gly Asn
245 250 255

Leu Ile Ala Leu Ser Leu Gly Leu Thr Pro Asn Phe Lys Ser Asn Phe
260 265 270

Asp Leu Ala Glu Asp Ala Lys Leu Gln Leu Ser Lys Asp Thr Tyr Asp
275 280 285

Asp Asp Leu Asp Asn Leu Leu Ala Gln Ile Gly Asp Gln Tyr Ala Asp
290 295 300

Leu Phe Leu Ala Ala Lys Asn Leu Ser Asp Ala Ile Leu Leu Ser Asp
305 310 315 320

Ile Leu Arg Val Asn Thr Glu Ile Thr Lys Ala Pro Leu Ser Ala Ser
325 330 335

Met Ile Lys Arg Tyr Asp Glu His His Gln Asp Leu Thr Leu Leu Lys
340 345 350

-continued

```
Ala Leu Val Arg Gln Gln Leu Pro Glu Lys Tyr Lys Glu Ile Phe Phe
        355                 360                 365

Asp Gln Ser Lys Asn Gly Tyr Ala Gly Tyr Ile Asp Gly Gly Ala Ser
    370                 375                 380

Gln Glu Glu Phe Tyr Lys Phe Ile Lys Pro Ile Leu Glu Lys Met Asp
385                 390                 395                 400

Gly Thr Glu Glu Leu Leu Val Lys Leu Asn Arg Glu Asp Leu Leu Arg
                405                 410                 415

Lys Gln Arg Thr Phe Asp Asn Gly Ser Ile Pro His Gln Ile His Leu
            420                 425                 430

Gly Glu Leu His Ala Ile Leu Arg Arg Gln Glu Asp Phe Tyr Pro Phe
        435                 440                 445

Leu Lys Asp Asn Arg Glu Lys Ile Glu Lys Ile Leu Thr Phe Arg Ile
    450                 455                 460

Pro Tyr Tyr Val Gly Pro Leu Ala Arg Gly Asn Ser Arg Phe Ala Trp
465                 470                 475                 480

Met Thr Arg Lys Ser Glu Glu Thr Ile Thr Pro Trp Asn Phe Glu Glu
                485                 490                 495

Val Val Asp Lys Gly Ala Ser Ala Gln Ser Phe Ile Glu Arg Met Thr
            500                 505                 510

Asn Phe Asp Lys Asn Leu Pro Asn Glu Lys Val Leu Pro Lys His Ser
        515                 520                 525

Leu Leu Tyr Glu Tyr Phe Thr Val Tyr Asn Glu Leu Thr Lys Val Lys
    530                 535                 540

Tyr Val Thr Glu Gly Met Arg Lys Pro Ala Phe Leu Ser Gly Glu Gln
545                 550                 555                 560

Lys Lys Ala Ile Val Asp Leu Leu Phe Lys Thr Asn Arg Lys Val Thr
                565                 570                 575

Val Lys Gln Leu Lys Glu Asp Tyr Phe Lys Lys Ile Glu Cys Phe Asp
            580                 585                 590

Ser Val Glu Ile Ser Gly Val Glu Asp Arg Phe Asn Ala Ser Leu Gly
        595                 600                 605

Thr Tyr His Asp Leu Leu Lys Ile Ile Lys Asp Lys Asp Phe Leu Asp
    610                 615                 620

Asn Glu Glu Asn Glu Asp Ile Leu Glu Asp Ile Val Leu Thr Leu Thr
625                 630                 635                 640

Leu Phe Glu Asp Arg Glu Met Ile Glu Glu Arg Leu Lys Thr Tyr Ala
                645                 650                 655

His Leu Phe Asp Asp Lys Val Met Lys Gln Leu Lys Arg Arg Arg Tyr
            660                 665                 670

Thr Gly Trp Gly Arg Leu Ser Arg Lys Leu Ile Asn Gly Ile Arg Asp
        675                 680                 685

Lys Gln Ser Gly Lys Thr Ile Leu Asp Phe Leu Lys Ser Asp Gly Phe
    690                 695                 700

Ala Asn Arg Asn Phe Met Gln Leu Ile His Asp Asp Ser Leu Thr Phe
705                 710                 715                 720

Lys Glu Asp Ile Gln Lys Ala Gln Val Ser Gly Gln Gly Asp Ser Leu
                725                 730                 735

His Glu His Ile Ala Asn Leu Ala Gly Ser Pro Ala Ile Lys Lys Gly
            740                 745                 750

Ile Leu Gln Thr Val Lys Val Val Asp Glu Leu Val Lys Val Met Gly
        755                 760                 765

Arg His Lys Pro Glu Asn Ile Val Ile Glu Met Ala Arg Glu Asn Gln
```

```
    770                 775                 780

Thr Thr Gln Lys Gly Gln Lys Asn Ser Arg Glu Arg Met Lys Arg Ile
785                 790                 795                 800

Glu Glu Gly Ile Lys Glu Leu Gly Ser Gln Ile Leu Lys Glu His Pro
                805                 810                 815

Val Glu Asn Thr Gln Leu Gln Asn Glu Lys Leu Tyr Leu Tyr Tyr Leu
            820                 825                 830

Gln Asn Gly Arg Asp Met Tyr Val Asp Gln Glu Leu Asp Ile Asn Arg
        835                 840                 845

Leu Ser Asp Tyr Asp Val Asp His Ile Val Pro Gln Ser Phe Leu Lys
    850                 855                 860

Asp Asp Ser Ile Asp Asn Lys Val Leu Thr Arg Ser Asp Lys Asn Arg
865                 870                 875                 880

Gly Lys Ser Asp Asn Val Pro Ser Glu Glu Val Val Lys Lys Met Lys
                885                 890                 895

Asn Tyr Trp Arg Gln Leu Leu Asn Ala Lys Leu Ile Thr Gln Arg Lys
            900                 905                 910

Phe Asp Asn Leu Thr Lys Ala Glu Arg Gly Gly Leu Ser Glu Leu Asp
        915                 920                 925

Lys Ala Gly Phe Ile Lys Arg Gln Leu Val Glu Thr Arg Gln Ile Thr
    930                 935                 940

Lys His Val Ala Gln Ile Leu Asp Ser Arg Met Asn Thr Lys Tyr Asp
945                 950                 955                 960

Glu Asn Asp Lys Leu Ile Arg Glu Val Lys Val Ile Thr Leu Lys Ser
                965                 970                 975

Lys Leu Val Ser Asp Phe Arg Lys Asp Phe Gln Phe Tyr Lys Val Arg
            980                 985                 990

Glu Ile Asn Asn Tyr His His Ala  His Asp Ala Tyr Leu  Asn Ala Val
        995                 1000                1005

Val Gly  Thr Ala Leu Ile Lys  Lys Tyr Pro Lys Leu  Glu Ser Glu
    1010                1015                1020

Phe Val  Tyr Gly Asp Tyr Lys  Val Tyr Asp Val Arg  Lys Met Ile
    1025                1030                1035

Ala Lys  Ser Glu Gln Glu Ile  Gly Lys Ala Thr Ala  Lys Tyr Phe
    1040                1045                1050

Phe Tyr  Ser Asn Ile Met Asn  Phe Phe Lys Thr Glu  Ile Thr Leu
    1055                1060                1065

Ala Asn  Gly Glu Ile Arg Lys  Arg Pro Leu Ile Glu  Thr Asn Gly
    1070                1075                1080

Glu Thr  Gly Glu Ile Val Trp  Asp Lys Gly Arg Asp  Phe Ala Thr
    1085                1090                1095

Val Arg  Lys Val Leu Ser Met  Pro Gln Val Asn Ile  Val Lys Lys
    1100                1105                1110

Thr Glu  Val Gln Thr Gly Gly  Phe Ser Lys Glu Ser  Ile Leu Pro
    1115                1120                1125

Lys Arg  Asn Ser Asp Lys Leu  Ile Ala Arg Lys Lys  Asp Trp Asp
    1130                1135                1140

Pro Lys  Lys Tyr Gly Gly Phe  Asp Ser Pro Thr Val  Ala Tyr Ser
    1145                1150                1155

Val Leu  Val Val Ala Lys Val  Glu Lys Gly Lys Ser  Lys Lys Leu
    1160                1165                1170

Lys Val  Lys Glu Leu Leu Gly  Ile Thr Ile Met Glu  Arg Ser Ser
    1175                1180                1185
```

```
Phe Glu  Lys Asn Pro Ile Asp  Phe Leu Glu Ala Lys  Gly Tyr Lys
    1190                 1195                 1200

Glu Val  Lys Lys Asp Leu Ile  Ile Lys Leu Pro Lys  Tyr Ser Leu
    1205                 1210                 1215

Phe Glu  Leu Glu Asn Gly Arg  Lys Arg Met Leu Ala  Ser Ala Gly
    1220                 1225                 1230

Glu Leu  Gln Lys Gly Asn Glu  Leu Ala Leu Pro Ser  Lys Tyr Val
    1235                 1240                 1245

Asn Phe  Leu Tyr Leu Ala Ser  His Tyr Glu Lys Leu  Lys Gly Ser
    1250                 1255                 1260

Pro Glu  Asp Asn Glu Gln Lys  Gln Leu Phe Val Glu  Gln His Lys
    1265                 1270                 1275

His Tyr  Leu Asp Glu Ile Ile  Glu Gln Ile Ser Glu  Phe Ser Lys
    1280                 1285                 1290

Arg Val  Ile Leu Ala Asp Ala  Asn Leu Asp Lys Val  Leu Ser Ala
    1295                 1300                 1305

Tyr Asn  Lys His Arg Asp Lys  Pro Ile Arg Glu Gln  Ala Glu Asn
    1310                 1315                 1320

Ile Ile  His Leu Phe Thr Leu  Thr Asn Leu Gly Ala  Pro Ala Ala
    1325                 1330                 1335

Phe Lys  Tyr Phe Asp Thr Thr  Ile Asp Arg Lys Arg  Tyr Thr Ser
    1340                 1345                 1350

Thr Lys  Glu Val Leu Asp Ala  Thr Leu Ile His Gln  Ser Ile Thr
    1355                 1360                 1365

Gly Leu  Tyr Glu Thr Arg Ile  Asp Leu Ser Gln Leu  Gly Gly Asp
    1370                 1375                 1380

Lys Arg  Pro Ala Ala Thr Lys  Lys Ala Gly Gln Ala  Lys Lys Lys
    1385                 1390                 1395

Lys
```

<210> SEQ ID NO 21
<211> LENGTH: 104
<212> TYPE: RNA
<213> ORGANISM: Artificial
<220> FEATURE:
<223> OTHER INFORMATION: CRISPR-gRNA-hPCSK9-ETH1

<400> SEQUENCE: 21

```
ggggugcuag ccuugcguuc cgguuuuaga gcuagaaaua gcaaguuaaa auaaggcuag     60

uccguuauca acuugaaaaa guggcaccga gucggugcuu uuuu                     104
```

<210> SEQ ID NO 22
<211> LENGTH: 104
<212> TYPE: RNA
<213> ORGANISM: Artificial
<220> FEATURE:
<223> OTHER INFORMATION: CRISPR-gRNA-hPCSK9-ETH2

<400> SEQUENCE: 22

```
ggucuuggug agguaucccc ggguuuuaga gcuagaaaua gcaaguuaaa auaaggcuag     60

uccguuauca acuugaaaaa guggcaccga gucggugcuu uuuu                     104
```

<210> SEQ ID NO 23
<211> LENGTH: 104
<212> TYPE: RNA
<213> ORGANISM: Artificial
<220> FEATURE:

<223> OTHER INFORMATION: CRISPR-gRNA-hPCSK9-ETH3

<400> SEQUENCE: 23
gggucgugcu ggucaccgcu gcguuuuaga gcuagaaaua gcaaguuaaa auaaggcuag 60
uccguuauca acuugaaaaa guggcaccga gucggugcuu uuuu 104

<210> SEQ ID NO 24
<211> LENGTH: 104
<212> TYPE: RNA
<213> ORGANISM: Artificial
<220> FEATURE:
<223> OTHER INFORMATION: CRISPR-gRNA-hPCSK9-ETH4

<400> SEQUENCE: 24
ggcaccgacu ucaacagcgu gcguuuuaga gcuagaaaua gcaaguuaaa auaaggcuag 60
uccguuauca acuugaaaaa guggcaccga gucggugcuu uuuu 104

<210> SEQ ID NO 25
<211> LENGTH: 104
<212> TYPE: RNA
<213> ORGANISM: Artificial
<220> FEATURE:
<223> OTHER INFORMATION: CRISPR-gRNA-hPCSK9-ETH5

<400> SEQUENCE: 25
ggaugcuggg auaauucgcu ccguuuuaga gcuagaaaua gcaaguuaaa auaaggcuag 60
uccguuauca acuugaaaaa guggcaccga gucggugcuu uuuu 104

<210> SEQ ID NO 26
<211> LENGTH: 104
<212> TYPE: RNA
<213> ORGANISM: Artificial
<220> FEATURE:
<223> OTHER INFORMATION: CRISPR-gRNA-hPCSK9-ETH6

<400> SEQUENCE: 26
ggggcugaug aggccgcaca ugguuuuaga gcuagaaaua gcaaguuaaa auaaggcuag 60
uccguuauca acuugaaaaa guggcaccga gucggugcuu uuuu 104

<210> SEQ ID NO 27
<211> LENGTH: 69
<212> TYPE: DNA
<213> ORGANISM: Artificial
<220> FEATURE:
<223> OTHER INFORMATION: start codon and a FLAG tag

<400> SEQUENCE: 27
atggactata aggaccacga cggagactac aaggatcatg atattgatta caaagacgat 60
gacgataag 69

<210> SEQ ID NO 28
<211> LENGTH: 69
<212> TYPE: RNA
<213> ORGANISM: Artificial
<220> FEATURE:
<223> OTHER INFORMATION: start codon and a FLAG tag

<400> SEQUENCE: 28
auggacuaua aggaccacga cggagacuac aaggaucaug auauugauua caaagacgau 60
gacgauaag 69

<210> SEQ ID NO 29
<211> LENGTH: 36
<212> TYPE: RNA
<213> ORGANISM: Artificial
<220> FEATURE:
<223> OTHER INFORMATION: CYBA 5' UTR

<400> SEQUENCE: 29
cgcgccuagc agugucccag ccggguucgu gucgcc 36

<210> SEQ ID NO 30
<211> LENGTH: 64
<212> TYPE: DNA
<213> ORGANISM: Artificial
<220> FEATURE:
<223> OTHER INFORMATION: CYBA 3' UTR

<400> SEQUENCE: 30
ccucgccccg gaccugcccu cccgccaggu gcacccacct gcaauaaaug cagcgaagcc 60
ggga 64

<210> SEQ ID NO 31
<211> LENGTH: 4484
<212> TYPE: DNA
<213> ORGANISM: Artificial
<220> FEATURE:
<223> OTHER INFORMATION: polynucleotide sequence

<400> SEQUENCE: 31
gggagaccca agctggctag cgtttaaact taagcttgcc accatggact ataaggacca 60
cgacggagac tacaaggatc atgatattga ttacaaagac gatgacgata agatggcccc 120
aaagaagaag cggaaggtcg gtatccacgg agtcccagca gccgacaaga agtacagcat 180
cggcctggac atcggcacca actctgtggg ctgggccgtg atcaccgacg agtacaaggt 240
gcccagcaag aaattcaagg tgctgggcaa caccgaccgg cacagcatca agaagaacct 300
gatcggagcc ctgctgttcg acagcggcga aacagccgag gccacccggc tgaagagaac 360
cgccagaaga agatacacca gacggaagaa ccggatctgc tatctgcaag agatcttcag 420
caacgagatg gccaaggtgg acgacagctt cttccacaga ctggaagagt ccttcctggt 480
ggaagaggat aagaagcacg agcggcaccc catcttcggc aacatcgtgg acgaggtggc 540
ctaccacgag aagtacccca ccatctacca cctgagaaag aaactggtgg acagcaccga 600
caaggccgac ctgcggctga tctatctggc cctggcccac atgatcaagt tccggggcca 660
cttcctgatc gagggcgacc tgaaccccga caacagcgac gtggacaagc tgttcatcca 720
gctggtgcag acctacaacc agctgttcga ggaaaacccc atcaacgcca gcggcgtgga 780
cgccaaggcc atcctgtctg ccagactgag caagagcaga cggctggaaa atctgatcgc 840
ccagctgccc ggcgagaaga agaatggcct gttcggaaac ctgattgccc tgagcctggg 900
cctgaccccc aacttcaaga gcaacttcga cctggccgag gatgccaaac tgcagctgag 960
caaggacacc tacgacgacg acctggacaa cctgctggcc cagatcggcg accagtacgc 1020
cgacctgttt ctggccgcca agaacctgtc cgacgccatc ctgctgagcg acatcctgag 1080
agtgaacacc gagatcacca aggccccct gagcgcctct atgatcaaga gatacgacga 1140
gcaccaccag gacctgaccc tgctgaaagc tctcgtgcgg cagcagctgc ctgagaagta 1200
caaagagatt ttcttcgacc agagcaagaa cggctacgcc ggctacattg acggcggagc 1260
cagccaggaa gagttctaca agttcatcaa gcccatcctg gaaaagatgg acggcaccga 1320

-continued

```
ggaactgctc gtgaagctga acagagagga cctgctgcgg aagcagcgga ccttcgacaa   1380
cggcagcatc ccccaccaga tccacctggg agagctgcac gccattctgc ggcggcagga   1440
agatttttac ccattcctga aggacaaccg ggaaaagatc gagaagatcc tgaccttccg   1500
catcccctac tacgtgggcc ctctggccag gggaaacagc agattcgcct ggatgaccag   1560
aaagagcgag gaaaccatca cccccctggaa cttcgaggaa gtggtggaca agggcgcttc   1620
cgcccagagc ttcatcgagc ggatgaccaa cttcgataag aacctgccca acgagaaggt   1680
gctgcccaag cacagcctgc tgtacgagta cttcaccgtg tataacgagc tgaccaaagt   1740
gaaatacgtg accgagggaa tgagaaagcc cgccttcctg agcggcgagc agaaaaaggc   1800
catcgtggac ctgctgttca agaccaaccg gaaagtgacc gtgaagcagc tgaaagagga   1860
ctacttcaag aaaatcgagt gcttcgactc cgtggaaatc tccggcgtgg aagatcggtt   1920
caacgcctcc ctgggcacat accacgatct gctgaaaatt atcaaggaca aggacttcct   1980
ggacaatgag gaaaacgagg acattctgga agatatcgtg ctgaccctga cactgtttga   2040
ggacagagag atgatcgagg aacggctgaa aacctatgcc cacctgttcg acgacaaagt   2100
gatgaagcag ctgaagcggc ggagatacac cggctggggc aggctgagcc ggaagctgat   2160
caacggcatc cgggacaagc agtccggcaa gacaatcctg gatttcctga agtccgacgg   2220
cttcgccaac agaaacttca tgcagctgat ccacgacgac agcctgacct ttaaagagga   2280
catccagaaa gcccaggtgt ccggccaggg cgatagcctg cacgagcaca ttgccaatct   2340
ggccggcagc cccgccatta agaagggcat cctgcagaca gtgaaggtgg tggacgagct   2400
cgtgaaagtg atgggccggc acaagcccga gaacatcgtg atcgaaatgg ccagagagaa   2460
ccagaccacc cagaagggac agaagaacag ccgcgagaga atgaagcgga tcgaagaggg   2520
catcaaagag ctgggcagcc agatcctgaa agaacacccc gtggaaaaca cccagctgca   2580
gaacgagaag ctgtacctgt actacctgca gaatgggcgg gatatgtacg tggaccagga   2640
actggacatc aaccggctgt ccgactacga tgtggaccat atcgtgcctc agagctttct   2700
gaaggacgac tccatcgaca acaaggtgct gaccagaagc gacaagaacc ggggcaagag   2760
cgacaacgtg ccctccgaag aggtcgtgaa gaagatgaag aactactggc ggcagctgct   2820
gaacgccaag ctgattaccc agagaaagtt cgacaatctg accaaggccg agagaggcgg   2880
cctgagcgaa ctggataagg ccggcttcat caagagacag ctggtggaaa cccggcagat   2940
cacaaagcac gtggcacaga tcctggactc ccggatgaac actaagtacg acgagaatga   3000
caagctgatc cgggaagtga aagtgatcac cctgaagtcc aagctggtgt ccgatttccg   3060
gaaggatttc cagttttaca aagtgcgcga gatcaacaac taccaccacg cccacgacgc   3120
ctacctgaac gccgtcgtgg gaaccgccct gatcaaaaag taccctaagc tggaaagcga   3180
gttcgtgtac ggcgactaca aggtgtacga cgtgcggaag atgatcgcca agagcgagca   3240
ggaaatcggc aaggctaccg ccaagtactt cttctacagc aacatcatga actttttcaa   3300
gaccgagatt accctggcca acggcgagat ccggaagcgg cctctgatcg agacaaacgg   3360
cgaaaccggg gagatcgtgt gggataaggg ccgggatttt gccaccgtgc ggaaagtgct   3420
gagcatgccc caagtgaata tcgtgaaaaa gaccgaggtg cagacaggcg gcttcagcaa   3480
agagtctatc ctgcccaaga ggaacagcga taagctgatc gccagaaaga aggactggga   3540
ccctaagaag tacggcggct tcgacagccc caccgtggcc tattctgtgc tggtggtggc   3600
caaagtggaa aagggcaagt ccaagaaact gaagagtgtg aaagagctgc tggggatcac   3660
catcatggaa agaagcagct tcgagaagaa tcccatcgac tttctggaag ccaagggcta   3720
```

caaagaagtg aaaaaggacc tgatcatcaa gctgcctaag tactccctgt tcgagctgga 3780
aaacggccgg aagagaatgc tggcctctgc cggcgaactg cagaagggaa acgaactggc 3840
cctgccctcc aaatatgtga acttcctgta cctggccagc cactatgaga agctgaaggg 3900
ctcccccgag gataatgagc agaaacagct gtttgtggaa cagcacaagc actacctgga 3960
cgagatcatc gagcagatca gcgagttctc caagagagtg atcctggccg acgctaatct 4020
ggacaaagtg ctgtccgcct acaacaagca ccgggataag cccatcagag agcaggccga 4080
gaatatcatc cacctgttta ccctgaccaa tctgggagcc cctgccgcct tcaagtactt 4140
tgacaccacc atcgaccgga agaggtacac cagcaccaaa gaggtgctgg acgccaccct 4200
gatccaccag agcatcaccg gcctgtacga gacacggatc gacctgtctc agctgggagg 4260
cgacaaaagg ccggcggcca cgaaaaaggc cggccaggca aaaaagaaaa agtaagaatt 4320
cctaggatcc actagtccag tgtggtggaa ttctgcagaa aaaaaaaaaa aaaaaaaaaa 4380
aaaaaaaaaa aaaaaaaaaa aaaaaaaaaa aaaaaaaaaa aaaaaaaaaa aaaaaaaaaa 4440
aaaaaaaaaa aaaaaaaaaa aaaaaaaaaa aaaaaaaagc ggcc 4484

<210> SEQ ID NO 32
<211> LENGTH: 4221
<212> TYPE: DNA
<213> ORGANISM: Artificial
<220> FEATURE:
<223> OTHER INFORMATION: polynucleotide sequence

<400> SEQUENCE: 32
gggagacgcc accatggccc caaagaagaa gcggaaggtc ggtatccacg gagtcccagc 60
agccgacaag aagtacagca tcggcctgga catcggcacc aactctgtgg gctgggccgt 120
gatcaccgac gagtacaagg tgcccagcaa gaaattcaag gtgctgggca acaccgaccg 180
gcacagcatc aagaagaacc tgatcggagc cctgctgttc gacagcggcg aaacagccga 240
ggccacccgg ctgaagagaa ccgccagaag aagatacacc agacggaaga accggatctg 300
ctatctgcaa gagatcttca gcaacgagat ggccaaggtg gacgacagct tcttccacag 360
actggaagag tccttcctgg tggaagagga taagaagcac gagcggcacc ccatcttcgg 420
caacatcgtg gacgaggtgg cctaccacga gaagtacccc accatctacc acctgagaaa 480
gaaactggtg gacagcaccg acaaggccga cctgcggctg atctatctgg ccctggccca 540
catgatcaag ttccggggcc acttcctgat cgagggcgac ctgaaccccg acaacagcga 600
cgtggacaag ctgttcatcc agctggtgca gacctacaac cagctgttcg aggaaaaccc 660
catcaacgcc agcggcgtgg acgccaaggc catcctgtct gccagactga gcaagagcag 720
acggctggaa aatctgatcg cccagctgcc cggcgagaag aagaatggcc tgttcggaaa 780
cctgattgcc ctgagcctgg gcctgacccc caacttcaag agcaacttcg acctggccga 840
ggatgccaaa ctgcagctga gcaaggacac ctacgacgac gacctggaca acctgctggc 900
ccagatcggc gaccagtacg ccgacctgtt tctggccgcc aagaacctgt ccgacgccat 960
cctgctgagc gacatcctga gagtgaacac cgagatcacc aaggcccccc tgagcgcctc 1020
tatgatcaag agatacgacg agcaccacca ggacctgacc ctgctgaaag ctctcgtgcg 1080
gcagcagctg cctgagaagt acaaagagat tttcttcgac cagagcaaga acggctacgc 1140
cggctacatt gacggcggag ccagccagga agagttctac aagttcatca agcccatcct 1200
ggaaaagatg gacggcaccg aggaactgct cgtgaagctg aacagagagg acctgctgcg 1260

-continued

```
gaagcagcgg accttcgaca acggcagcat cccccaccag atccacctgg gagagctgca   1320
cgccattctg cggcggcagg aagattttta cccattcctg aaggacaacc gggaaaagat   1380
cgagaagatc ctgaccttcc gcatccccta ctacgtgggc cctctggcca ggggaaacag   1440
cagattcgcc tggatgacca gaaagagcga ggaaaccatc accccctgga acttcgagga   1500
agtggtggac aagggcgctt ccgcccagag cttcatcgag cggatgacca acttcgataa   1560
gaacctgccc aacgagaagg tgctgcccaa gcacagcctg ctgtacgagt acttcaccgt   1620
gtataacgag ctgaccaaag tgaaatacgt gaccgaggga atgagaaagc ccgccttcct   1680
gagcggcgag cagaaaaagg ccatcgtgga cctgctgttc aagaccaacc ggaaagtgac   1740
cgtgaagcag ctgaaagagg actacttcaa gaaaatcgag tgcttcgact ccgtggaaat   1800
ctccggcgtg gaagatcggt tcaacgcctc cctgggcaca taccacgatc tgctgaaaat   1860
tatcaaggac aaggacttcc tggacaatga ggaaaacgag gacattctgg aagatatcgt   1920
gctgaccctg acactgtttg aggacagaga gatgatcgag gaacggctga aaacctatgc   1980
ccacctgttc gacgacaaag tgatgaagca gctgaagcgg cggagataca ccggctgggg   2040
caggctgagc cggaagctga tcaacggcat ccgggacaag cagtccggca agacaatcct   2100
ggatttcctg aagtccgacg gcttcgccaa cagaaacttc atgcagctga tccacgacga   2160
cagcctgacc tttaaagagg acatccagaa agcccaggtg tccggccagg gcgatagcct   2220
gcacgagcac attgccaatc tggccggcag ccccgccatt aagaagggca tcctgcagac   2280
agtgaaggtg gtggacgagc tcgtgaaagt gatgggccgg cacaagcccg agaacatcgt   2340
gatcgaaatg gccagagaga accagaccac ccagaaggga cagaagaaca gccgcgagag   2400
aatgaagcgg atcgaagagg gcatcaaaga gctgggcagc cagatcctga aagaacaccc   2460
cgtggaaaac acccagctgc agaacgagaa gctgtacctg tactacctgc agaatgggcg   2520
ggatatgtac gtggaccagg aactggacat caaccggctg tccgactacg atgtggacca   2580
tatcgtgcct cagagctttc tgaaggacga ctccatcgac aacaaggtgc tgaccagaag   2640
cgacaagaac cggggcaaga gcgacaacgt gccctccgaa gaggtcgtga agaagatgaa   2700
gaactactgg cggcagctgc tgaacgccaa gctgattacc cagagaaagt tcgacaatct   2760
gaccaaggcc gagagaggcg gcctgagcga actggataag gccggcttca tcaagagaca   2820
gctggtggaa acccggcaga tcacaaagca cgtggcacag atcctggact cccggatgaa   2880
cactaagtac gacgagaatg acaagctgat ccgggaagtg aaagtgatca ccctgaagtc   2940
caagctggtg tccgatttcc ggaaggattt ccagttttac aaagtgcgcg agatcaacaa   3000
ctaccaccac gcccacgacg cctacctgaa cgccgtcgtg ggaaccgccc tgatcaaaaa   3060
gtaccctaag ctggaaagcg agttcgtgta cggcgactac aaggtgtacg acgtgcggaa   3120
gatgatcgcc aagagcgagc aggaaatcgg caaggctacc gccaagtact tcttctacag   3180
caacatcatg aactttttca agaccgagat taccctggcc aacggcgaga tccggaagcg   3240
gcctctgatc gagacaaacg gcgaaaccgg ggagatcgtg tgggataagg gccgggattt   3300
tgccaccgtg cggaaagtgc tgagcatgcc ccaagtgaat atcgtgaaaa agaccgaggt   3360
gcagacaggc ggcttcagca aagagtctat cctgcccaag aggaacagcg ataagctgat   3420
cgccagaaag aaggactggg accctaagaa gtacggcggc ttcgacagcc ccaccgtggc   3480
ctattctgtg ctggtggtgg ccaaagtgga aaagggcaag tccaagaaac tgaagagtgt   3540
gaaagagctg ctggggatca ccatcatgga aagaagcagc ttcgagaaga atcccatcga   3600
ctttctggaa gccaagggct acaaagaagt gaaaaaggac ctgatcatca agctgcctaa   3660
```

gtactccctg ttcgagctgg aaaacggccg gaagagaatg ctggcctctg ccggcgaact 3720
gcagaaggga aacgaactgg ccctgccctc caaatatgtg aacttcctgt acctggccag 3780
ccactatgag aagctgaagg gctcccccga ggataatgag cagaaacagc tgtttgtgga 3840
acagcacaag cactacctgg acgagatcat cgagcagatc agcgagttct ccaagagagt 3900
gatcctggcc gacgctaatc tggacaaagt gctgtccgcc tacaacaagc accgggataa 3960
gcccatcaga gagcaggccg agaatatcat ccacctgttt accctgacca atctgggagc 4020
ccctgccgcc ttcaagtact ttgacaccac catcgaccgg aagaggtaca ccagcaccaa 4080
agaggtgctg gacgccaccc tgatccacca gagcatcacc ggcctgtacg agacacggat 4140
cgacctgtct cagctgggag gcgacaaaag gccggcggcc acgaaaaagg ccggccaggc 4200
aaaaaagaaa aagtaagaat t 4221

<210> SEQ ID NO 33
<211> LENGTH: 4251
<212> TYPE: DNA
<213> ORGANISM: Artificial
<220> FEATURE:
<223> OTHER INFORMATION: polynucleotide sequence

<400> SEQUENCE: 33
gggagactct tctggtcccc acagactcag agagaacgcc accatggccc caaagaagaa 60
gcggaaggtc ggtatccacg gagtcccagc agccgacaag aagtacagca tcggcctgga 120
catcggcacc aactctgtgg gctgggccgt gatcaccgac gagtacaagg tgcccagcaa 180
gaaattcaag gtgctgggca acaccgaccg gcacagcatc aagaagaacc tgatcggagc 240
cctgctgttc gacagcggcg aaacagccga ggccacccgg ctgaagagaa ccgccagaag 300
aagatacacc agacggaaga accggatctg ctatctgcaa gagatcttca gcaacgagat 360
ggccaaggtg gacgacagct tcttccacag actggaagag tccttcctgg tggaagagga 420
taagaagcac gagcggcacc ccatcttcgg caacatcgtg gacgaggtgg cctaccacga 480
gaagtacccc accatctacc acctgagaaa gaaactggtg gacagcaccg acaaggccga 540
cctgcggctg atctatctgg ccctggccca catgatcaag ttccggggcc acttcctgat 600
cgagggcgac ctgaaccccg acaacagcga cgtggacaag ctgttcatcc agctggtgca 660
gacctacaac cagctgttcg aggaaaaccc catcaacgcc agcggcgtgg acgccaaggc 720
catcctgtct gccagactga gcaagagcag acggctggaa aatctgatcg cccagctgcc 780
cggcgagaag aagaatggcc tgttcggaaa cctgattgcc ctgagcctgg gcctgacccc 840
caacttcaag agcaacttcg acctggccga ggatgccaaa ctgcagctga gcaaggacac 900
ctacgacgac gacctggaca acctgctggc ccagatcggc gaccagtacg ccgacctgtt 960
tctggccgcc aagaacctgt ccgacgccat cctgctgagc gacatcctga gagtgaacac 1020
cgagatcacc aaggcccccc tgagcgcctc tatgatcaag agatacgacg agcaccacca 1080
ggacctgacc ctgctgaaag ctctcgtgcg gcagcagctg cctgagaagt acaaagagat 1140
tttcttcgac cagagcaaga acggctacgc cggctacatt gacggcggag ccagccagga 1200
agagttctac aagttcatca agcccatcct ggaaaagatg gacggcaccg aggaactgct 1260
cgtgaagctg aacagagagg acctgctgcg gaagcagcgg accttcgaca acggcagcat 1320
cccccaccag atccacctgg gagagctgca cgccattctg cggcggcagg aagattttta 1380
cccattcctg aaggacaacc gggaaaagat cgagaagatc ctgaccttcc gcatccccta 1440

```
ctacgtgggc cctctggcca ggggaaacag cagattcgcc tggatgacca gaaagagcga   1500
ggaaaccatc accccctgga acttcgagga agtggtggac aagggcgctt ccgcccagag   1560
cttcatcgag cggatgacca acttcgataa gaacctgccc aacgagaagg tgctgcccaa   1620
gcacagcctg ctgtacgagt acttcaccgt gtataacgag ctgaccaaag tgaaatacgt   1680
gaccgaggga atgagaaagc ccgccttcct gagcggcgag cagaaaaagg ccatcgtgga   1740
cctgctgttc aagaccaacc ggaaagtgac cgtgaagcag ctgaaagagg actacttcaa   1800
gaaaatcgag tgcttcgact ccgtggaaat ctccggcgtg gaagatcggt tcaacgcctc   1860
cctgggcaca taccacgatc tgctgaaaat tatcaaggac aaggacttcc tggacaatga   1920
ggaaaacgag gacattctgg aagatatcgt gctgaccctg acactgtttg aggacagaga   1980
gatgatcgag gaacggctga aaacctatgc ccacctgttc gacgacaaag tgatgaagca   2040
gctgaagcgg cggagataca ccggctgggg caggctgagc cggaagctga tcaacggcat   2100
ccgggacaag cagtccggca agacaatcct ggatttcctg aagtccgacg gcttcgccaa   2160
cagaaacttc atgcagctga tccacgacga cagcctgacc tttaaagagg acatccagaa   2220
agcccaggtg tccggccagg gcgatagcct gcacgagcac attgccaatc tggccggcag   2280
ccccgccatt aagaagggca tcctgcagac agtgaaggtg gtggacgagc tcgtgaaagt   2340
gatgggccgg cacaagcccg agaacatcgt gatcgaaatg gccagagaga accagaccac   2400
ccagaaggga cagaagaaca gccgcgagag aatgaagcgg atcgaagagg gcatcaaaga   2460
gctgggcagc cagatcctga aagaacaccc cgtggaaaac acccagctgc agaacgagaa   2520
gctgtacctg tactacctgc agaatgggcg ggatatgtac gtggaccagg aactggacat   2580
caaccggctg tccgactacg atgtggacca tatcgtgcct cagagctttc tgaaggacga   2640
ctccatcgac aacaaggtgc tgaccagaag cgacaagaac cggggcaaga gcgacaacgt   2700
gccctccgaa gaggtcgtga agaagatgaa gaactactgg cggcagctgc tgaacgccaa   2760
gctgattacc cagagaaagt tcgacaatct gaccaaggcc gagagaggcg gcctgagcga   2820
actggataag gccggcttca tcaagagaca gctggtggaa acccggcaga tcacaaagca   2880
cgtggcacag atcctggact cccggatgaa cactaagtac gacgagaatg acaagctgat   2940
ccgggaagtg aaagtgatca ccctgaagtc caagctggtg tccgatttcc ggaaggattt   3000
ccagttttac aaagtgcgcg agatcaacaa ctaccaccac gcccacgacg cctacctgaa   3060
cgccgtcgtg ggaaccgccc tgatcaaaaa gtaccctaag ctggaaagcg agttcgtgta   3120
cggcgactac aaggtgtacg acgtgcggaa gatgatcgcc aagagcgagc aggaaatcgg   3180
caaggctacc gccaagtact tcttctacag caacatcatg aactttttca agaccgagat   3240
taccctggcc aacggcgaga tccggaagcg gcctctgatc gagacaaacg gcgaaaccgg   3300
ggagatcgtg tgggataagg gccgggattt tgccaccgtg cggaaagtgc tgagcatgcc   3360
ccaagtgaat atcgtgaaaa agaccgaggt gcagacaggc ggcttcagca aagagtctat   3420
cctgcccaag aggaacagcg ataagctgat cgccagaaag aaggactggg accctaagaa   3480
gtacggcggc ttcgacagcc ccaccgtggc ctattctgtg ctggtggtgg ccaaagtgga   3540
aaagggcaag tccaagaaac tgaagagtgt gaaagagctg ctggggatca ccatcatgga   3600
aagaagcagc ttcgagaaga atcccatcga ctttctggaa gccaagggct acaaagaagt   3660
gaaaaaggac ctgatcatca agctgcctaa gtactccctg ttcgagctgg aaaacggccg   3720
gaagagaatg ctggcctctg ccggcgaact gcagaaggga aacgaactgg ccctgccctc   3780
caaatatgtg aacttcctgt acctggccag ccactatgag aagctgaagg gctcccccga   3840
```

ggataatgag cagaaacagc tgtttgtgga acagcacaag cactacctgg acgagatcat 3900
cgagcagatc agcgagttct ccaagagagt gatcctggcc gacgctaatc tggacaaagt 3960
gctgtccgcc tacaacaagc accgggataa gcccatcaga gagcaggccg agaatatcat 4020
ccacctgttt accctgacca atctgggagc ccctgccgcc ttcaagtact ttgacaccac 4080
catcgaccgg aagaggtaca ccagcaccaa agaggtgctg gacgccaccc tgatccacca 4140
gagcatcacc ggcctgtacg agacacggat cgacctgtct cagctgggag gcgacaaaag 4200
gccggcggcc acgaaaaagg ccggccaggc aaaaaagaaa aagtaagaat t 4251

<210> SEQ ID NO 34
<211> LENGTH: 4222
<212> TYPE: DNA
<213> ORGANISM: Artificial
<220> FEATURE:
<223> OTHER INFORMATION: polynucleotide sequence

<400> SEQUENCE: 34
gggagactgc caagatggcc ccaaagaaga agcggaaggt cggtatccac ggagtcccag 60
cagccgacaa gaagtacagc atcggcctgg acatcggcac caactctgtg ggctgggccg 120
tgatcaccga cgagtacaag gtgcccagca agaaattcaa ggtgctgggc aacaccgacc 180
ggcacagcat caagaagaac ctgatcggag ccctgctgtt cgacagcggc gaaacagccg 240
aggccacccg gctgaagaga accgccagaa gaagatacac cagacggaag aaccggatct 300
gctatctgca agagatcttc agcaacgaga tggccaaggt ggacgacagc ttcttccaca 360
gactggaaga gtccttcctg gtggaagagg ataagaagca cgagcggcac cccatcttcg 420
gcaacatcgt ggacgaggtg gcctaccacg agaagtaccc caccatctac cacctgagaa 480
agaaactggt ggacagcacc gacaaggccg acctgcggct gatctatctg gccctggccc 540
acatgatcaa gttccggggc cacttcctga tcgagggcga cctgaacccc gacaacagcg 600
acgtggacaa gctgttcatc cagctggtgc agacctacaa ccagctgttc gaggaaaacc 660
ccatcaacgc cagcggcgtg gacgccaagg ccatcctgtc tgccagactg agcaagagca 720
gacggctgga aaatctgatc gcccagctgc ccggcgagaa gaagaatggc ctgttcggaa 780
acctgattgc cctgagcctg ggcctgaccc ccaacttcaa gagcaacttc gacctggccg 840
aggatgccaa actgcagctg agcaaggaca cctacgacga cgacctggac aacctgctgg 900
cccagatcgg cgaccagtac gccgacctgt ttctggccgc caagaacctg tccgacgcca 960
tcctgctgag cgacatcctg agagtgaaca ccgagatcac caaggccccc ctgagcgcct 1020
ctatgatcaa gagatacgac gagcaccacc aggacctgac cctgctgaaa gctctcgtgc 1080
ggcagcagct gcctgagaag tacaaagaga ttttcttcga ccagagcaag aacggctacg 1140
ccggctacat tgacggcgga gccagccagg aagagttcta caagttcatc aagcccatcc 1200
tggaaaagat ggacggcacc gaggaactgc tcgtgaagct gaacagagag gacctgctgc 1260
ggaagcagcg gaccttcgac aacggcagca tcccccacca gatccacctg ggagagctgc 1320
acgccattct gcggcggcag gaagattttt acccattcct gaaggacaac cgggaaaaga 1380
tcgagaagat cctgaccttc cgcatcccct actacgtggg ccctctggcc aggggaaaca 1440
gcagattcgc ctggatgacc agaaagagcg aggaaaccat cacccccctgg aacttcgagg 1500 aagtggtgga caagggcgct tccgcccaga gcttcatcga gcggatgacc aacttcgata 1560
agaacctgcc caacgagaag gtgctgccca agcacagcct gctgtacgag tacttcaccg 1620

-continued

```
tgtataacga gctgaccaaa gtgaaatacg tgaccgaggg aatgagaaag cccgccttcc   1680
tgagcggcga gcagaaaaag gccatcgtgg acctgctgtt caagaccaac cggaaagtga   1740
ccgtgaagca gctgaaagag gactacttca agaaaatcga gtgcttcgac tccgtggaaa   1800
tctccggcgt ggaagatcgg ttcaacgcct ccctgggcac ataccacgat ctgctgaaaa   1860
ttatcaagga caaggacttc ctggacaatg aggaaaacga ggacattctg gaagatatcg   1920
tgctgaccct gacactgttt gaggacagag agatgatcga ggaacggctg aaaacctatg   1980
cccacctgtt cgacgacaaa gtgatgaagc agctgaagcg gcggagatac accggctggg   2040
gcaggctgag ccggaagctg atcaacggca tccgggacaa gcagtccggc aagacaatcc   2100
tggatttcct gaagtccgac ggcttcgcca acagaaactt catgcagctg atccacgacg   2160
acagcctgac ctttaaagag gacatccaga aagcccaggt gtccggccag ggcgatagcc   2220
tgcacgagca cattgccaat ctggccggca gccccgccat taagaagggc atcctgcaga   2280
cagtgaaggt ggtggacgag ctcgtgaaag tgatgggccg gcacaagccc gagaacatcg   2340
tgatcgaaat ggccagagag aaccagacca cccagaaggg acagaagaac agccgcgaga   2400
gaatgaagcg gatcgaagag ggcatcaaag agctgggcag ccagatcctg aaagaacacc   2460
ccgtggaaaa cacccagctg cagaacgaga agctgtacct gtactacctg cagaatgggc   2520
gggatatgta cgtggaccag gaactggaca tcaaccggct gtccgactac gatgtggacc   2580
atatcgtgcc tcagagcttt ctgaaggacg actccatcga caacaaggtg ctgaccagaa   2640
gcgacaagaa ccggggcaag agcgacaacg tgccctccga agaggtcgtg aagaagatga   2700
agaactactg gcggcagctg ctgaacgcca agctgattac ccagagaaag ttcgacaatc   2760
tgaccaaggc cgagagaggc ggcctgagcg aactggataa ggccggcttc atcaagagac   2820
agctggtgga aacccggcag atcacaaagc acgtggcaca gatcctggac tcccggatga   2880
acactaagta cgacgagaat gacaagctga tccgggaagt gaaagtgatc accctgaagt   2940
ccaagctggt gtccgatttc cggaaggatt tccagtttta caaagtgcgc gagatcaaca   3000
actaccacca cgcccacgac gcctacctga acgccgtcgt gggaaccgcc ctgatcaaaa   3060
agtaccctaa gctggaaagc gagttcgtgt acggcgacta caaggtgtac gacgtgcgga   3120
agatgatcgc caagagcgag caggaaatcg gcaaggctac cgccaagtac ttcttctaca   3180
gcaacatcat gaactttttc aagaccgaga ttaccctggc caacggcgag atccggaagc   3240
ggcctctgat cgagacaaac ggcgaaaccg gggagatcgt gtgggataag ggccgggatt   3300
ttgccaccgt gcggaaagtg ctgagcatgc cccaagtgaa tatcgtgaaa aagaccgagg   3360
tgcagacagg cggcttcagc aaagagtcta tcctgcccaa gaggaacagc gataagctga   3420
tcgccagaaa gaaggactgg gaccctaaga agtacggcgg cttcgacagc cccaccgtgg   3480
cctattctgt gctggtggtg gccaaagtgg aaaagggcaa gtccaagaaa ctgaagagtg   3540
tgaaagagct gctggggatc accatcatgg aaagaagcag cttcgagaag aatcccatcg   3600
actttctgga agccaagggc tacaaagaag tgaaaaagga cctgatcatc aagctgccta   3660
agtactccct gttcgagctg gaaaacggcc ggaagagaat gctggcctct gccggcgaac   3720
tgcagaaggg aaacgaactg gccctgccct ccaaatatgt gaacttcctg tacctggcca   3780
gccactatga gaagctgaag ggctcccccg aggataatga gcagaaacag ctgtttgtgg   3840
aacagcacaa gcactacctg gacgagatca tcgagcagat cagcgagttc tccaagagag   3900
tgatcctggc cgacgctaat ctggacaaag tgctgtccgc ctacaacaag caccgggata   3960
agcccatcag agagcaggcc gagaatatca tccacctgtt taccctgacc aatctgggag   4020
```

cccctgccgc cttcaagtac tttgacacca ccatcgaccg gaagaggtac accagcacca 4080
aagaggtgct ggacgccacc ctgatccacc agagcatcac cggcctgtac gagacacgga 4140
tcgacctgtc tcagctggga ggcgacaaaa ggccggcggc cacgaaaaag gccggccagg 4200
caaaaaagaa aaagtaagaa tt 4222

<210> SEQ ID NO 35
<211> LENGTH: 4484
<212> TYPE: DNA
<213> ORGANISM: Artificial
<220> FEATURE:
<223> OTHER INFORMATION: polynucleotide sequence

<400> SEQUENCE: 35
gggagaccca agctggctag cgtttaaact taagcttgcc accatggact ataaggacca 60
cgacggagac tacaaggatc atgatattga ttacaaagac gatgacgata agatggcccc 120
aaagaagaag cggaaggtcg gtatccacgg agtcccagca gccgacaaga agtacagcat 180
cggcctggcc atcggcacca actctgtggg ctgggccgtg atcaccgacg agtacaaggt 240
gcccagcaag aaattcaagg tgctgggcaa caccgaccgg cacagcatca agaagaacct 300
gatcggagcc ctgctgttcg acagcggcga aacagccgag gccacccggc tgaagagaac 360
cgccagaaga agatacacca gacggaagaa ccggatctgc tatctgcaag agatcttcag 420
caacgagatg gccaaggtgg acgacagctt cttccacaga ctggaagagt ccttcctggt 480
ggaagaggat aagaagcacg agcggcaccc catcttcggc aacatcgtgg acgaggtggc 540
ctaccacgag aagtacccca ccatctacca cctgagaaag aaactggtgg acagcaccga 600
caaggccgac ctgcggctga tctatctggc cctggcccac atgatcaagt tccggggcca 660
cttcctgatc gagggcgacc tgaaccccga caacagcgac gtggacaagc tgttcatcca 720
gctggtgcag acctacaacc agctgttcga ggaaaacccc atcaacgcca gcggcgtgga 780
cgccaaggcc atcctgtctg ccagactgag caagagcaga cggctggaaa atctgatcgc 840
ccagctgccc ggcgagaaga agaatggcct gttcggaaac ctgattgccc tgagcctggg 900
cctgaccccc aacttcaaga gcaacttcga cctggccgag gatgccaaac tgcagctgag 960
caaggacacc tacgacgacg acctggacaa cctgctggcc cagatcggcg accagtacgc 1020
cgacctgttt ctggccgcca agaacctgtc cgacgccatc ctgctgagcg acatcctgag 1080
agtgaacacc gagatcacca aggcccccct gagcgcctct atgatcaaga gatacgacga 1140
gcaccaccag gacctgaccc tgctgaaagc tctcgtgcgg cagcagctgc ctgagaagta 1200
caaagagatt ttcttcgacc agagcaagaa cggctacgcc ggctacattg acggcggagc 1260
cagccaggaa gagttctaca agttcatcaa gcccatcctg gaaaagatgg acggcaccga 1320
ggaactgctc gtgaagctga acagagagga cctgctgcgg aagcagcgga ccttcgacaa 1380
cggcagcatc ccccaccaga tccacctggg agagctgcac gccattctgc ggcggcagga 1440
agatttttac ccattcctga aggacaaccg ggaaaagatc gagaagatcc tgaccttccg 1500
catcccctac tacgtgggcc ctctggccag gggaaacagc agattcgcct ggatgaccag 1560
aaagagcgag gaaaccatca cccccctggaa cttcgaggaa gtggtggaca agggcgcttc 1620
cgcccagagc ttcatcgagc ggatgaccaa cttcgataag aacctgccca acgagaaggt 1680
gctgcccaag cacagcctgc tgtacgagta cttcaccgtg tataacgagc tgaccaaagt 1740
gaaatacgtg accgagggaa tgagaaagcc cgccttcctg agcggcgagc agaaaaaggc 1800

-continued

```
catcgtggac ctgctgttca agaccaaccg gaaagtgacc gtgaagcagc tgaaagagga   1860
ctacttcaag aaaatcgagt gcttcgactc cgtggaaatc tccggcgtgg aagatcggtt   1920
caacgcctcc ctgggcacat accacgatct gctgaaaatt atcaaggaca aggacttcct   1980
ggacaatgag gaaaacgagg acattctgga agatatcgtg ctgaccctga cactgtttga   2040
ggacagagag atgatcgagg aacggctgaa aacctatgcc cacctgttcg acgacaaagt   2100
gatgaagcag ctgaagcggc ggagatacac cggctggggc aggctgagcc ggaagctgat   2160
caacggcatc cgggacaagc agtccggcaa gacaatcctg gatttcctga agtccgacgg   2220
cttcgccaac agaaacttca tgcagctgat ccacgacgac agcctgacct ttaaagagga   2280
catccagaaa gcccaggtgt ccggccaggg cgatagcctg cacgagcaca ttgccaatct   2340
ggccggcagc cccgccatta agaagggcat cctgcagaca gtgaaggtgg tggacgagct   2400
cgtgaaagtg atgggccggc acaagcccga gaacatcgtg atcgaaatgg ccagagagaa   2460
ccagaccacc cagaagggac agaagaacag ccgcgagaga atgaagcgga tcgaagaggg   2520
catcaaagag ctgggcagcc agatcctgaa agaacacccc gtggaaaaca cccagctgca   2580
gaacgagaag ctgtacctgt actacctgca gaatgggcgg gatatgtacg tggaccagga   2640
actggacatc aaccggctgt ccgactacga tgtggaccat atcgtgcctc agagctttct   2700
gaaggacgac tccatcgaca acaaggtgct gaccagaagc gacaagaacc ggggcaagag   2760
cgacaacgtg ccctccgaag aggtcgtgaa gaagatgaag aactactggc ggcagctgct   2820
gaacgccaag ctgattaccc agagaaagtt cgacaatctg accaaggccg agagaggcgg   2880
cctgagcgaa ctggataagg ccggcttcat caagagacag ctggtggaaa cccggcagat   2940
cacaaagcac gtggcacaga tcctggactc ccggatgaac actaagtacg acgagaatga   3000
caagctgatc cgggaagtga aagtgatcac cctgaagtcc aagctggtgt ccgatttccg   3060
gaaggatttc cagttttaca aagtgcgcga gatcaacaac taccaccacg cccacgacgc   3120
ctacctgaac gccgtcgtgg gaaccgccct gatcaaaaag taccctaagc tggaaagcga   3180
gttcgtgtac ggcgactaca aggtgtacga cgtgcggaag atgatcgcca agagcgagca   3240
ggaaatcggc aaggctaccg ccaagtactt cttctacagc aacatcatga actttttcaa   3300
gaccgagatt accctggcca acggcgagat ccggaagcgg cctctgatcg agacaaacgg   3360
cgaaaccggg gagatcgtgt gggataaggg ccgggatttt gccaccgtgc ggaaagtgct   3420
gagcatgccc caagtgaata tcgtgaaaaa gaccgaggtg cagacaggcg gcttcagcaa   3480
agagtctatc ctgcccaaga ggaacagcga taagctgatc gccagaaaga aggactggga   3540
ccctaagaag tacggcggct tcgacagccc caccgtggcc tattctgtgc tggtggtggc   3600
caaagtggaa aagggcaagt ccaagaaact gaagagtgtg aaagagctgc tggggatcac   3660
catcatggaa agaagcagct tcgagaagaa tcccatcgac tttctggaag ccaagggcta   3720
caaagaagtg aaaaaggacc tgatcatcaa gctgcctaag tactccctgt tcgagctgga   3780
aaacggccgg aagagaatgc tggcctctgc cggcgaactg cagaagggaa acgaactggc   3840
cctgccctcc aaatatgtga acttcctgta cctggccagc cactatgaga agctgaaggg   3900
ctcccccgag gataatgagc agaaacagct gtttgtggaa cagcacaagc actacctgga   3960
cgagatcatc gagcagatca gcgagttctc caagagagtg atcctggccg acgctaatct   4020
ggacaaagtg ctgtccgcct acaacaagca ccgggataag cccatcagag agcaggccga   4080
gaatatcatc cacctgttta ccctgaccaa tctgggagcc cctgccgcct tcaagtactt   4140
tgacaccacc atcgaccgga agaggtacac cagcaccaaa gaggtgctgg acgccaccct   4200
```

gatccaccag agcatcaccg gcctgtacga gacacggatc gacctgtctc agctgggagg 4260
cgacaaaagg ccggcggcca cgaaaaaggc cggccaggca aaaaagaaaa agtaagaatt 4320
cctaggatcc actagtccag tgtggtggaa ttctgcagaa aaaaaaaaaa aaaaaaaaaa 4380
aaaaaaaaaa aaaaaaaaaa aaaaaaaaaa aaaaaaaaaa aaaaaaaaaa aaaaaaaaaa 4440
aaaaaaaaaa aaaaaaaaaa aaaaaaaaaa aaaaaaaagc ggcc 4484

<210> SEQ ID NO 36
<211> LENGTH: 4221
<212> TYPE: DNA
<213> ORGANISM: Artificial
<220> FEATURE:
<223> OTHER INFORMATION: polynucleotide sequence

<400> SEQUENCE: 36
gggagacgcc accatggccc caaagaagaa gcggaaggtc ggtatccacg gagtcccagc 60
agccgacaag aagtacagca tcggcctggc catcggcacc aactctgtgg gctgggccgt 120
gatcaccgac gagtacaagg tgcccagcaa gaaattcaag gtgctgggca acaccgaccg 180
gcacagcatc aagaagaacc tgatcggagc cctgctgttc gacagcggcg aaacagccga 240
ggccacccgg ctgaagagaa ccgccagaag aagatacacc agacggaaga accggatctg 300
ctatctgcaa gagatcttca gcaacgagat ggccaaggtg gacgacagct tcttccacag 360
actggaagag tccttcctgg tggaagagga taagaagcac gagcggcacc ccatcttcgg 420
caacatcgtg gacgaggtgg cctaccacga gaagtacccc accatctacc acctgagaaa 480
gaaactggtg gacagcaccg acaaggccga cctgcggctg atctatctgg ccctggccca 540
catgatcaag ttccggggcc acttcctgat cgagggcgac ctgaaccccg acaacagcga 600
cgtggacaag ctgttcatcc agctggtgca gacctacaac cagctgttcg aggaaaaccc 660
catcaacgcc agcggcgtgg acgccaaggc catcctgtct gccagactga gcaagagcag 720
acggctggaa aatctgatcg cccagctgcc cggcgagaag aagaatggcc tgttcggaaa 780
cctgattgcc ctgagcctgg gcctgacccc caacttcaag agcaacttcg acctggccga 840
ggatgccaaa ctgcagctga gcaaggacac ctacgacgac gacctggaca acctgctggc 900
ccagatcggc gaccagtacg ccgacctgtt tctggccgcc aagaacctgt ccgacgccat 960
cctgctgagc gacatcctga gagtgaacac cgagatcacc aaggcccccc tgagcgcctc 1020
tatgatcaag agatacgacg agcaccacca ggacctgacc ctgctgaaag ctctcgtgcg 1080
gcagcagctg cctgagaagt acaaagagat tttcttcgac cagagcaaga acggctacgc 1140
cggctacatt gacggcggag ccagccagga agagttctac aagttcatca agcccatcct 1200
ggaaaagatg gacggcaccg aggaactgct cgtgaagctg aacagagagg acctgctgcg 1260
gaagcagcgg accttcgaca acggcagcat cccccaccag atccacctgg gagagctgca 1320
cgccattctg cggcggcagg aagattttta cccattcctg aaggacaacc gggaaaagat 1380
cgagaagatc ctgaccttcc gcatccccta ctacgtgggc cctctggcca ggggaaacag 1440
cagattcgcc tggatgacca gaaagagcga ggaaaccatc accccctgga acttcgagga 1500
agtggtggac aagggcgctt ccgcccagag cttcatcgag cggatgacca acttcgataa 1560
gaacctgccc aacgagaagg tgctgcccaa gcacagcctg ctgtacgagt acttcaccgt 1620
gtataacgag ctgaccaaag tgaaatacgt gaccgaggga atgagaaagc ccgccttcct 1680
gagcggcgag cagaaaaagg ccatcgtgga cctgctgttc aagaccaacc ggaaagtgac 1740

-continued

```
cgtgaagcag ctgaaagagg actacttcaa gaaaatcgag tgcttcgact ccgtggaaat   1800
ctccggcgtg gaagatcggt tcaacgcctc cctgggcaca taccacgatc tgctgaaaat   1860
tatcaaggac aaggacttcc tggacaatga ggaaaacgag gacattctgg aagatatcgt   1920
gctgaccctg acactgtttg aggacagaga gatgatcgag gaacggctga aaacctatgc   1980
ccacctgttc gacgacaaag tgatgaagca gctgaagcgg cggagataca ccggctgggg   2040
caggctgagc cggaagctga tcaacggcat ccgggacaag cagtccggca agacaatcct   2100
ggatttcctg aagtccgacg gcttcgccaa cagaaacttc atgcagctga tccacgacga   2160
cagcctgacc tttaaagagg acatccagaa agcccaggtg tccggccagg gcgatagcct   2220
gcacgagcac attgccaatc tggccggcag ccccgccatt aagaagggca tcctgcagac   2280
agtgaaggtg gtggacgagc tcgtgaaagt gatgggccgg cacaagcccg agaacatcgt   2340
gatcgaaatg gccagagaga accagaccac ccagaaggga cagaagaaca gccgcgagag   2400
aatgaagcgg atcgaagagg gcatcaaaga gctgggcagc cagatcctga aagaacaccc   2460
cgtggaaaac acccagctgc agaacgagaa gctgtacctg tactacctgc agaatgggcg   2520
ggatatgtac gtggaccagg aactggacat caaccggctg tccgactacg atgtggacca   2580
tatcgtgcct cagagctttc tgaaggacga ctccatcgac aacaaggtgc tgaccagaag   2640
cgacaagaac cggggcaaga gcgacaacgt gccctccgaa gaggtcgtga agaagatgaa   2700
gaactactgg cggcagctgc tgaacgccaa gctgattacc cagagaaagt tcgacaatct   2760
gaccaaggcc gagagaggcg gcctgagcga actggataag gccggcttca tcaagagaca   2820
gctggtggaa acccggcaga tcacaaagca cgtggcacag atcctggact cccggatgaa   2880
cactaagtac gacgagaatg acaagctgat ccgggaagtg aaagtgatca ccctgaagtc   2940
caagctggtg tccgatttcc ggaaggattt ccagttttac aaagtgcgcg agatcaacaa   3000
ctaccaccac gcccacgacg cctacctgaa cgccgtcgtg ggaaccgccc tgatcaaaaa   3060
gtaccctaag ctggaaagcg agttcgtgta cggcgactac aaggtgtacg acgtgcggaa   3120
gatgatcgcc aagagcgagc aggaaatcgg caaggctacc gccaagtact tcttctacag   3180
caacatcatg aactttttca agaccgagat taccctggcc aacggcgaga tccggaagcg   3240
gcctctgatc gagacaaacg gcgaaaccgg ggagatcgtg tgggataagg gccgggattt   3300
tgccaccgtg cggaaagtgc tgagcatgcc ccaagtgaat atcgtgaaaa agaccgaggt   3360
gcagacaggc ggcttcagca aagagtctat cctgcccaag aggaacagcg ataagctgat   3420
cgccagaaag aaggactggg accctaagaa gtacggcggc ttcgacagcc ccaccgtggc   3480
ctattctgtg ctggtggtgg ccaaagtgga aaagggcaag tccaagaaac tgaagagtgt   3540
gaaagagctg ctggggatca ccatcatgga aagaagcagc ttcgagaaga atcccatcga   3600
ctttctggaa gccaagggct acaaagaagt gaaaaaggac ctgatcatca agctgcctaa   3660
gtactccctg ttcgagctgg aaaacggccg gaagagaatg ctggcctctg ccggcgaact   3720
gcagaaggga aacgaactgg ccctgccctc caaatatgtg aacttcctgt acctggccag   3780
ccactatgag aagctgaagg gctcccccga ggataatgag cagaaacagc tgtttgtgga   3840
acagcacaag cactacctgg acgagatcat cgagcagatc agcgagttct ccaagagagt   3900
gatcctggcc gacgctaatc tggacaaagt gctgtccgcc tacaacaagc accgggataa   3960
gcccatcaga gagcaggccg agaatatcat ccacctgttt accctgacca atctgggagc   4020
ccctgccgcc ttcaagtact ttgacaccac catcgaccgg aagaggtaca ccagcaccaa   4080
agaggtgctg gacgccaccc tgatccacca gagcatcacc ggcctgtacg agacacggat   4140
```

cgacctgtct cagctgggag gcgacaaaag gccggcggcc acgaaaaagg ccggccaggc 4200
aaaaaagaaa aagtaagaat t 4221

<210> SEQ ID NO 37
<211> LENGTH: 4251
<212> TYPE: DNA
<213> ORGANISM: Artificial
<220> FEATURE:
<223> OTHER INFORMATION: polynucleotide sequence

<400> SEQUENCE: 37
gggagactct tctggtcccc acagactcag agagaacgcc accatggccc caaagaagaa 60
gcggaaggtc ggtatccacg gagtcccagc agccgacaag aagtacagca tcggcctggc 120
catcggcacc aactctgtgg gctgggccgt gatcaccgac gagtacaagg tgcccagcaa 180
gaaattcaag gtgctgggca acaccgaccg gcacagcatc aagaagaacc tgatcggagc 240
cctgctgttc gacagcggcg aaacagccga ggccacccgg ctgaagagaa ccgccagaag 300
aagatacacc agacggaaga accggatctg ctatctgcaa gagatcttca gcaacgagat 360
ggccaaggtg gacgacagct tcttccacag actggaagag tccttcctgg tggaagagga 420
taagaagcac gagcggcacc ccatcttcgg caacatcgtg gacgaggtgg cctaccacga 480
gaagtacccc accatctacc acctgagaaa gaaactggtg gacagcaccg acaaggccga 540
cctgcggctg atctatctgg ccctggccca catgatcaag ttccggggcc acttcctgat 600
cgagggcgac ctgaaccccg acaacagcga cgtggacaag ctgttcatcc agctggtgca 660
gacctacaac cagctgttcg aggaaaaccc catcaacgcc agcggcgtgg acgccaaggc 720
catcctgtct gccagactga gcaagagcag acggctggaa aatctgatcg cccagctgcc 780
cggcgagaag aagaatggcc tgttcggaaa cctgattgcc ctgagcctgg gcctgacccc 840
caacttcaag agcaacttcg acctggccga ggatgccaaa ctgcagctga gcaaggacac 900
ctacgacgac gacctggaca acctgctggc ccagatcggc gaccagtacg ccgacctgtt 960
tctggccgcc aagaacctgt ccgacgccat cctgctgagc gacatcctga gagtgaacac 1020
cgagatcacc aaggcccccc tgagcgcctc tatgatcaag agatacgacg agcaccacca 1080
ggacctgacc ctgctgaaag ctctcgtgcg gcagcagctg cctgagaagt acaaagagat 1140
tttcttcgac cagagcaaga acggctacgc cggctacatt gacggcggag ccagccagga 1200
agagttctac aagttcatca agcccatcct ggaaaagatg gacggcaccg aggaactgct 1260
cgtgaagctg aacagagagg acctgctgcg gaagcagcgg accttcgaca acggcagcat 1320
cccccaccag atccacctgg gagagctgca cgccattctg cggcggcagg aagattttta 1380
cccattcctg aaggacaacc gggaaaagat cgagaagatc ctgaccttcc gcatccccta 1440
ctacgtgggc cctctggcca ggggaaacag cagattcgcc tggatgacca gaaagagcga 1500
ggaaaccatc accccctgga acttcgagga agtggtggac aagggcgctt ccgcccagag 1560
cttcatcgag cggatgacca acttcgataa gaacctgccc aacgagaagg tgctgcccaa 1620
gcacagcctg ctgtacgagt acttcaccgt gtataacgag ctgaccaaag tgaaatacgt 1680
gaccgaggga atgagaaagc ccgccttcct gagcggcgag cagaaaaagg ccatcgtgga 1740
cctgctgttc aagaccaacc ggaaagtgac cgtgaagcag ctgaaagagg actacttcaa 1800
gaaaatcgag tgcttcgact ccgtggaaat ctccggcgtg gaagatcggt tcaacgcctc 1860
cctgggcaca taccacgatc tgctgaaaat tatcaaggac aaggacttcc tggacaatga 1920

-continued

```
ggaaaacgag gacattctgg aagatatcgt gctgaccctg acactgtttg aggacagaga   1980
gatgatcgag gaacggctga aaacctatgc ccacctgttc gacgacaaag tgatgaagca   2040
gctgaagcgg cggagataca ccggctgggg caggctgagc cggaagctga tcaacggcat   2100
ccgggacaag cagtccggca agacaatcct ggatttcctg aagtccgacg gcttcgccaa   2160
cagaaacttc atgcagctga tccacgacga cagcctgacc tttaaagagg acatccagaa   2220
agcccaggtg tccggccagg gcgatagcct gcacgagcac attgccaatc tggccggcag   2280
ccccgccatt aagaagggca tcctgcagac agtgaaggtg gtggacgagc tcgtgaaagt   2340
gatgggccgg cacaagcccg agaacatcgt gatcgaaatg gccagagaga accagaccac   2400
ccagaaggga cagaagaaca gccgcgagag aatgaagcgg atcgaagagg gcatcaaaga   2460
gctgggcagc cagatcctga aagaacaccc cgtggaaaac acccagctgc agaacgagaa   2520
gctgtacctg tactacctgc agaatgggcg ggatatgtac gtggaccagg aactggacat   2580
caaccggctg tccgactacg atgtggacca tatcgtgcct cagagctttc tgaaggacga   2640
ctccatcgac aacaaggtgc tgaccagaag cgacaagaac cggggcaaga gcgacaacgt   2700
gccctccgaa gaggtcgtga agaagatgaa gaactactgg cggcagctgc tgaacgccaa   2760
gctgattacc cagagaaagt tcgacaatct gaccaaggcc gagagaggcg gcctgagcga   2820
actggataag gccggcttca tcaagagaca gctggtggaa acccggcaga tcacaaagca   2880
cgtggcacag atcctggact cccggatgaa cactaagtac gacgagaatg acaagctgat   2940
ccgggaagtg aaagtgatca ccctgaagtc caagctggtg tccgatttcc ggaaggattt   3000
ccagttttac aaagtgcgcg agatcaacaa ctaccaccac gcccacgacg cctacctgaa   3060
cgccgtcgtg ggaaccgccc tgatcaaaaa gtaccctaag ctggaaagcg agttcgtgta   3120
cggcgactac aaggtgtacg acgtgcggaa gatgatcgcc aagagcgagc aggaaatcgg   3180
caaggctacc gccaagtact tcttctacag caacatcatg aactttttca agaccgagat   3240
taccctggcc aacggcgaga tccggaagcg gcctctgatc gagacaaacg gcgaaaccgg   3300
ggagatcgtg tgggataagg gccgggattt tgccaccgtg cggaaagtgc tgagcatgcc   3360
ccaagtgaat atcgtgaaaa agaccgaggt gcagacaggc ggcttcagca aagagtctat   3420
cctgcccaag aggaacagcg ataagctgat cgccagaaag aaggactggg accctaagaa   3480
gtacggcggc ttcgacagcc ccaccgtggc ctattctgtg ctggtggtgg ccaaagtgga   3540
aaagggcaag tccaagaaac tgaagagtgt gaaagagctg ctggggatca ccatcatgga   3600
aagaagcagc ttcgagaaga atcccatcga ctttctggaa gccaagggct acaaagaagt   3660
gaaaaaggac ctgatcatca agctgcctaa gtactccctg ttcgagctgg aaaacggccg   3720
gaagagaatg ctggcctctg ccggcgaact gcagaaggga aacgaactgg ccctgccctc   3780
caaatatgtg aacttcctgt acctggccag ccactatgag aagctgaagg gctcccccga   3840
ggataatgag cagaaacagc tgtttgtgga acagcacaag cactacctgg acgagatcat   3900
cgagcagatc agcgagttct ccaagagagt gatcctggcc gacgctaatc tggacaaagt   3960
gctgtccgcc tacaacaagc accgggataa gcccatcaga gagcaggccg agaatatcat   4020
ccacctgttt accctgacca atctgggagc ccctgccgcc ttcaagtact ttgacaccac   4080
catcgaccgg aagaggtaca ccagcaccaa agaggtgctg gacgccaccc tgatccacca   4140
gagcatcacc ggcctgtacg agacacggat cgacctgtct cagctgggag gcgacaaaag   4200
gccggcggcc acgaaaaagg ccggccaggc aaaaaagaaa aagtaagaat t            4251
```

<210> SEQ ID NO 38
<211> LENGTH: 4222
<212> TYPE: DNA
<213> ORGANISM: Artificial
<220> FEATURE:
<223> OTHER INFORMATION: polynucleotide sequence

<400> SEQUENCE: 38
gggagactgc caagatggcc ccaaagaaga agcggaaggt cggtatccac ggagtcccag 60
cagccgacaa gaagtacagc atcggcctgg ccatcggcac caactctgtg ggctgggccg 120
tgatcaccga cgagtacaag gtgcccagca agaaattcaa ggtgctgggc aacaccgacc 180
ggcacagcat caagaagaac ctgatcggag ccctgctgtt cgacagcggc gaaacagccg 240
aggccacccg gctgaagaga accgccagaa gaagatacac cagacggaag aaccggatct 300
gctatctgca agagatcttc agcaacgaga tggccaaggt ggacgacagc ttcttccaca 360
gactggaaga gtccttcctg gtggaagagg ataagaagca cgagcggcac cccatcttcg 420
gcaacatcgt ggacgaggtg gcctaccacg agaagtaccc caccatctac cacctgagaa 480
agaaactggt ggacagcacc gacaaggccg acctgcggct gatctatctg gccctggccc 540
acatgatcaa gttccggggc cacttcctga tcgagggcga cctgaacccc gacaacagcg 600
acgtggacaa gctgttcatc cagctggtgc agacctacaa ccagctgttc gaggaaaacc 660
ccatcaacgc cagcggcgtg gacgccaagg ccatcctgtc tgccagactg agcaagagca 720
gacggctgga aaatctgatc gcccagctgc ccggcgagaa gaagaatggc ctgttcggaa 780
acctgattgc cctgagcctg ggcctgaccc ccaacttcaa gagcaacttc gacctggccg 840
aggatgccaa actgcagctg agcaaggaca cctacgacga cgacctggac aacctgctgg 900
cccagatcgg cgaccagtac gccgacctgt ttctggccgc caagaacctg tccgacgcca 960
tcctgctgag cgacatcctg agagtgaaca ccgagatcac caaggccccc ctgagcgcct 1020
ctatgatcaa gagatacgac gagcaccacc aggacctgac cctgctgaaa gctctcgtgc 1080
ggcagcagct gcctgagaag tacaaagaga ttttcttcga ccagagcaag aacggctacg 1140
ccggctacat tgacggcgga gccagccagg aagagttcta caagttcatc aagcccatcc 1200
tggaaaagat ggacggcacc gaggaactgc tcgtgaagct gaacagagag gacctgctgc 1260
ggaagcagcg gaccttcgac aacggcagca tcccccacca gatccacctg ggagagctgc 1320
acgccattct gcggcggcag gaagattttt acccattcct gaaggacaac cgggaaaaga 1380
tcgagaagat cctgaccttc cgcatcccct actacgtggg ccctctggcc aggggaaaca 1440
gcagattcgc ctggatgacc agaaagagcg aggaaaccat caccccctgg aacttcgagg 1500
aagtggtgga caagggcgct tccgcccaga gcttcatcga gcggatgacc aacttcgata 1560
agaacctgcc caacgagaag gtgctgccca agcacagcct gctgtacgag tacttcaccg 1620
tgtataacga gctgaccaaa gtgaaatacg tgaccgaggg aatgagaaag cccgccttcc 1680
tgagcggcga gcagaaaaag gccatcgtgg acctgctgtt caagaccaac cggaaagtga 1740
ccgtgaagca gctgaaagag gactacttca agaaaatcga gtgcttcgac tccgtggaaa 1800
tctccggcgt ggaagatcgg ttcaacgcct ccctgggcac ataccacgat ctgctgaaaa 1860
ttatcaagga caaggacttc ctggacaatg aggaaaacga ggacattctg gaagatatcg 1920
tgctgaccct gacactgttt gaggacagag agatgatcga ggaacggctg aaaacctatg 1980
cccacctgtt cgacgacaaa gtgatgaagc agctgaagcg gcggagatac accggctggg 2040
gcaggctgag ccggaagctg atcaacggca tccgggacaa gcagtccggc aagacaatcc 2100
tggatttcct gaagtccgac ggcttcgcca acagaaactt catgcagctg atccacgacg 2160
acagcctgac ctttaaagag gacatccaga aagcccaggt gtccggccag ggcgatagcc 2220
tgcacgagca cattgccaat ctggccggca gccccgccat taagaagggc atcctgcaga 2280
cagtgaaggt ggtggacgag ctcgtgaaag tgatgggccg gcacaagccc gagaacatcg 2340
tgatcgaaat ggccagagag aaccagacca cccagaaggg acagaagaac agccgcgaga 2400
gaatgaagcg gatcgaagag ggcatcaaag agctgggcag ccagatcctg aaagaacacc 2460
ccgtggaaaa cacccagctg cagaacgaga agctgtacct gtactacctg cagaatgggc 2520
gggatatgta cgtggaccag gaactggaca tcaaccggct gtccgactac gatgtggacc 2580
atatcgtgcc tcagagcttt ctgaaggacg actccatcga caacaaggtg ctgaccagaa 2640
gcgacaagaa ccggggcaag agcgacaacg tgccctccga agaggtcgtg aagaagatga 2700
agaactactg gcggcagctg ctgaacgcca agctgattac ccagagaaag ttcgacaatc 2760
tgaccaaggc cgagagaggc ggcctgagcg aactggataa ggccggcttc atcaagagac 2820
agctggtgga aacccggcag atcacaaagc acgtggcaca gatcctggac tcccggatga 2880
acactaagta cgacgagaat gacaagctga tccgggaagt gaaagtgatc accctgaagt 2940
ccaagctggt gtccgatttc cggaaggatt tccagtttta caaagtgcgc gagatcaaca 3000
actaccacca cgcccacgac gcctacctga acgccgtcgt gggaaccgcc ctgatcaaaa 3060
agtaccctaa gctggaaagc gagttcgtgt acggcgacta caaggtgtac gacgtgcgga 3120
agatgatcgc caagagcgag caggaaatcg gcaaggctac cgccaagtac ttcttctaca 3180
gcaacatcat gaactttttc aagaccgaga ttaccctggc caacggcgag atccggaagc 3240
ggcctctgat cgagacaaac ggcgaaaccg gggagatcgt gtgggataag ggccgggatt 3300
ttgccaccgt gcggaaagtg ctgagcatgc cccaagtgaa tatcgtgaaa aagaccgagg 3360
tgcagacagg cggcttcagc aaagagtcta tcctgcccaa gaggaacagc gataagctga 3420
tcgccagaaa gaaggactgg gaccctaaga agtacggcgg cttcgacagc cccaccgtgg 3480
cctattctgt gctggtggtg gccaaagtgg aaaagggcaa gtccaagaaa ctgaagagtg 3540
tgaaagagct gctggggatc accatcatgg aaagaagcag cttcgagaag aatcccatcg 3600
actttctgga agccaagggc tacaaagaag tgaaaaagga cctgatcatc aagctgccta 3660
agtactccct gttcgagctg gaaaacggcc ggaagagaat gctggcctct gccggcgaac 3720
tgcagaaggg aaacgaactg gccctgccct ccaaatatgt gaacttcctg tacctggcca 3780
gccactatga gaagctgaag ggctcccccg aggataatga gcagaaacag ctgtttgtgg 3840
aacagcacaa gcactacctg gacgagatca tcgagcagat cagcgagttc tccaagagag 3900
tgatcctggc cgacgctaat ctggacaaag tgctgtccgc ctacaacaag caccgggata 3960
agcccatcag agagcaggcc gagaatatca tccacctgtt taccctgacc aatctgggag 4020
cccctgccgc cttcaagtac tttgacacca ccatcgaccg gaagaggtac accagcacca 4080
aagaggtgct ggacgccacc ctgatccacc agagcatcac cggcctgtac gagacacgga 4140
tcgacctgtc tcagctggga ggcgacaaaa ggccggcggc cacgaaaaag gccggccagg 4200
caaaaaagaa aaagtaagaa tt 4222

<210> SEQ ID NO 39
<211> LENGTH: 100
<212> TYPE: RNA
<213> ORGANISM: Artificial
<220> FEATURE:
<223> OTHER INFORMATION: Hgh 3' UTR

<400> SEQUENCE: 39
cggguggcau cccugugacc ccucccccagu gccucuccug gcccuggaag uugccacucc 60
agugcccacc agccuugucc uaauaaaauu aaguugcauc 100

<210> SEQ ID NO 40
<211> LENGTH: 104
<212> TYPE: RNA
<213> ORGANISM: Artificial
<220> FEATURE:
<223> OTHER INFORMATION: CRISPR-gRNA-eGFP-ETH1

<400> SEQUENCE: 40
gggggcacgg gcagcuugcc ggguuuuaga gcuagaaaua gcaaguuaaa auaaggcuag 60
uccguuauca acuugaaaaa guggcaccga gucggugcuu uuuu 104

<210> SEQ ID NO 41
<211> LENGTH: 104
<212> TYPE: RNA
<213> ORGANISM: Artificial
<220> FEATURE:
<223> OTHER INFORMATION: CRISPR-gRNA-eGFP-ETH2

<400> SEQUENCE: 41 ggggguggugc agaugaacuu caguuuuaga gcuagaaaua gcaaguuaaa auaaggcuag 60
uccguuauca acuugaaaaa guggcaccga gucggugcuu uuuu 104

<210> SEQ ID NO 42
<211> LENGTH: 104
<212> TYPE: RNA
<213> ORGANISM: Artificial
<220> FEATURE:
<223> OTHER INFORMATION: CRISPR-gRNA-eGFP-ETH3

<400> SEQUENCE: 42
gggggcgagg agcuguucac cgguuuuaga gcuagaaaua gcaaguuaaa auaaggcuag 60
uccguuauca acuugaaaaa guggcaccga gucggugcuu uuuu 104

<210> SEQ ID NO 43
<211> LENGTH: 104
<212> TYPE: RNA
<213> ORGANISM: Artificial
<220> FEATURE:
<223> OTHER INFORMATION: CRISPR-gRNA-eGFP-ETH4

<400> SEQUENCE: 43
ggcaugcccg aaggcuacgu ccguuuuaga gcuagaaaua gcaaguuaaa auaaggcuag 60
uccguuauca acuugaaaaa guggcaccga gucggugcuu uuuu 104

<210> SEQ ID NO 44
<211> LENGTH: 104
<212> TYPE: RNA
<213> ORGANISM: Artificial
<220> FEATURE:
<223> OTHER INFORMATION: CRISPR-gRNA-eGFP-ETH5

<400> SEQUENCE: 44
ggcggccaug auauagacgu ugguuuuaga gcuagaaaua gcaaguuaaa auaaggcuag 60
uccguuauca acuugaaaaa guggcaccga gucggugcuu uuuu 104

<210> SEQ ID NO 45

<211> LENGTH: 104
<212> TYPE: RNA
<213> ORGANISM: Artificial
<220> FEATURE:
<223> OTHER INFORMATION: CRISPR-gRNA-eGFP-ETH6

<400> SEQUENCE: 45
ggagcguguc cggcgagggc gaguuuuaga gcuagaaaua gcaaguuaaa auaaggcuag 60
uccguuauca acuugaaaaa guggcaccga gucggugcuu uuuu 104

<210> SEQ ID NO 46
<211> LENGTH: 43
<212> TYPE: DNA
<213> ORGANISM: Artificial
<220> FEATURE:
<223> OTHER INFORMATION: 5' UTR pVAXA120-Cas9 plasmid/vector

<400> SEQUENCE: 46
gggagaccca agctggctag cgtttaaact taagcttgcc acc 43

<210> SEQ ID NO 47
<211> LENGTH: 169
<212> TYPE: DNA
<213> ORGANISM: Artificial
<220> FEATURE:
<223> OTHER INFORMATION: 3p-UTR

<400> SEQUENCE: 47
gaattcctag gatccactag tccagtgtgg tggaattctg cagaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa aaaaaaaaaa aaaaaaaaaa aaaaaaaaaa aaagcggcc 169

<210> SEQ ID NO 48
<211> LENGTH: 4203
<212> TYPE: DNA
<213> ORGANISM: Artificial
<220> FEATURE:
<223> OTHER INFORMATION: codon optimized wildtype Cas9

<400> SEQUENCE: 48
atggccccaa agaagaagcg gaaggtcggt atccacggag tcccagcagc cgacaagaag 60
tacagcatcg gcctggacat cggcaccaac tctgtgggct gggccgtgat caccgacgag 120
tacaaggtgc ccagcaagaa attcaaggtg ctgggcaaca ccgaccggca cagcatcaag 180
aagaacctga tcggagccct gctgttcgac agcggcgaaa cagccgaggc cacccggctg 240
aagagaaccg ccagaagaag atacaccaga cggaagaacc ggatctgcta tctgcaagag 300
atcttcagca acgagatggc caaggtggac gacagcttct tccacagact ggaagagtcc 360
ttcctggtgg aagaggataa gaagcacgag cggcacccca tcttcggcaa catcgtggac 420
gaggtggcct accacgagaa gtaccccacc atctaccacc tgagaaagaa actggtggac 480
agcaccgaca aggccgacct gcggctgatc tatctggccc tggcccacat gatcaagttc 540
cggggccact tcctgatcga gggcgacctg aaccccgaca acagcgacgt ggacaagctg 600
ttcatccagc tggtgcagac ctacaaccag ctgttcgagg aaaaccccat caacgccagc 660
ggcgtggacg ccaaggccat cctgtctgcc agactgagca agagcagacg gctggaaaat 720
ctgatcgccc agctgcccgg cgagaagaag aatggcctgt tcggaaacct gattgccctg 780
agcctgggcc tgacccccaa cttcaagagc aacttcgacc tggccgagga tgccaaactg 840
cagctgagca aggacaccta cgacgacgac ctggacaacc tgctggccca gatcggcgac 900

-continued

```
cagtacgccg acctgtttct ggccgccaag aacctgtccg acgccatcct gctgagcgac    960
atcctgagag tgaacaccga gatcaccaag gccccccctga gcgcctctat gatcaagaga   1020
tacgacgagc accaccagga cctgaccctg ctgaaagctc tcgtgcggca gcagctgcct   1080
gagaagtaca aagagatttt cttcgaccag agcaagaacg gctacgccgg ctacattgac   1140
ggcggagcca gccaggaaga gttctacaag ttcatcaagc ccatcctgga aaagatggac   1200
ggcaccgagg aactgctcgt gaagctgaac agagaggacc tgctgcggaa gcagcggacc   1260
ttcgacaacg gcagcatccc ccaccagatc cacctgggag agctgcacgc cattctgcgg   1320
cggcaggaag atttttaccc attcctgaag gacaaccggg aaaagatcga gaagatcctg   1380
accttccgca tcccctacta cgtgggccct ctggccaggg gaaacagcag attcgcctgg   1440
atgaccagaa agagcgagga aaccatcacc ccctggaact tcgaggaagt ggtggacaag   1500
ggcgcttccg cccagagctt catcgagcgg atgaccaact tcgataagaa cctgcccaac   1560
gagaaggtgc tgcccaagca cagcctgctg tacgagtact tcaccgtgta taacgagctg   1620
accaaagtga aatacgtgac cgagggaatg agaaagcccg ccttcctgag cggcgagcag   1680
aaaaaggcca tcgtggacct gctgttcaag accaaccgga aagtgaccgt gaagcagctg   1740
aaagaggact acttcaagaa aatcgagtgc ttcgactccg tggaaatctc cggcgtggaa   1800
gatcggttca acgcctccct gggcacatac cacgatctgc tgaaaattat caaggacaag   1860
gacttcctgg acaatgagga aaacgaggac attctggaag atatcgtgct gaccctgaca   1920
ctgtttgagg acagagagat gatcgaggaa cggctgaaaa cctatgccca cctgttcgac   1980
gacaaagtga tgaagcagct gaagcggcgg agatacaccg gctggggcag gctgagccgg   2040
aagctgatca acggcatccg ggacaagcag tccggcaaga caatcctgga tttcctgaag   2100
tccgacggct tcgccaacag aaacttcatg cagctgatcc acgacgacag cctgaccttt   2160
aaagaggaca tccagaaagc ccaggtgtcc ggccagggcg atagcctgca cgagcacatt   2220
gccaatctgg ccggcagccc cgccattaag aagggcatcc tgcagacagt gaaggtggtg   2280
gacgagctcg tgaaagtgat gggccggcac aagcccgaga acatcgtgat cgaaatggcc   2340
agagagaacc agaccaccca gaagggacag aagaacagcc gcgagagaat gaagcggatc   2400
gaagagggca tcaaagagct gggcagccag atcctgaaag aacaccccgt ggaaaacacc   2460
cagctgcaga acgagaagct gtacctgtac tacctgcaga atgggcggga tatgtacgtg   2520
gaccaggaac tggacatcaa ccggctgtcc gactacgatg tggaccatat cgtgcctcag   2580
agctttctga aggacgactc catcgacaac aaggtgctga ccagaagcga caagaaccgg   2640
ggcaagagcg acaacgtgcc ctccgaagag gtcgtgaaga agatgaagaa ctactggcgg   2700
cagctgctga acgccaagct gattacccag agaaagttcg acaatctgac caaggccgag   2760
agaggcggcc tgagcgaact ggataaggcc ggcttcatca agagacagct ggtggaaacc   2820
cggcagatca caaagcacgt ggcacagatc ctggactccc ggatgaacac taagtacgac   2880
gagaatgaca agctgatccg ggaagtgaaa gtgatcaccc tgaagtccaa gctggtgtcc   2940
gatttccgga aggatttcca gttttacaaa gtgcgcgaga tcaacaacta ccaccacgcc   3000
cacgacgcct acctgaacgc cgtcgtggga accgccctga tcaaaaagta ccctaagctg   3060
gaaagcgagt tcgtgtacgg cgactacaag gtgtacgacg tgcggaagat gatcgccaag   3120
agcgagcagg aaatcggcaa ggctaccgcc aagtacttct tctacagcaa catcatgaac   3180
tttttcaaga ccgagattac cctggccaac ggcgagatcc ggaagcggcc tctgatcgag   3240
```

```
acaaacggcg aaaccgggga gatcgtgtgg gataagggcc gggattttgc caccgtgcgg   3300
aaagtgctga gcatgcccca agtgaatatc gtgaaaaaga ccgaggtgca gacaggcggc   3360
ttcagcaaag agtctatcct gcccaagagg aacagcgata agctgatcgc cagaaagaag   3420
gactgggacc ctaagaagta cggcggcttc gacagcccca ccgtggccta ttctgtgctg   3480
gtggtggcca aagtggaaaa gggcaagtcc aagaaactga agagtgtgaa agagctgctg   3540
gggatcacca tcatggaaag aagcagcttc gagaagaatc ccatcgactt tctggaagcc   3600
aagggctaca aagaagtgaa aaaggacctg atcatcaagc tgcctaagta ctccctgttc   3660
gagctggaaa acggccggaa gagaatgctg gcctctgccg gcgaactgca gaagggaaac   3720
gaactggccc tgccctccaa atatgtgaac ttcctgtacc tggccagcca ctatgagaag   3780
ctgaagggct cccccgagga taatgagcag aaacagctgt ttgtggaaca gcacaagcac   3840
tacctggacg agatcatcga gcagatcagc gagttctcca agagagtgat cctggccgac   3900
gctaatctgg acaaagtgct gtccgcctac aacaagcacc gggataagcc catcagagag   3960
caggccgaga atatcatcca cctgtttacc ctgaccaatc tgggagcccc tgccgccttc   4020
aagtactttg acaccaccat cgaccggaag aggtacacca gcaccaaaga ggtgctggac   4080
gccaccctga tccaccagag catcaccggc ctgtacgaga cacggatcga cctgtctcag   4140
ctgggaggcg acaaaaggcc ggcggccacg aaaaaggccg gccaggcaaa aaagaaaaag   4200
taa                                                                 4203
```

```
<210> SEQ ID NO 49
<211> LENGTH: 4203
<212> TYPE: DNA
<213> ORGANISM: Artificial
<220> FEATURE:
<223> OTHER INFORMATION: codon optimized D10A Cas9

<400> SEQUENCE: 49
```

```
atggccccaa agaagaagcg gaaggtcggt atccacggag tcccagcagc cgacaagaag     60
tacagcatcg gcctggccat cggcaccaac tctgtgggct gggccgtgat caccgacgag    120
tacaaggtgc ccagcaagaa attcaaggtg ctgggcaaca ccgaccggca cagcatcaag    180
aagaacctga tcggagccct gctgttcgac agcggcgaaa cagccgaggc cacccggctg    240
aagagaaccg ccagaagaag atacaccaga cggaagaacc ggatctgcta tctgcaagag    300
atcttcagca acgagatggc caaggtggac gacagcttct tccacagact ggaagagtcc    360
ttcctggtgg aagaggataa gaagcacgag cggcacccca tcttcggcaa catcgtggac    420
gaggtggcct accacgagaa gtaccccacc atctaccacc tgagaaagaa actggtggac    480
agcaccgaca aggccgacct gcggctgatc tatctggccc tggcccacat gatcaagttc    540
cggggccact tcctgatcga gggcgacctg aaccccgaca acagcgacgt ggacaagctg    600
ttcatccagc tggtgcagac ctacaaccag ctgttcgagg aaaaccccat caacgccagc    660
ggcgtggacg ccaaggccat cctgtctgcc agactgagca agagcagacg gctggaaaat    720
ctgatcgccc agctgcccgg cgagaagaag aatggcctgt tcggaaacct gattgccctg    780
agcctgggcc tgacccccaa cttcaagagc aacttcgacc tggccgagga tgccaaactg    840
cagctgagca aggacaccta cgacgacgac ctggacaacc tgctggccca gatcggcgac    900
cagtacgccg acctgtttct ggccgccaag aacctgtccg acgccatcct gctgagcgac    960
atcctgagag tgaacaccga gatcaccaag gccccctga gcgcctctat gatcaagaga   1020
tacgacgagc accaccagga cctgaccctg ctgaaagctc tcgtgcggca gcagctgcct   1080
```

-continued

```
gagaagtaca aagagatttt cttcgaccag agcaagaacg gctacgccgg ctacattgac   1140
ggcggagcca gccaggaaga gttctacaag ttcatcaagc ccatcctgga aaagatggac   1200
ggcaccgagg aactgctcgt gaagctgaac agagaggacc tgctgcggaa gcagcggacc   1260
ttcgacaacg gcagcatccc ccaccagatc cacctgggag agctgcacgc cattctgcgg   1320
cggcaggaag atttttaccc attcctgaag gacaaccggg aaaagatcga gaagatcctg   1380
accttccgca tcccctacta cgtgggccct ctggccaggg gaaacagcag attcgcctgg   1440
atgaccagaa agagcgagga aaccatcacc ccctggaact tcgaggaagt ggtggacaag   1500
ggcgcttccg cccagagctt catcgagcgg atgaccaact tcgataagaa cctgcccaac   1560
gagaaggtgc tgcccaagca cagcctgctg tacgagtact tcaccgtgta taacgagctg   1620
accaaagtga aatacgtgac cgagggaatg agaaagcccg ccttcctgag cggcgagcag   1680
aaaaaggcca tcgtggacct gctgttcaag accaaccgga aagtgaccgt gaagcagctg   1740
aaagaggact acttcaagaa aatcgagtgc ttcgactccg tggaaatctc cggcgtggaa   1800
gatcggttca acgcctccct gggcacatac cacgatctgc tgaaaattat caaggacaag   1860
gacttcctgg acaatgagga aaacgaggac attctggaag atatcgtgct gaccctgaca   1920
ctgtttgagg acagagagat gatcgaggaa cggctgaaaa cctatgccca cctgttcgac   1980
gacaaagtga tgaagcagct gaagcggcgg agatacaccg gctggggcag gctgagccgg   2040
aagctgatca acggcatccg ggacaagcag tccggcaaga caatcctgga tttcctgaag   2100
tccgacggct tcgccaacag aaacttcatg cagctgatcc acgacgacag cctgaccttt   2160
aaagaggaca tccagaaagc ccaggtgtcc ggccagggcg atagcctgca cgagcacatt   2220
gccaatctgg ccggcagccc cgccattaag aagggcatcc tgcagacagt gaaggtggtg   2280
gacgagctcg tgaaagtgat gggccggcac aagcccgaga acatcgtgat cgaaatggcc   2340
agagagaacc agaccaccca gaagggacag aagaacagcc gcgagagaat gaagcggatc   2400
gaagagggca tcaaagagct gggcagccag atcctgaaag aacaccccgt ggaaaacacc   2460
cagctgcaga acgagaagct gtacctgtac tacctgcaga atgggcggga tatgtacgtg   2520
gaccaggaac tggacatcaa ccggctgtcc gactacgatg tggaccatat cgtgcctcag   2580
agctttctga aggacgactc catcgacaac aaggtgctga ccagaagcga caagaaccgg   2640
ggcaagagcg acaacgtgcc ctccgaagag gtcgtgaaga agatgaagaa ctactggcgg   2700
cagctgctga acgccaagct gattacccag agaaagttcg acaatctgac caaggccgag   2760
agaggcggcc tgagcgaact ggataaggcc ggcttcatca agagacagct ggtggaaacc   2820
cggcagatca caaagcacgt ggcacagatc ctggactccc ggatgaacac taagtacgac   2880
gagaatgaca agctgatccg ggaagtgaaa gtgatcaccc tgaagtccaa gctggtgtcc   2940
gatttccgga aggatttcca gttttacaaa gtgcgcgaga tcaacaacta ccaccacgcc   3000
cacgacgcct acctgaacgc cgtcgtggga accgccctga tcaaaaagta ccctaagctg   3060
gaaagcgagt tcgtgtacgg cgactacaag gtgtacgacg tgcggaagat gatcgccaag   3120
agcgagcagg aaatcggcaa ggctaccgcc aagtacttct tctacagcaa catcatgaac   3180
tttttcaaga ccgagattac cctggccaac ggcgagatcc ggaagcggcc tctgatcgag   3240
acaaacggcg aaaccgggga gatcgtgtgg gataagggcc gggattttgc caccgtgcgg   3300
aaagtgctga gcatgcccca agtgaatatc gtgaaaaaga ccgaggtgca gacaggcggc   3360
ttcagcaaag agtctatcct gcccaagagg aacagcgata agctgatcgc cagaaagaag   3420
```

gactgggacc ctaagaagta cggcggcttc gacagcccca ccgtggccta ttctgtgctg 3480
gtggtggcca aagtggaaaa gggcaagtcc aagaaactga agagtgtgaa agagctgctg 3540
gggatcacca tcatggaaag aagcagcttc gagaagaatc ccatcgactt tctggaagcc 3600
aagggctaca aagaagtgaa aaaggacctg atcatcaagc tgcctaagta ctccctgttc 3660
gagctggaaa acggccggaa gagaatgctg gcctctgccg gcgaactgca gaagggaaac 3720
gaactggccc tgccctccaa atatgtgaac ttcctgtacc tggccagcca ctatgagaag 3780
ctgaagggct cccccgagga taatgagcag aaacagctgt ttgtggaaca gcacaagcac 3840
tacctggacg agatcatcga gcagatcagc gagttctcca agagagtgat cctggccgac 3900
gctaatctgg acaaagtgct gtccgcctac aacaagcacc gggataagcc catcagagag 3960
caggccgaga atatcatcca cctgtttacc ctgaccaatc tgggagcccc tgccgccttc 4020
aagtactttg acaccaccat cgaccggaag aggtacacca gcaccaaaga ggtgctggac 4080
gccaccctga tccaccagag catcaccggc ctgtacgaga cacggatcga cctgtctcag 4140
ctgggaggcg acaaaaggcc ggcggccacg aaaaaggccg gccaggcaaa aaagaaaaag 4200
taa 4203

<210> SEQ ID NO 50
<211> LENGTH: 4203
<212> TYPE: DNA
<213> ORGANISM: Artificial
<220> FEATURE:
<223> OTHER INFORMATION: D10A H841A Cas9 (referred to as dCas9)

<400> SEQUENCE: 50
atggccccaa agaagaagcg gaaggtcggt atccacggag tcccagcagc cgacaagaag 60
tacagcatcg gcctggccat cggcaccaac tctgtgggct gggccgtgat caccgacgag 120
tacaaggtgc ccagcaagaa attcaaggtg ctgggcaaca ccgaccggca cagcatcaag 180
aagaacctga tcggagccct gctgttcgac agcggcgaaa cagccgaggc cacccggctg 240
aagagaaccg ccagaagaag atacaccaga cggaagaacc ggatctgcta tctgcaagag 300
atcttcagca acgagatggc caaggtggac gacagcttct tccacagact ggaagagtcc 360
ttcctggtgg aagaggataa gaagcacgag cggcacccca tcttcggcaa catcgtggac 420
gaggtggcct accacgagaa gtaccccacc atctaccacc tgagaaagaa actggtggac 480
agcaccgaca aggccgacct gcggctgatc tatctggccc tggcccacat gatcaagttc 540
cggggccact tcctgatcga gggcgacctg aaccccgaca acagcgacgt ggacaagctg 600
ttcatccagc tggtgcagac ctacaaccag ctgttcgagg aaaaccccat caacgccagc 660
ggcgtggacg ccaaggccat cctgtctgcc agactgagca agagcagacg gctggaaaat 720
ctgatcgccc agctgcccgg cgagaagaag aatggcctgt tcggaaacct gattgccctg 780
agcctgggcc tgacccccaa cttcaagagc aacttcgacc tggccgagga tgccaaactg 840
cagctgagca aggacaccta cgacgacgac ctggacaacc tgctggccca gatcggcgac 900
cagtacgccg acctgtttct ggccgccaag aacctgtccg acgccatcct gctgagcgac 960
atcctgagag tgaacaccga gatcaccaag gccccccctga gcgcctctat gatcaagaga 1020
tacgacgagc accaccagga cctgaccctg ctgaaagctc tcgtgcggca gcagctgcct 1080
gagaagtaca aagagatttt cttcgaccag agcaagaacg gctacgccgg ctacattgac 1140
ggcggagcca gccaggaaga gttctacaag ttcatcaagc ccatcctgga aaagatggac 1200
ggcaccgagg aactgctcgt gaagctgaac agagaggacc tgctgcggaa gcagcggacc 1260

-continued

```
ttcgacaacg gcagcatccc ccaccagatc cacctgggag agctgcacgc cattctgcgg   1320
cggcaggaag atttttaccc attcctgaag gacaaccggg aaaagatcga gaagatcctg   1380
accttccgca tcccctacta cgtgggccct ctggccaggg gaaacagcag attcgcctgg   1440
atgaccagaa agagcgagga aaccatcacc ccctggaact tcgaggaagt ggtggacaag   1500
ggcgcttccg cccagagctt catcgagcgg atgaccaact tcgataagaa cctgcccaac   1560
gagaaggtgc tgcccaagca cagcctgctg tacgagtact tcaccgtgta taacgagctg   1620
accaaagtga aatacgtgac cgagggaatg agaaagcccg ccttcctgag cggcgagcag   1680
aaaaaggcca tcgtggacct gctgttcaag accaaccgga aagtgaccgt gaagcagctg   1740
aaagaggact acttcaagaa aatcgagtgc ttcgactccg tggaaatctc cggcgtggaa   1800
gatcggttca acgcctccct gggcacatac cacgatctgc tgaaaattat caaggacaag   1860
gacttcctgg acaatgagga aaacgaggac attctggaag atatcgtgct gaccctgaca   1920
ctgtttgagg acagagagat gatcgaggaa cggctgaaaa cctatgccca cctgttcgac   1980
gacaaagtga tgaagcagct gaagcggcgg agatacaccg gctggggcag gctgagccgg   2040
aagctgatca acggcatccg ggacaagcag tccggcaaga caatcctgga tttcctgaag   2100
tccgacggct tcgccaacag aaacttcatg cagctgatcc acgacgacag cctgaccttt   2160
aaagaggaca tccagaaagc ccaggtgtcc ggccagggcg atagcctgca cgagcacatt   2220
gccaatctgg ccggcagccc cgccattaag aagggcatcc tgcagacagt gaaggtggtg   2280
gacgagctcg tgaaagtgat gggccggcac aagcccgaga acatcgtgat cgaaatggcc   2340
agagagaacc agaccaccca gaagggacag aagaacagcc gcgagagaat gaagcggatc   2400
gaagagggca tcaaagagct gggcagccag atcctgaaag aacaccccgt ggaaaacacc   2460
cagctgcaga acgagaagct gtacctgtac tacctgcaga atgggcggga tatgtacgtg   2520
gaccaggaac tggacatcaa ccggctgtcc gactacgatg tggacgccat cgtgcctcag   2580
agctttctga aggacgactc catcgacaac aaggtgctga ccagaagcga caagaaccgg   2640
ggcaagagcg acaacgtgcc ctccgaagag gtcgtgaaga agatgaagaa ctactggcgg   2700
cagctgctga acgccaagct gattacccag agaaagttcg acaatctgac caaggccgag   2760
agaggcggcc tgagcgaact ggataaggcc ggcttcatca agagacagct ggtggaaacc   2820
cggcagatca caaagcacgt ggcacagatc ctggactccc ggatgaacac taagtacgac   2880
gagaatgaca agctgatccg ggaagtgaaa gtgatcaccc tgaagtccaa gctggtgtcc   2940
gatttccgga aggatttcca gttttacaaa gtgcgcgaga tcaacaacta ccaccacgcc   3000
cacgacgcct acctgaacgc cgtcgtggga accgccctga tcaaaaagta ccctaagctg   3060
gaaagcgagt tcgtgtacgg cgactacaag gtgtacgacg tgcggaagat gatcgccaag   3120
agcgagcagg aaatcggcaa ggctaccgcc aagtacttct tctacagcaa catcatgaac   3180
tttttcaaga ccgagattac cctggccaac ggcgagatcc ggaagcggcc tctgatcgag   3240
acaaacggcg aaaccgggga gatcgtgtgg gataagggcc gggattttgc caccgtgcgg   3300
aaagtgctga gcatgcccca agtgaatatc gtgaaaaaga ccgaggtgca gacaggcggc   3360
ttcagcaaag agtctatcct gcccaagagg aacagcgata agctgatcgc cagaaagaag   3420
gactgggacc ctaagaagta cggcggcttc gacagcccca ccgtggccta ttctgtgctg   3480
gtggtggcca aagtggaaaa gggcaagtcc aagaaactga agagtgtgaa agagctgctg   3540
gggatcacca tcatggaaag aagcagcttc gagaagaatc ccatcgactt tctggaagcc   3600
```

-continued

```
aagggctaca aagaagtgaa aaaggacctg atcatcaagc tgcctaagta ctccctgttc   3660

gagctggaaa acggccggaa gagaatgctg gcctctgccg gcgaactgca gaagggaaac   3720

gaactggccc tgccctccaa atatgtgaac ttcctgtacc tggccagcca ctatgagaag   3780

ctgaagggct cccccgagga taatgagcag aaacagctgt ttgtggaaca gcacaagcac   3840

tacctggacg agatcatcga gcagatcagc gagttctcca agagagtgat cctggccgac   3900

gctaatctgg acaaagtgct gtccgcctac aacaagcacc gggataagcc catcagagag   3960

caggccgaga atatcatcca cctgtttacc ctgaccaatc tgggagcccc tgccgccttc   4020

aagtactttg acaccaccat cgaccggaag aggtacacca gcaccaaaga ggtgctggac   4080

gccaccctga tccaccagag catcaccggc ctgtacgaga cacggatcga cctgtctcag   4140

ctgggaggcg acaaaaggcc ggcggccacg aaaaaggccg gccaggcaaa aaagaaaaag   4200

taa                                                                 4203
```

<210> SEQ ID NO 51
<211> LENGTH: 4203
<212> TYPE: RNA
<213> ORGANISM: Artificial
<220> FEATURE:
<223> OTHER INFORMATION: D10A H841A Cas9

<400> SEQUENCE: 51

```
auggccccaa agaagaagcg gaaggucggu auccacggag ucccagcagc cgacaagaag     60

uacagcaucg gccuggccau cggcaccaac ucugugggcu gggccgugau caccgacgag    120

uacaaggugc ccagcaagaa auucaaggug cugggcaaca ccgaccggca cagcaucaag    180

aagaaccuga ucggagcccu gcuguucgac agcggcgaaa cagccgaggc cacccggcug    240

aagagaaccg ccagaagaag auacaccaga cggaagaacc ggaucugcua ucugcaagag    300

aucuucagca acgagauggc caagguggac gacagcuucu uccacagacu ggaagagucc    360

uuccuggugg aagaggauaa gaagcacgag cggcacccca ucuucggcaa caucguggac    420

gagguggccu accacgagaa guaccccacc aucuaccacc ugagaaagaa acugguggac    480

agcaccgaca aggccgaccu gcggcugauc uaucuggccc uggcccacau gaucaaguuc    540

cggggccacu uccugaucga gggcgaccug aaccccgaca acagcgacgu ggacaagcug    600

uucauccagc uggugcagac cuacaaccag cuguucgagg aaaaccccau caacgccagc    660

ggcguggacg ccaaggccau ccugucugcc agacugagca agagcagacg gcuggaaaau    720

cugaucgccc agcugcccgg cgagaagaag aauggccugu ucggaaaccu gauugcccug    780

agccugggcc ugacccccaa cuucaagagc aacuucgacc uggccgagga ugccaaacug    840

cagcugagca aggacaccua cgacgacgac cuggacaacc ugcuggccca gaucggcgac    900

caguacgccg accuguuucu ggccgccaag aaccuguccg acgccauccu gcugagcgac    960

auccugagag ugaacaccga gaucaccaag gcccccccuga gcgccucuau gaucaagaga   1020

uacgacgagc accaccagga ccugacccug cugaaagcuc ucgugcggca gcagcugccu   1080

gagaaguaca aagagauuuu cuucgaccag agcaagaacg gcuacgccgg cuacauugac   1140

ggcggagcca gccaggaaga guucuacaag uucaucaagc ccauccugga aaagauggac   1200

ggcaccgagg aacugcucgu gaagcugaac agagaggacc ugcugcggaa gcagcggacc   1260

uucgacaacg gcagcauccc ccaccagauc caccugggag agcugcacgc cauucugcgg   1320

cggcaggaag auuuuuaccc auuccugaag gacaaccggg aaaagaucga gaagauccug   1380

accuuccgca uccccuacua cgugggcccu cuggccaggg gaaacagcag auucgccugg   1440
```

-continued

```
augaccagaa agagcgagga aaccaucacc cccuggaacu ucgaggaagu gguggacaag   1500
ggcgcuuccg cccagagcuu caucgagcgg augaccaacu ucgauaagaa ccugcccaac   1560
gagaaggugc ugcccaagca cagccugcug uacgaguacu ucaccgugua uaacgagcug   1620
accaaaguga aauacgugac cgagggaaug agaaagcccg ccuuccugag cggcgagcag   1680
aaaaaggcca ucguggaccu gcuguucaag accaaccgga aagugaccgu gaagcagcug   1740
aaagaggacu acuucaagaa aaucgagugc uucgacuccg uggaaaucuc cggcguggaa   1800
gaucgguuca acgccucccu gggcacauac cacgaucugc ugaaaauuau caaggacaag   1860
gacuuccugg acaaugagga aaacgaggac auucuggaag auaucgugcu gacccugaca   1920
cuguuugagg acagagagau gaucgaggaa cggcugaaaa ccuaugccca ccuguucgac   1980
gacaaaguga ugaagcagcu gaagcggcgg agauacaccg gcuggggcag gcugagccgg   2040
aagcugauca acggcauccg ggacaagcag uccggcaaga caauccugga uuuccugaag   2100
uccgacggcu ucgccaacag aaacuucaug cagcugaucc acgacgacag ccugaccuuu   2160
aaagaggaca uccagaaagc ccaggugucc ggccagggcg auagccugca cgagcacauu   2220
gccaaucugg ccggcagccc cgccauuaag aagggcaucc ugcagacagu gaagguggug   2280
gacgagcucg ugaaagugau gggccggcac aagcccgaga acaucgugau cgaaauggcc   2340
agagagaacc agaccaccca gaagggacag aagaacagcc gcgagagaau gaagcggauc   2400
gaagagggca ucaaagagcu gggcagccag auccugaaag aacaccccgu ggaaaacacc   2460
cagcugcaga acgagaagcu guaccuguac uaccugcaga augggcggga uauguacgug   2520
gaccaggaac uggacaucaa ccggcugucc gacuacgaug uggacgccau cgugccucag   2580
agcuuucuga aggacgacuc caucgacaac aaggugcuga ccagaagcga caagaaccgg   2640
ggcaagagcg acaacgugcc cuccgaagag gucgugaaga agaugaagaa cuacuggcgg   2700
cagcugcuga acgccaagcu gauuacccag agaaaguucg acaaucugac caaggccgag   2760
agaggcggcc ugagcgaacu ggauaaggcc ggcuucauca agagacagcu gguggaaacc   2820
cggcagauca caaagcacgu ggcacagauc cuggacuccc ggaugaacac uaaguacgac   2880
gagaaugaca agcugauccg ggaagugaaa gugaucaccc ugaaguccaa gcuggugucc   2940
gauuuccgga aggauuucca guuuuacaaa gugcgcgaga ucaacaacua ccaccacgcc   3000
cacgacgccu accugaacgc cgucguggga accgcccuga ucaaaaagua cccuaagcug   3060
gaaagcgagu ucguguacgg cgacuacaag guguacgacg ugcggaagau gaucgccaag   3120
agcgagcagg aaaucggcaa ggcuaccgcc aaguacuucu ucuacagcaa caucaugaac   3180
uuuuucaaga ccgagauuac ccuggccaac ggcgagaucc ggaagcggcc ucugaucgag   3240
acaaacggcg aaaccgggga gaucgugugg gauaagggcc gggauuuugc caccgugcgg   3300
aaagugcuga gcaugcccca agugaauauc gugaaaaaga ccgaggugca gacaggcggc   3360
uucagcaaag agucuauccu gcccaagagg aacagcgaua agcugaucgc cagaaagaag   3420
gacugggacc cuaagaagua cggcggcuuc gacagcccca ccguggccua uucugugcug   3480
gugguggcca aaguggaaaa gggcaagucc aagaaacuga agagugugaa agagcugcug   3540
gggaucacca ucauggaaag aagcagcuuc gagaagaauc ccaucgacuu ucuggaagcc   3600
aagggcuaca aagaagugaa aaaggaccug aucaucaagc ugccuaagua cucccuguuc   3660
gagcuggaaa acggccggaa gagaaugcug gccucugccg gcgaacugca gaagggaaac   3720
gaacuggccc ugcccuccaa auaugugaac uuccuguacc uggccagcca cuaugagaag   3780
```

```
cugaagggcu cccccgagga uaaugagcag aaacagcugu uuguggaaca gcacaagcac   3840

uaccuggacg agaucaucga gcagaucagc gaguucucca agagagugau ccuggccgac   3900

gcuaaucugg acaaagugcu guccgccuac aacaagcacc gggauaagcc caucagagag   3960

caggccgaga auaucaucca ccuguuuacc cugaccaauc ugggagcccc ugccgccuuc   4020

aaguacuuug acaccaccau cgaccggaag agguacacca gcaccaaaga ggugcuggac   4080

gccacccuga uccaccagag caucaccggc cuguacgaga cacggaucga ccugucucag   4140

cugggaggcg acaaaaggcc ggcggccacg aaaaaggccg gccaggcaaa aaagaaaaag   4200

uaa                                                                 4203


<210> SEQ ID NO 52
<211> LENGTH: 4272
<212> TYPE: DNA
<213> ORGANISM: Artificial
<220> FEATURE:
<223> OTHER INFORMATION: FLAGtagged wildtype Cas9

<400> SEQUENCE: 52

atggactata aggaccacga cggagactac aaggatcatg atattgatta caaagacgat     60

gacgataaga tggccccaaa gaagaagcgg aaggtcggta tccacggagt cccagcagcc    120

gacaagaagt acagcatcgg cctggacatc ggcaccaact ctgtgggctg ggccgtgatc    180

accgacgagt acaaggtgcc cagcaagaaa ttcaaggtgc tgggcaacac cgaccggcac    240

agcatcaaga agaacctgat cggagccctg ctgttcgaca gcggcgaaac agccgaggcc    300

acccggctga agagaaccgc cagaagaaga tacaccagac ggaagaaccg gatctgctat    360

ctgcaagaga tcttcagcaa cgagatggcc aaggtggacg acagcttctt ccacagactg    420

gaagagtcct tcctggtgga agaggataag aagcacgagc ggcaccccat cttcggcaac    480

atcgtggacg aggtggccta ccacgagaag taccccacca tctaccacct gagaaagaaa    540

ctggtggaca gcaccgacaa ggccgacctg cggctgatct atctggccct ggcccacatg    600

atcaagttcc ggggccactt cctgatcgag ggcgacctga accccgacaa cagcgacgtg    660

gacaagctgt tcatccagct ggtgcagacc tacaaccagc tgttcgagga aaaccccatc    720

aacgccagcg gcgtggacgc caaggccatc ctgtctgcca gactgagcaa gagcagacgg    780

ctggaaaatc tgatcgccca gctgcccggc gagaagaaga atggcctgtt cggaaacctg    840

attgccctga gcctgggcct gacccccaac ttcaagagca acttcgacct ggccgaggat    900

gccaaactgc agctgagcaa ggacacctac gacgacgacc tggacaacct gctggcccag    960

atcggcgacc agtacgccga cctgtttctg gccgccaaga acctgtccga cgccatcctg   1020

ctgagcgaca tcctgagagt gaacaccgag atcaccaagg ccccccctgag cgcctctatg   1080

atcaagagat acgacgagca ccaccaggac ctgaccctgc tgaaagctct cgtgcggcag   1140

cagctgcctg agaagtacaa agagattttc ttcgaccaga gcaagaacgg ctacgccggc   1200

tacattgacg gcggagccag ccaggaagag ttctacaagt tcatcaagcc catcctggaa   1260

aagatggacg gcaccgagga actgctcgtg aagctgaaca gagaggacct gctgcggaag   1320

cagcggacct tcgacaacgg cagcatcccc caccagatcc acctgggaga gctgcacgcc   1380

attctgcggc ggcaggaaga tttttaccca ttcctgaagg acaaccggga aaagatcgag   1440

aagatcctga ccttccgcat cccctactac gtgggccctc tggccagggg aaacagcaga   1500

ttcgcctgga tgaccagaaa gagcgaggaa accatcaccc cctggaactt cgaggaagtg   1560

gtggacaagg gcgcttccgc ccagagcttc atcgagcgga tgaccaactt cgataagaac   1620
```

-continued

```
ctgcccaacg agaaggtgct gcccaagcac agcctgctgt acgagtactt caccgtgtat   1680
aacgagctga ccaaagtgaa atacgtgacc gagggaatga gaaagcccgc cttcctgagc   1740
ggcgagcaga aaaaggccat cgtggacctg ctgttcaaga ccaaccggaa agtgaccgtg   1800
aagcagctga aagaggacta cttcaagaaa atcgagtgct tcgactccgt ggaaatctcc   1860
ggcgtggaag atcggttcaa cgcctccctg ggcacatacc acgatctgct gaaaattatc   1920
aaggacaagg acttcctgga caatgaggaa aacgaggaca ttctggaaga tatcgtgctg   1980
accctgacac tgtttgagga cagagagatg atcgaggaac ggctgaaaac ctatgcccac   2040
ctgttcgacg acaaagtgat gaagcagctg aagcggcgga gatacaccgg ctggggcagg   2100
ctgagccgga agctgatcaa cggcatccgg gacaagcagt ccggcaagac aatcctggat   2160
ttcctgaagt ccgacggctt cgccaacaga aacttcatgc agctgatcca cgacgacagc   2220
ctgaccttta aagaggacat ccagaaagcc caggtgtccg gccagggcga tagcctgcac   2280
gagcacattg ccaatctggc cggcagcccc gccattaaga agggcatcct gcagacagtg   2340
aaggtggtgg acgagctcgt gaaagtgatg ggccggcaca agcccgagaa catcgtgatc   2400
gaaatggcca gagagaacca gaccacccag aagggacaga agaacagccg cgagagaatg   2460
aagcggatcg aagagggcat caaagagctg ggcagccaga tcctgaaaga acaccccgtg   2520
gaaaacaccc agctgcagaa cgagaagctg tacctgtact acctgcagaa tgggcgggat   2580
atgtacgtgg accaggaact ggacatcaac cggctgtccg actacgatgt ggaccatatc   2640
gtgcctcaga gctttctgaa ggacgactcc atcgacaaca aggtgctgac cagaagcgac   2700
aagaaccggg gcaagagcga caacgtgccc tccgaagagg tcgtgaagaa gatgaagaac   2760
tactggcggc agctgctgaa cgccaagctg attacccaga gaaagttcga caatctgacc   2820
aaggccgaga gaggcggcct gagcgaactg gataaggccg gcttcatcaa gagacagctg   2880
gtggaaaccc ggcagatcac aaagcacgtg gcacagatcc tggactcccg gatgaacact   2940
aagtacgacg agaatgacaa gctgatccgg gaagtgaaag tgatcaccct gaagtccaag   3000
ctggtgtccg atttccggaa ggatttccag ttttacaaag tgcgcgagat caacaactac   3060
caccacgccc acgacgccta cctgaacgcc gtcgtgggaa ccgccctgat caaaaagtac   3120
cctaagctgg aaagcgagtt cgtgtacggc gactacaagg tgtacgacgt gcggaagatg   3180
atcgccaaga gcgagcagga aatcggcaag gctaccgcca agtacttctt ctacagcaac   3240
atcatgaact tttcaagac cgagattacc ctggccaacg gcgagatccg gaagcggcct   3300
ctgatcgaga caaacggcga aaccggggag atcgtgtggg ataagggccg ggattttgcc   3360
accgtgcgga aagtgctgag catgccccaa gtgaatatcg tgaaaaagac cgaggtgcag   3420
acaggcggct tcagcaaaga gtctatcctg cccaagagga acagcgataa gctgatcgcc   3480
agaaagaagg actgggaccc taagaagtac ggcggcttcg acagccccac cgtggcctat   3540
tctgtgctgg tggtggccaa agtggaaaag ggcaagtcca agaaactgaa gagtgtgaaa   3600
gagctgctgg ggatcaccat catggaaaga agcagcttcg agaagaatcc catcgacttt   3660
ctggaagcca agggctacaa agaagtgaaa aaggacctga tcatcaagct gcctaagtac   3720
tccctgttcg agctggaaaa cggccggaag agaatgctgg cctctgccgg cgaactgcag   3780
aagggaaacg aactggccct gccctccaaa tatgtgaact tcctgtacct ggccagccac   3840
tatgagaagc tgaagggctc ccccgaggat aatgagcaga aacagctgtt tgtggaacag   3900
cacaagcact acctggacga gatcatcgag cagatcagcg agttctccaa gagagtgatc   3960
```

ctggccgacg ctaatctgga caaagtgctg tccgcctaca acaagcaccg ggataagccc 4020
atcagagagc aggccgagaa tatcatccac ctgtttaccc tgaccaatct gggagcccct 4080
gccgccttca agtactttga caccaccatc gaccggaaga ggtacaccag caccaaagag 4140
gtgctggacg ccaccctgat ccaccagagc atcaccggcc tgtacgagac acggatcgac 4200
ctgtctcagc tgggaggcga caaaaggccg gcggccacga aaaaggccgg ccaggcaaaa 4260
aagaaaaagt aa 4272

<210> SEQ ID NO 53
<211> LENGTH: 4233
<212> TYPE: DNA
<213> ORGANISM: Artificial
<220> FEATURE:
<223> OTHER INFORMATION: HA-tagged D10A Cas9

<400> SEQUENCE: 53
atgtacccat acgatgttcc agattacgct atggccccaa agaagaagcg gaaggtcggt 60
atccacggag tcccagcagc cgacaagaag tacagcatcg gcctggccat cggcaccaac 120
tctgtgggct gggccgtgat caccgacgag tacaaggtgc ccagcaagaa attcaaggtg 180
ctgggcaaca ccgaccggca cagcatcaag aagaacctga tcggagccct gctgttcgac 240
agcggcgaaa cagccgaggc cacccggctg aagagaaccg ccagaagaag atacaccaga 300
cggaagaacc ggatctgcta tctgcaagag atcttcagca acgagatggc caaggtggac 360
gacagcttct tccacagact ggaagagtcc ttcctggtgg aagaggataa gaagcacgag 420
cggcacccca tcttcggcaa catcgtggac gaggtggcct accacgagaa gtaccccacc 480
atctaccacc tgagaaagaa actggtggac agcaccgaca aggccgacct gcggctgatc 540
tatctggccc tggcccacat gatcaagttc cggggccact tcctgatcga gggcgacctg 600
aaccccgaca acagcgacgt ggacaagctg ttcatccagc tggtgcagac ctacaaccag 660
ctgttcgagg aaaaccccat caacgccagc ggcgtggacg ccaaggccat cctgtctgcc 720
agactgagca agagcagacg gctggaaaat ctgatcgccc agctgcccgg cgagaagaag 780
aatggcctgt tcggaaacct gattgccctg agcctgggcc tgacccccaa cttcaagagc 840
aacttcgacc tggccgagga tgccaaactg cagctgagca aggacaccta cgacgacgac 900
ctggacaacc tgctggccca gatcggcgac cagtacgccg acctgtttct ggccgccaag 960
aacctgtccg acgccatcct gctgagcgac atcctgagag tgaacaccga gatcaccaag 1020 gccccccctga gcgcctctat gatcaagaga tacgacgagc accaccagga cctgaccctg 1080
ctgaaagctc tcgtgcggca gcagctgcct gagaagtaca aagagatttt cttcgaccag 1140
agcaagaacg gctacgccgg ctacattgac ggcggagcca gccaggaaga gttctacaag 1200
ttcatcaagc ccatcctgga aaagatggac ggcaccgagg aactgctcgt gaagctgaac 1260
agagaggacc tgctgcggaa gcagcggacc ttcgacaacg gcagcatccc ccaccagatc 1320
cacctgggag agctgcacgc cattctgcgg cggcaggaag atttttaccc attcctgaag 1380
gacaaccggg aaaagatcga gaagatcctg accttccgca tcccctacta cgtgggccct 1440
ctggccaggg gaaacagcag attcgcctgg atgaccagaa agagcgagga aaccatcacc 1500
ccctggaact tcgaggaagt ggtggacaag ggcgcttccg cccagagctt catcgagcgg 1560
atgaccaact tcgataagaa cctgcccaac gagaaggtgc tgcccaagca cagcctgctg 1620
tacgagtact tcaccgtgta taacgagctg accaaagtga aatacgtgac cgagggaatg 1680
agaaagcccg ccttcctgag cggcgagcag aaaaaggcca tcgtggacct gctgttcaag 1740
accaaccgga aagtgaccgt gaagcagctg aaagaggact acttcaagaa aatcgagtgc 1800
ttcgactccg tggaaatctc cggcgtggaa gatcggttca acgcctccct gggcacatac 1860
cacgatctgc tgaaaattat caaggacaag gacttcctgg acaatgagga aaacgaggac 1920
attctggaag atatcgtgct gaccctgaca ctgtttgagg acagagagat gatcgaggaa 1980
cggctgaaaa cctatgccca cctgttcgac gacaaagtga tgaagcagct gaagcggcgg 2040
agatacaccg gctggggcag gctgagccgg aagctgatca acggcatccg ggacaagcag 2100
tccggcaaga caatcctgga tttcctgaag tccgacggct tcgccaacag aaacttcatg 2160
cagctgatcc acgacgacag cctgaccttt aaagaggaca tccagaaagc ccaggtgtcc 2220
ggccagggcg atagcctgca cgagcacatt gccaatctgg ccggcagccc cgccattaag 2280
aagggcatcc tgcagacagt gaaggtggtg gacgagctcg tgaaagtgat gggccggcac 2340
aagcccgaga acatcgtgat cgaaatggcc agagagaacc agaccaccca gaagggacag 2400
aagaacagcc gcgagagaat gaagcggatc gaagagggca tcaaagagct gggcagccag 2460
atcctgaaag aacaccccgt ggaaaacacc cagctgcaga acgagaagct gtacctgtac 2520
tacctgcaga atgggcggga tatgtacgtg gaccaggaac tggacatcaa ccggctgtcc 2580
gactacgatg tggaccatat cgtgcctcag agctttctga aggacgactc catcgacaac 2640
aaggtgctga ccagaagcga caagaaccgg ggcaagagcg acaacgtgcc ctccgaagag 2700
gtcgtgaaga agatgaagaa ctactggcgg cagctgctga acgccaagct gattacccag 2760
agaaagttcg acaatctgac caaggccgag agaggcggcc tgagcgaact ggataaggcc 2820
ggcttcatca agagacagct ggtggaaacc cggcagatca caaagcacgt ggcacagatc 2880
ctggactccc ggatgaacac taagtacgac gagaatgaca agctgatccg ggaagtgaaa 2940
gtgatcaccc tgaagtccaa gctggtgtcc gatttccgga aggatttcca gttttacaaa 3000
gtgcgcgaga tcaacaacta ccaccacgcc cacgacgcct acctgaacgc cgtcgtggga 3060
accgccctga tcaaaaagta ccctaagctg gaaagcgagt tcgtgtacgg cgactacaag 3120
gtgtacgacg tgcggaagat gatcgccaag agcgagcagg aaatcggcaa ggctaccgcc 3180
aagtacttct tctacagcaa catcatgaac tttttcaaga ccgagattac cctggccaac 3240
ggcgagatcc ggaagcggcc tctgatcgag acaaacggcg aaaccgggga gatcgtgtgg 3300
gataagggcc gggattttgc caccgtgcgg aaagtgctga gcatgcccca agtgaatatc 3360
gtgaaaaaga ccgaggtgca gacaggcggc ttcagcaaag agtctatcct gcccaagagg 3420
aacagcgata agctgatcgc cagaaagaag gactgggacc ctaagaagta cggcggcttc 3480
gacagcccca ccgtggccta ttctgtgctg gtggtggcca aagtggaaaa gggcaagtcc 3540
aagaaactga agagtgtgaa agagctgctg gggatcacca tcatggaaag aagcagcttc 3600
gagaagaatc ccatcgactt tctggaagcc aagggctaca aagaagtgaa aaaggacctg 3660
atcatcaagc tgcctaagta ctccctgttc gagctggaaa acggccggaa gagaatgctg 3720
gcctctgccg gcgaactgca gaagggaaac gaactggccc tgccctccaa atatgtgaac 3780
ttcctgtacc tggccagcca ctatgagaag ctgaagggct cccccgagga taatgagcag 3840
aaacagctgt ttgtggaaca gcacaagcac tacctggacg agatcatcga gcagatcagc 3900
gagttctcca agagagtgat cctggccgac gctaatctgg acaaagtgct gtccgcctac 3960
aacaagcacc gggataagcc catcagagag caggccgaga atatcatcca cctgtttacc 4020
ctgaccaatc tgggagcccc tgccgccttc aagtactttg acaccaccat cgaccggaag 4080

```
aggtacacca gcaccaaaga ggtgctggac gccaccctga tccaccagag catcaccggc   4140

ctgtacgaga cacggatcga cctgtctcag ctgggaggcg acaaaaggcc ggcggccacg   4200

aaaaaggccg gccaggcaaa aaagaaaaag taa                                 4233


<210> SEQ ID NO 54
<211> LENGTH: 4272
<212> TYPE: DNA
<213> ORGANISM: Artificial
<220> FEATURE:
<223> OTHER INFORMATION: FLAG-tagged D10A H841A Cas9

<400> SEQUENCE: 54

atggactata aggaccacga cggagactac aaggatcatg atattgatta caaagacgat     60

gacgataaga tggccccaaa gaagaagcgg aaggtcggta tccacggagt cccagcagcc    120

gacaagaagt acagcatcgg cctggccatc ggcaccaact ctgtgggctg ggccgtgatc    180

accgacgagt acaaggtgcc cagcaagaaa ttcaaggtgc tgggcaacac cgaccggcac    240

agcatcaaga agaacctgat cggagccctg ctgttcgaca gcggcgaaac agccgaggcc    300

acccggctga agagaaccgc cagaagaaga tacaccagac ggaagaaccg gatctgctat    360

ctgcaagaga tcttcagcaa cgagatggcc aaggtggacg acagcttctt ccacagactg    420

gaagagtcct tcctggtgga agaggataag aagcacgagc ggcaccccat cttcggcaac    480

atcgtggacg aggtggccta ccacgagaag taccccacca tctaccacct gagaaagaaa    540

ctggtggaca gcaccgacaa ggccgacctg cggctgatct atctggccct ggcccacatg    600

atcaagttcc ggggccactt cctgatcgag ggcgacctga accccgacaa cagcgacgtg    660

gacaagctgt tcatccagct ggtgcagacc tacaaccagc tgttcgagga aaaccccatc    720

aacgccagcg gcgtggacgc caaggccatc ctgtctgcca gactgagcaa gagcagacgg    780

ctggaaaatc tgatcgccca gctgcccggc gagaagaaga atggcctgtt cggaaacctg    840

attgccctga gcctgggcct gacccccaac ttcaagagca acttcgacct ggccgaggat    900

gccaaactgc agctgagcaa ggacacctac gacgacgacc tggacaacct gctggcccag    960

atcggcgacc agtacgccga cctgtttctg gccgccaaga acctgtccga cgccatcctg   1020

ctgagcgaca tcctgagagt gaacaccgag atcaccaagg ccccccctgag cgcctctatg   1080

atcaagagat acgacgagca ccaccaggac ctgaccctgc tgaaagctct cgtgcggcag   1140

cagctgcctg agaagtacaa agagattttc ttcgaccaga gcaagaacgg ctacgccggc   1200

tacattgacg gcggagccag ccaggaagag ttctacaagt tcatcaagcc catcctggaa   1260

aagatggacg gcaccgagga actgctcgtg aagctgaaca gagaggacct gctgcggaag   1320

cagcggacct tcgacaacgg cagcatcccc caccagatcc acctgggaga gctgcacgcc   1380

attctgcggc ggcaggaaga tttttaccca ttcctgaagg acaaccggga aaagatcgag   1440

aagatcctga ccttccgcat ccccctactac gtgggccctc tggccagggg aaacagcaga   1500

ttcgcctgga tgaccagaaa gagcgaggaa accatcaccc cctggaactt cgaggaagtg   1560

gtggacaagg gcgcttccgc ccagagcttc atcgagcgga tgaccaactt cgataagaac   1620

ctgcccaacg agaaggtgct gcccaagcac agcctgctgt acgagtactt caccgtgtat   1680

aacgagctga ccaaagtgaa atacgtgacc gagggaatga gaaagcccgc cttcctgagc   1740

ggcgagcaga aaaaggccat cgtggacctg ctgttcaaga ccaaccggaa agtgaccgtg   1800

aagcagctga aagaggacta cttcaagaaa atcgagtgct tcgactccgt ggaaatctcc   1860

ggcgtggaag atcggttcaa cgcctccctg ggcacatacc acgatctgct gaaaattatc   1920
```

```
aaggacaagg acttcctgga caatgaggaa aacgaggaca ttctggaaga tatcgtgctg   1980
accctgacac tgtttgagga cagagagatg atcgaggaac ggctgaaaac ctatgcccac   2040
ctgttcgacg acaaagtgat gaagcagctg aagcggcgga gatacaccgg ctggggcagg   2100
ctgagccgga agctgatcaa cggcatccgg gacaagcagt ccggcaagac aatcctggat   2160
ttcctgaagt ccgacggctt cgccaacaga aacttcatgc agctgatcca cgacgacagc   2220
ctgaccttta aagaggacat ccagaaagcc caggtgtccg gccagggcga tagcctgcac   2280
gagcacattg ccaatctggc cggcagcccc gccattaaga agggcatcct gcagacagtg   2340
aaggtggtgg acgagctcgt gaaagtgatg ggccggcaca agcccgagaa catcgtgatc   2400
gaaatggcca gagagaacca gaccacccag aagggacaga agaacagccg cgagagaatg   2460
aagcggatcg aagagggcat caaagagctg ggcagccaga tcctgaaaga acaccccgtg   2520
gaaaacaccc agctgcagaa cgagaagctg tacctgtact acctgcagaa tgggcgggat   2580
atgtacgtgg accaggaact ggacatcaac cggctgtccg actacgatgt ggacgccatc   2640
gtgcctcaga gctttctgaa ggacgactcc atcgacaaca aggtgctgac cagaagcgac   2700
aagaaccggg gcaagagcga caacgtgccc tccgaagagg tcgtgaagaa gatgaagaac   2760
tactggcggc agctgctgaa cgccaagctg attacccaga gaaagttcga caatctgacc   2820
aaggccgaga gaggcggcct gagcgaactg gataaggccg gcttcatcaa gagacagctg   2880
gtggaaaccc ggcagatcac aaagcacgtg gcacagatcc tggactcccg gatgaacact   2940
aagtacgacg agaatgacaa gctgatccgg gaagtgaaag tgatcaccct gaagtccaag   3000
ctggtgtccg atttccggaa ggatttccag ttttacaaag tgcgcgagat caacaactac   3060
caccacgccc acgacgccta cctgaacgcc gtcgtgggaa ccgccctgat caaaaagtac   3120
cctaagctgg aaagcgagtt cgtgtacggc gactacaagg tgtacgacgt gcggaagatg   3180
atcgccaaga gcgagcagga aatcggcaag gctaccgcca agtacttctt ctacagcaac   3240
atcatgaact ttttcaagac cgagattacc ctggccaacg gcgagatccg gaagcggcct   3300
ctgatcgaga caaacggcga aaccggggag atcgtgtggg ataagggccg ggattttgcc   3360
accgtgcgga aagtgctgag catgccccaa gtgaatatcg tgaaaaagac cgaggtgcag   3420
acaggcggct tcagcaaaga gtctatcctg cccaagagga acagcgataa gctgatcgcc   3480
agaaagaagg actgggaccc taagaagtac ggcggcttcg acagccccac cgtggcctat   3540
tctgtgctgg tggtggccaa agtggaaaag ggcaagtcca agaaactgaa gagtgtgaaa   3600
gagctgctgg ggatcaccat catggaaaga agcagcttcg agaagaatcc catcgacttt   3660
ctggaagcca agggctacaa agaagtgaaa aaggacctga tcatcaagct gcctaagtac   3720
tccctgttcg agctggaaaa cggccggaag agaatgctgg cctctgccgg cgaactgcag   3780
aagggaaacg aactggccct gccctccaaa tatgtgaact tcctgtacct ggccagccac   3840
tatgagaagc tgaagggctc ccccgaggat aatgagcaga aacagctgtt tgtggaacag   3900
cacaagcact acctggacga gatcatcgag cagatcagcg agttctccaa gagagtgatc   3960
ctggccgacg ctaatctgga caaagtgctg tccgcctaca acaagcaccg ggataagccc   4020
atcagagagc aggccgagaa tatcatccac ctgtttaccc tgaccaatct gggagcccct   4080
gccgccttca agtactttga caccaccatc gaccggaaga ggtacaccag caccaaagag   4140
gtgctggacg ccaccctgat ccaccagagc atcaccggcc tgtacgagac acggatcgac   4200
ctgtctcagc tgggaggcga caaaaggccg gcggccacga aaaaggccgg ccaggcaaaa   4260
```

aagaaaaagt aa 4272

<210> SEQ ID NO 55
<211> LENGTH: 13
<212> TYPE: DNA
<213> ORGANISM: Artificial
<220> FEATURE:
<223> OTHER INFORMATION: Minimal 5' UTR

<400> SEQUENCE: 55
gggagacgcc acc 13

<210> SEQ ID NO 56
<211> LENGTH: 43
<212> TYPE: DNA
<213> ORGANISM: Artificial
<220> FEATURE:
<223> OTHER INFORMATION: hAg 5' UTR

<400> SEQUENCE: 56
gggagactct tctggtcccc acagactcag agagaacgcc acc 43

<210> SEQ ID NO 57
<211> LENGTH: 13
<212> TYPE: DNA
<213> ORGANISM: Artificial
<220> FEATURE:
<223> OTHER INFORMATION: TISU 5' UTR

<400> SEQUENCE: 57
gggagacgcc aag 13

<210> SEQ ID NO 58
<211> LENGTH: 14
<212> TYPE: DNA
<213> ORGANISM: Artificial
<220> FEATURE:
<223> OTHER INFORMATION: TISU+T 5' UTR

<400> SEQUENCE: 58
gggagactgc caag 14

<210> SEQ ID NO 59
<211> LENGTH: 43
<212> TYPE: RNA
<213> ORGANISM: Artificial
<220> FEATURE:
<223> OTHER INFORMATION: 5p-UTR 5' UTR

<400> SEQUENCE: 59
gggagaccca agcuggcuag cguuuaaacu uaagcuugcc acc 43

<210> SEQ ID NO 60
<211> LENGTH: 169
<212> TYPE: RNA
<213> ORGANISM: Artificial
<220> FEATURE:
<223> OTHER INFORMATION: 3p-UTR 3' UTR

<400> SEQUENCE: 60
gaauuccuag gauccacuag uccagugugg uggaauucug cagaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa aaaaaaaaaa aaaaaaaaaa aaaaaaaaaa aaagcggcc 169

<210> SEQ ID NO 61
<211> LENGTH: 4272
<212> TYPE: RNA
<213> ORGANISM: Artificial
<220> FEATURE:
<223> OTHER INFORMATION: FLAG-tagged wildtype Cas9

<400> SEQUENCE: 61
auggacuaua aggaccacga cggagacuac aaggaucaug auauugauua caaagacgau 60
gacgauaaga uggccccaaa gaagaagcgg aaggucggua uccacggagu cccagcagcc 120
gacaagaagu acagcaucgg ccuggacauc ggcaccaacu cugugggcug ggccgugauc 180
accgacgagu acaaggugcc cagcaagaaa uucaaggugc ugggcaacac cgaccggcac 240
agcaucaaga agaaccugau cggagcccug cuguucgaca gcggcgaaac agccgaggcc 300
acccggcuga agagaaccgc cagaagaaga uacaccagac ggaagaaccg gaucugcuau 360
cugcaagaga ucuucagcaa cgagauggcc aagguggacg acagcuucuu ccacagacug 420
gaagaguccu uccuggugga agaggauaag aagcacgagc ggcaccccau cuucggcaac 480
aucguggacg agguggccua ccacgagaag uaccccacca ucuaccaccu gagaaagaaa 540
cugguggaca gcaccgacaa ggccgaccug cggcugaucu aucuggcccu ggcccacaug 600
aucaaguucc ggggccacuu ccugaucgag ggcgaccuga accccgacaa cagcgacgug 660
gacaagcugu ucauccagcu ggugcagacc uacaaccagc uguucgagga aaaccccauc 720
aacgccagcg gcguggacgc caaggccauc cugucugcca gacugagcaa gagcagacgg 780
cuggaaaauc ugaucgccca gcugcccggc gagaagaaga auggccuguu cggaaaccug 840
auugcccuga gccugggccu gacccccaac uucaagagca acuucgaccu ggccgaggau 900
gccaaacugc agcugagcaa ggacaccuac gacgacgacc uggacaaccu gcuggcccag 960
aucggcgacc aguacgccga ccuguuucug gccgccaaga accuguccga cgccauccug 1020
cugagcgaca uccugagagu gaacaccgag aucaccaagg ccccccugag cgccucuaug 1080
aucaagagau acgacgagca ccaccaggac cugacccugc ugaaagcucu cgugcggcag 1140
cagcugccug agaaguacaa agagauuuuc uucgaccaga gcaagaacgg cuacgccggc 1200
uacauugacg gcggagccag ccaggaagag uucuacaagu ucaucaagcc cauccuggaa 1260
aagauggacg gcaccgagga acugcucgug aagcugaaca gagaggaccu gcugcggaag 1320
cagcggaccu ucgacaacgg cagcaucccc caccagaucc accugggaga gcugcacgcc 1380
auucugcggc ggcaggaaga uuuuuaccca uuccugaagg acaaccggga aaagaucgag 1440
aagauccuga ccuuccgcau ccccuacuac guggggcccuc uggccagggg aaacagcaga 1500
uucgccugga ugaccagaaa gagcgaggaa accaucaccc ccuggaacuu cgaggaagug 1560
guggacaagg gcgcuuccgc ccagagcuuc aucgagcgga ugaccaacuu cgauaagaac 1620
cugcccaacg agaaggugcu gcccaagcac agccugcugu acgaguacuu caccguguau 1680
aacgagcuga ccaaagugaa auacgugacc gagggaauga gaaagcccgc cuuccugagc 1740
ggcgagcaga aaaaggccau cguggaccug cuguucaaga ccaaccggaa agugaccgug 1800
aagcagcuga aagaggacua cuucaagaaa aucgagugcu ucgacuccgu ggaaaucucc 1860
ggcguggaag aucgguucaa cgccucccug ggcacauacc acgaucugcu gaaaauuauc 1920
aaggacaagg acuuccugga caaugaggaa aacgaggaca uucuggaaga uaucgugcug 1980
acccugacac uguuugagga cagagagaug aucgaggaac ggcugaaaac cuaugcccac 2040
cuguucgacg acaaagugau gaagcagcug aagcggcgga gauacaccgg cuggggcagg 2100

-continued

```
cugagccgga agcugaucaa cggcauccgg gacaagcagu ccggcaagac aauccuggau   2160
uuccugaagu ccgacggcuu cgccaacaga aacuucaugc agcugaucca cgacgacagc   2220
cugaccuuua aagaggacau ccagaaagcc caggugccg gccagggcga uagccugcac   2280
gagcacauug ccaaucuggc cggcagcccc gccauuaaga agggcauccu gcagacagug   2340
aagguggugg acgagcucgu gaaagugaug ggccggcaca agcccgagaa caucgugauc   2400
gaaauggcca gagagaacca gaccacccag aagggacaga agaacagccg cgagagaaug   2460
aagcggaucg aagagggcau caaagagcug ggcagccaga uccugaaaga acaccccgug   2520
gaaaacaccc agcugcagaa cgagaagcug uaccuguacu accugcagaa ugggcgggau   2580
auguacgugg accaggaacu ggacaucaac cggcuguccg acuacgaugu ggaccauauc   2640
gugccucaga gcuuucugaa ggacgacucc aucgacaaca aggugcugac cagaagcgac   2700
aagaaccggg gcaagagcga caacgugccc uccgaagagg ucgugaagaa gaugaagaac   2760
uacuggcggc agcugcugaa cgccaagcug auuacccaga gaaaguucga caaucugacc   2820
aaggccgaga gaggcggccu gagcgaacug gauaaggccg gcuucaucaa gagacagcug   2880
guggaaaccc ggcagaucac aaagcacgug gcacagaucc uggacucccg gaugaacacu   2940
aaguacgacg agaaugacaa gcugauccgg gaagugaaag ugaucacccu gaaguccaag   3000
cugguguccg auuuccggaa ggauuuccag uuuuacaaag ugcgcgagau caacaacuac   3060
caccacgccc acgacgccua ccugaacgcc gucgugggaa ccgcccugau caaaaaguac   3120
ccuaagcugg aaagcgaguu cguguacggc gacuacaagg uguacgacgu gcggaagaug   3180
aucgccaaga gcgagcagga aaucggcaag gcuaccgcca aguacuucuu cuacagcaac   3240
aucaugaacu uuuucaagac cgagauuacc cuggccaacg gcgagauccg gaagcggccu   3300
cugaucgaga caaacggcga aaccggggag aucguguggg auaagggccg ggauuuugcc   3360
accgugcgga aagugcugag caugccccaa gugaauaucg ugaaaaagac cgaggugcag   3420
acaggcggcu ucagcaaaga gucuauccug cccaagagga acagcgauaa gcugaucgcc   3480
agaaagaagg acugggaccc uaagaaguac ggcggcuucg acagccccac cguggccuau   3540
ucugugcugg ugguggccaa aguggaaaag ggcaagucca agaaacugaa gagugugaaa   3600
gagcugcugg ggaucaccau cauggaaaga agcagcuucg agaagaaucc caucgacuuu   3660
cuggaagcca agggcuacaa agaagugaaa aaggaccuga ucaucaagcu gccuaaguac   3720
ucccuguucg agcuggaaaa cggccggaag agaaugcugg ccucugccgg cgaacugcag   3780
aagggaaacg aacuggcccu gcccuccaaa uaugugaacu uccuguaccu ggccagccac   3840
uaugagaagc ugaagggcuc ccccgaggau aaugagcaga aacagcuguu uguggaacag   3900
cacaagcacu accuggacga gaucaucgag cagaucagcg aguucuccaa gagagugauc   3960
cuggccgacg cuaaucugga caaagugcug uccgccuaca acaagcaccg ggauaagccc   4020
aucagagagc aggccgagaa uaucauccac cuguuuaccc ugaccaaucu gggagccccu   4080
gccgccuuca aguacuuuga caccaccauc gaccggaaga gguacaccag caccaaagag   4140
gugcuggacg ccacccugau ccaccagagc aucaccggcc uguacgagac acggaucgac   4200
cugucucagc ugggaggcga caaaaggccg gcggccacga aaaaggccgg ccaggcaaaa   4260
aagaaaaagu aa                                                       4272
```

<210> SEQ ID NO 62
<211> LENGTH: 4233
<212> TYPE: RNA
<213> ORGANISM: Artificial
<220> FEATURE:
<223> OTHER INFORMATION: Hatagged D10A Cas9

<400> SEQUENCE: 62

```
auguacccau acgauguucc agauuacgcu auggccccaa agaagaagcg gaaggucggu     60
auccacggag ucccagcagc cgacaagaag uacagcaucg gccuggccau cggcaccaac    120
ucugugggcu gggccgugau caccgacgag uacaaggugc ccagcaagaa auucaaggug    180
cugggcaaca ccgaccggca cagcaucaag aagaaccuga ucggagcccu gcuguucgac    240
agcggcgaaa cagccgaggc cacccggcug aagagaaccg ccagaagaag auacaccaga    300
cggaagaacc ggaucugcua ucugcaagag aucuucagca acgagauggc caagguggac    360
gacagcuucu uccacagacu ggaagagucc uuccuggugg aagaggauaa gaagcacgag    420
cggcacccca ucuucggcaa caucguggac gagguggccu accacgagaa guaccccacc    480
aucuaccacc ugagaaagaa acugguggac agcaccgaca aggccgaccu gcggcugauc    540
uaucuggccc uggcccacau gaucaaguuc cggggccacu uccugaucga gggcgaccug    600
aaccccgaca acagcgacgu ggacaagcug uucauccagc uggugcagac cuacaaccag    660
cuguucgagg aaaaccccau caacgccagc ggcguggacg ccaaggccau ccugucugcc    720
agacugagca agagcagacg gcuggaaaau cugaucgccc agcugcccgg cgagaagaag    780
aauggccugu ucggaaaccu gauugcccug agccugggcc ugacccccaa cuucaagagc    840
aacuucgacc uggccgagga ugccaaacug cagcugagca aggacaccua cgacgacgac    900
cuggacaacc ugcuggccca gaucggcgac caguacgccg accuguuucu ggccgccaag    960
aaccuguccg acgccauccu gcugagcgac auccugagag ugaacaccga gaucaccaag   1020
gccccccuga gcgccucuau gaucaagaga uacgacgagc accaccagga ccugacccug   1080
cugaaagcuc ucgugcggca gcagcugccu gagaaguaca aagagauuuu cuucgaccag   1140
agcaagaacg gcuacgccgg cuacauugac ggcggagcca gccaggaaga guucuacaag   1200
uucaucaagc ccauccugga aaagauggac ggcaccgagg aacugcucgu gaagcugaac   1260
agagaggacc ugcugcggaa gcagcggacc uucgacaacg gcagcauccc ccaccagauc   1320
caccugggag agcugcacgc cauucugcgg cggcaggaag auuuuuaccc auuccugaag   1380
gacaaccggg aaaagaucga gaagauccug accuuccgca uccccuacua cgugggcccu   1440
cuggccaggg gaaacagcag auucgccugg augaccagaa agagcgagga aaccaucacc   1500
cccuggaacu ucgaggaagu gguggacaag ggcgcuuccg cccagagcuu caucgagcgg   1560
augaccaacu ucgauaagaa ccugcccaac gagaaggugc ugcccaagca cagccugcug   1620
uacgaguacu ucaccgugua uaacgagcug accaaaguga aauacgugac cgagggaaug   1680
agaaagcccg ccuuccugag cggcgagcag aaaaaggcca ucguggaccu gcuguucaag   1740
accaaccgga aagugaccgu gaagcagcug aaagaggacu acuucaagaa aaucgagugc   1800
uucgacuccg uggaaaucuc cggcguggaa gaucgguuca acgccucccu gggcacauac   1860
cacgaucugc ugaaaauuau caaggacaag gacuuccugg acaaugagga aaacgaggac   1920
auucuggaag auaucgugcu gacccugaca cuguuugagg acagagagau gaucgaggaa   1980
cggcugaaaa ccuaugccca ccuguucgac gacaaaguga ugaagcagcu gaagcggcgg   2040
agauacaccg gcuggggcag gcugagccgg aagcugauca acggcauccg ggacaagcag   2100
uccggcaaga caauccugga uuuccugaag uccgacggcu ucgccaacag aaacuucaug   2160
cagcugaucc acgacgacag ccugaccuuu aaagaggaca uccagaaagc ccaggugucc   2220
```

ggccagggcg auagccugca cgagcacauu gccaaucugg ccggcagccc cgccauuaag 2280
aagggcaucc ugcagacagu gaagguggug gacgagcucg ugaaagugau gggccggcac 2340
aagcccgaga acaucgugau cgaaauggcc agagagaacc agaccaccca gaagggacag 2400
aagaacagcc gcgagagaau gaagcggauc gaagagggca ucaaagagcu gggcagccag 2460
auccugaaag aacaccccgu ggaaaacacc cagcugcaga acgagaagcu guaccuguac 2520
uaccugcaga augggcggga uauguacgug gaccaggaac uggacaucaa ccggcugucc 2580
gacuacgaug uggaccauau cgugccucag agcuuucuga aggacgacuc caucgacaac 2640
aaggugcuga ccagaagcga caagaaccgg ggcaagagcg acaacgugcc cuccgaagag 2700
gucgugaaga agaugaagaa cuacuggcgg cagcugcuga acgccaagcu gauuacccag 2760
agaaaguucg acaaucugac caaggccgag agaggcggcc ugagcgaacu ggauaaggcc 2820
ggcuucauca agagacagcu gguggaaacc cggcagauca caaagcacgu ggcacagauc 2880
cuggacuccc ggaugaacac uaaguacgac gagaaugaca agcugauccg ggaagugaaa 2940
gugaucaccc ugaaguccaa gcuggugucc gauuuccgga aggauuucca guuuuacaaa 3000
gugcgcgaga ucaacaacua ccaccacgcc cacgacgccu accugaacgc cgucguggga 3060
accgcccuga ucaaaaagua cccuaagcug gaaagcgagu ucguguacgg cgacuacaag 3120
guguacgacg ugcggaagau gaucgccaag agcgagcagg aaaucggcaa ggcuaccgcc 3180
aaguacuucu ucuacagcaa caucaugaac uuuuucaaga ccgagauuac ccuggccaac 3240
ggcgagaucc ggaagcggcc ucugaucgag acaaacggcg aaaccgggga gaucgugugg 3300
gauaagggcc gggauuuugc caccgugcgg aaagugcuga gcaugcccca agugaauauc 3360
gugaaaaaga ccgaggugca gacaggcggc uucagcaaag agucuauccu gcccaagagg 3420
aacagcgaua agcugaucgc cagaaagaag gacugggacc cuaagaagua cggcggcuuc 3480
gacagcccca ccguggccua uucugugcug gugguggcca aaguggaaaa gggcaagucc 3540
aagaaacuga agagugugaa agagcugcug gggaucacca ucauggaaag aagcagcuuc 3600
gagaagaauc ccaucgacuu ucuggaagcc aagggcuaca aagaagugaa aaaggaccug 3660
aucaucaagc ugccuaagua cucccuguuc gagcuggaaa acggccggaa gagaaugcug 3720
gccucugccg gcgaacugca gaagggaaac gaacuggccc ugcccuccaa auaugugaac 3780
uuccuguacc uggccagcca cuaugagaag cugaagggcu cccccgagga uaaugagcag 3840
aaacagcugu uuguggaaca gcacaagcac uaccuggacg agaucaucga gcagaucagc 3900
gaguucucca agagagugau ccuggccgac gcuaaucugg acaaagugcu guccgccuac 3960
aacaagcacc gggauaagcc caucagagag caggccgaga auaucaucca ccuguuuacc 4020
cugaccaauc ugggagcccc ugccgccuuc aaguacuuug acaccaccau cgaccggaag 4080
agguacacca gcaccaaaga ggugcuggac gccacccuga uccaccagag caucaccggc 4140
cuguacgaga cacggaucga ccugucucag cugggaggcg acaaaaggcc ggcggccacg 4200
aaaaaggccg gccaggcaaa aaagaaaaag uaa 4233

<210> SEQ ID NO 63
<211> LENGTH: 4272
<212> TYPE: RNA
<213> ORGANISM: Artificial
<220> FEATURE:
<223> OTHER INFORMATION: FLAG-tagged D10A H841A Cas9

<400> SEQUENCE: 63
auggacuaua aggaccacga cggagacuac aaggaucaug auauugauua caaagacgau 60

```
gacgauaaga uggccccaaa gaagaagcgg aaggucggua uccacggagu cccagcagcc    120
gacaagaagu acagcaucgg ccuggccauc ggcaccaacu cugugggcug ggccgugauc    180
accgacgagu acaaggugcc cagcaagaaa uucaaggugc ugggcaacac cgaccggcac    240
agcaucaaga agaaccugau cggagcccug cuguucgaca gcggcgaaac agccgaggcc    300
acccggcuga agagaaccgc cagaagaaga uacaccagac ggaagaaccg gaucugcuau    360
cugcaagaga ucuucagcaa cgagauggcc aagguggacg acagcuucuu ccacagacug    420
gaagaguccu uccuggugga agaggauaag aagcacgagc ggcaccccau cuucggcaac    480
aucguggacg agguggccua ccacgagaag uaccccacca ucuaccaccu gagaaagaaa    540
cugguggaca gcaccgacaa ggccgaccug cggcugaucu aucuggcccu ggcccacaug    600
aucaaguucc ggggccacuu ccugaucgag ggcgaccuga accccgacaa cagcgacgug    660
gacaagcugu ucauccagcu ggugcagacc uacaaccagc uguucgagga aaaccccauc    720
aacgccagcg gcguggacgc caaggccauc cugucugcca gacugagcaa gagcagacgg    780
cuggaaaauc ugaucgccca gcugcccggc gagaagaaga auggccuguu cggaaaccug    840
auugcccuga gccugggccu gacccccaac uucaagagca acuucgaccu ggccgaggau    900
gccaaacugc agcugagcaa ggacaccuac gacgacgacc uggacaaccu gcuggcccag    960
aucggcgacc aguacgccga ccuguuucug gccgccaaga accuguccga cgccauccug   1020
cugagcgaca uccugagagu gaacaccgag aucaccaagg ccccccugag cgccucuaug   1080
aucaagagau acgacgagca ccaccaggac cugacccugc ugaaagcucu cgugcggcag   1140
cagcugccug agaaguacaa agagauuuuc uucgaccaga gcaagaacgg cuacgccggc   1200
uacauugacg gcggagccag ccaggaagag uucuacaagu ucaucaagcc cauccuggaa   1260
aagauggacg gcaccgagga acugcucgug aagcugaaca gagaggaccu gcugcggaag   1320
cagcggaccu ucgacaacgg cagcaucccc caccagaucc accugggaga gcugcacgcc   1380
auucugcggc ggcaggaaga uuuuuaccca uuccugaagg acaaccggga aaagaucgag   1440
aagauccuga ccuuccgcau ccccuacuac guggggcccuc uggccagggg aaacagcaga   1500
uucgccugga ugaccagaaa gagcgaggaa accaucaccc ccuggaacuu cgaggaagug   1560
guggacaagg gcgcuuccgc ccagagcuuc aucgagcgga ugaccaacuu cgauaagaac   1620
cugcccaacg agaaggugcu gcccaagcac agccugcugu acgaguacuu caccguguau   1680
aacgagcuga ccaaagugaa auacgugacc gagggaauga gaaagcccgc cuuccugagc   1740
ggcgagcaga aaaaggccau cguggaccug cuguucaaga ccaaccggaa agugaccgug   1800
aagcagcuga aagaggacua cuucaagaaa aucgagugcu ucgacuccgu ggaaaucucc   1860
ggcguggaag aucgguucaa cgccucccug ggcacauacc acgaucugcu gaaaauuauc   1920
aaggacaagg acuuccugga caaugaggaa aacgaggaca uucuggaaga uaucgugcug   1980
acccugacac uguuugagga cagagagaug aucgaggaac ggcugaaaac cuaugcccac   2040
cuguucgacg acaaagugau gaagcagcug aagcggcgga gauacaccgg cuggggcagg   2100
cugagccgga agcugaucaa cggcauccgg gacaagcagu ccggcaagac aauccuggau   2160
uuccugaagu ccgacggcuu cgccaacaga aacuucaugc agcugaucca cgacgacagc   2220
cugaccuuua aagaggacau ccagaaagcc cagguguccg gccagggcga uagccugcac   2280
gagcacauug ccaaucuggc cggcagcccc gccauuaaga agggcauccu gcagacagug   2340
aagguggugg acgagcucgu gaaagugaug ggccggcaca agcccgagaa caucgugauc   2400
```

gaaauggcca gagagaacca gaccacccag aagggacaga agaacagccg cgagagaaug 2460
aagcggaucg aagagggcau caaagagcug ggcagccaga uccugaaaga acaccccgug 2520
gaaaacaccc agcugcagaa cgagaagcug uaccuguacu accugcagaa ugggcgggau 2580
auguacgugg accaggaacu ggacaucaac cggcuguccg acuacgaugu ggacgccauc 2640
gugccucaga gcuuucugaa ggacgacucc aucgacaaca aggugcugac cagaagcgac 2700
aagaaccggg gcaagagcga caacgugccc uccgaagagg ucgugaagaa gaugaagaac 2760
uacuggcggc agcugcugaa cgccaagcug auuacccaga gaaaguucga caaucugacc 2820
aaggccgaga gaggcggccu gagcgaacug gauaaggccg gcuucaucaa gagacagcug 2880
guggaaaccc ggcagaucac aaagcacgug gcacagaucc uggacucccg gaugaacacu 2940
aaguacgacg agaaugacaa gcugauccgg gaagugaaag ugaucacccu gaaguccaag 3000 cuggugucog auuuccggaa ggauuuccag uuuuacaaag ugcgcgagau caacaacuac 3060
caccacgccc acgacgccua ccugaacgcc gucgugggaa ccgcccugau caaaaaguac 3120
ccuaagcugg aaagcgaguu cguguacggc gacuacaagg uguacgacgu gcggaagaug 3180
aucgccaaga gcgagcagga aaucggcaag gcuaccgcca aguacuucuu cuacagcaac 3240
aucaugaacu uuuucaagac cgagauuacc cuggccaacg gcgagauccg gaagcggccu 3300
cugaucgaga caaacggcga aaccggggag aucguguggg auaagggccg ggauuuugcc 3360
accgugcgga aagugcugag caugccccaa gugaauaucg ugaaaaagac cgaggugcag 3420
acaggcggcu ucagcaaaga gucuauccug cccaagagga acagcgauaa gcugaucgcc 3480
agaaagaagg acugggaccc uaagaaguac ggcggcuucg acagccccac cguggccuau 3540
ucugugcugg ugguggccaa aguggaaaag ggcaagucca agaaacugaa gagugugaaa 3600
gagcugcugg ggaucaccau cauggaaaga agcagcuucg agaagaaucc caucgacuuu 3660
cuggaagcca agggcuacaa agaagugaaa aaggaccuga ucaucaagcu gccuaaguac 3720
ucccuguucg agcuggaaaa cggccggaag agaaugcugg ccucugccgg cgaacugcag 3780
aagggaaacg aacuggcccu gcccuccaaa uaugugaacu uccuguaccu ggccagccac 3840
uaugagaagc ugaagggcuc ccccgaggau aaugagcaga aacagcuguu uguggaacag 3900
cacaagcacu accuggacga gaucaucgag cagaucagcg aguucuccaa gagagugauc 3960
cuggccgacg cuaaucugga caaagugcug uccgccuaca acaagcaccg ggauaagccc 4020
aucagagagc aggccgagaa uaucauccac cuguuuaccc ugaccaaucu gggagccccu 4080
gccgccuuca aguacuuuga caccaccauc gaccggaaga gguacaccag caccaaagag 4140
gugcuggacg ccacccugau ccaccagagc aucaccggcc uguacgagac acggaucgac 4200
cugucucagc ugggaggcga caaaaggccg gcggccacga aaaaggccgg ccaggcaaaa 4260
aagaaaaagu aa 4272

<210> SEQ ID NO 64
<211> LENGTH: 66
<212> TYPE: RNA
<213> ORGANISM: Artificial
<220> FEATURE:
<223> OTHER INFORMATION: alpha-GLOBIN 5' UTR (HBA2)

<400> SEQUENCE: 64
cauaaacccu ggcgcgcucg cgggccggca cucuucuggu ccccacagac ucagagagaa 60
cccacc 66

-continued

<210> SEQ ID NO 65
<211> LENGTH: 30
<212> TYPE: RNA
<213> ORGANISM: Artificial
<220> FEATURE:
<223> OTHER INFORMATION: alpha-GLOBIN 5' UTR ETH

<400> SEQUENCE: 65
ucuucugguc cccacagacu cagagagaac 30

<210> SEQ ID NO 66
<211> LENGTH: 129
<212> TYPE: DNA
<213> ORGANISM: Artificial
<220> FEATURE:
<223> OTHER INFORMATION: NLS referred to as rpL23a

<400> SEQUENCE: 66
gtgcacagcc acaagaagaa gaagatcaga accagcccca ccttcagaag acccaagacc 60
ctgagactga gaagacagcc caagtacccc agaaagagcg cccccagaag aaacaagctg 120
gaccactac 129

<210> SEQ ID NO 67
<211> LENGTH: 36
<212> TYPE: DNA
<213> ORGANISM: Artificial
<220> FEATURE:
<223> OTHER INFORMATION: NLS referred to as TAT

<400> SEQUENCE: 67
ggcagaaaga agagaagaca gagaagaaga gccccc 36

<210> SEQ ID NO 68
<211> LENGTH: 141
<212> TYPE: DNA
<213> ORGANISM: Artificial
<220> FEATURE:
<223> OTHER INFORMATION: NLS referred to as IBB domain

<400> SEQUENCE: 68
caccggatca agagcttcaa gaacaagggc cgggacgtgg aaaccatgcg gcggcacaga 60
aacgaagtga ccgtggaact gcggaagaac aagcgggacg agcatctgct gaagaaacgg 120
aacgtgcccc aggaagagag c 141

<210> SEQ ID NO 69
<211> LENGTH: 42
<212> TYPE: DNA
<213> ORGANISM: Artificial
<220> FEATURE:
<223> OTHER INFORMATION: NLS referred to as SwitchII-Ran

<400> SEQUENCE: 69
gacacagccg gccaggagaa attcggtgga ctgagagatg gc 42

<210> SEQ ID NO 70
<211> LENGTH: 129
<212> TYPE: RNA
<213> ORGANISM: Artificial
<220> FEATURE:
<223> OTHER INFORMATION: NLS referred to as rpL23a

<400> SEQUENCE: 70
gugcacagcc acaagaagaa gaagaucaga accagcccca ccuucagaag acccaagacc 60

-continued cugagacuga gaagacagcc caaguacccc agaaagagcg cccccagaag aaacaagcug 120
gaccacuac 129

<210> SEQ ID NO 71
<211> LENGTH: 36
<212> TYPE: DNA
<213> ORGANISM: Artificial
<220> FEATURE:
<223> OTHER INFORMATION: NLS referred to as TAT

<400> SEQUENCE: 71
ggcagaaaga agagaagaca gagaagaaga gccccc 36

<210> SEQ ID NO 72
<211> LENGTH: 141
<212> TYPE: RNA
<213> ORGANISM: Artificial
<220> FEATURE:
<223> OTHER INFORMATION: NLS referred to as IBB domain

<400> SEQUENCE: 72
caccggauca agagcuucaa gaacaagggc cgggacgugg aaaccaugcg gcggcacaga 60
aacgaaguga ccguggaacu gcggaagaac aagcgggacg agcaucugcu gaagaaacgg 120
aacgugcccc aggaagagag c 141

<210> SEQ ID NO 73
<211> LENGTH: 42
<212> TYPE: RNA
<213> ORGANISM: Artificial
<220> FEATURE:
<223> OTHER INFORMATION: NLS referred to as SwitchII-Ran

<400> SEQUENCE: 73
gacacagccg gccaggagaa auucggugga cugagagaug gc 42

<210> SEQ ID NO 74
<211> LENGTH: 82
<212> TYPE: RNA
<213> ORGANISM: Artificial
<220> FEATURE:
<223> OTHER INFORMATION: tracer RNA (trRNA) sequence

<400> SEQUENCE: 74
guuuuagagc uagaaauagc aaguuaaaau aaggcuaguc cguuaucaac uugaaaaagu 60
ggcaccgagu cggugcuuuu uu 82

<210> SEQ ID NO 75
<211> LENGTH: 7
<212> TYPE: DNA
<213> ORGANISM: Artificial
<220> FEATURE:
<223> OTHER INFORMATION: 5' UTR referred to as Minimal, without promoter sequence

<400> SEQUENCE: 75 cgccacc 7

<210> SEQ ID NO 76
<211> LENGTH: 37
<212> TYPE: RNA
<213> ORGANISM: Artificial
<220> FEATURE:
<223> OTHER INFORMATION: 5' UTR referred to as hAg, without promoter sequence

<400> SEQUENCE: 76
cucuucuggu ccccacagac ucagagagaa cgccacc 37

<210> SEQ ID NO 77
<211> LENGTH: 7
<212> TYPE: DNA
<213> ORGANISM: Artificial
<220> FEATURE:
<223> OTHER INFORMATION: 5' UTR referred to as TISU, without promoter sequence

<400> SEQUENCE: 77 cgccaag 7

<210> SEQ ID NO 78
<211> LENGTH: 8
<212> TYPE: RNA
<213> ORGANISM: Artificial
<220> FEATURE:
<223> OTHER INFORMATION: 5' UTR referred to as TISU+T, without promoter sequence

<400> SEQUENCE: 78 cugccaag 8

<210> SEQ ID NO 79
<211> LENGTH: 1400
<212> TYPE: PRT
<213> ORGANISM: Artificial
<220> FEATURE:
<223> OTHER INFORMATION: D10A H841A Cas9

<400> SEQUENCE: 79

Met Ala Pro Lys Lys Lys Arg Lys Val Gly Ile His Gly Val Pro Ala
1 5 10 15

Ala Asp Lys Lys Tyr Ser Ile Gly Leu Ala Ile Gly Thr Asn Ser Val
20 25 30

Gly Trp Ala Val Ile Thr Asp Glu Tyr Lys Val Pro Ser Lys Lys Phe
35 40 45

Lys Val Leu Gly Asn Thr Asp Arg His Ser Ile Lys Lys Asn Leu Ile
50 55 60

Gly Ala Leu Leu Phe Asp Ser Gly Glu Thr Ala Glu Ala Thr Arg Leu
65 70 75 80

Lys Arg Thr Ala Arg Arg Arg Tyr Thr Arg Arg Lys Asn Arg Ile Cys
85 90 95

Tyr Leu Gln Glu Ile Phe Ser Asn Glu Met Ala Lys Val Asp Asp Ser
100 105 110

Phe Phe His Arg Leu Glu Glu Ser Phe Leu Val Glu Glu Asp Lys Lys
115 120 125

His Glu Arg His Pro Ile Phe Gly Asn Ile Val Asp Glu Val Ala Tyr
130 135 140

His Glu Lys Tyr Pro Thr Ile Tyr His Leu Arg Lys Lys Leu Val Asp
145 150 155 160

Ser Thr Asp Lys Ala Asp Leu Arg Leu Ile Tyr Leu Ala Leu Ala His
165 170 175

Met Ile Lys Phe Arg Gly His Phe Leu Ile Glu Gly Asp Leu Asn Pro
180 185 190

Asp Asn Ser Asp Val Asp Lys Leu Phe Ile Gln Leu Val Gln Thr Tyr
195 200 205

-continued

```
Asn Gln Leu Phe Glu Glu Asn Pro Ile Asn Ala Ser Gly Val Asp Ala
    210                 215                 220

Lys Ala Ile Leu Ser Ala Arg Leu Ser Lys Ser Arg Arg Leu Glu Asn
225                 230                 235                 240

Leu Ile Ala Gln Leu Pro Gly Glu Lys Lys Asn Gly Leu Phe Gly Asn
                245                 250                 255

Leu Ile Ala Leu Ser Leu Gly Leu Thr Pro Asn Phe Lys Ser Asn Phe
            260                 265                 270

Asp Leu Ala Glu Asp Ala Lys Leu Gln Leu Ser Lys Asp Thr Tyr Asp
        275                 280                 285

Asp Asp Leu Asp Asn Leu Leu Ala Gln Ile Gly Asp Gln Tyr Ala Asp
    290                 295                 300

Leu Phe Leu Ala Ala Lys Asn Leu Ser Asp Ala Ile Leu Leu Ser Asp
305                 310                 315                 320

Ile Leu Arg Val Asn Thr Glu Ile Thr Lys Ala Pro Leu Ser Ala Ser
                325                 330                 335

Met Ile Lys Arg Tyr Asp Glu His His Gln Asp Leu Thr Leu Leu Lys
            340                 345                 350

Ala Leu Val Arg Gln Gln Leu Pro Glu Lys Tyr Lys Glu Ile Phe Phe
        355                 360                 365

Asp Gln Ser Lys Asn Gly Tyr Ala Gly Tyr Ile Asp Gly Gly Ala Ser
    370                 375                 380

Gln Glu Glu Phe Tyr Lys Phe Ile Lys Pro Ile Leu Glu Lys Met Asp
385                 390                 395                 400

Gly Thr Glu Glu Leu Leu Val Lys Leu Asn Arg Glu Asp Leu Leu Arg
                405                 410                 415

Lys Gln Arg Thr Phe Asp Asn Gly Ser Ile Pro His Gln Ile His Leu
            420                 425                 430

Gly Glu Leu His Ala Ile Leu Arg Arg Gln Glu Asp Phe Tyr Pro Phe
        435                 440                 445

Leu Lys Asp Asn Arg Glu Lys Ile Glu Lys Ile Leu Thr Phe Arg Ile
    450                 455                 460

Pro Tyr Tyr Val Gly Pro Leu Ala Arg Gly Asn Ser Arg Phe Ala Trp
465                 470                 475                 480

Met Thr Arg Lys Ser Glu Glu Thr Ile Thr Pro Trp Asn Phe Glu Glu
                485                 490                 495

Val Val Asp Lys Gly Ala Ser Ala Gln Ser Phe Ile Glu Arg Met Thr
            500                 505                 510

Asn Phe Asp Lys Asn Leu Pro Asn Glu Lys Val Leu Pro Lys His Ser
        515                 520                 525

Leu Leu Tyr Glu Tyr Phe Thr Val Tyr Asn Glu Leu Thr Lys Val Lys
    530                 535                 540

Tyr Val Thr Glu Gly Met Arg Lys Pro Ala Phe Leu Ser Gly Glu Gln
545                 550                 555                 560

Lys Lys Ala Ile Val Asp Leu Leu Phe Lys Thr Asn Arg Lys Val Thr
                565                 570                 575

Val Lys Gln Leu Lys Glu Asp Tyr Phe Lys Lys Ile Glu Cys Phe Asp
            580                 585                 590

Ser Val Glu Ile Ser Gly Val Glu Asp Arg Phe Asn Ala Ser Leu Gly
        595                 600                 605

Thr Tyr His Asp Leu Leu Lys Ile Ile Lys Asp Lys Asp Phe Leu Asp
    610                 615                 620
```

-continued

```
Asn Glu Glu Asn Glu Asp Ile Leu Glu Asp Ile Val Leu Thr Leu Thr
625                 630                 635                 640

Leu Phe Glu Asp Arg Glu Met Ile Glu Glu Arg Leu Lys Thr Tyr Ala
                645                 650                 655

His Leu Phe Asp Asp Lys Val Met Lys Gln Leu Lys Arg Arg Arg Tyr
            660                 665                 670

Thr Gly Trp Gly Arg Leu Ser Arg Lys Leu Ile Asn Gly Ile Arg Asp
        675                 680                 685

Lys Gln Ser Gly Lys Thr Ile Leu Asp Phe Leu Lys Ser Asp Gly Phe
    690                 695                 700

Ala Asn Arg Asn Phe Met Gln Leu Ile His Asp Asp Ser Leu Thr Phe
705                 710                 715                 720

Lys Glu Asp Ile Gln Lys Ala Gln Val Ser Gly Gln Gly Asp Ser Leu
                725                 730                 735

His Glu His Ile Ala Asn Leu Ala Gly Ser Pro Ala Ile Lys Lys Gly
            740                 745                 750

Ile Leu Gln Thr Val Lys Val Val Asp Glu Leu Val Lys Val Met Gly
        755                 760                 765

Arg His Lys Pro Glu Asn Ile Val Ile Glu Met Ala Arg Glu Asn Gln
    770                 775                 780

Thr Thr Gln Lys Gly Gln Lys Asn Ser Arg Glu Arg Met Lys Arg Ile
785                 790                 795                 800

Glu Glu Gly Ile Lys Glu Leu Gly Ser Gln Ile Leu Lys Glu His Pro
                805                 810                 815

Val Glu Asn Thr Gln Leu Gln Asn Glu Lys Leu Tyr Leu Tyr Tyr Leu
            820                 825                 830

Gln Asn Gly Arg Asp Met Tyr Val Asp Gln Glu Leu Asp Ile Asn Arg
        835                 840                 845

Leu Ser Asp Tyr Asp Val Asp Ala Ile Val Pro Gln Ser Phe Leu Lys
    850                 855                 860

Asp Asp Ser Ile Asp Asn Lys Val Leu Thr Arg Ser Asp Lys Asn Arg
865                 870                 875                 880

Gly Lys Ser Asp Asn Val Pro Ser Glu Glu Val Val Lys Lys Met Lys
                885                 890                 895

Asn Tyr Trp Arg Gln Leu Leu Asn Ala Lys Leu Ile Thr Gln Arg Lys
            900                 905                 910

Phe Asp Asn Leu Thr Lys Ala Glu Arg Gly Gly Leu Ser Glu Leu Asp
        915                 920                 925

Lys Ala Gly Phe Ile Lys Arg Gln Leu Val Glu Thr Arg Gln Ile Thr
    930                 935                 940

Lys His Val Ala Gln Ile Leu Asp Ser Arg Met Asn Thr Lys Tyr Asp
945                 950                 955                 960

Glu Asn Asp Lys Leu Ile Arg Glu Val Lys Val Ile Thr Leu Lys Ser
                965                 970                 975

Lys Leu Val Ser Asp Phe Arg Lys Asp Phe Gln Phe Tyr Lys Val Arg
            980                 985                 990

Glu Ile Asn Asn Tyr His His Ala  His Asp Ala Tyr Leu  Asn Ala Val
        995                 1000                 1005

Val Gly  Thr Ala Leu Ile Lys  Lys Tyr Pro Lys Leu  Glu Ser Glu
    1010                 1015                 1020

Phe Val  Tyr Gly Asp Tyr Lys  Val Tyr Asp Val Arg  Lys Met Ile
    1025                 1030                 1035

Ala Lys  Ser Glu Gln Glu Ile  Gly Lys Ala Thr Ala  Lys Tyr Phe
```

```
    1040                1045                1050

Phe Tyr  Ser Asn Ile Met Asn  Phe Phe Lys Thr Glu  Ile Thr Leu
    1055                1060                1065

Ala Asn  Gly Glu Ile Arg Lys  Arg Pro Leu Ile Glu  Thr Asn Gly
    1070                1075                1080

Glu Thr  Gly Glu Ile Val Trp  Asp Lys Gly Arg Asp  Phe Ala Thr
    1085                1090                1095

Val Arg  Lys Val Leu Ser Met  Pro Gln Val Asn Ile  Val Lys Lys
    1100                1105                1110

Thr Glu  Val Gln Thr Gly Gly  Phe Ser Lys Glu Ser  Ile Leu Pro
    1115                1120                1125

Lys Arg  Asn Ser Asp Lys Leu  Ile Ala Arg Lys Lys  Asp Trp Asp
    1130                1135                1140

Pro Lys  Lys Tyr Gly Gly Phe  Asp Ser Pro Thr Val  Ala Tyr Ser
    1145                1150                1155

Val Leu  Val Val Ala Lys Val  Glu Lys Gly Lys Ser  Lys Lys Leu
    1160                1165                1170

Lys Ser  Val Lys Glu Leu Leu  Gly Ile Thr Ile Met  Glu Arg Ser
    1175                1180                1185

Ser Phe  Glu Lys Asn Pro Ile  Asp Phe Leu Glu Ala  Lys Gly Tyr
    1190                1195                1200

Lys Glu  Val Lys Lys Asp Leu  Ile Ile Lys Leu Pro  Lys Tyr Ser
    1205                1210                1215

Leu Phe  Glu Leu Glu Asn Gly  Arg Lys Arg Met Leu  Ala Ser Ala
    1220                1225                1230

Gly Glu  Leu Gln Lys Gly Asn  Glu Leu Ala Leu Pro  Ser Lys Tyr
    1235                1240                1245

Val Asn  Phe Leu Tyr Leu Ala  Ser His Tyr Glu Lys  Leu Lys Gly
    1250                1255                1260

Ser Pro  Glu Asp Asn Glu Gln  Lys Gln Leu Phe Val  Glu Gln His
    1265                1270                1275

Lys His  Tyr Leu Asp Glu Ile  Ile Glu Gln Ile Ser  Glu Phe Ser
    1280                1285                1290

Lys Arg  Val Ile Leu Ala Asp  Ala Asn Leu Asp Lys  Val Leu Ser
    1295                1300                1305

Ala Tyr  Asn Lys His Arg Asp  Lys Pro Ile Arg Glu  Gln Ala Glu
    1310                1315                1320

Asn Ile  Ile His Leu Phe Thr  Leu Thr Asn Leu Gly  Ala Pro Ala
    1325                1330                1335

Ala Phe  Lys Tyr Phe Asp Thr  Thr Ile Asp Arg Lys  Arg Tyr Thr
    1340                1345                1350

Ser Thr  Lys Glu Val Leu Asp  Ala Thr Leu Ile His  Gln Ser Ile
    1355                1360                1365

Thr Gly  Leu Tyr Glu Thr Arg  Ile Asp Leu Ser Gln  Leu Gly Gly
    1370                1375                1380

Asp Lys  Arg Pro Ala Ala Thr  Lys Lys Ala Gly Gln  Ala Lys Lys
    1385                1390                1395

Lys Lys
    1400
```

<210> SEQ ID NO 80
<211> LENGTH: 7
<212> TYPE: RNA
<213> ORGANISM: Artificial

-continued

```
<220> FEATURE:
<223> OTHER INFORMATION: alternative 5' UTR, without promoter sequence

<400> SEQUENCE: 80

ugccaag                                                              7


<210> SEQ ID NO 81
<211> LENGTH: 43
<212> TYPE: RNA
<213> ORGANISM: Artificial
<220> FEATURE:
<223> OTHER INFORMATION: 5' UTR referred to as CYBA without promoter
      sequence

<400> SEQUENCE: 81

ccgcgccuag caguguccca gccggguucg ugucgccgcc acc                     43


<210> SEQ ID NO 82
<211> LENGTH: 6
<212> TYPE: DNA
<213> ORGANISM: Artificial
<220> FEATURE:
<223> OTHER INFORMATION: alternative 5' UTR, without promoter sequence

<400> SEQUENCE: 82

gccacc                                                               6


<210> SEQ ID NO 83
<211> LENGTH: 36
<212> TYPE: RNA
<213> ORGANISM: Artificial
<220> FEATURE:
<223> OTHER INFORMATION: alternative 5' UTR, without promoter sequence

<400> SEQUENCE: 83

ucuucugguc cccacagacu cagagagaac gccacc                             36


<210> SEQ ID NO 84
<211> LENGTH: 6
<212> TYPE: DNA
<213> ORGANISM: Artificial
<220> FEATURE:
<223> OTHER INFORMATION: alternative 5' UTR, without promoter sequence

<400> SEQUENCE: 84

gccaag                                                               6
```

CAS9 MRNAS

CROSS-REFERENCE TO RELATED APPLICATIONS

This application claims priority to U.S. Provisional Patent Application No. 62/357,106, filed Jun. 30, 2016, which is incorporated by reference herein in its entirety.

BACKGROUND OF THE DISCLOSURE

Gene editing technology has emerged as a potentially game changing technology with broad therapeutic applicability across targets and disease states. The Cas9 family of enzymes, including mutants that result in single-stranded breaks or which bind but do not nick nucleic acid, is one of the enzymes being widely investigated for use in CRISPR systems.

One of the challenges to be solved to implement CRISPR-Cas9 technology is how to deliver the protein component (Cas9 family member) and the RNA component(s) (e.g., the sgRNA). The present disclosure addresses, specifically, various compositions and methods for delivering Cas9 activity (alone or in combination with other components of the CRISPR-Cas9 system).

SUMMARY OF THE DISCLOSURE

The present disclosure provides polyribonucleotides and polynucleotides, including modified polyribonucleotides and polynucleotides, in each case encoding Cas9 related proteins. Such polyribonucleotides and polynucleotides include DNA and RNA, such as mRNA, and may be provided in isolated and/or purified form. Moreover, polynucleotides of the disclosure may be provided in the context of a vector, plasmid, or longer polynucleotide, in each case, further comprising other sequences. Similarly, polyribonucleotides of the disclosure may be provided in the context of a longer nucleotide and may further comprise other sequences.

Polyribonucleotides and polynucleotides of the disclosure have numerous uses, including in vitro or ex vivo uses in cells in culture, as well as in vivo uses in subjects.

In one aspect, the disclosure provides a polyribonucleotide comprising a sequence which encodes a Cas9 protein (e.g., a Cas9 coding sequence). Exemplary Cas9 proteins and Cas9 coding sequences are described herein, and can be readily selected for use in the claimed invention. In some embodiments, the polyribonucleotide, optionally modified, is codon optimized and encodes a Cas9 protein, such as a Cas9 protein (or variant) described herein. In some embodiments, the polyribonucleotide is a modified polyribonucleotide comprising a combination of unmodified and modified ribonucleotides. For example, in some embodiments, 30-45% of the uridines in the polyribonucleotide are analogs of uridine and 5-10% of the cytidines in the polyribonucleotide are analogs of cytidine. Other percentages of modified uridines and cytidines are also contemplated, as described herein.

In another aspect, the disclosure provides a modified polyribonucleotide comprising a sequence which encodes a Cas9 protein (as described above and herein), wherein the modified polyribonucleotide contains a combination of unmodified and modified ribonucleotides, wherein the modified polyribonucleotide is made using an input mixture of ribonucleotides, wherein 30-45% of uridines in said input mixture are analogs of uridine and 5-10% of cytidines in said input mixture are analogs of cytidine. Other percentages of modified uridines and cytidines are also contemplated, as described herein.

In some embodiments of any of the foregoing or other aspects and embodiments of the disclosure, the polyribonucleotide or modified polyribonucleotide comprises a primary sequence that is at least 95% identical (e.g., at least 95, 96, 97, 98, 99 or 100% identical) to SEQ ID NO: 1 (e.g., to the sequence set forth in SEQ ID NO 1). In some embodiments, the polyribonucleotide is a modified polyribonucleotide having a level of modification selected from any such level set forth herein.

In some embodiments of any of the foregoing or other aspects and embodiments of the disclosure, the polyribonucleotide or modified polyribonucleotide encodes a Cas9 polypeptide with altered activity relative to wildtype Cas9. In some embodiments, the Cas9 polypeptide is Cas9 D10A.

In some embodiments of any of the foregoing or other aspects and embodiments of the disclosure, the polyribonucleotide or modified polyribonucleotide comprises a primary sequence that is at least 95% identical (e.g., at least 95, 96, 97, 98, 99 or 100% identical) to SEQ ID NO: 2 (e.g., to the sequence set forth in SEQ ID NO 2). In some embodiments, the polyribonucleotide is a modified polyribonucleotide having a level of modification selected from any such level set forth herein.

In another aspect, the disclosure provides a polyribonucleotide or modified polyribonucleotide comprising a primary sequence at least 99% identical (e.g., 99% or 100% identical) to a sequence selected from the group consisting of SEQ ID NOs: 11-18. In certain embodiments such primary sequence comprises or does not comprise a FLAG tag, a HA tag, or a similar epitope tag (e.g., optionally percent identity is determined without including such a tag).

In some embodiment, the polyribonucleotide is a modified polyribonucleotide containing a combination of unmodified and modified ribonucleotides, wherein 5-50% of the uridines are analogs of uridine and 5-50% of the cytidines are analogs of cytidine.

In some embodiments of any of the foregoing or following aspects and embodiments, the polyribonucleotide encoding a Cas9 protein is a modified polyribonucleotide containing a combination of unmodified and modified ribonucleotides, wherein 5-50% of the uridines are analogs of uridine and 5-50% of the cytidines are analogs of cytidine. In some embodiments, 25-45% of uridines are analogs of uridine and 5-20% of cytidines are analogs of cytidine. In some embodiments, 30-40% of uridines are analogs of uridine and 5-10% of cytidines are analogs of cytidine.

In another aspect, the disclosure provides a polyribonucleotide or a modified polyribonucleotide comprising a primary sequence at least 95% identical to SEQ ID NO: 1. In embodiments wherein the polyribonucleotide is a modified polyribonucleotide, the modified polyribonucleotide contains a combination of unmodified and modified ribonucleotides, wherein the modified polyribonucleotide is made using an input mixture of ribonucleotides, wherein 5-50% of uridines in the input mixture are analogs of uridine and 5-50% of cytidines in the input mixture are analogs of cytidine. In other embodiments, 25-45% of uridines in said mixture are analogs of uridine and 5-20% of cytidines in said mixture are analogs of cytidine. In other embodiments, 30-40% of uridines in said mixture are analogs of uridine and 5-10% of cytidines in said mixture are analogs of cytidine.

In some embodiments of any of the foregoing or following aspect and embodiments of the disclosure, the polyribonucleotide or modified polyribonucleotide comprises a primary sequence that is identical to SEQ ID NO: 2.

In some embodiments of any of the foregoing or following aspect and embodiments of the disclosure, the modified polyribonucleotide is codon-optimized for expression in mammalian cells.

In some embodiments of any of the foregoing or following aspect and embodiments of the disclosure, the polyribonucleotide or modified polyribonucleotide further comprises a 3' UTR, a 5' UTR, or a 3' UTR and a 5' UTR, and wherein the UTR(s) may optionally aid(s) in enhancing expression or increasing stability of a Cas9 protein in cells.

In some embodiments of any of the foregoing or following aspect and embodiments of the disclosure, 5' UTR comprises one or more sequences selected from the group consisting of SEQ ID NOs: 75-78, 80-84 and 29, wherein the ribonucleotides of the 5' UTR are positioned upstream (5') of the ribonucleotides encoding the Cas9 protein, such as the ribonucleotides of SEQ ID NOs: 1 or 2, and 3' from ribonucleotides corresponding to a portion of a promoter sequence, for example, directly 3' with less than 40 contiguous nucleotides intervening. In other embodiments, the 5' UTR are directly 3' from ribonucleotides corresponding to a portion of the promoter without any intervening nucleotides.

In some embodiments of any of the foregoing or following aspect and embodiments of the disclosure, the 5' UTR and the portion of a promoter together comprise or consist essentially of SEQ ID NO: 7, SEQ ID NO: 8, SEQ ID NO: 9, or SEQ ID NO: 10.

In some embodiments of any of the foregoing or following aspect and embodiments of the disclosure, the 3' UTR comprises one or more copies of a 3' UTR sequence selected from the group consisting of SEQ ID NOs: 30 and 39, wherein the ribonucleotides of the 3' UTR are positioned downstream (3') of the ribonucleotides encoding the Cas9 protein, such as the ribonucleotides of SEQ ID NOs: 1 or 2, for example, directly downstream with less than 40 contiguous nucleotides intervening. In some embodiments, the ribonucleotides of the 3' UTR are positioned directly downstream (3') of the ribonucleotides encoding the Cas9 protein, such as the ribonucleotides of SEQ ID NOs: 1 or 2, for example, with no nucleotides intervening.

In some embodiments of any of the foregoing or following aspect and embodiments of the disclosure, the 3' UTR comprises one copy of SEQ ID NO: 30, two copies of SEQ ID NO: 30, one copy of SEQ ID NO: 39, or two copies of SEQ ID NO: 39.

In some embodiments of any of the foregoing or following aspects and embodiments of the disclosure, the polyribonucleotide or modified polyribonucleotide further comprises a portion of a promoter sequence, wherein the ribonucleotides of the portion of a promoter sequence are positioned upstream (5') of the ribonucleotides of the 5' UTR and/or Cas9 coding sequence(s). In some embodiments, the promoter sequence is selected from the group consisting of SEQ ID NOs: 3-6. In some embodiments, the sequence designated as promoter sequence may not include the final guanosine nucleotide, said guanosine nucleotide being the transcription start site and thus also part of the 5' UTR. In some embodiments, the sequence designated as promoter sequence may not include the single or several nucleotide(s) beginning with and following after the nucleotide that is the transcription start site, said single or several nucleotide(s) thus also being part of the 5' UTR. In some embodiments, the portion of the promoter sequence included in the 5' UTR corresponds to a region transcribed by a DNA-dependent RNA-polymerase.

In another aspect, the disclosure provides a polyribonucleotide comprising a primary polyribonucleotide sequence that is at least 99% or is 100% identical to a sequence selected from any of SEQ ID NO: 11-18, in the presence or absence of polyribonucleotide encoding a FLAG tag, an HA tag or other epitope tag. In some embodiments, the polyribonucleotide further comprises SEQ ID NO: 28.

In some embodiments of any of the foregoing or following aspect and embodiments of the disclosure, the polyribonucleotide further comprises at least one 5' cap structure. In some embodiments of any of the foregoing or following aspect and embodiments of the disclosure, the polyribonucleotide further comprises a polyA tail at the 3' end of the polyribonucleotide, and wherein the polyA tail comprises at least 100 bases.

In some embodiments of any of the foregoing or following aspect and embodiments of the disclosure, the polyribonucleotide is a modified polyribonucleotide, wherein the level of modification, the bases modified, and the potential analog are selected as described herein.

In another aspect, the disclosure provides a polynucleotide comprising a sequence selected from the group consisting of SEQ ID NO: 31-38. In some embodiments, the polynucleotide further comprises SEQ ID NO: 27.

In another aspect, the disclosure provides a vector comprising a polynucleotide encoding a polyribonucleotide encoding Cas9, as described herein, such as a vector comprising a sequence selected from the group consisting of SEQ ID NO: 31-38. Also provided is a host cell comprising the vector and a method of producing polyribonucleotides encoding Cas9 protein.

In another aspect or in some embodiments of any of the foregoing or following, the disclosure provides a polyribonucleotide encoding a polypeptide comprising an amino acid sequence with at least 95% (e.g., at least 95, 96, 97, 98, 99, or 100%) identity to any one of SEQ ID NOs: 19-20. In some embodiments, the polyribonucleotide is codon optimized. In some embodiments, the polyribonucleotide is a modified polyribonucleotide containing a combination of unmodified and modified ribonucleotides, wherein the modified polyribonucleotide is made using an input mixture of ribonucleotides, wherein 30-40% of uridines in said input mixture are analogs of uridine and 5-10% of cytidines in said input mixture are analogs of cytidine. Other percentages of modified ribonucleotides are similarly contemplated and disclosed herein.

In some embodiments of any of the foregoing or following aspects and embodiments of the disclosure, the modified polyribonucleotide is one or more beneficial properties as compared to an unmodified polyribonucleotide having the same primary sequence or compared to some other control or comparator. Exemplary beneficial properties may include increased translational efficiency, enhanced stability, and/or diminished immunogenicity.

In another aspect, the disclosure provides compositions comprising a polynucleotide or polyribonucleotide of the disclosure formulated with one or more pharmaceutically acceptable carriers and/or excipients.

In another aspect, the disclosure provides a composition comprising a polyribonucleotide or modified polyribonucleotide encoding a Cas9 related protein and one or more sgRNAs (single guide RNAs) for targeting a gene of interest, the sgRNA comprising:

a. a first region comprising a guide sequence of 20-25 ribonucleotides (e.g., region with complementarity to a target gene), and b. a second region positioned at the 3' end of the first region. Such a composition may be further formulated with one or more pharmaceutically acceptable carriers and/or excipients.

In another aspect, the disclosure provides a method for cleaving, nicking, or binding to DNA, comprising administering to a subject or contacting cells with the composition of the disclosure, comprising a polyribonucleotide encoding Cas9 related protein and an sgRNA that comprises a sequence complementary to a gene targeted for cleaving, nicking, or binding.

In some embodiments, after administering the composition to a patient, cells of the patient display decreased expression of the gene targeted for cleaving, nicking, or binding.

In some embodiments of any of the foregoing or following aspects or embodiments, the modified polyribonucleotide and sgRNA are formulated in a nanoparticle or nanocapsule. In other embodiments, the modified polyribonucleotide and sgRNA are formulated in a cationic lipid, cationic polymer, or nanoemulsion.

In some embodiments of any of the foregoing or following aspects or embodiments, the first region of the sgRNA comprises a guide sequence complementary to a segment of a gene of interest.

In some embodiments of any of the foregoing or following aspects or embodiments, the second region of the sgRNA comprises a sequence that is greater than or equal to 95% identical to SEQ ID NO: 74. In some embodiments, the second region comprises a sequence identical to SEQ ID NO: 74.

In some embodiments of any of the foregoing or following aspects or embodiments, the sgRNA targets PCSK9. In some embodiments, the sgRNA consists essentially of a sequence selected from the list consisting of SEQ ID NOs: 21-26.

In some embodiments of any of the foregoing or following aspects and embodiments of the disclosure, the modified polyribonucleotide comprises one or more copies of a nuclear localization sequence (NLS), wherein the NLS(s) are selected from the group consisting essentially of SEQ ID NOs: 70-73.

In some embodiments of any of the foregoing or following aspects or embodiments, analogs are selected from amongst the analogs disclosed herein. In some embodiments, uridine analogs are selected from the group consisting of pseudouridine, 2-thiouridine, 5-iodouridine, and 5-methyluridine. In some embodiments, cytidine analogs are selected from the group consisting of 5-methylcytidine, 2'-amino-2'-deoxycytidine, 2'-fluoro-2'-deoxycytidine, and 5-iodocytidine.

In some embodiments of any of the foregoing or following aspects or embodiments, modified polyribonucleotides of the disclosure do not comprise 5-methylcytidine and/or pseudouridine and/or the analogs do not comprise 5-methylcytidine and/or pseudouridine.

In some embodiments of any of the foregoing or following aspects or embodiments, modified polyribonucleotide of the disclosure do not comprise analogs of adenosine and analogs of guanosine.

The disclosure contemplates all combinations of any of the foregoing aspects and embodiments, as well as combinations with any of the embodiments set forth in the detailed description and examples. The disclosure contemplates polynucleotides encoding Cas9 and, in some embodiments, modified polynucleotides encoding Cas9 that comprise or are derived from any one of the sequences corresponding to SEQ ID NOs: 1-18, 27-39, 46-78, and 80, as well as polyribonucleotide and modified polyribonucleotide sequences encoding all amino acid sequences listed herein (SEQ ID NOs: 19-20 and 79).

BRIEF DESCRIPTION OF THE DRAWINGS

FIG. 3A shows Insertion/Deletion (Indel) analysis of the PCSK9 genomic locus after HepG2 cells were transfected with modified polyribonucleotides encoding Cas9 and (i) either one of two sgRNAs with PCSK9 complementarity or (ii) no sgRNA. FIG. 3B shows densitometry measurements of the Indel analysis gel from FIG. 3A.

FIG. 4A shows Insertion/Deletion (Indel) analysis of the PCSK9 genomic locus after AML12 cells were transfected with modified polyribonucleotides encoding Cas9 and (i) either one of two sgRNAs with PCSK9 complementarity or (ii) no sgRNA. FIG. 4B shows densitometry measurements of the Indel analysis gel from FIG. 4A.

FIG. 5A shows a graph of eGFP fluorescence signal detected in eGFP-expressing HepG2 cells by flow cytometry 24 hours after co-transfection with modified polyribonucleotides encoding either (i) wildtype Cas9 or (ii) D10A Cas9 in combination with various sgRNAs with complementarity to the eGFP locus. FIG. 5B shows an image of eGFP positive HepG2 cells.

FIG. 7 shows a Western blot against Cas9 (top) and HSP90 (control, bottom) run on a Wet-Blot 3-8% Tris-Acetate gel. Lysates were obtained from HEK293 cells transfected with Cas9-encoding modified polyribonucleotides comprising several different 5' UTR sequences. The Min pVax lane corresponds to samples transfected with modified polyribonucleotide comprising the 5p-UTR (015-T05), the minimal lane corresponds to samples transfected with modified polyribonucleotide comprising the minimal UTR (015-T06), the haGlobin lane corresponds to samples transfected with modified polyribonucleotide comprising the hAg UTR (015-T07), the TEE lane corresponds to samples transfected with modified polyribonucleotide comprising the TISU+T UTR (015-T08), and the TriLink lane corresponds to samples transfected with COMP polyribonucleotide. The eGFP lane corresponds to samples transfected with eGFP-expressing polyribonucleotide. The Untr. lane corresponds to samples that were not transfected with polyribonucleotide.

DETAILED DESCRIPTION OF THE DISCLOSURE

Overview

Figure 1:
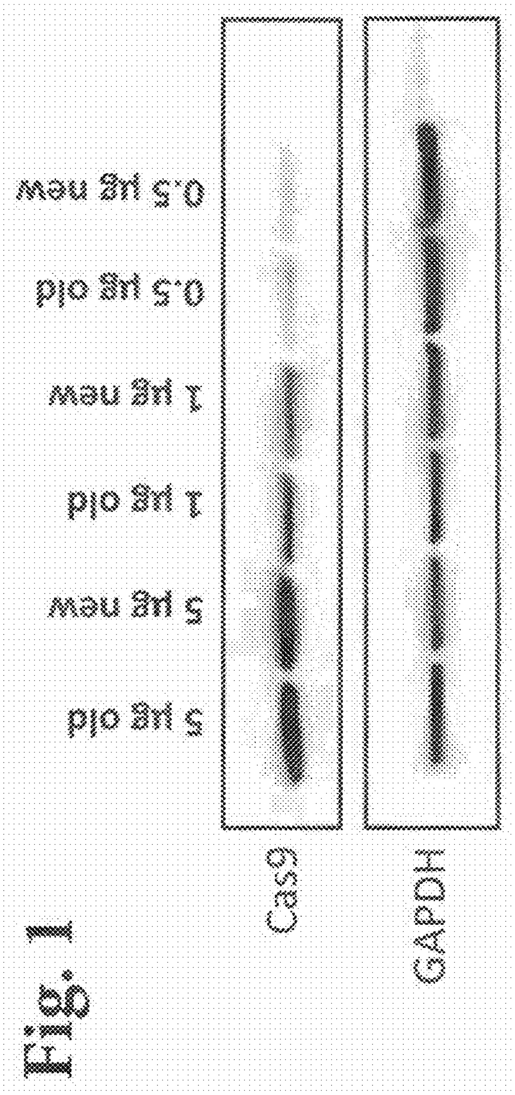
FIG. 1 shows a Western blot against Cas9 protein (top), and GAPDH (control, bottom) obtained from cells transfected with varying amounts of one of two batches of modified polyribonucleotides encoding Cas9.

In recent years, CRISPR (Clustered Regularly Interspaced Short Palindromic Repeats) systems were discovered in bacteria and archaea (Barrangou, R., et al. (2007). Science, 315, 1709-1712). CRISPR systems function as bacterial/archaeal adaptive immune systems that target and cleave foreign DNA in a sequence-specific manner. A bacterial cell under attack from a phage or plasmid first integrates a portion of the invading DNA into the CRISPR loci of the bacterial genome, which contains multiple such portions of foreign DNA separated by repeat DNA. The CRISPR locus is transcribed into CRISPR RNA (crRNA). Three types of CRISPR systems have been identified (K. S. Makarova et al., Nat. Rev. Microbiol. 9, 467 (2011)). In the most studied type II system, a trans-activating CRISPR RNA (trRNA) is transcribed that base-pairs with the repeat sequences of the crRNA (Jinek, M., et al. (2012) Science, 337, 816-821). CRISPR-associated (Cas) protein 9 (Cas9) is an endonuclease that binds to the crRNA and trRNA, cleaving the crRNA to produce a mature crRNA with a single foreign sequence portion and repeat sequence annealed to the trRNA. Cas9, in complex with the mature crRNA and trRNA, recognizes and cleaves sequences complementary to the crRNA (Jinek, M., et al. (2012) Science, 337, 816-821). Researchers have determined that the Cas9:crRNA:trRNA complex is sufficient to recognize and cleave target DNA sequences, and that a single guide RNA (sgRNA), comprising both crRNA and trRNA, can function to direct Cas9 binding and activity (Jinek, M., et al. (2012) Science, 337, 816-821).

Using Cas9 and an appropriate sgRNA, double-stranded breaks can be introduced into the genome in a site-specific manner. The double-stranded breaks Cas9 introduces can be repaired by non-homologous end joining, producing insertions and deletions that disrupt expression of the cleaved gene, or by homologous recombination which, if provided with a donor DNA with homology to the cleaved site, can introduce desired replacement sequences at the cleaved site (Gong, C., et al. (2005) Nat. Struct. Mol. Biol. 12, 304-312; Hsu P D. et al. Cell. 2014; 157: 1262-1278; Merkert S, Martin U. Stem Cell Research. 2016; 16: 377-386). Cong et al. developed a mutant form of Cas9, D10A Cas9, that nicks target DNA sequences instead of cleaving them, promoting homology-based repair, and also demonstrated that transforming cells with multiple sgRNAs could target multiple genomic loci with Cas9 simultaneously (Cong L., et al. (2013) Science, 339, 819-823). Paired complexes of Cas9D10A have also been developed that further improve the specificity of Cas9 targeting (Ran, F. A., et al. (2013) Cell, 154, 1380-1389). Other Cas9 variant polypeptides have also been developed, for example, H841A D10A Cas9 (dCas9), which lacks nuclease activity but retains site-specific DNA binding activity, and have been shown to be useful for targeting fused effector domains to specific sites in the genome (Maeder, Morgan L et al. Nature methods 10.10 (2013): 977-979.

Several groups have attempted to use CRISPR/Cas9 for gene therapy and other therapeutic goals in human patients and animal models of disease (See, e.g., Nguyen, T. H., Anegon, Ignacio. EMBO Molecular Medicine (2016) 8, 439-441). Such efforts revealed that use of CRISPR/Cas9 systems for therapeutic goals may be limited by the available delivery methods and the disadvantages associated with said methods (Maresch, Roman et al. Nature Communications 7 (2016): 10770.

The present disclosure provides polyribonucleotides, polynucleotides and compositions that are useful for improving delivery of Cas9 activity. In some embodiments, these may be combined with sgRNAs and applied in vitro, ex vivo or in vivo to target a Cas9 related protein to a specific site for any of a number of research, cell based, animal or human applications, including therapeutic applications.

Before continuing to describe the present disclosure in further detail, it is to be understood that this disclosure is not limited to specific compositions or process steps, as such may vary. It must be noted that, as used in this specification and the appended claims, the singular form “a”, “an” and “the” include plural referents unless the context clearly dictates otherwise.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

As used herein, the term “polynucleotide” is generally used to refer to a nucleic acid (e.g., DNA or RNA). When RNA, such as mRNA, is specifically being referred to, the term polyribonucleotide may be used. The terms polynucleotide, polyribonucleotide, nucleic acid, ribo nucleic acid, DNA, RNA, mRNA, and the like include such molecules that may be comprised of standard or unmodified residues; nonstandard or modified residues (e.g., analogs); and mixtures of standard and nonstandard (e.g., analogs) residues. In certain embodiments a polynucleotide or a polyribonucleotide is a modified polynucleotide or a polyribonucleotide For purposes of determining percentage identity of a first sequence relative to a second sequence, an analog (e.g., methylcytidine) matches cytidine, etc. In certain embodiments, the term “primary sequence” may be used to refer to a polynucleotide sequence without regard to whether or the level of modification, such that a primary sequence identical to CUCUCUA would include that sequence regardless of whether any or all of the recited nucleotides are modified (e.g., analogs of any more or more of C, U and A may be present and would be considered the same primary sequence).

Polynucleotides and polyribonucleotides of the disclosure refer, unless context indicates otherwise, to polynucleotides or polyribonucleotides encoding a Cas9 protein family member (e.g., a Cas9 related protein, as described herein). Such polynucleotides and polyribonucleotides comprising a Cas9 coding sequence may optionally comprise other nucleotide sequences, as described herein.

Polyribonucleotides

The present disclosure provides polyribonucleic acid molecules, preferably modified polyribonucleic acid molecules, which encode a protein of the Cas protein family, preferably a Cas9-related protein, including a wildtype Cas9 or a Cas9 protein having one or more substitutions, such as substitutions or mutations that alter its nucleic acid nicking activity. The terms nucleic acid and polynucleotide are used interchangeably and include any compound and/or substance that comprises a polymer of nucleotides. The term nucleotide includes deoxynucleotides and ribonucleotides. The terms ribonucleic acid and polyribonucleotide are used interchangeably and, in certain embodiments, include any compound and/or substance that comprises a polymer of nucleotides wherein greater than 50% of the nucleotides are ribonucleotides. In certain embodiments, polyribonucletodies comprise a polymer of nucleotides wherein greater than 60%, 70%, 75%, 80%, 90%, greater than 95%, greater than 99% or 100% of the nucleotides are ribonucleotides. Polyribonucleotides wherein one or more nucleotides are modified nucleotides may be referred to as modified polyribonucleotides. However, the term polyribonucleotides may include modified polyribonucleotides.

The present disclosure also contemplates polyribonucleotides that may comprise one, several, or all of the features disclosed in the various embodiments herein. The present disclosure contemplates polyribonucleotides that may comprise one or more untranslated regions (UTRs) as disclosed herein. The present disclosure contemplates polyribonucleotides that encode Cas family proteins, such as Cas9 or Cas9-related proteins. The present disclosure contemplates polyribonucleotides comprising Cas9 coding sequences. The present disclosure contemplates polyribonucleotides comprising one or more analogs of the canonical nucleotides (i.e. analogs of cytidine, uridine, adenosine, and/or guanosine; modified nucleotides), naturally or non-naturally occurring; such polyribonucleotides contain a mixture of modified and unmodified nucleotides. The present disclosure contemplates polyribonucleotides wherein 30-45% of the uridines are analogs of uridine and 5-10% of the cytidines are analogs of cytidine. The present disclosure contemplates compositions of polyribonucleotides with or without one or more single guide RNAs (sgRNAs), and methods of formulating and using said compositions. In certain embodiments, such as several of those contemplated in the Exemplification, treating a cell or cells with a modified polyribonucleotide encoding Cas9 and a sgRNA targeting a gene results in a decrease in expression of the targeted gene.

Polyribonucleotides and polynucleotides described herein that may encode a Cas9 related protein, alone or together with additional sequence, may be referred to as polynucleotides or polyribonucleotides of the disclosure. In certain embodiments, polyribonucleotides described herein may comprise Cas9 or Cas9-related coding sequences. In certain embodiments, polyribonucleotides described herein may comprise fragments of Cas9 coding sequences. In certain embodiments, polyribonucleotides described herein may encode truncated variants of Cas9 polypeptides.

The sequence of the polyribonucleotides can be derived from, for example, any suitable nucleic acid that comprises the genetic information of a gene of interest. Examples of nucleic acids include genomic DNA, RNA, or cDNA from any bacterial or archaeal cell comprising the Cas family of genes or a Cas9-encoding gene. The polynucleotides can be derived from nucleic acids carrying mutated genes and polymorphisms. A polyribonucleotide of the present disclosure comprises a sequence encoding a Cas protein (e.g., a coding sequence). In certain embodiments, the sequence (e.g., DNA sequence and/or RNA sequence) is a codon optimized sequence, such as a codon optimized sequence to facilitate expression in a mammalian system. The polyribonucleotide may further comprise an untranslated sequence positioned upstream (5') of the Cas9-related protein encoding region's start codon, an untranslated sequence positioned downstream (3') of the Cas9-related protein encoding region's stop codon, or both an untranslated sequence positioned upstream (5') of the Cas9-related protein encoding region's start codon and an untranslated sequence positioned downstream (3') of the Cas9-related protein encoding region's stop codon. For each polyribonucleotide (RNA) sequence listed in the present disclosure, the corresponding polydeoxyribonucleotide (DNA) sequence is contemplated and vice versa. In a preferred embodiment, a polyribonucleotide of the present disclosure may be a modified polyribonucleotide.

Modified Ribonucleotides

In addition to the four classical ribonucleotides, namely, adenosine, guanosine, cytidine and uridine, there exist numerous analogs of each of these nucleobases. Sometimes throughout and in the literature, these analogs, or polyribonucleotides that include one or more of these analogs, are referred to as modified (e.g., modified nucleotides or modified ribonucleotides). Some analogs differ from the above canonical nucleobases, but yet can exist in nature. Other analogs are non-naturally occurring. Either type of analog is contemplated.

In certain embodiments, polyribonucleotides of the disclosure comprise nucleotide analogs (e.g., the polyribonucleotide comprises a modified polyribonucleotide). Exemplary nucleotide analogs are provided below (e.g., analogs of U; analogs of C; analogs of A; analogs of G). In addition, in certain embodiments, a polyribonucleotide or other nucleic acid of the disclosure may also comprise (in addition to or alternatively) modifications in the phosphodiester backbone or in the linkage between nucleobases. Exemplary nucleic acids that can form part or all of a polyribonucleotide of the disclosure include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a beta-D-ribo configuration, alpha-LNA having an alpha-L-ribo configuration (a diastereomer of LNA), 2'-amino-LNA having a 2'-amino functionalization, and 2'-amino-alpha-LNA having a 2'-amino functionalization) or hybrids thereof. In certain embodiments, a modification may be on one or more nucleoside(s) or the backbone of thepolynucleotide molecule. In certain embodiments, a modification may be on both a nucleoside and a backbone linkage. In certain embodiments, a modification may be engineered into a polynucleotide in vitro. In certain embodiments, a modified nucleotide may also be synthesized post-transcriptionally by covalent modification of the natural nucleotides.

A polyribonucleotide of the disclosure can be a modified polyribonucleotide and, in certain embodiments, can comprise analogs of purines and/or analogs of pyrimidines. In certain embodiments, a modified polyribonucleotide of the disclosure comprises a pyrimidine analog, such as an analog of uridine and/or an analog of cytidine. In certain embodiments, a modified polyribonucleotide of the disclosure comprises an analog of uridine and an analog of cytidine. In certain embodiments, the modified polyribonucleotide does not comprise analogs of adenosine and/or analogs of guanosine. In certain embodiments, the polyribonucleotide comprises a single type of analog of uridine and a single type of analog of cytidine (e.g., one type of analog, not a single molecule of analog—the single analog may be present at any of several percentages described herein). In other embodiments, the polyribonucleotide comprises more than one type of analog of uridine and/or cytidine and, optionally and if present, one or more analogs of adenosine and/or guanosine (or none of either or both).

In some cases a modified uridine (e.g., analog of uridine) is selected from 2-thiouridine, 5'-methyluridine, pseudouridine, 5-iodouridine (15U), 4-thiouridine (S4U), 5-bromouridine (Br5U), 2'-methyl-2'-deoxyuridine (U2'm), 2'-amino-2'-deoxyuridine (U2'$NH_2$), 2'-azido-2'-deoxyuridine (U2'$N_3$), and 2'-fluoro-2'-deoxyuridine (U2'F). In some cases, a modified cytidine (e.g., analog of cytidine) is selected from 5-methylcytidine, 3-methylcytidine, 2-thiocytidine, 2'-methyl-2'-deoxycytidine (C2'm), 2'-amino-2'-deoxycytidine (C2'NH2), 2'-fluoro-2'-deoxycytidine (C2'F), 5-iodocytidine (I5C), 5-bromocytidine (Br5C) and 2'-azido-2'-deoxycytidine (C2'N3). Note that when referring to analogs, the foregoing also refers to analogs in their 5' triphosphate form. In certain embodiments, the cytidine analog is 5-iodocytidine and the uridine analog is 5-iodouridine.

In some embodiments, the polyribonucleotide is a modified polyribonucleotide. In some cases, the modified polyribonucleotide is at least 25% more stable as compared to a non-modified (or unmodified) polyribonucleotide. In some cases, the modified polyribonucleotide can be at least 30% more stable, at least 35% more stable, at least 40% more stable, at least 45% more stable, at least 50% more stable, at least 55% more stable, at least 60% more stable, at least 65% more stable, at least 70% more stable, at least 75% more stable, at least 80% more stable, at least 85% more stable, at least 90% more stable, or at least 95% more stable as compared to a non-modified polyribonucleotide. In certain embodiments, stability is measured in vivo. In certain embodiments, stability is measured in vitro. In certain embodiments, stability is quantified by measuring the half-life of the polyribonucleotide.

A polyribonucleotide of the disclosure can have nucleotides that have been modified in the same form or else a mixture of different modified nucleotides. The modified nucleotides can have modifications that are naturally or not naturally occurring in messenger RNA. A mixture of various modified nucleotides can be used. For example one or more modified nucleotides within a polyribonucleotide can have natural modifications, while another part has modifications that are not naturally found in mRNA. Additionally, some modified nucleotides can have a base modification, while other modified nucleotides have a sugar modification. In the same way, it is possible that all modifications are base modifications or all modifications are sugar modifications or any suitable mixture thereof. In some cases, the stability of the modified polyribonucleotide can be selectively optimized by changing the nature of modified bases within the modified polyribonucleotide.

Non-limiting examples of analogs of U are shown in TABLE 1.

TABLE 1

| Name | Base modification (5'-position) | Sugar modification (2'-position) | Naturally in mRNA |
|---|---|---|---|
| 5-methyluridine (m5U) | $CH_3$ | — | No |
| 5-iodouridine (I5U) | I | — | No |
| 5-bromouridine (Br5U) | Br | — | No |
| 2-thiouridine (S2U) | S (in 2 position) | — | No |
| 4-thiouridine (S4U) | S (in 4 position) | — | No |
| 2'-methyl-2'-deoxyuridine (U2'm) | — | $CH_3$ | Yes |
| 2'-amino-2'-deoxyuridine (U2'NH2) | — | $NH_2$ | No |
| 2'-azido-2'-deoxyuridine (U2'N3) | — | $N_3$ | No |
| 2'-fluoro-2'-deoxyuridine (U2'F) | — | F | No |

Non-limiting examples of analogs of C are shown in TABLE 2.

TABLE 2

| Name | Base modification (5'-position) | Sugar modification (2'-position) | Naturally in mRNA |
|---|---|---|---|
| 5-methylcytidine (m5C) | $CH_3$ | — | Yes |
| 5-iodocytidine (I5C) | I | — | No |
| 5-bromocytidine (Br5C) | Br | — | No |
| 2-thiocytidine (S2C) | S (in 2 position) | — | No |
| 2'-methyl-2'-deoxycytidine (C2'm) | — | $CH_3$ | Yes |
| 2'-amino-2'-deoxycytidine (C2'NH2) | — | $NH_2$ | No |
| 2'-azido-2'-deoxycytidine (C2'N3) | — | $N_3$ | No |
| 2'-fluoro-2'-deoxycytidine (C2'F) | — | F | No |

Non-limiting examples of analogs of A are shown in TABLE 3.

TABLE 3

| Name | Base modification (5'-position) | Sugar modification (2'-position) | Naturally in mRNA |
|---|---|---|---|
| N6-methyladenosine (m6A) | $CH_3$ (in 6 position) | — | Yes |
| N1-methyladenosine (m1A) | $CH_3$ (in 1 position) | — | No |
| 2'-0-methyladenosine (A2'm) | — | $CH_3$ | Yes |
| 2'-amino-2'-deoxyadenosine (A2'NH2) | — | $NH_2$ | No |
| 2'-azido-2'-deoxyadenosine (A2'N3) | — | $N_3$ | No |
| 2'-fluoro-2'-deoxyadenosine (A2'F) | — | F | No |

Non-limiting examples of analogs of G are shown in TABLE 4.

TABLE 4

| Name | Base modification (5'-position) | Sugar modification (2'-position) | Naturally in mRNA |
|---|---|---|---|
| N1-methylguanosine (m1G) | $CH_3$ (in position 1) | | No |
| 2'-0-methylguanosine (G2'm) | — | $CH_3$ | Yes |

TABLE 4-continued

| Name | Base modification (5'-position) | Sugar modification (2'-position) | Naturally in mRNA |
|---|---|---|---|
| 2'-amino-3'-deoxyguanosine (G2'NH2) | — | $NH_2$ | No |
| 2'-azido-2'-deoxyguanosine (G2'N3) | — | $N_3$ | No |
| 2'-fluoro-2'-deoxyguanosine (G2'F) | — | F | No |

In certain embodiments, an analog (e.g., a modified nucleotide) can be selected from the group comprising pyridin-4-one ribonucleoside, 5-iodouridine, 5-iodocytidine, 5-aza-uridine, 2'-amino-2'-deoxycytidine, 2'-fluor-2'-deoxycytidine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formyl cytidine, 5-methylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl)adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-ethyl-guanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In certain embodiments, a modified polyribonucleotide of the disclosure does not include pseudouridine. In certain embodiments, a modified polyribonucleotide of the disclosure does not include 5-methyl cytidine. In certain embodiments, a modified polyribonucleotide of the disclosure does not include 5-methyl uridine. In certain embodiments, a modified polyribonucleotide of the disclosure comprises analogs of U and analogs of C, wherein such analogs of U may all be the same analog or may be different analogs (e.g., more than one type of analog), and wherein such analogs of C may all be the same analog or may be different analogs (e.g., more than one type of analog). In certain embodiments, a modified polyribonucleotide of the disclosure does not include analogs of adenosine and analogs of guanosine.

As described in detail herein, when a polyribonucleotide comprises a modified polyribonucleotide, analogs may be present as a certain proportion of the nucleotides in the compound (e.g., a given percentage of a given nucleobase may be analog, as described herein).

Modified Polyribonucleotides

A polyribonucleotide that comprises at least one modified nucleotide is a modified polyribonucleotide. In certain embodiments, at least about 5% of the modified polyribonucleotide includes analogs of (e.g., modified, or non-natural) adenosine, cytidine, guanosine, or uridine, such as the analog nucleotides described herein. In some cases, at least about 5%, 10%, 15%, 20%, 25%, 30%, 40%, 45%, 50% of the modified polyribonucleotide includes analogs of adenosine, cytidine, guanosine, or uridine. In some cases, at most about 50%, 45%, 40%, 35%, 30%, 25%, 20%, 15%, 10%, 5%, of the modified polyribonucleotide includes non-naturally occurring adenosine, cytidine, guanosine, or uridine.

In certain embodiments a modified polyribonucleotide of the present disclosure contains a combination of modified and unmodified nucleotides. Preferably, a modified polyribonucleotide molecule of the present disclosure contains a combination of modified and unmodified nucleotides as described in US 2012/0195936 A1, hereby incorporated by reference in its entirety. Such modified polyribonucleotide molecules are also known and commercialized as "SNIM®-RNA". The RNA molecule described in US 2012/0195936 A1 is reported to show an increased stability and diminished immunogenicity. In certain embodiments, in such a modified polyribonucleotide molecule, 5 to 50% of the cytidines are analogs of C and 5 to 50% of the uridines are analogs of U. In certain embodiments, in such a modified polyribonucleotide molecule 5 to 40% of the cytidines are analogs of C and 5 to 40% of the uridines are analogs of U. In certain embodiments, in such a modified polyribonucleotide molecule 5 to 30% of the cytidines are analogs of C and 5 to 30% of the uridines are analogs of U. In certain embodiments, in such a modified polyribonucleotide molecule 10 to 30% of the cytidines are analogs of C and 10 to 30% of the uridines are analogs of U. In certain embodiments, in such a modified polyribonucleotide molecule 5 to 20% of the cytidines are analogs of C and 5 to 20% of the uridines are analogs of U. In certain embodiments, in such a modified polyribonucleotide molecule 5 to 10% of the cytidine nucleotides and 5 to 10% of the uridine nucleotides are modified. In certain embodiments, in such a modified polyribonucleotide molecule 25% of the cytidine nucleotides and 25% of the uridine nucleotides are modified. In certain embodiments, the adenosine- and guanosine-containing nucleotides can be unmodified. In certain embodiments, the adenosine and guanosine nucleotides can be unmodified or partially modified, and they are preferably present in unmodified form.

As noted above, in certain embodiments, analogs of U refers to a single type of analog of U. In certain embodiments, analogs of U refers to two or more types of analogs of U. In certain embodiments, analogs of C refers to a single type of analog of C. In certain embodiments, analogs of C refers to two or more types of analogs of C.

In certain embodiments, the percentage of cytidines in a polyribonucleotide that are analogs of cytidine is not the same as the percentage of uridines in the polyribonucleotide that are analogs of uridine. In certain embodiments, the percentage of analogs of cytidine is lower than the percentage of analogs of uridine. As noted above, this may be in the presence or the absence of analogs of adenosine and guanosine but, in certain embodiments, is in the absence of analogs of adenosine and analogs of guanosine. In certain embodiments, polyribonucleotides of the disclosure comprises less than 15%, less than 10%, less than 5% or less than 2% analogs of adenosine, analogs of guanosine or both.

In certain embodiments, a polyribonucleotide of the disclosure comprises analogs of cytidine and analogs of uridine, and 5 to 20% of the cytidines are analogs of cytidine and 25 to 45% of the uridines are analogs of uridine. In other words, the polyribonucleotide comprises modified and unmodified cytidines and modified and unmodified uridines, and 5 to 20% of the cytidines comprise analogs of cytidine while 25 to 45% of the uridines comprise analogs of uridine. In other embodiments, the polyribonucleotide comprises 5 to 10% analogs of cytidine and 30 to 40% analogs of uridine, such as 7-9% analogs of cytidine, such as about 7, 7.5 or 8% and, such as 32-38% analogs of uridine, such as about 33, 34, 35, 36%.

In certain embodiments, any of the analogs of uridine and analogs of cytidine described herein may be used, optionally excluding pseudouridine. In certain embodiments, the analog of cytidine comprises or consists of (e.g., in the case of consists of, it is the single analog type used) 5-iodocytidine and the analog of uridine comprises or consists of (e.g., in the case of consists of, it is the single analog type used) 5-iodouridine.

In certain embodiments of any of the foregoing, the percentage of analogs of a given nucleotide refers to input percentage (e.g., the percentage of analogs in a starting reaction, such as a starting in vitro transcription reaction). In certain embodiments of any of the foregoing, the percentage of analogs of a given nucleotide refers to output (e.g., the percentage in a synthesized or transcribed compound).

The polyribonucleotide molecules of the present disclosure may be produced recombinantly in in vivo systems by methods known to a person skilled in the art. Alternatively, the modified polyribonucleotide molecules of the present disclosure may be produced in an in vitro system using, for example, an in vitro transcription system. In vitro transcription systems are commonly known and usually require a purified linear DNA template containing a DNA sequence "encoding" the RNA molecule wherein said DNA sequence is under the control of an appropriate promoter. Moreover, an in vitro transcription system also commonly requires ribonucleoside triphosphates, a buffer system that includes DTT and magnesium ions, and an appropriate RNA polymerase which provides the enzymatic activity for the in vitro transcription of the DNA sequence into a corresponding RNA molecule of the present disclosure.

An in vitro transcription system capable of producing polyribonucleotides requires an input mixture of modified and unmodified nucleoside triphosphates to produce modified polyribonucleotides with the desired properties of the present disclosure. In certain embodiments, 5 to 50% of the cytidines are analogs of cytidine in such an input mixture and 5 to 50% of the uridines are analogs of uridine in such an input mixture. In certain embodiments, 5 to 40% of the cytidines are analogs of cytidine in such an input mixture and 5 to 40% of the uridines are analogs of uridine in such an input mixture. In certain embodiments, 5 to 30% of the cytidines are analogs of cytidine in such a mixture and 5 to 30% of the uridines are analogs of uridine in such an input mixture. In certain embodiments, 5 to 30% of the cytidines are analogs of cytidine in such mixture and 10 to 30% of the uridines are analogs of uridine in such mixture. In certain embodiments, 5 to 20% of the cytidines are analogs of cytidine in such an input mixture and 5 to 20% of the uridines are analogs of uridine in such an input mixture. In certain embodiments, 5 to 10% of the cytidines are analogs of cytidine in such an input mixture and 5 to 10% of the uridines are analogs of uridine in such an input mixture. In certain embodiments, 25% of the cytidines are analogs of cytidine in such an input mixture and 25% of the uridines are analogs of uridine in such an input mixture. In certain embodiments, the input mixture does not comprise analogs of adenosine and/or guanosine. In other embodiments, optionally, the input mixture comprises one or more analogs of adenosine and/or guanosine (or none of either or both).

In certain embodiments, the percentage of cytidines in an input mixture that are analogs of cytidine is not the same as the percentage of uridines in an input mixture that are analogs of uridine. In certain embodiments, the percentage of analogs of cytidine in an input mixture is lower than the percentage of analogs of uridine in an input mixture. As noted above, this may be in the presence or the absence of analogs of adenosine and guanosine in the input mixture but, in certain embodiments, is in the absence of analogs of adenosine and analogs of guanosine in the input mixture.

In certain embodiments, an input mixture of nucleotides for an in vitro transcription system that produces a polyribonucleotide of the disclosure comprises analogs of cytidine and analogs of uridine, and 5 to 20% of the cytidines of the input mixture are analogs of cytidine and and 25 to 45% of the uridines of the input mixture are analogs of uridine. In other words, the input mixture comprises modified and unmodified cytidines and modified and unmodified uridines, and 5 to 20% of the cytidines of the input mixture comprise analogs of cytidine while 25 to 45% of the uridines of the input mixture comprise analogs of uridine. In other embodiments, the input mixture comprises 5 to 10% analogs of cytidine and 30 to 40% analogs of uridine, such as 7-9% analogs of cytidine, such as 7, 7.5 or 8% and, such as 32-38% analogs of uridine, such as 33, 34, 35, 36%.

In certain embodiments, any of the analogs of uridine and analogs of cytidine described herein may be used, optionally excluding pseudouridine. In certain embodiments, the analog of cytidine comprises or consists of (e.g., it is the single C analog type used) 5-iodocytidine and the analog of uridine comprises or consists of (e.g., it is the single U analog type used) 5-iodouridine.

Exemplary analogs are described in the tables above. It should be understood that for modified polyribonucleotides encoding Cas9, the analogs and level of modification is, unless indicated otherwise, considered across the entire polyribonucleotide encoding Cas9, including 5' and 3' untranslated regions (e.g., the level of modification is based on input ratios of analogs in an in vitro transcription reaction such that analogs may be incorporated at positions that are transcribed).

The modified polyribonucleotide molecules may be chemically synthesized, for example by conventional chemical synthesis on an automated nucleotide sequence synthesizer using a solid-phase support and standard techniques.

Translation efficiency is the rate at which a polyribonucleotide is translated into polypeptides or proteins within cells.

The translation efficiency of a given polyribonucleotide can be measured as the number of proteins or polypeptides which are translated per polyribonucleotde per unit time. Translation is the process in which cellular ribosomes create proteins by translating the coding region of a polyribonucleotide into the specific primary amino acid sequence of a protein; translation is well-known to those skilled in the art.

In certain embodiments, the translation efficiency of a modified polyribonucleotide molecule of the present disclosure is higher in comparison to a translation efficiency of an unmodified polyribonucleotide molecule of the same primary sequence that does not comprise nucleotide analogs (i.e. modified nucleotides). Accordingly, the number of Cas proteins or polypeptides translated from the Cas gene of a modified polyribonucleotide per modified polyribonucleotide per time unit may be higher than the number of Cas proteins or polypeptides translated from the Cas gene of the unmodified polyribonucleotide molecule of the same primary sequence that does not comprise nucleotide analogs (i.e. modified nucleotides) per polyribonucleotide per time unit. In other words, in certain embodiments, a modified polyribonucleotide of the present disclosure may be translated more efficiently in the cells of a subject as compared to the unmodified polyribonucleotide molecule of the same primary sequence that does not comprise nucleotide analogs (i.e. modified nucleotides).

In other embodiments, the translation efficiency is the same or substantially the same. This may be cell-type specific. Nevertheless, other differences may be apparent, such as decreased immunogenicity for modified polyribonucleotides, improved stability, increased half-life, and the like.

The translation efficiency can be determined by methods known in the art and as outlined in the following. Translation efficiency, in the context of the present disclosure, is the rate at which a polyribonucleotide is translated into protein within a cell at a given time point in relation to the amount of polyribonucleotide encoding said protein in said cell at the same time point. Thus, the translation efficiency is equal to the quantity of polyribonucleotide being translated into a protein within a cell at a given time point divided by the total quantity of polyribonucleotide encoding said protein within said cell at said time point. Both parameters, i.e., the quantity of polyribonucleotide being translated into a protein as well as the total quantity of polyribonucleotide encoding said protein, can be determined by methods known in the art. As a non-limiting example, the quantity of polyribonucleotide translated into a protein within a cell can be determined by flow cytometry while the total quantity of polyribonucleotide encoding said protein can be measured by qPCR.

The stability of an mRNA is a measure of how long it exists in a cell before being degraded. mRNA is degraded in vivo by a number of pathways known in the art. The stability of an mRNA can be measured as the half-life of the mRNA. An mRNA half-life is the time required for the quantity of that mRNA present in a sample or (a) cell(s) to reduce by half.

In certain embodiments, modified polyribonucleotide molecules of the present disclosure have enhanced stability in cells of a subject as compared to unmodified polyribonucleotide molecules of the same primary sequence that do not comprise nucleotide analogs (i.e. modified nucleotides). Accordingly, the half-life of a modified polyribonucleotide of the present disclosure is preferably longer (i.e. a greater time period) than the half-life of unmodified polyribonucleotide molecules of the same primary sequence that do not comprise nucleotide analogs (i.e. modified nucleotides). In certain embodiments, enhanced stability may be difficult to observe in cells in culture and may only become apparent in vivo. In other embodiments, stability is the same or substantially the same.

Untranslated Regions

A polyribonucleotide or a modified polyribonucleotide of the disclosure can comprise one or more untranslated regions. Similar to as described above, sequence in one or both untranslated regions may be optionally modified and, if modified, may be modified at the same percentages and for the same residues as described above, all of which is equally applicable here. An untranslated region can comprise any number of modified or unmodified nucleotides. Untranslated regions (UTRs) of a gene are transcribed but not translated into a polypeptide.

In some cases, a UTR can enhance expression of an associated gene and thus the expression of the protein that gene encodes. In a modified polyribonucleotide of the present disclosure, a UTR can enhance expression of a Cas protein or Cas9 protein, such as any of the Cas9 related proteins described herein. “Enhance expression” may include one or both of the following effects: increase the stability of the nucleic acid molecule, and increase the efficiency of translation. A UTR can also comprise sequences that ensure controlled down-regulation of the associated transcript in case the polyribonucleotide molecules are misdirected to undesired organs or sites.

UTRs are positioned upstream (5') of the start codon of a modified polyribonucleotide of the disclosure and/or downstream (3') of the stop codon of a modified polyribonucleotide of the disclosure. UTRs are also encoded in a DNA sequence, as will be discussed below. As used in the present disclosure, the 5' untranslated region (5' UTR) (also known as a Leader Sequence or Leader RNA) is the region that is directly upstream from the start codon. In a ribonucleotide, the 5' UTR begins at the transcription start site and ends one nucleotide (nt) before the start codon (usually AUG) of the coding region. Native UTRs naturally occurring in messages of prokaryotes, and the length of such 5' UTR tends to be 3-10 nucleotides long. In contrast, native UTRs naturally occurring in eukaryotes it tends to be longer, generally from 100 to several thousand nucleotides long (although they can be shorter). The 5' UTR, once transcribed, may contain, inter alia, sequences which correspond to (residual 3') parts of the promoter as well as a so-called Kozak sequence. A Kozak sequence may be required for ribosome recognition and translation of many genes. Kozak sequences can have the consensus CCR(A/G)CC, where R is a purine (adenine or guanine) that is located three bases upstream of the start codon (AUG). 5' UTRs may form secondary structures which are involved in binding of translation elongation factor. In some cases, one can increase the stability and protein production of the engineered polynucleotide molecules of the disclosure by engineering the features typically found in abundantly expressed genes of specific target organs. For example, introduction of a 5'UTR of liver-expressed mRNA, such as albumin, serum amyloid A, Apolipoprotein AB/E, transferrin, alpha fetoprotein, erythropoietin, or Factor VIII, can be used to increase expression of a modified polyribonucleotide in a liver. Likewise, use of a 5' UTR from muscle proteins (MyoD, Myosin, Myoglobin, Myogenin, Herculin), for endothelial cells (Tie-1, CD36), for myeloid cells (C/EBP, AML1, G-CSF, GM-CSF, CD1 lb, MSR, Fr-1, i-NOS), for leukocytes (CD45, CD18), for adipose tissue (CD36, GLUT4, ACRP30, adiponectin) and for lung epithelial cells (SP-A/B/C/D) can be used to increase expression of a modified polynucleotide in a desired cell or tissue. In some cases a UTR of the disclosure can be derived from the sequence of a cytochrome b-245 alpha polypeptide (CYBA); in such a case, a 5' UTR of the disclosure can comprise SEQ ID NO: 29 or 81, and a 3' UTR of the disclosure can comprise SEQ ID NO: 30. In some cases a UTR of the disclosure can be derived from an α-globin gene; in such a case, a 5' UTR of the disclosure can comprise sequences derived from an α-globin gene, with (SEQ ID NOs: 8, 64) or without (SEQ ID NOs: 65, 76, 83) a portion of an upstream promoter sequence. In some cases a 5' UTR of the disclosure can comprise a TISU element with (SEQ ID NO: 9) or without (SEQ ID NO: 77, 84) a portion of an upstream promoter sequence. In some cases a 5' UTR of the disclosure can comprise a TISU+T element with (SEQ ID NO: 10) or without (SEQ ID NO: 78 or 80) a portion of an upstream promoter sequence. In some cases a 5' UTR of the disclosure can comprise a 3' UTR derived from the sequence of human growth hormone (hGH) (SEQ ID NO: 39).

In certain embodiments, a modified polyribonucleotide of the disclosure comprises one or more UTRs selected from the sequences listed in Table 5.

TABLE 5

UTRs

| UTR | RNA sequence (from 5' to 3') |
|---|---|
| CYBA 5' | CGCGCCUAGCAGUGUCCCAGCCGGGUUCGUGUCGCC (SEQ ID NO: 29) |
| CYBA 3' | CCUCGCCCCGGACCUGCCCUCCCGCCAGGUGCACCCACCTGC**AAUAAA**UGC AGCGAAGCCGGGA (SEQ ID NO: 30) |
| α-globin 5' UTR (hAg) | GGGAGACUCU UCUGGUCCCCACAGACUCAG AGAGAACGCCACC (SEQ ID NO: 8) |
| α-globin 5' UTR (HBA2) | cauaaacccuggcgcgcucgcgggccggcacucuucugguccccacagacucagagagaacccacc (SEQ ID NO: 64) |
| α-globin 5' UTR ETH | ucuucugguccccacagacucagagagaac (SEQ ID NO: 65) |
| hGH 3' UTR | CGGGUGGCAUCCCUGUGACCCCUCCCCAGUGCCUCUCCUGGCCCUGGAAG UUGCCACUCCAGUGCCCACCAGCCUUGUCCUAAUAAAAUUAAGUUGCAUC (SEQ ID NO: 39) |
| Minimal 5' UTR | GGGAGACGCCACC (SEQ ID NO: 7) |
| TISU 5' UTR | GGGAGACGCCAAG (SEQ ID NO: 9) |
| TISU + T 5' UTR | GGGAGACUGCCAAG (SEQ ID NO: 10) |

As used in the present disclosure, the 3' untranslated region (3'-UTR) relates to the section of a modified polyribonucleotide that immediately follows the translation termination codon (the stop codon) of a sequence encoding a Cas family protein. As used in the present disclosure, the 3' UTR may comprise regulatory regions which are known to influence polyadenylation and stability of a polyribonucleotide. A 3'-UTR can also comprise AU-rich elements (AREs). A 3'-UTR of the present disclosure can comprise the sequence AAUAAA that directs addition of several to several hundred adenine residues called the poly(A) tail to the end of the coding region of a polyribonucleotide.

3' UTRs may have stretches of adenosines and uridines embedded therein. These AU rich signatures are particularly prevalent in genes with high rates of turnover. Based on their sequence features and functional properties, the AU rich elements (AREs) can be separated into classes: Class I AREs contain several dispersed copies of an AUUUA motif within U-rich regions. C-Myc and MyoD contain class I AREs. Class II AREs possess two or more overlapping UUAUUUA (U/A)(U/A) nonamers. Molecules containing this type of AREs include GM-CSF and TNF-α. Class III ARES are less well defined. These U rich regions do not contain an AUUUA motif c-Jun and Myogenin are two well-studied examples of this class. Proteins binding to the AREs may destabilize the messenger, whereas members of the ELAV family, such as HuR, may increase the stability of mRNA. HuR may bind to AREs of all the three classes. Engineering the HuR specific binding sites into the 3' UTR of nucleic acid molecules can lead to HuR binding and thus, stabilization of the message in vivo.

Engineering of 3' UTR AU rich elements (AREs) can be used to modulate the stability of a polyribonucleotide of the disclosure encoding a Cas9. One or more copies of an ARE can be engineered into a polyribonucleotide to modulate the stability of a polyribonucleotide. AREs can be identified, removed or mutated to increase the intracellular stability and thus increase translation and production of the resultant protein. Transfection experiments can be conducted in relevant cell lines, using engineered polyribonucleotides and protein production can be assayed at various time points post-transfection. For example, cells can be transfected with different ARE-engineering molecules and by using an ELISA kit to the relevant protein and assaying protein produced at 6 hours, 12 hours, 24 hours, 48 hours, and 7 days post-transfection.

A 3' UTR of a modified polyribonucleotide encoding a Cas9 protein of the present disclosure may also contain a poly-A tail. A poly-A tail is a long sequence of adenine nucleotides (often 100 or even several hundred) added to the 3' end of a pre-mRNA by a process called polyadenylation. As used herein, a poly-A tail relates to a sequence of adenine nucleotides located at the 3' end of the polyribonucleotide. A 3' UTR of a polyribonucleotide of the present disclosure may comprise a sequence for a poly-A tail or said 3' UTR may comprise polyadenylation signal sequences that signal polyadenylation of the polyribonucleotide intracellularly. Thus, the present disclosure relates to any of the above-described polyribonucleotides, wherein the polyribonucleotide comprises a poly-A tail at the 3' end.

A modified polyribonucleotide of the disclosure encoding Cas9 can comprise an engineered 5' cap, or a 5' cap can be added to a polyribonucleotide intracellularly. The 5' cap structure of an mRNA can be involved in binding to the mRNA Cap Binding Protein (CBP), which is responsible for mRNA stability in the cell and translation competency through the association of CBP with poly(A) binding protein to form the mature cyclic mRNA species. The 5' cap structure can also be involved in nuclear export, increases in mRNA stability, and in assisting the removal of 5' proximal introns during mRNA splicing.

A modified polyribonucleotide can be 5'-end capped generating a 5'-ppp-5'-triphosphate linkage between a terminal guanosine cap residue and the 5'-terminal transcribed sense nucleotide of the polyribonucleotide molecule. The cap-structure can comprise a modified or unmodified 7-methyl-guanosine linked to the first nucleotide via a 5'-5' triphosphate bridge. This 5'-guanylate cap can then be methylated to generate an N7-methyl-guanylate residue. The ribose sugars of the terminal and/or anteterminal transcribed nucleotides of the 5'end of the polyribonucleotide may optionally also be 2'-O-methylated. 5'-decapping through hydrolysis and cleavage of the guanylate cap structure may target a nucleic acid molecule, such as an polyribonucleotide molecule of the disclosure, for degradation.

In some cases, a cap can comprise further modifications, including the methylation of the 2' hydroxy-groups of the first 2 ribose sugars of the 5' end of the polyribonucleotide. For instance, an eukaryotic cap-1 has a methylated 2'-hydroxy group on the first ribose sugar, while a cap-2 has methylated 2'-hydroxy groups on the first two ribose sugars. The 5' cap can be chemically similar to the 3' end of an polyribonucleotide molecule (the 5' carbon of the cap ribose is bonded, and the 3' unbonded). Such double modification can provides significant resistance to 5' exonucleases. Non-limiting examples of 5' cap structures that can be used with an engineered polyribonucleotide include, but are not limited to, 7mG(5)ppp(5)N, pN2p (cap 0), 7mG(5)ppp(5) NImpNp (cap 1), and 7mG(5')-ppp(5')NImpN2mp (cap 2).

Modifications to the modified polyribonucleotide of the present disclosure may generate a non-hydrolyzable cap structure preventing decapping and thus increasing polyribonucleotide half-life. Because cap structure hydrolysis requires cleavage of 5'-ppp-5'phosphorodiester linkages, modified nucleotides may be used during the capping reaction. For example, a Vaccinia Capping Enzyme from New England Biolabs (Ipswich, Mass.) may be used with a-thio-guanosine nucleotides according to the manufacturer's instructions to create a phosphorothioate linkage in the 5'-ppp-5' cap. Additional modified guanosine nucleotides may be used such as a-methyl-phosphonate and seleno-phosphate nucleotides. Additional modifications include, but are not limited to, 2'-O-methylation of the ribose sugars of 5'-terminal and/or 5'-anteterminal nucleotides of the mRNA on the 2'-hydroxyl group of the sugar ring. Multiple distinct 5'-cap structures can be used to generate the 5'-cap of a polyribonucleotide.

The modified polyribonucleotide may be capped post-transcriptionally, According to the present disclosure, 5' terminal caps may include endogenous caps or cap analogues.

Further, a modified polyribonucleotide can contain one or more internal ribosome entry site(s) (IRES). IRES sequences can initiate protein synthesis in the absence of the 5' cap structure. An IRES sequence can also be the sole ribosome binding site, or it can serve as one of multiple ribosome binding sites of a polyribonucleotide. Modified polyribonucleotides containing more than one functional ribosome binding site can encode several peptides or polypeptides that are translated by the ribosomes ("polycistronic or multicistronic polyribonucleotides"). A modified polyribonucleotide described here can comprise at least one IRES sequence, two IRES sequences, three IRES sequences, four IRES sequences, five IRES sequences, six IRES sequences, seven IRES sequences, eight IRES sequences, nine IRES sequences, ten IRES sequences, or another suitable number are present in a modified polyribonucleotide. Examples of IRES sequences that can be used according to the present disclosure include without limitation, those from picornaviruses (e.g., FMDV), pest viruses (CFFV), polio viruses (PV), encephalomyocarditis viruses (ECMV), foot-and-mouth disease viruses (FMDV), hepatitis C viruses (HCV), classical swine fever viruses (CSFV), murine leukemia virus (MLV), simian immune deficiency viruses (SIV) or cricket paralysis viruses (CrPV). An IRES sequence can be derived, for example, from commercially available vectors such as the IRES sequences available from Clontech™, GeneCopoeia™, Sigma-Aldrich™. IRES sequences can be, for example, at least 150 bases or base pairs, 200 bases or base pairs, 300 bases or base pairs, 400 bases or base pairs, 500 bases or base pairs, 600 bases or base pairs, 700 bases or base pairs, 800 bases or base pairs, 900 bases or base pairs, 1000 bases or base pairs, 2000 bases or base pairs, 3000 bases or base pairs, 4000 bases or base pairs, 5000 bases or base pairs, or 10000 bases or base pairs. IRES sequences can be at most 10000 bases or base pairs, 5000 bases or base pairs, 4000 bases or base pairs, 3000 bases or base pairs, 2000 bases or base pairs, 1000 bases or base pairs, 900 bases or base pairs, 800 bases or base pairs, 700 bases or base pairs, 600 bases or base pairs, 500 bases or base pairs, 400 bases or base pairs, 300 bases or base pairs, 200 bases or base pairs, 100 bases or base pairs, 50 bases or base pairs, or 10 bases or base pairs. In certain embodiments, a polyribonucleotide of the disclosure may comprise an m7GpppG cap, an internal ribosome entry site (IRES) and/or a polyA tail at the 3' end in particular in order to improve translation. The RNA can have further regions promoting translation.

A polynucleotide sequence that may transcribe a modified polyribonucleotide of the disclosure can comprise one or more promoter sequences and any associated regulatory sequences, either a whole promoter and associated regulatory sequences or a fragment thereof. mRNA is transcribed from a gene by a DNA-dependent RNA polymerase, which begins transcribing at the transcription start site (TSS). The position of the TSS is determined by the specific promoter sequence and any other regulatory sequences upstream of the start codon of the gene. The TSS may be within the promoter sequence. Thus the 5' UTR of a modified polyribonucleotide may comprise a portion of a promoter sequence. The promoter sequence and any associated regulatory sequence or portion thereof can be positioned at the 5' end of the 5' UTR. A promoter sequence and/or an associated regulatory sequence can comprise any number of modified or unmodified nucleotides. Promoter sequences and/or any associated regulatory sequences can comprise, for example, at least 150 bases or base pairs, 200 bases or base pairs, 300 bases or base pairs, 400 bases or base pairs, 500 bases or base pairs, 600 bases or base pairs, 700 bases or base pairs, 800 bases or base pairs, 900 bases or base pairs, 1000 bases or base pairs, 2000 bases or base pairs, 3000 bases or base pairs, 4000 bases or base pairs, 5000 bases or base pairs, or at least 10000 bases or base pairs. A promoter sequence and/or an associated regulatory sequence can comprise any number of modified or unmodified nucleotides, for example, at most 10000 bases or base pairs, 5000 bases or base pairs, 4000 bases or base pairs, 3000 bases or base pairs, 2000 bases or base pairs, 1000 bases or base pairs, 900 bases or base pairs, 800 bases or base pairs, 700 bases or base pairs, 600 bases or base pairs, 500 bases or base pairs, 400 bases or base pairs, 300 bases or base pairs, 200 bases or base pairs, or 100 bases or base pairs. DNA sequences of promoters of the disclosure include, but are not limited to, the sequences listed in Table 6. As the present disclosure also concerns modified polyribonucleotides, RNA sequences versions of the promoters listed in Table 6 may be found in Table 6.

TABLE 6

| Promoter Name | RNA Sequence and SEQ ID NO. |
|---|---|
| T7 | UAAUACGACUCACUAUAG (SEQ ID NO: 3) |
| T3 | AAUUAACCCUCACUAAAG (SEQ ID NO: 4) |
| SP6 | AUUUAGGUGACACUAUAG (SEQ ID NO: 5) |
| K11 | AAUUAGGGCACACUAUAGGGA (SEQ ID NO: 6) |

In certain embodiments, a modified polyribonucleotide molecule of the present disclosure comprises a 5' UTR comprising the nucleotide sequence of SEQ ID NO: 29 or 81 or a sequence which shows 1 to 4 substitutions (or, in certain embodiments, additions or deletions) in comparison to SEQ ID NO: 29 or 81. In some embodiments, such a polyribonucleotide has the same or higher translation efficiency compared to a polyribonucleotide without the 5' UTR. In another embodiment, a modified polyribonucleotide molecule of the present disclosure comprises a 5' UTR comprising two or more copies of the nucleotide sequence of SEQ ID NO: 29 or 81 or a sequence which shows 1 to 4 substitutions (or, in certain embodiments, additions or deletions) in comparison to SEQ ID NO: 29 or 81. In some embodiments, such a polyribonucleotide has the same or higher translation efficiency compared to a polyribonucleotide without the 5' UTR.

In certain embodiments, a modified polyribonucleotide molecule of the present disclosure comprises a 3' UTR comprising the nucleotide sequence of SEQ ID NO: 30 or a sequence which shows 1 to 4 substitutions (or, in certain embodiments, additions or deletions) in comparison to SEQ ID NO: 30. In some embodiments, such a polyribonucleotide has the same or higher translation efficiency compared to a polyribonucleotide without the 3' UTR. In another embodiment, a modified polyribonucleotide molecule of the present disclosure comprises a 3' UTR comprising two or more copies of the nucleotide sequence of SEQ ID NO: 30 or a sequence which shows 1 to 4 substitutions (or, in certain embodiments, additions or deletions) in comparison to SEQ ID NO: 30. In some embodiments, the polyribonucleotide has the same or higher translation efficiency compared to a polyribonucleotide without the 3' UTR.

In certain embodiments, a modified polyribonucleotide molecule of the present disclosure comprises a 5' UTR comprising the nucleotide sequence of SEQ ID NO: 8 or a sequence which shows 1 to 4 substitutions (or, in certain embodiments, additions or deletions) in comparison to SEQ ID NO: 8. In certain embodiments, the polyribonucleotide has the same or higher translation efficiency compared to a polyribonucleotide without the 5' UTR. In another embodiment, a modified polyribonucleotide molecule of the present disclosure comprises a 5' UTR comprising two or more copies of the nucleotide sequence of SEQ ID NO: 76 or a sequence which shows 1 to 4 substitutions (or, in certain embodiments, additions or deletions) in comparison to SEQ ID NO: 76. In another embodiment, a modified polyribonucleotide molecule of the present disclosure comprises a 5' UTR comprising two or more copies of the nucleotide sequence of SEQ ID NO: 83 or a sequence which shows 1 to 4 substitutions (or, in certain embodiments, additions or deletions) in comparison to SEQ ID NO: 83. In certain embodiments, the polyribonucleotide has the same or higher translation efficiency compared to a polyribonucleotide without the 5' UTR.

In certain embodiments, a modified polyribonucleotide molecule of the present disclosure comprises a 5' UTR comprising the nucleotide sequence of SEQ ID NO: 64 or a sequence which shows 1 to 4 substitutions (or, in certain embodiments, additions or deletions) in comparison to SEQ ID NO: 64. In certain embodiments, the polyribonucleotide has the same or higher translation efficiency compared to a polyribonucleotide without the 5' UTR. In another embodiment, a modified polyribonucleotide molecule of the present disclosure comprises a 5' UTR comprising two or more copies of the nucleotide sequence of SEQ ID NO: 64 or a sequence which shows 1 to 4 substitutions (or, in certain embodiments, additions or deletions) in comparison to SEQ ID NO: 64. In certain embodiments, the polyribonucleotide has the same or higher translation efficiency compared to a polyribonucleotide without the 5' UTR.

In certain embodiments, a modified polyribonucleotide molecule of the present disclosure comprises a 5' UTR comprising the nucleotide sequence of SEQ ID NO: 65 or a sequence which shows 1 to 4 substitutions (or, in certain embodiments, additions or deletions) in comparison to SEQ ID NO: 65. In certain embodiments, the polyribonucleotide has the same or higher translation efficiency compared to a polyribonucleotide without the 5' UTR. In another embodiment, a modified polyribonucleotide molecule of the present disclosure comprises a 5' UTR comprising two or more copies of the nucleotide sequence of SEQ ID NO: 65 or a sequence which shows 1 to 4 substitutions (or, in certain embodiments, additions or deletions) in comparison to SEQ ID NO: 65. In certain embodiments, the polyribonucleotide has the same or higher translation efficiency compared to a polyribonucleotide without the 5' UTR.

In certain embodiments, a modified polyribonucleotide molecule of the present disclosure comprises a 3' UTR comprising the nucleotide sequence of SEQ ID NO: 39 or a sequence which shows 1 to 4 substitutions (or, in certain embodiments, additions or deletions) in comparison to SEQ ID NO: 39. In certain embodiments, the polyribonucleotide has the same or higher translation efficiency compared to a polyribonucleotide without the 3' UTR. In another embodiment, a modified polyribonucleotide molecule of the present disclosure comprises a 3' UTR comprising two or more copies of the nucleotide sequence of SEQ ID NO: 39 or a sequence which shows 1 to 4 substitutions (or, in certain embodiments, additions or deletions) in comparison to SEQ ID NO: 39. In certain embodiments, the polyribonucleotide has the same or higher translation efficiency compared to a polyribonucleotide without the 3' UTR.

In certain embodiments, a modified polyribonucleotide molecule of the present disclosure comprises a 5' UTR comprising the nucleotide sequence of SEQ ID NO: 7 or a sequence which shows 1 to 4 substitutions (or, in certain embodiments, additions or deletions) in comparison to SEQ ID NO: 7. In certain embodiments, the polyribonucleotide has the same or higher translation efficiency compared to a polyribonucleotide without the 5' UTR. In another embodiment, a modified polyribonucleotide molecule of the present disclosure comprises a 5' UTR comprising two or more copies of the nucleotide sequence of SEQ ID NO: 75 or a sequence which shows 1 to 4 substitutions (or, in certain embodiments, additions or deletions) in comparison to SEQ ID NO: 75. In another embodiment, a modified polyribonucleotide molecule of the present disclosure comprises a 5' UTR comprising two or more copies of the nucleotide sequence of SEQ ID NO: 82 or a sequence which shows 1 to 4 substitutions (or, in certain embodiments, additions or deletions) in comparison to SEQ ID NO: 82. In certain embodiments, the polyribonucleotide has the same or higher translation efficiency compared to a polyribonucleotide without the 5' UTR.

In certain embodiments, a modified polyribonucleotide molecule of the present disclosure comprises a 5' UTR comprising the nucleotide sequence of SEQ ID NO: 9 or a sequence which shows 1 to 4 substitutions (or, in certain embodiments, additions or deletions) in comparison to SEQ ID NO: 9. In certain embodiments, the polyribonucleotide has the same or higher translation efficiency compared to a polyribonucleotide without the 5' UTR. In another embodiment, a modified polyribonucleotide molecule of the present disclosure comprises a 5' UTR comprising two or more copies of the nucleotide sequence of SEQ ID NO: 77 or a sequence which shows 1 to 4 substitutions (or, in certain embodiments, additions or deletions) in comparison to SEQ ID NO: 77. In another embodiment, a modified polyribonucleotide molecule of the present disclosure comprises a 5' UTR comprising two or more copies of the nucleotide sequence of SEQ ID NO: 84 or a sequence which shows 1 to 4 substitutions (or, in certain embodiments, additions or deletions) in comparison to SEQ ID NO: 84. In certain embodiments, the polyribonucleotide has the same or higher translation efficiency compared to a polyribonucleotide without the 5' UTR.

In certain embodiments, a modified polyribonucleotide molecule of the present disclosure comprises a 5' UTR comprising the nucleotide sequence of SEQ ID NO: 10 or a sequence which shows 1 to 4 substitutions (or, in certain embodiments, additions or deletions) in comparison to SEQ ID NO: 10. In certain embodiments, the polyribonucleotide has the same or higher translation efficiency compared to a polyribonucleotide without the 5' UTR. In another embodiment, a modified polyribonucleotide molecule of the present disclosure comprises a 5' UTR comprising two or more copies of the nucleotide sequence of SEQ ID NO: 78 or a sequence which shows 1 to 4 substitutions (or, in certain embodiments, additions or deletions) in comparison to SEQ ID NO: 78. In another embodiment, a modified polyribonucleotide molecule of the present disclosure comprises a 5' UTR comprising two or more copies of the nucleotide sequence of SEQ ID NO: 80 or a sequence which shows 1 to 4 substitutions (or, in certain embodiments, additions or deletions) in comparison to SEQ ID NO: 80. In certain embodiments, the polyribonucleotide has the same or higher translation efficiency compared to a polyribonucleotide without the 5' UTR.

"Two or more" in the above embodiments means that the modified polyribonucleotide molecule may comprise a UTR comprising two, three, or four copies of the specified sequence, or a sequence which shows 1 to 4 substitutions (or, in certain embodiments, additions or deletions) in comparison to the specified sequence. Alternatively, the modified polyribonucleotide molecule may also comprise five or even more copies of the specified sequence within the UTR.

In certain embodiments, the 3' UTR comprises one or more copies of a 3' UTR sequence selected from the group consisting of SEQ ID NOs: 30 and 39, wherein the ribonucleotides of the 3' UTR are positioned downstream (3') of the ribonucleotides encoding the Cas9 protein, such as the ribonucleotides of SEQ ID NOs: 1 or 2, for example, directly downstream with less than 40 contiguous nucleotides intervening, less than 30, less than 20, less than 10, less than 5, less than 3, 3, 2, 1 or no contiguous nucleotides intervening.

In certain embodiments, the 5' UTR comprises one or more sequences selected from the group consisting of SEQ ID NOs: 75-78, 80-84 and 29, wherein the ribonucleotides of the 5' UTR are positioned upstream (5') of the ribonucleotides encoding the Cas9 protein, such as the ribonucleotides of SEQ ID NOs: 1 or 2, and 3' from ribonucleotides corresponding to a portion of a promoter sequence, for example, directly 3' with less than 40 contiguous nucleotides intervening, less than 30, less than 20, less than 10, less than 5, less than 3, 3, 2, 1 or no contiguous nucleotides intervening.

In certain embodiments, the modified polyribonucleotide of the disclosure encoding Cas9 contains a combination of unmodified and modified ribonucleotides, wherein 30-45% of the uridines are analogs of uridine and 5-10% of the cytidines are analogs of cytidine. In certain embodiments, the modified polyribonucleotide contains a combination of unmodified and modified ribonucleotides, wherein 30-45% of uridines in said input mixture are analogs of uridine and 5-10% of cytidines in said input mixture are analogs of cytidine. Also contemplated are such modified polyribonucleotides having any of the analogs described herein or percentages or modified residues, as disclosed herein (e.g., type of analog and/or percentage of modification and/or presence or absence of particular modifications). In some embodiments, a polyribonucleotide of the disclosure encodes a Cas9 protein, such as a Cas9 protein described herein, or a protein comprising an amino acid sequence at least 90%, 91%, 92%, 93%, 94%, 95%, 96%, 97%, 98%, 99% or 100% identical thereto.

The present disclosure is not particularly limited to modified polyribonucleotides comprising UTRs listed in Table 5, but may also relate to (an) UTR sequence(s) which comprise(s) a sequence which shows (a) nucleotide(s) addition(s) or deletion(s) in comparison to sequences listed in Table 5. The addition of (a) nucleotide(s) can be flanking. Thus, the additional nucleotide(s) may be added at the 3'-end or 5'-end of the UTR(s) of the present disclosure. The additional nucleotide(s) comprise polynucleotide chains of up to 0 (no changes), 1, 2, 3, 4, 5, 6, 7, 8, 9 or 10 nucleotides, preferably of up to 20 nucleotides or even more preferably of up to 30 nucleotides. In light of the rationale that the addition of nucleotides is likely not to change the above functional properties of the UTR(s) of the disclosure the addition of the nucleotides may also have a length of up to 40, 50, 60, 70, 80, 90, or even 100 nucleotides or even more, up to 200, 300, 400 or 500 nucleotides as long as these sequences have a similar capability (in terms of the above-described translation efficiency) as sequences described in Table 5, preferably higher translation efficiency as in Table 5 defined above.

Alternatively, or in addition to these flanking additions of (a) nucleotide(s) the addition of (a) nucleotide(s) can be interspersed. Thus, the additional nucleotide(s) may be added/inserted within the nucleotide sequence of the UTR(s) of the present disclosure. These nucleotide(s) insertions comprise 1, 2, or 3 nucleotides and, in some embodiments, result in sequences having a similar capability (in terms of the above-described translation efficiency) as sequences of Table 5, preferably higher translation efficiency as sequences of Table 5 as defined above.

A modified polyribonucleotide according to the present disclosure may not only comprise the three main modules of (i) Cas protein encoding sequence, (ii) 5' UTR, and/or (iii) 3' UTR. Rather, it may be desirable that between the individual modules (a) linker moiety/moieties and/or (a) multiple cloning site(s) is/are placed which may, e.g., facilitate the construction of the modified polyribonucleotide. Suitable linker moieties and multiple cloning sites are known to the skilled person.

The position of the UTR modules within the modified polyribonucleotide molecule of the present disclosure in relation to the Cas protein encoding sequence is not particularly limited and, accordingly, between the individual UTRs and Cas protein encoding sequence of the modified polyribonucleotide molecule of the present disclosure there may be a spacing or a gap filled with one or more nucleotides G, A, U and/or C which are not part of the UTRs or the Cas protein encoding sequence.

"One or more nucleotides G, A, U and/or C" in this context means that the spacing or gap between the individual UTR(s) and the Cas protein encoding sequence of the modified polyribonucleotide molecule of the present disclosure is/are filled with 1, 2, 3, 4, 5, 6, 7, 8, 9 or 10 nucleotides G, A, U and/or C. In certain embodiments, the spacing or gap between the individual UTR(s) and the Cas protein encoding sequence of the modified polyribonucleotide molecule of the present disclosure are filled with 20, 30, 40, 50, 60, 70, 80, 90, 100 or 110 or more nucleotides G, A, U and/or C.

In certain embodiments, the 5' UTR(s), within the modified polyribonucleotide molecule of the present disclosure in relation to the Cas protein encoding sequence is directly placed adjacent to the start codon of the coding region without any spacing or gap in between, i.e., directly upstream of the start codon of the coding region of the Cas protein encoding sequence.

In another embodiment, the 3' UTR, within the modified polyribonucleotide molecule of the present disclosure in relation to the Cas protein encoding sequence is directly placed adjacent to the termination codon (i.e., the stop codon) of the coding region without any spacing or gap in between, i.e., directly downstream of the termination codon/stop codon of the coding region of the Cas protein encoding sequence.

In certain embodiments, the 5' UTR(s), within the modified polyribonucleotide molecule of the present disclosure in relation to the Cas protein encoding sequence is directly placed adjacent to the start codon of the coding region without any spacing or gap in between, i.e., directly upstream of the start codon of the coding region of the Cas protein encoding sequence, and the 3' UTR, within the modified polyribonucleotide molecule of the present disclosure in relation to the Cas protein encoding sequence is directly placed adjacent to the termination codon (i.e., the stop codon) of the coding region without any spacing or gap in between, i.e., directly downstream of the termination codon/stop codon of the coding region of the Cas protein encoding sequence.

In certain embodiments, the modified polyribonucleotide of the present disclosure encodes a Cas protein, wherein said modified polynucleotide includes a codon sequence that is optimized for translation within cells of the subject exposed to the modified polyribonucleotide.

Other non-UTR sequences can be incorporated into the 5' (or 3' UTR) UTRs of the modified polyribonucleotides of the present disclosure. The 5' and/or 3' UTRs can provide stability and/or translation efficiency of polyribonucleotides. For example, introns or portions of intron sequences can be incorporated into the flanking regions of a polyribonucleotide. Incorporation of intronic sequences can also increase the rate of translation of the modified polyribonucleotide.

An untranslated region can comprise any number of nucleotides. An untranslated region can comprise a length of about 1 to about 10 bases or base pairs, about 10 to about 20 bases or base pairs, about 20 to about 50 bases or base pairs, about 50 to about 100 bases or base pairs, about 100 to about 500 bases or base pairs, about 500 to about 1000 bases or base pairs, about 1000 to about 2000 bases or base pairs, about 2000 to about 3000 bases or base pairs, about 3000 to about 4000 bases or base pairs, about 4000 to about 5000 bases or base pairs, about 5000 to about 6000 bases or base pairs, about 6000 to about 7000 bases or base pairs, about 7000 to about 8000 bases or base pairs, about 8000 to about 9000 bases or base pairs, or about 9000 to about 10000 bases or base pairs in length. An untranslated region can comprise a length of for example, at least 1 base or base pair, 2 bases or base pairs, 3 bases or base pairs, 4 bases or base pairs, 5 bases or base pairs, 6 bases or base pairs, 7 bases or base pairs, 8 bases or base pairs, 9 bases or base pairs, 10 bases or base pairs, 20 bases or base pairs, 30 bases or base pairs, 40 bases or base pairs, 50 bases or base pairs, 60 bases or base pairs, 70 bases or base pairs, 80 bases or base pairs, 90 bases or base pairs, 100 bases or base pairs, 200 bases or base pairs, 300 bases or base pairs, 400 bases or base pairs, 500 bases or base pairs, 600 bases or base pairs, 700 bases or base pairs, 800 bases or base pairs, 900 bases or base pairs, 1000 bases or base pairs, 2000 bases or base pairs, 3000 bases or base pairs, 4000 bases or base pairs, 5000 bases or base pairs, 6000 bases or base pairs, 7000 bases or base pairs, 8000 bases or base pairs, 9000 bases or base pairs, or 10000 bases or base pairs in length.

A modified polyribonucleotide of the disclosure can comprise one or more introns.

A modified polyribonucleotide of the disclosure can comprise a poly-A sequence. A poly-A sequence (e.g., poly-A tail) can comprise any number of nucleotides. A poly-A sequence can comprise a length of about 1 to about 10 bases or base pairs, about 10 to about 20 bases or base pairs, about 20 to about 50 bases or base pairs, about 50 to about 100 bases or base pairs, about 100 to about 500 bases or base pairs, or even more than 500.

In some cases, a percentage of the nucleotides in a poly-A sequence are modified nucleotides. For instance, in some cases, fewer than 99%, 95%, 90%, 85%, 80%, 75%, 70%, 65%, 60%, 55%, 50%, 45%, 40%, 35%, 30%, 25%, 20%, 15%, 10%, 5% or 1% of the nucleotides in a poly-A sequence are modified nucleotides. In some cases, all of the nucleotides in a poly-A are modified nucleotides.

A linker sequence can comprise any number of nucleotides. A linker can be attached to the modified nucleobase at an N-3 or C-5 position. The linker attached to the nucleobase can be diethylene glycol, dipropylene glycol, triethylene glycol, tripropylene glycol, tetraethylene glycol, tetraethylene glycol, divalent alkyl, alkenyl, alkynyl moiety, ester, amide, or an ether moiety. A linker sequence can comprise a length of about 1 to about 10 bases or base pairs, about 10 to about 20 bases or base pairs, about 20 to about 50 bases or base pairs, about 50 to about 100 bases or base pairs, about 100 to about 500 bases or base pairs, about 500 to about 1000 bases or base pairs, about 1000 to about 2000 bases or base pairs, about 2000 to about 3000 bases or base pairs, about 3000 to about 4000 bases or base pairs, about 4000 to about 5000 bases or base pairs, about 5000 to about 6000 bases or base pairs, about 6000 to about 7000 bases or base pairs, about 7000 to about 8000 bases or base pairs, about 8000 to about 9000 bases or base pairs, or about 9000 to about 10000 bases or base pairs in length. A linker sequence can comprise a length of for example, at least 1 base or base pair, 2 bases or base pairs, 3 bases or base pairs, 4 bases or base pairs, 5 bases or base pairs, 6 bases or base pairs, 7 bases or base pairs, 8 bases or base pairs, 9 bases or base pairs, 10 bases or base pairs, 20 bases or base pairs, 30 bases or base pairs, 40 bases or base pairs, 50 bases or base pairs, 60 bases or base pairs, 70 bases or base pairs, 80 bases or base pairs, 90 bases or base pairs, 100 bases or base pairs, 200 bases or base pairs, 300 bases or base pairs, 400 bases or base pairs, 500 bases or base pairs, 600 bases or base pairs, 700 bases or base pairs, 800 bases or base pairs, 900 bases or base pairs, 1000 bases or base pairs, 2000 bases or base pairs, 3000 bases or base pairs, 4000 bases or base pairs, 5000 bases or base pairs, 6000 bases or base pairs, 7000 bases or base pairs, 8000 bases or base pairs, 9000 bases or base pairs, or at least 10000 bases or base pairs in length. A linker at most 10000 bases or base pairs, 5000 bases or base pairs, 4000 bases or base pairs, 3000 bases or base pairs, 2000 bases or base pairs, 1000 bases or base pairs, 900 bases or base pairs, 800 bases or base pairs, 700 bases or base pairs, 600 bases or base pairs, 500 bases or base pairs, 400 bases or base pairs, 300 bases or base pairs, 200 bases or base pairs, or 100 bases or base pairs in length.

In some cases, a percentage of the nucleotides in a linker sequence are modified nucleotides. For instance, in some cases, fewer than 99%, 95%, 90%, 85%, 80%, 75%, 70%, 65%, 60%, 55%, 50%, 45%, 40%, 35%, 30%, 25%, 20%, 15%, 10%, 5% or 1% of the nucleotides in a linker sequence are modified nucleotides. In some cases, all of the nucleotides in a linker sequence are modified nucleotides.

In some cases, a modified polyribonucleotide can include at least one stop codon before the 3'untranslated region (UTR). In some cases, a modified polyribonucleotide includes multiple stop codons. The stop codon can be selected from TGA, TAA and TAG. The stop codon may comprise modified or unmodified nucleotides. In some cases, the modified polyribonucleotide includes the stop codon TGA and one additional stop codon. In some cases, the modified polyribonucleotide includes the addition of the TAA stop codon.

Encoded Cas-related Polypeptides

The present disclosure provides polyribonucleotide molecules, preferably modified polyribonucleotide molecules comprising modified nucleotides (i.e. non-naturally occurring or analogs of uridine, cytidine, guanosine, and adenosine), which encode a protein of the Cas protein family, preferably a Cas9-related protein. An encoded Cas polypeptide is a polymer chain comprised of amino acid residue monomers which are joined together through amide bonds (peptide bonds). A polyribonucleotide that is translated within a subject's body can generate an ample supply of encoded Cas protein within a cell, a tissue, or across many cells and tissues of a subject. In some cases, a polyribonucleotide can be translated in vivo within the cytosol of a specific target cell(s) type or target tissue. In some cases, a modified polyribonucleotide of the present disclosure can be translated in vivo to provide a Cas family protein or a Cas9-related protein. In some cases, a polyribonucleotide can be translated in vivo in various non-target cell types or target tissue(s). Non-limiting examples of cells that can be target or non-target cells include: a) skin cells, e.g.: keratinocytes, melanocytes, urothelial cells; b) neural cells, e.g.: neurons, Schwann cells, oligodentrocytes, astrocytes; c) liver cells, e.g.: hepatocytes; d) intestinal cells, e.g.: globlet cell, enterocytes; e) blood cells; e.g.: lymphoid or myeloid cells. Non-limiting examples of tissues include connective tissue, muscle tissue, nervous tissue, or epithelial tissue. In some cases, a target cell or a target tissue is a cancerous cell, tissue, or organ.

A polynucleotide sequence encoding a Cas family protein can be derived from one or more bacterial species. For example, a polynucleotide sequence can be derived from *Streptococcus pyogenes, Coriobacterium glomerans, Olsenella uli, Lactobacillus casei, Belliella baltica, Capnocytophaga canimorsus, Riemerella anatipestifer, Zunongwangia profunda, Filifactor alocis, Finegoldia magna, Acidaminococcus intestine, Wolinella succinogenes, Acidothermus cellulolyticus, Gluconaceteobacter diazotrophicus, Tistrella mobilis, Dinoroseobacter shibae, Parvibaculum lavamentivorans, Candidatus Puniceispirillum marinum, Fluviicola taffensis, Ornithobacterium rhinotracheale, Weeksella virosa, Verminephrobacter eiseniae, Alicychphilus dentrificans, Nitratifractor salsuginis, Helicobacter cinaedi, Elusimicrobium minutum, Fibrobacter succinogenes, Ilyobacter polytropus, gamma proteobacterium, Actinobacillus suis, Ignavibacterium album, Akkermansia musimphila, Streptococcus thermophiles, Campylobacter jejuni, Neisseria meningitides*, or *Legionella pneumophila*, or any bacterial species that possesses a CRISPR system, for example as disclosed in Chylinski et al. Nucleic Acids Res. 2014. 42:10, 6091-6105. A polynucleotide sequence can be a chimeric combination of the sequence of one or more species.

Unmodified sequences of exemplary Cas9 polyribonucleotides may be found in U.S. Pat. Nos. 8,999,641, 8,993,233, 8,945,839, 8,932,814, 8,906,616, 8,895,308, 8,889,418, 8,889,356, 8,871,445, 8,865,406, 8,795,965, 8,771,945, and 8,697,359, incorporated by reference herein. In certain embodiments, a modified polyribonucleotide of the present disclosure encodes an ortholog or homolog of a Cas9 protein of described or referred to herein.

In some embodiments, the modified polyribonucleotide of the present disclosure encodes a Cas9 protein. Cas9 proteins comprise a family of endonucleases that bind base-paired crRNA and trRNA use complementarity between crRNA and target double-stranded DNA to bind and cleave the double-stranded DNA (Jinek et al. 2012). Cas9 proteins comprise two endonuclease domains, a RuvC domain and an HNH domain. The HNH domain cuts the DNA strand complementary to the crRNA, while the RuvC domain cuts the non-complementary DNA strand. Jinek et al. also showed that crRNA and sgRNA can be combined into a single guide RNA, sgRNA, capable of guiding Cas9 cleavage of target DNA.

Wildtype Cas9 proteins introduce double-stranded breaks into target DNA. Cas9 proteins comprising point mutations in the active sites of one or both endonuclease domains have been shown to possess attenuated or no DNA cleaving activity. For example, the D10A amino acid substitution creates a Cas9 with an inactive RuvC domain; D10A Cas9 nicks target DNA. Another example of a mutant Cas9 protein is the D10A H841A Cas9 (dCas9); with substitutions in the active sites of both the RuvC and HNH domains, dCas9 binds to target DNA but does not cut either DNA strand. While not wishing to be limited by the above listing, the present disclosure contemplates polyribonucleotides encoding wildtype Cas9 as well as mutant Cas9 proteins comprising amino acid substitutions such as those that alter Cas9 activity, structure, target DNA specificity, target DNA binding affinity. In certain embodiments, a modified polyribonucleotide of the disclosure encodes wildtype Cas9, D10A Cas9, or dCas9. In certain embodiments, a modified polyribonucleotide of the disclosure encodes a variant Cas9 protein with one or more amino acid substitutions, domain truncations, and/or additional sequences or domains attached to the Cas9 sequence by protein fusion.

Without wishing to be limited by any single or several mechanisms, the present disclosure contemplates modes of action of a Cas9 protein encoded by a modified polyribonucleotide. In certain embodiments, a Cas9 protein encoded by a modified polyribonucleotide of the present disclosure cleaves double stranded DNA in a subject cell or in cells of a patient to whom a modified polyribonucleotide has been administered. "Cleave" is known by those skilled in the art to mean creating a double-stranded break (DSB) in DNA. A Cas9 protein encoded by a modified polyribonucleotide of the present disclosure may cleave DNA in a sequence specific manner acting with a co-administered sgRNA which base-pairs with a target sequence in the DNA of a subject cell or in cells of a patient to whom a modified polyribonucleotide has been administered. A DSB created by the action of a Cas9 protein encoded by a modified polyribonucleotide of the present disclosure may be repaired by non-homologous end joining (NHEJ), thereby introducing an insertion or deletion in the DNA at the target site. Such an insertion or deletion may decrease or abolish expression of the gene in which the insertion or deletion occurred. Thus a Cas9 protein encoded by a modified polyribonucleotide may decrease expression of a target gene with a sequence complementary to a co-administered sgRNA.

A DSB created by the action of a Cas9 protein encoded by a modified polyribonucleotide of the present disclosure may alternatively be repaired by homology directed repair (e.g. by homologous recombination). In the presence of a DNA construct comprising a desired sequence flanked by regions homologous to the regions flanking the DSB site, homology directed repair may insert the desired sequence at the site of the DSB. Such an insertion may decrease or abolish expression of the gene in which the insertion occurred, and may also introduce a new gene to the treated cell. Thus a Cas9 protein encoded by a modified polyribonucleotide may decrease expression of a target gene with a sequence complementary to a co-administered sgRNA and may also additionally introduce a new gene to a treated cell, which may then be expressed in said cell.

In certain embodiments, a Cas9 protein with a single functional endonuclease domain and a single non-functional endonuclease domain (for example, D10A Cas9) encoded by a modified polyribonucleotide of the present disclosure nicks double stranded DNA in a subject cell or in cells of a patient to whom a modified polyribonucleotide has been administered. "Nick" is known by those skilled in the art to mean creating a single-stranded break (SSB) in DNA. In certain embodiments, a Cas9 protein with a single functional endonuclease domain and a single non-functional endonuclease domain encoded by a modified polyribonucleotide of the present disclosure may nick DNA in a sequence specific manner acting with a co-administered sgRNA which base-pairs with a target sequence in the DNA of a subject cell or in cells of a patient to whom a modified polyribonucleotide has been administered. Such an SSB may be repaired by homology directed repair (e.g. by homologous recombination). In the presence of a DNA construct comprising a desired sequence flanked by regions homologous to the regions flanking the SSB site, homology directed repair may insert the desired sequence at the site of the SSB. Such an insertion may decrease or abolish expression of the gene in which the insertion occurred, and may also introduce a new gene to the treated cell. Thus a Cas9 protein encoded by a modified polyribonucleotide may decrease expression of a target gene with a sequence complementary to a co-administered sgRNA and may also additionally introduce a new gene to a treated cell, which may then be expressed in said cell.

In certain embodiments, a Cas9 protein with two non-functional endonuclease domains (for example, D10A H841A Cas9) encoded by a modified polyribonucleotide of the present disclosure binds to double stranded DNA but does not nick or cleave the DNA in a subject cell or in cells of a patient to whom a modified polyribonucleotide has been administered. In certain embodiments, a Cas9 protein with two non-functional endonuclease domains encoded by a modified polyribonucleotide of the present disclosure may bind DNA in a sequence specific manner acting with a co-administered sgRNA which base-pairs with a target sequence in the DNA of a subject cell or in cells of a patient to whom a modified polyribonucleotide has been administered. A Cas9 protein encoded by a modified polyribonucleotide may be a fusion protein, comprising one or more heterologous domains. Thus in certain embodiments, through binding a target sequence in the DNA of a subject or in cells of a patient to whom a modified polyribonucleotide has been administered, a Cas9 protein that is also a fusion protein can bring a heterologous domain into close proximity to a target DNA sequence. Heterologous domains may have diverse structures and functions. Heterologous domains that recruit transcription proteins and increase expression of a desired gene or genes are contemplated by the present disclosure. Heterologous domains that recruit inhibitory proteins that decrease expression of a desired gene or genes are contemplated by the present disclosure.

In certain embodiments, a modified polyribonucleotide of the disclosure encodes a wildtype Cas9 protein. In certain embodiments, a modified polyribonucleotide of the disclosure that encodes a wildtype Cas9 protein has been codon optimized for expression in mammalian cells. In certain embodiments, a modified polyribonucleotide of the disclosure comprises a sequence greater than or equal to 75%, 80%, 85%, 90%, 95%, 96%, 97%, 98%, or 99% identical to SEQ ID NO: 1. In certain embodiments, a modified polyribonucleotide of the disclosure comprises a sequence identical to SEQ ID NO: 1. In certain embodiments, a modified polyribonucleotide of the disclosure that encodes a D10A Cas9 protein has been codon optimized for expression in mammalian cells. In certain embodiments, a modified polyribonucleotide of the disclosure comprises a sequence greater than or equal to 75%, 80%, 85%, 90%, 95%, 96%, 97%, 98%, or 99% identical to SEQ ID NO: 2. In certain embodiments, a modified polyribonucleotide of the disclosure comprises a sequence identical to SEQ ID NO: 2. In certain embodiments, a modified polyribonucleotide of the disclosure that encodes a D10A H841A Cas9 protein has been codon optimized for expression in mammalian cells. In certain embodiments, a modified polyribonucleotide of the disclosure comprises a sequence greater than or equal to 75%, 80%, 85%, 90%, 95%, 95%, 97%, 98%, or 99% identical to SEQ ID NO: 51. In certain embodiments, a modified polyribonucleotide of the disclosure comprises a sequence identical to SEQ ID NO: 51. In certain embodiments, a protein encoded by a modified polyribonucleotide of the disclosure may have a post-translational modification. In certain embodiments, the modified polyribonucleotide contains a combination of unmodified and modified ribonucleotides, wherein 30-45% of the uridines are analogs of uridine and 5-10% of the cytidines are analogs of cytidine. In certain embodiments, the modified polyribonucleotide contains a combination of unmodified and modified ribonucleotides, wherein 30-45% of uridines in said input mixture are analogs of uridine and 5-10% of cytidines in said input mixture are analogs of cytidine Also contemplated is such modified polyribonucleotides having any of the analogs described herein or percentages or modified residues, as disclosed herein (e.g., type of analog and/or percentage of modification and/or presence or absence of particular modifications). In some embodiments, a polyribonucleotide of the disclosure encodes a Cas9 protein, such as a Cas9 protein described herein, or a protein comprising an amino acid sequence at least 90%, 91%, 92%, 93%, 94%, 95%, 96%, 97%, 98%, 99% or 100% identical thereto.

Non-limiting examples of Cas9-encoding ribonucleotide sequences that can be a part of a polynucleotide of the disclosure are disclosed in TABLE 7.

TABLE 7

| Name | Sequence Number |
|---|---|
| Wildtype Cas9 | SEQ ID NO: 1 |
| D10A Cas9 | SEQ ID NO: 2 |
| D10A H841A Cas9 | SEQ ID NO: 51 |

Non-limiting examples of Cas9 polypeptide sequences that can be encoded by a modified polyribonucleotide of the disclosure are disclosed in TABLE 8.

TABLE 8

| Name | Sequence Number |
|---|---|
| Wildtype Cas9 | SEQ ID NO: 19 |
| D10A Cas9 | SEQ ID NO: 20 |
| D10A H841A Cas9 | SEQ ID NO: 79 |

The present disclosure also contemplates modified polyribonucleotides encoding other Cas9 polypeptides and modified polyribonucleotides comprising other Cas9 coding sequences. Examples of such Cas9-related sequences can be found in Ran et al. Nature 2015 Apr. 9; 520(7546): 186-191, hereby incorporated by reference in its entirety.

Immunogenicity

The use of modified polyribonucleotides may increase stability and/or decrease immunogenicity versus unmodified polyribonucleotides. Thus, in some embodiments, use of a modified polyribonucleotide encoding a Cas9 is preferred. Numerous methods for evaluating immunogenicity are known in the art. For example, one method is determining expression of inflammatory markers in cells following administration of a polyribonucleotide of the disclosure encoding Cas9 versus expression or concentration of inflammatory markers in response to an ummodified polyribonucleotide having the same sequence. Cytokines which are associated with inflammation, such as for example TNF-α, IFN-α, IFN-β, IL-8, IL-6, IL-12 or other cytokines known to those skilled in the art may be evaluated. The expression of DC activation markers can also be used for the estimation of immunogenicity. A further indication of an immunological reaction is the detection of binding to the Toll-like receptors TLR-3, TLR-7, or TLR-8, and/or to helicase RIG-1.

The immunogenicity is as a rule determined in relation to a control. In a common method, either the modified polyribonucleotide according to the disclosure or a polyribonucleotidethat is unmodified or modified in another way is administered to cells and the secretion of inflammatory markers in a defined time interval as a reaction to the administration of the polyribonucleotide is measured. As the standard used for comparison, either unmodified polyribonucleotide can be used, in which case the immune response should be lower, or polyribonucleotide which is known to cause little or no immune response, in which case the immune response to the modified polyribonucleotide according to the disclosure should then lie in the same range and not be elevated. With the modified polyribonucleotide according to the disclosure it is possible to lower the immune response compared to unmodified polyribonucleotide by at least 30%, as a rule at least 50% or even 75% or even to prevent it completely.

The immunogenicity can be determined by measurement of the aforesaid factors, in particular by measurement of the TNF-α and IL-8 levels and the binding capacity to TLR-3, TLR-7, TLR-8 and helicase RIG-1. In order thereby to establish whether a polyribonucleotidehas the desired low immunogenicity, the quantity of one or more of the aforesaid factors after administration of the polyribonucleotide concerned can be measured. Thus for example a quantity of the polyribonucleotide to be tested can be administered to mice via the caudal vein or i.p. and then one or more of the aforesaid factors can be measured in the blood after a predefined period, e.g. after 7 or 14 days. The quantity of factor is then related to the quantity of factor which is present in the blood of untreated animals. For the determination of the immunogenicity it has been found very valuable to determine the binding capacity to TLR-3, TLR-7, TLR-8 and/or helicase RIG-1. The TNF-α levels and IL-8 levels also provide very good indications. With the modified polyribonucleotide according to the disclosure, it is possible to lower the binding capacity to TLR-3, TLR-7, TLR-8 and RIG-1 by at least 50% compared to unmodified RNA. As a rule it is possible to lower the binding to said factors by at least 75% or even by 80%. In preferred embodiments, the binding capacity to TLR-3, TLR-7, TLR-8 and RIG-1 lies in the same range for the modified polyribonucleotide according to the disclosure and for animals to which no mRNA was administered. In other words, the modified polyribonucleotide according to the disclosure causes practically no inflammatory or immunological reactions.

In some embodiments, modified polyribonucleotides encoding Cas9 according to the disclosure have reduced immunogenicity versus a non-modified comparator.

In some embodiments, any of the polyribonucleotides encoding Cas9 described herein may be described based on a decreased level of immunogenicity, or based on other function properties described herein.

Further properties of the polyribonucleotides encoding Cas9 according to the disclosure which may be used are its efficiency and stability. Transcription efficiency, transfection efficiency, translation efficiency and duration of protein expression may be evaluated to see whether it is at least comparable to unmodified polyribonucleotide or, in some cases or for some properties, improved.

Examples of modified polyribonucleotide sequences of the disclosure include SEQ ID Nos. 11-18. In certain embodiments, the modified polyribonucleotide contains a combination of unmodified and modified ribonucleotides, wherein 30-45% of the uridines are analogs of uridine and 5-10% of the cytidines are analogs of cytidine. In certain embodiments, the modified polyribonucleotide contains a combination of unmodified and modified ribonucleotides, wherein 30-45% of uridines in said input mixture are analogs of uridine and 5-10% of cytidines in said input mixture are analogs of cytidine. In certain embodiments, the cytidine analog is 5-iodocytidine and the uridine analog is 5-iodouridine. Also contemplated is such modified polyribonucleotides having any of the analogs described herein or percentages or modified residues, as disclosed herein (e.g., type of analog and/or percentage of modification and/or presence or absence of particular modifications). In some embodiments, a polyribonucleotide of the disclosure encodes a Cas9 protein, such as a Cas9 protein described herein, or a protein comprising an amino acid sequence at least 90%, 91%, 92%, 93%, 94%, 95%, 96%, 97%, 98%, 99% or 100% identical thereto.

Single Guide RNAs (sgRNAs)

Bacterial Type II CRISPR systems consist, minimally, of Cas9, a specificity determining crRNA, and a trans-activating trRNA that base-pairs with a segment of the crRNA (Cong et al. 2013, Hsu et al. Nat. Biotechnol. 2013 September; 31(9): 827-832). crRNA and trRNA can be fused into a single guide RNA, sgRNA, that mimics the natural crRNA:trRNA hybrid. A crRNA:trRNA or a sgRNA sequence can bind to Cas9, and crRNA:trRNA or sgRNA sequence complementarity to a target sequence (e.g., DNA of a target gene) determines Cas9 target specificity.

In certain embodiments, an sgRNA of the present disclosure comprises a polyribonucleotide between 50 and 150 ribonucleotides long (Hsu et al. 2013). In certain embodiments, an sgRNA of the present disclosure comprises a polyribonucleotide 102 ribonucleotides long (Jinek et al. 2012). In certain embodiments, from 5' to 3', a sgRNA comprises a first region comprising a guide sequence, and a second region comprising a Cas9 binding sequence and a transcription terminator sequence (Larson et al. Nat. Protoc. 2013. November: 8(11): 2180-2196). The guide sequence comprises 20-25 ribonucleotides; the complementarity of the guide sequence to other DNA sequences specifies a target for a Cas9 protein's DNA binding and/or endonuclease activity(ies). The Cas9 binding sequence comprises a hairpin loop formed by 42 ribonucleotides folded back on and annealing to itself; the Cas9 binding sequence aids in sgRNA binding to Cas9. The transcription terminator sequence comprises a further hairpin loop formed by 40 ribonucleotides folded back on and annealing to itself. A number of algorithms for the design of sgRNAs targeting specific genes or DNA sequences are available and known to those skilled in the art (Cong et al.; Larson et al.; GeneArt, ThermoFisher). When designing sgRNAs, maintaining the stability of the sgRNA secondary structure is important for Cas9:sgRNA binding. Using an appropriate algorithm, a sgRNA guide sequence can also be customized to target a specific gene or other DNA sequence and to minimize off-target Cas9 activity due to guide sequence complementarity to other sequences.

In certain embodiments, a modified polyribonucleotide of the present disclosure encoding Cas9 can be combined with an sgRNA as described herein. In certain embodiments, the sgRNA may comprise a tracer RNA (trRNA) sequence that encompasses the Cas9 binding sequence and transcription terminator sequence described above. In certain embodiments, the trRNA sequence is greater than 70%, 75%, 80%, 85%, 90%, 95%, 97%, 98%, 99%, or 100% identical to the sequence of SEQ ID NO: 74. In certain embodiments, the sgRNA comprises, from 5' to 3', a guide sequence 20-25 nucleotides long with complementarity to a target gene, and a trRNA sequence, wherein the trRNA sequence is greater than 70%, 75%, 80%, 85%, 90%, 95%, 97%, 98%, 99%, or 100% identical to the sequence of SEQ ID NO: 74. In certain embodiments, the sgRNA comprises zero, one, two, or three nucleotides 5' of the guide sequence. In certain embodiments, the zero, one, two, or three nucleotides 5' of the guide sequence are guanosine nucleotides.

In certain non-limiting examples, a sgRNA that can be combined with a modified polyribonucleotide of the present disclosure comprises a guide sequence that targets the PCSK9 gene, which is described in further detail elsewhere in the present disclosure. In other non-limiting examples, a sgRNA that can be combined with a modified polyribonucleotide of the present disclosure comprises a guide sequence that targets the eGFP gene. Examples of said sgRNAs can be found in Tables 12 and 13 in the Exemplification.

In certain embodiments, a modified polyribonucleotide of the present disclosure can be administered in conjunction with a sgRNA, either simultaneously in a single administration event or in separate administration events. In certain embodiments, a modified polyribonucleotide of the present disclosure can be co-transfected into a cell or cells of a subject with a sgRNA. In certain embodiments, a modified polyribonucleotide can be formulated with a sgRNA into a composition, e.g., formulated in a cationic lipid, cationic polymer, or nanoemulsion. In certain embodiments, the composition can be administered to a subject or contact cells to cleave, nick, or bind to DNA wherein the sgRNA targets Cas9 to a target gene or DNA sequence by sequence complementarity. In certain embodiments, the composition can be used in a method comprising administering to a subject or contacting cells to cleave, nick, or bind to DNA wherein the sgRNA targets Cas9 to a target gene or DNA sequence by sequence complementarity. In certain embodiments, administering the composition to a patient leads to a decrease in expression of the gene targeted for cleavage, nicking, or binding by modified polyribonucleotide encoded Cas9 and sgRNA. Examples of modified polyribonucleotide sequences of the disclosure include SEQ ID Nos. 11-18. In certain embodiments, the modified polyribonucleotide contains a combination of unmodified and modified ribonucleotides, wherein 30-45% of the uridines are analogs of uridine and 5-10% of the cytidines are analogs of cytidine. In certain embodiments, the modified polyribonucleotide contains a combination of unmodified and modified ribonucleotides, wherein 30-45% of uridines in said input mixture are analogs of uridine and 5-10% of cytidines in said input mixture are analogs of cytidine. In certain embodiments, the cytidine analog is 5-iodocytidine and the uridine analog is 5-iodouridine. Also contemplated is such modified polyribonucleotides having any of the analogs described herein or percentages or modified residues, as disclosed herein (e.g., type of analog and/or percentage of modification and/or presence or absence of particular modifications). In some embodiments, a polyribonucleotide of the disclosure encodes a Cas9 protein, such as a Cas9 protein described herein, or a protein comprising an amino acid sequence at least 90%, 91%, 92%, 93%, 94%, 95%, 96%, 97%, 98%, 99% or 100% identical thereto.

Pharmaceutical Aspects

In a further aspect, the present disclosure relates to compositions for delivering a polyribonucleotide encoding Cas9, according to the disclosure, preferably a modified polyribonucleotide, to tissue or into a target cell. Optionally, the Cas9 encoding polyribonucleotide is delivered (in the same or a different composition) with, for example, a polynucleotide that includes a complementarity region to a target gene, such as an sgRNA. Said delivery can be in vivo or in vitro.

Polyribonucleotides may be delivered as "naked" RNA or in combination with a delivery agent, e.g., a carrier, an encapsulating agent, a polymeric material, such as polyethylenimine (PEI), a nanoparticle, or a lipidoid. In certain embodiments, the Cas9 encoding polyribonucleotide and additional target-specific polynucleotide are co-formulated, such as in a nanoparticle or lipidoid. An exemplary co-formulated composition is provided in the examples. Methods and compositions for delivery of polyribonucleotides of the disclosure may be found, for example, in U.S. Pat. No. 8,871,230, U.S. Patent Application Publication No. 20150126589, and PCT Publication No. WO2014207231, incorporated by reference herein.

The present disclosure also relates to a method for delivering a polyribonucleotide, preferably a modified polyribonucleotide, to a target cell or tissue comprising the step of bringing a composition according to the disclosure into contact with the target cell or tissue. Such a method can be carried out in vitro or in vivo and administration may be local or systemic. The bringing into contact may be achieved by means and methods known to the person skilled in the art. For example, if the method is carried out in vitro, the bringing into contact can be achieved by cultivating the cells in the presence of the composition in the culture medium or by adding the composition to the cells. If the method is carried out in vivo, the bringing into contact with cells or tissues can, e.g., be achieved by the administration of the composition to an individual by routes of administration known to the person skilled in the art, in particular by any route of administration that is usually employed in the field of genetic therapy. Possible ways of formulating the composition and of administering it to an individual are also described further below.

The term "in vivo" refers to any application which is effected to the body of a living organism wherein said organism is preferably multicellular, more preferably a mammal and most preferably a human. The term "in vitro" or "ex vivo" refers to any application performed outside an organism, including to cells or tissues isolated and outside of an organism, e.g. cells, tissues and organs, wherein said organism is preferably multicellular, more preferably a mammal and most preferably a human.

The present disclosure also relates to a pharmaceutical composition comprising the composition of the disclosure and optionally a pharmaceutically acceptable carrier and/or diluent. The term "pharmaceutical composition" refers to a pharmaceutically acceptable form of the composition of the present disclosure which can be administered to a subject.

The term "pharmaceutically acceptable form" means that the composition is formulated as a pharmaceutical composition, wherein said pharmaceutical composition may further comprise a pharmaceutically acceptable carrier and/or diluent. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well-known conventional methods. These pharmaceutical compositions can be administered to the subject at a suitable dose. The dosage regimen will be determined by the attending physician and clinical factors. As is well known in the medical arts, dosages for any one subject depend upon many factors, including the subject's size, body surface area, age, the particular compound to be administered, sex, time and route of administration, general health, and other drugs being administered concurrently. A typical dose of active substances can be, for example, in the range of 1 ng to several grams. Applied to polyribonucleotide therapy, the dosage of an polyribonucleotide for expression or for inhibition of expression should correspond to this range; however, doses below or above this exemplary range are envisioned, especially considering the aforementioned factors. Generally, the regimen as a regular administration of the pharmaceutical composition should be in the range of 0.1 pg to 10 mg units per kilogram of body weight per day. If the regimen is a continuous infusion, it should also be in the range of 1 pg to 10 mg units per kilogram of body weight, respectively. Progress can be monitored by periodic assessment. Dosages will vary but a preferred dosage for intravenous administration of polyribonucleotides as constituents of the composition of the present disclosure is from approximately $10^6$ to $10^{19}$ copies of the polyribonucleotidemolecule.

The term "administered" encompasses any method suitable for introducing the composition into the body of a subject. Administration of the suitable compositions may be effected in different ways, e.g., by intravenous, intraarterial, intraperitoneal, subcutaneous, transdermal, intrathecal, intramuscular, topical, intradermal, intranasal, pulmonary by inhalation or intrabronchial or oral or rectal administration. The compositions of the present disclosure may in particular be administered as a gene-activated matrix such as described by Shea et al. (Shea et al. 1999, Nat Biotechnol, 17, 551-554) and in EP1 198489. In principle, the pharmaceutical compositions of the disclosure may be administered locally or systemically. Administration will preferably be parenterally, e.g., intravenously, although other ways of administration are within the scope of the disclosure. Administration directly to the target site, e.g., by catheter to a site in a blood vessel, is also conceivable. Administration can, for example, also occur by direct injection into a target site such as a tumor. Also within the scope of the disclosure is administration by aerosolization or nebulization or oral administration. Preparations for parenteral administration include sterile aqueous or non-aqueous solutions, suspensions, and emulsions. Examples of non-aqueous solvents are propylene glycol, polyethylene glycol, fluorocarbons, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition may comprise further agents such as interleukins or interferons depending on the intended use of the pharmaceutical composition.

Examples of polyribonucleotide sequences of the disclosure to be formulated and/or administered include SEQ ID Nos. 11-18. In certain embodiments, the polyribonucleotide is a modified polyribonucleotide containing a combination of unmodified and modified ribonucleotides, as described herein, for example wherein 30-45% of the uridines are analogs of uridine and 5-10% of the cytidines are analogs of cytidine. In certain embodiments, the modified polyribonucleotide contains a combination of unmodified and modified ribonucleotides, wherein 30-45% of uridines in said input mixture are analogs of uridine and 5-10% of cytidines in said input mixture are analogs of cytidine. In certain embodiments, the cytidine analog is 5-iodocytidine and the uridine analog is 5-iodouridine. Also contemplated is such modified polyribonucleotides having any of the analogs described herein or percentages or modified residues, as disclosed herein (e.g., type of analog and/or percentage of modification and/or presence or absence of particular modifications). In some embodiments, a polyribonucleotide of the disclosure encodes a Cas9 protein, such as a Cas9 protein described herein, or a protein comprising an amino acid sequence at least 90%, 91%, 92%, 93%, 94%, 95%, 96%, 97%, 98%, 99% or 100% identical thereto.

Vectors, Host Cells and Expression

The present disclosure provides nucleic acid molecules, including DNA molecules, which encode a protein of the Cas protein family, preferably a Cas9-related protein, including a wildtype Cas9 or a Cas9 protein having one or more substitutions, such as substitutions or mutations that alter its nucleic acid nicking activity. For each DNA (polydeoxyribonucleotide or polynucleotide) sequence listed in the present disclosure, the corresponding RNA (polyribonucleotide) sequence is contemplated and vice versa. Examples of DNA sequences of the disclosure include SEQ ID Nos. 31-38, 48-50, and 52-54, and these are specifically contemplated (e.g., the disclosure provides polynucleotides comprising a nucleic acid sequence set forth in any of the foregoing, as well as sequences at least 90%, 91%, 92%, 93%, 94%, 95%, 96%, 97%, 98%, or 99% identical to any one or more of the foregoing). In certain embodiments, the polynucleotides sequence encoding a Cas9 related protein is codon optimized for expression in a mammalian system. As a result, in certain embodiments, a polyribonucleotide encoding a Cas9 related protein is codon optimized.

The sequence of the polynucleotides can be derived from, for example, any suitable nucleic acid that comprises the genetic information of a gene of interest. Examples of nucleic acids include genomic DNA, RNA, or cDNA from any bacterial or archaeal cell comprising the Cas family of genes or a Cas9-encoding gene. The polynucleotides can be derived from nucleic acids carrying mutated genes and polymorphisms. A polynucleotide of the present disclosure comprises a sequence encoding a Cas protein. In certain embodiments, the sequence (e.g., DNA sequence and/or RNA sequence) is a codon optimized sequence, such as a codon optimized sequence to facilitate expression in a mammalian system. The polynucleotide may further comprise an untranslated sequence positioned upstream (5') of the Cas9-related protein encoding region's start codon, an untranslated sequence positioned downstream (3') of the Cas9-related protein encoding region's stop codon, or both an untranslated sequence positioned upstream (5') of the Cas9-related protein encoding region's start codon and an untranslated sequence positioned downstream (3') of the Cas9-related protein encoding region's stop codon. In a certain embodiments, a polynucleotide of the present disclosure may be a modified polynucleotide.

In certain embodiments, the Cas9 nucleic acids may be operably linked to one or more regulatory nucleotide sequences in an expression construct, such as a vector or plasmid. In certain embodiments, such constructs are DNA constructs. Regulatory nucleotide sequences will generally be appropriate for a host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the disclosure. The promoters may be either naturally occurring promoters, or hybrid promoters that combine elements of more than one promoter. An expression construct may be present in a cell on an episome, such as a plasmid, or the expression construct may be inserted in a chromosome. In some embodiments, the expression vector contains a selectable marker gene to allow the selection of transformed host cells. Selectable marker genes are well known in the art and will vary with the host cell used. In certain aspects, this disclosure relates to an expression vector comprising a nucleotide sequence encoding a Cas9 polypeptide and operably linked to at least one regulatory sequence. Regulatory sequences are art-recognized and are selected to direct expression of the encoded polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

This present disclosure also pertains to a host cell transfected with a recombinant gene which encodes a Cas9 polypeptide of the disclosure. The host cell may be any prokaryotic or eukaryotic cell. For example, a Cas9 polypeptide may be expressed in bacterial cells such as *E. coli*, insect cells (e.g., using a baculovirus expression system), yeast, or mammalian cells. Other suitable host cells are known to those skilled in the art.

The present disclosure further pertains to methods of producing a Cas9 polypeptide of the disclosure. For example, a host cell transfected with an expression vector encoding a Cas9 polypeptide can be cultured under appropriate conditions to allow expression of the polypeptide to occur. The polypeptide may be secreted and isolated from a mixture of cells and medium containing the polypeptides. Alternatively, the polypeptides may be retained in the cytoplasm or in a membrane fraction and the cells harvested, lysed and the protein isolated. A cell culture includes host cells, media and other byproducts. Suitable media for cell culture are well known in the art. The polypeptides can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the polypeptides (e.g., a Cas9 polypeptide).

A recombinant Cas9 nucleic acid can be produced by ligating the cloned gene, or a portion thereof, into a vector suitable for expression in either prokaryotic cells, eukaryotic cells (yeast, avian, insect or mammalian), or both. Expression vehicles for production of a recombinant polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*. In certain embodiments, the mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press, 1989) Chapters 16 and 17. In some instances, it may be desirable to express the recombinant polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III). Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

In the present context, DNA constructs encoding a Cas9 protein of the disclosure are particularly suitable for generating polyribonucleotides. For example, such vectors may be used as the basis to transcribe, in vitro, a polyribonucleotide encoding a Cas9 related protein, such as a Cas9 protein (e.g., the polyribonucleotide comprising a Cas9 coding sequence). Methods for in vitro transcription are well known in the art. In certain embodiments, the polyribonucleotides are polyribonucleotides of the disclosure and comprise, for example, any of the Cas9 coding sequences described herein, in the presence or absence of a 5' and/or 3'-UTR, as described herein. In certain embodiments, the polyribonucleotide is modified, as described herein.

Nuclear Localization

The compartmentalization of the eukaryotic cell requires the import of all nuclearproteins from the cytoplasm into the nucleus and, vice versa, the export of all substances which are synthesized in the nucleus but required in the cytoplasm, e.g. transfer RNAs, messenger RNAs, and ribosomes. Nuclear import and export proceeds exclusively through the nuclear pore complex (NPC) via distinct pathways including the large importin β-like nuclear transport receptor family. These receptors shuttle between the nucleus and the cytoplasm thereby binding to the transport substrate either directly or through an adaptor molecule such as importin a (classic import). The shuttling receptors all cooperate with the RanGTPase system which is necessary to regulate their interaction with the cargoes.

The NPC is composed of a large multiprotein structure of almost cylindrical appearance measuring 125 nm in width and 150-200 nm in length occurring at a density of 1-10 NPCs/$\mu m^2$ in the nuclear membrane (Keminer and Peters, 1999). The NPC forms an aqueous channel through which all of the transport proceeds. However, the transport mode depends on the type of substrate which is transported through the NPC. Whereas small molecules such as metabolites pass the NPC through passive diffusion, the efficiency of this transport mode decreases as the molecular weight increases due to the limited diameter of apparently 9 nm of this transport channel. This theory is evidenced by the observation that proteins of a size of <20-30 kDa diffuse relatively rapid through the NPC whereas bovine serum albumin (68 kDa, ~7 nm in diameter) diffuses exceedingly slowly through the NPC. Thus the transport of large proteins into the nucleus requires an active and selective transport mode which is based on specific transport signals. The channel which allows such transport mode opens to diameter of up to ~45 nm (Lewin et al., 2000).

The nuclear transport receptors bind their transport cargo in the cytoplasm through nuclear localization sequences (NLS) and subsequently mediate their translocation via direct interaction with the NPC to the nuclear side, release the cargo and finally return to the cytoplasm to begin a new shuttling cycle. Directionality of the transport process is accomplished through a RanGTP concentration gradient across the nuclear envelope, i.e. low cytoplasmic and high nuclear RanGTP concentration. RanGTP binds to the dimeric transport complex consisting of the nuclear transport receptor and the cargo in the nucleus thereby dissociating the cargo from the nuclear transport receptor resulting in the release of the cargo in the nucleus. In some cases the nuclear transport receptor does not bind directly to the transport substrate but requires an adapter molecule such as importin a (Gorlich and Kutay, 1999).

With respect to nuclear translocation of Cas9, Cong et al. 2013 showed that efficient targeting of the Cas9 protein to the nucleus was achieved using 2 NLS elements. Studies with Cas9 have been done using either NLS from SV40 T antigen alone (1 copy each at N- and C-terminal respectively: Fuji et al. 2013 or 2 copies at either N- or C-terminal) or in combination with that from nucleoplasmin (Cong et al. 2013). Both SV40 and nucleoplasmid NLS function in an Importin-α dependent manner.

Having NLS elements which target different nuclear transport receptors and/or mechanisms may increase the efficiency of nuclear translocation of Cas9 especially in non-dividing cells (as is most often the case in vivo) or under conditions when either one or both Importin-α/β become limiting. Moreover, it has been previously shown that the nuclear accumulation of transportin increases with its cytoplasmic concentration (Ribbeck and Gorlich, 2001). Therefore, the likelihood of a nuclear transport event is expected to increase with the increase in the number of binding sites available in the cytoplasm.

In certain embodiments, modified polyribonucleotides of the present disclosure may comprise one or more NLS-encoding sequences. In certain embodiments, said one or more NLS-encoding sequences are positioned 5' of the start codon or 3' of the termination codon of the Cas9 coding sequence of the modified polyribonucleotide. In certain embodiments, said one or more NLS-encoding sequences is separated from the Cas9 coding sequence by 1, 2, 3, 4, or 5 intervening nucleotides. In further embodiments, said one or more NLS-encoding sequences is separated from the Cas9 coding sequence by less than 50 intervening nucleotides. In certain embodiments, a modified polyribonucleotide may comprise one NLS-encoding sequence 5' of the start codon of the Cas9 coding sequence and one NLS-encoding sequence 3' of the termination codon of the Cas9 coding sequence. In certain embodiments, a modified polyribonucleotide may comprise two NLS-encoding sequences 5' of the start codon of the Cas9 coding sequence. In certain embodiments, a modified polyribonucleotide may comprise two NLS-encoding sequences 3' of the termination codon of the Cas9 coding sequence.

In any of the above described embodiments, a modified polyribonucleotide comprising an NLS-encoding sequence may comprise an NLS-encoding sequence derived from rpL23a (i.e. BIB). In any of the above described embodiments, a modified polyribonucleotide comprising an NLS-encoding sequence may comprise an NLS-encoding sequence greater than 70%, 75%, 80%, 85%, 90%, 95%, 97%, 98%, 99%, or 100% identical to SEQ ID NO: 70. In any of the above described embodiments, a modified polyribonucleotide comprising an NLS-encoding sequence may comprise an NLS-encoding sequence derived from TAT. In any of the above described embodiments, a modified polyribonucleotide comprising an NLS-encoding sequence may comprise an NLS-encoding sequence greater than 70%, 75%, 80%, 85%, 90%, 95%, 97%, 98%, 99%, or 100% identical to SEQ ID NO: 71. In any of the above described embodiments, a modified polyribonucleotide comprising an NLS-encoding sequence may comprise an NLS-encoding sequence derived from IBB domain. In any of the above described embodiments, a modified polyribonucleotide comprising an NLS-encoding sequence may comprise an NLS-encoding sequence greater than 70%, 75%, 80%, 85%, 90%, 95%, 97%, 98%, 99%, or 100% identical to SEQ ID NO: 72. In any of the above described embodiments, a modified polyribonucleotide comprising an NLS-encoding sequence may comprise an NLS-encoding sequence derived from SwitchII Loop. In any of the above described embodiments, a modified polyribonucleotide comprising an NLS-encoding sequence may comprise an NLS-encoding sequence greater than 70%, 75%, 80%, 85%, 90%, 95%, 97%, 98%, 99%, or 100% identical to SEQ ID NO: 73. In certain embodiments, a modified polyribonucleotide of the present disclosure may comprise a single NLS-encoding sequence of a given type, multiple NLS-encoding sequences of a given type, or multiple NLS-encoding sequence comprising a mixture of more than one type, wherein a type refers to a NLS-encoding sequence described above and depicted as DNA nucleotide sequence in Table 9. —

TABLE 9

| NLS | Source NLS-encoding DNA Sequence and SEQ ID NO. |
|---|---|
| rpL23a | gtgcacagccacaagaagaagaagatcagaaccagccccaccttcag aagacccaagaccctgagactgagaagacagcccaagtaccccagaa agagcgcccccagaagaaacaagctggaccactac (SEQ ID NO: 66) |
| TAT | ggcagaaagaagagaagacagagaagaagagccccc (SEQ ID NO: 67) |
| IBB domain | CACCGGATCAAGAGCTTCAAGAACAAGGGCCGGGACGTGGAA ACCATGCGGCGGCACAGAAACGAAGTGACCGTGGAACTGCGG AAGAACAAGCGGGACGAGCATCTGCTGAAGAAACGGAACGTG CCCCAGGAAGAGAGC (SEQ ID NO: 68) |
| SwitchII-Ran | gacacagccggccaggagaaattcggtggactgagagatggc (SEQ ID NO: 69) |

Exemplary Methods—Treatments and Conditions

The methods, polyribonucleotides, polynucleotides, and pharmaceutical compositions of this disclosure provide numerous in vivo and in vitro methods, and may be useful to treat a condition. The treatment may comprise treating a subject (e.g., a patient with a disease and/or a lab animal with a condition and/or an animal model of a condition). Given the applicability of CRISPR technology to nearly any condition influenced by aberrant gene expression, the technology may be applied to virtually any condition—depending on the particular sgRNA sequence employed. Moreover, the disclosure contemplates in vivo, as well as ex vivo approaches, such as using CRISPR systems to modify blood cells ex vivo and then returning the modified blood cells to a subject.

Compositions containing polyribonucleotides encoding Cas9 family member, such as those compositions described herein, can be administered along with appropriate sgRNA, to a subject in need thereof. In certain embodiments, as shown herein, the Cas9 encoding polyribonucleotide and sgRNA (or other similar component containing a complementarity region) may be co-administered, such as co-transfected, optionally co-formulated for delivering in lipoplexes or nanoparticles. Alternatively, such compositions may be administered to a population of cells ex vivo and, following transduction and expansion of the cells, the cells may be administered to a subject in need thereof. The particular subject in need thereof will vary depending on the sgRNA used and the condition to be treated. By way of non-limiting example, Cas9-sgRNA compositions for targeting PCSK9 are provided.

In certain embodiments, modified polyribonucleotides encoding Cas9 of the disclosure, such as the specific examples described herein, can be used, for example, to treat a condition associated with coronary heart disease (CDH), imbalance of low density lipoprotein (LDL), imbalance of LDL cholesterol, and/or hypercholesterolemia. Proprotein convertase subtilisin-like kexin type-9 (PCSK9) is a circulating endoprotease secreted primarily from the liver (Lagace, T. PCSK9 and LDLR degradation: regulatory mechanisms in circulation and in cells. Curr. Opin. Lipidol. 2014 October; 25(5): 387-393). PCSK9 binds to LDL receptor (LDLR) and promotes its internalization and lysosomal degradation, thereby preventing LDLR from binding LDL and removing LDL cholesterol from circulation. Increased LDL cholesterol levels are the major risk factor for CDH. By administering a composition comprising a modified polyribonucleotide encoding Cas9 in combination with a suitable sgRNA with complementarity to PCSK9 to a patient, genetic alterations may be targeted to the PCSK9 gene. Cas9-related polypeptides encoded by modified polyribonucleotides of the present disclosure can create double-stranded breaks in chromosomal DNA at a particular locus, for example the PCSK9 gene locus, based on the sequence complementarity of an associated sgRNA. Cas9-related polypeptides encoded by modified polyribonucleotides of the present disclosure may create single-stranded nicks (i.e. single-stranded breaks) in chromosomal DNA at a particular locus, for example the PCSK9 gene locus, based on the sequence complementarity of an associated sgRNA. Cas9-related polypeptides encoded by modified polyribonucleotides of the present disclosure may bind (without cleaving or nicking) chromosomal DNA at a particular locus, for example the PCSK9 gene locus, based on the sequence complementarity of an associated sgRNA. Cas9 catalyzed insertions and deletions may decrease PCSK9 expression and thus decrease LDL cholesterol. Cas9 catalyzed double-stranded breaks and single-stranded nicks may, in the presence of an appropriate DNA construct with homology to the PCSK9 gene, insert by homology-directed repair a desired DNA sequence, with effects including (but not necessarily limited to): a decrease in PCSK9 expression, and decrease in LDL cholesterol. Cas9 binding to the PCSK9 gene locus may modulate the expression of PCSK9 or modulate functions related to PCSK9. Cas9 binding to the PCSK9 gene locus may decrease expression of PCSK9.

A modified polyribonucleotide, a method, and a pharmaceutical composition of the disclosure can be used, for example, to treat other diseases or conditions, such as those caused or exacerbated by mutation or misregulation of a single gene.

Examples of polyribonucleotide sequences of the disclosure for use with these methods include SEQ ID Nos. 11-18, as well as sequence at least 90%, 91%, 92%, 93%, 94%, 95%, 96%, 97%, 98%, or 99% identical to any one or more of the foregoing. In certain embodiments, the polyribonucleotides are modified polyribonucleotides containing a combination of unmodified and modified ribonucleotides, wherein 30-45% of the uridines are analogs of uridine and 5-10% of the cytidines are analogs of cytidine. In certain embodiments, the modified polyribonucleotide contains a combination of unmodified and modified ribonucleotides, wherein 30-45% of uridines in said input mixture are analogs of uridine and 5-10% of cytidines in said input mixture are analogs of cytidine. In certain embodiments, the cytidine analog is 5-iodocytidine and the uridine analog is 5-iodouridine. Also contemplated is such modified polyribonucleotides having any of the analogs described herein or percentages or modified residues, as disclosed herein (e.g., type of analog and/or percentage of modification and/or presence or absence of particular modifications). In some embodiments, a polyribonucleotide of the disclosure encodes a Cas9 protein, such as a Cas9 protein described herein, or a protein comprising an amino acid sequence at least 90%, 91%, 92%, 93%, 94%, 95%, 96%, 97%, 98%, 99% or 100% identical thereto.

Other Uses

The methods, modified polyribonucleotides, and pharmaceutical compositions of this disclosure provide a method to deliver Cas9 expression or activity into cells. The CRISPR technology may be applied to any gene of interest—depending on the particularly complementarity regions, sgRNA sequences employed, presence or absence of mutations in the Cas9 used, and other factors. Moreover, the disclosure contemplates in vivo, as well as ex vivo uses. In certain embodiments, modified polyribonucleotides encoding Cas9 of the disclosure, such as the specific examples described herein, can be used, for example, to develop a model of a disease by targeting a gene known to be involved in the disease. In certain embodiments, modified polyribonucleotides encoding Cas9 of the disclosure, such as the specific examples described herein, can be used, for example, to manipulate cell fate by targeting a gene known to be involved in the cell fate determination.

By administering a composition comprising a modified polyribonucleotide encoding Cas9 (e.g., comprising a Cas9 coding sequence) in combination with a suitable sgRNA with complementarity to a gene target in a cell or animal, genetic alterations may be targeted to any gene of interest to deliver Cas9 expression or activity, for example, to develop a model of gene regulation, gene deregulation, or disease or to manipulate cell fate. Cas9-related polypeptides encoded by modified polyribonucleotides of the present disclosure can create double-stranded breaks in chromosomal DNA at a particular locus, for example the PCSK9 gene locus, based on the sequence complementarity of an associated sgRNA. Cas9-related polypeptides encoded by modified polyribonucleotides of the present disclosure may create single-stranded nicks (i.e. single-stranded breaks) in chromosomal DNA at a particular locus, for example the PCSK9 gene locus, based on the sequence complementarity of an associated sgRNA. Cas9-related polypeptides encoded by modified polyribonucleotides of the present disclosure may bind (without cleaving or nicking) chromosomal DNA at a particular locus, for example the PCSK9 gene locus, based on the sequence complementarity of an associated sgRNA. Cas9 catalyzed insertions and deletions may decrease PCSK9 expression. Cas9 catalyzed double-stranded breaks and single-stranded nicks may, in the presence of an appropriate DNA construct with homology to the PCSK9 gene, insert by homology-directed repair a desired DNA sequence, with effects including (but not necessarily limited to): a decrease in PCSK9 expression. Cas9 binding to the PCSK9 gene locus may modulate the expression of PCSK9 or modulate functions related to PCSK9. Cas9 binding to the PCSK9 gene locus may decrease expression of PCSK9. References to PCSK9 are purely exemplary, as this technology can be readily applied to virtually any gene target.

Examples of polyribonucleotide sequences of the disclosure for use with these methods include SEQ ID Nos. 11-18, as well as sequences at least 90%, 91%, 92%, 93%, 94%, 95%, 96%, 97%, 98%, or 99% identical to any one or more of the foregoing. In certain embodiments, the polyribonucleotides are modified polyribonucleotide containing a combination of unmodified and modified ribonucleotides, wherein 30-45% of the uridines are analogs of uridine and 5-10% of the cytidines are analogs of cytidine. In certain embodiments, the modified polyribonucleotide contains a combination of unmodified and modified ribonucleotides, wherein 30-45% of uridines in said input mixture are analogs of uridine and 5-10% of cytidines in said input mixture are analogs of cytidine. In certain embodiments, the cytidine analog is 5-iodocytidine and the uridine analog is 5-iodouridine. Also contemplated is such modified polyribonucleotides having any of the analogs described herein or percentages or modified residues, as disclosed herein (e.g., type of analog and/or percentage of modification and/or presence or absence of particular modifications). In some embodiments, a polyribonucleotide of the disclosure encodes a Cas9 protein, such as a Cas9 protein described herein, or a protein comprising an amino acid sequence at least 90%, 91%, 92%, 93%, 94%, 95%, 96%, 97%, 98%, 99% or 100% identical thereto.

EXEMPLIFICATION

The disclosure now being generally described, it will be more readily understood by reference to the following examples, which are included merely for purposes of illustrating certain embodiments of the present disclosure. These examples are not intended to limit the disclosure.

Example 1: Cas9 Polynucleotide and Polyribonucleotide Construction

CRISPR/Cas9 systems are known to be useful for genome editing and for increasing or decreasing the expression of target genes. SNIM RNA technology has been shown to decrease immunological response to transformed RNA in target cells. We evaluated a variety of plasmids and polyribonucleotides encoding Cas9, including modified polyribonucleotides comprising a mixture of unmodified and modified ribonucleotides. Two DNA plasmid vectors derived from pVAXA120 were generated, one comprising the nucleotide sequence (codon optimized; SEQ ID NO: 48) encoding wildtype *S. pyogenes* Cas9 and one comprising the nucleotide sequence (codon optimized; SEQ ID NO: 49) encoding D10A *S. pyogenes* Cas9. Such DNA plasmid vectors can be constructed using methods known in the art. The Cas9 sequences used in the present disclosure were codon optimized for expression in mammalian cells and disclosed by Cong et al.

SEQ ID NO: 48 corresponds to the wildtype Cas9 DNA coding sequence as disclosed by Cong et al. (cited herein)

SEQ ID NO: 49 corresponds to the D10A Cas9 DNA coding sequence as disclosed by Cong et al. (the mutated codon corresponding to D10A is indicated with lower case letters).

The plasmids further comprise sequences positioned to append nuclear localization signal peptides and FLAG tags to the Cas9 proteins expressed. The DNA constructs created are listed in Table 10.

TABLE 10

| Plasmid Name | FLAG-Tag | 5' UTR | 3' UTR | Theoretical PolyA length (nt) | Bases after PolyA (nt) |
|---|---|---|---|---|---|
| pVAXA120-Cas9 | Yes | 5p-UTR (DNA - SEQ ID NO: 46) (RNA - SEQ ID NO: 59) | 3p-UTR (SEQ ID NO: 47) (RNA - SEQ ID NO: 60) | 120 | 6 |
| pVAXA120-Cas9_D10A | Yes | 5p-UTR (SEQ ID NO: 46) (RNA - SEQ ID NO: 59) | 3p-UTR (SEQ ID NO: 47) (RNA - SEQ ID NO: 60) | 120 | 6 |
| p128 | No | Minimal (DNA - SEQ ID NO: 55) (RNA - SEQ ID NO: 7) | 5'-GAATT-3' | — | — |
| p129 | No | hAg (DNA - SEQ ID NO: 56) (RNA - SEQ ID NO: 8) | No | — | — |
| p130 | No | TISU + T (DNA - SEQ ID NO: 58) (RNA - SEQ ID NO: 10) | No | — | — |

The following sequence (SEQ ID NO: 46) corresponds to 5p-UTR; specifically the DNA sequence of the 5' UTR of the pVAXA120-Cas9 plasmid/vector noted above. The depicted sequence corresponds to one strand of the double-stranded nucleic acid.

```
                                              (SEQ ID NO: 46)
1  GGGAGACCCA AGCTGGCTAG CGTTTAAACT TAAGCTTGCC ACC
```

The following sequence (SEQ ID NO: 55) corresponds to the Minimal 5' UTR; specifically the DNA sequence of the 5' UTR used in the p128 plasmid/vector noted above. The depicted sequence corresponds to one strand of the double stranded nucleic acid.

```
                                              (SEQ ID NO: 55)
      1           GGGAGACGCC ACC
```

The following sequence (SEQ ID NO: 56) corresponds to the hAg 5' UTR; specifically the DNA sequence of a 5' UTR derived from human alpha globin and used in the 5' UTR of the p129 plasmid/vector noted above. The depicted sequence corresponds to one strand of the double stranded nucleic acid.

```
                                              (SEQ ID NO: 56)
1  GGGAGACTCT TCTGGTCCCC ACAGACTCAG AGAGAACGCC ACC
```

The following sequence (SEQ ID NO: 58) corresponds to the TISU+T 5' UTR; specifically the DNA sequence of the 5' UTR used in the p130 plasmid/vector noted above. The depicted sequence corresponds to one strand of the double-stranded nucleic acid

```
                                          (SEQ ID NO: 58)
     1          GGGAGACTGC CAAG
```

The following sequence (SEQ ID NO: 47) corresponds to the 3p-UTR; specifically the DNA sequence of the 3' UTR used in the pVAXA120-Cas9 plasmid/vector described above. The depicted sequence corresponds to one strand of the double-stranded nucleic acid. Of note, this particular 3'UTR contains a polyA tail of approximately 120 nucleotides. Similar 3'UTRs without such a polyA tail, or with a longer or shorter polyA tail are also contemplated.

```
                                                  (SEQ ID NO: 47)
     1 GAATTCCTAg gatccACTAG TCCAGTGTGG TGGAATTCTG CAGAAAAAAA

    51 AAAAAAAAAA AAAAAAAAAA AAAAAAAAAA AAAAAAAAAA AAAAAAAAAA

   101 AAAAAAAAAA AAAAAAAAAA AAAAAAAAAA AAAAAAAAAA AAAAAAAAAA

   151 AAAAAAAAAA AAAGCGGCC
```

A series of plasmids were thus constructed to express various Cas9 protein encoding polyribonucleotides, each comprising various UTRs. The sequence of the DNA strand encoding the polyribonucleotides is as follows.

SEQ ID NO: 31 corresponds to a nucleic acid sequence, such as a DNA sequence, comprising the 5p-UTR 5' UTR (SEQ ID NO: 46), wildtype FLAG-tagged Cas9 (SEQ ID NO: 52), and the 3p-UTR 3' UTR (SEQ ID NO: 47).

SEQ ID NO: 35 corresponds to a nucleic acid sequence, such as a DNA sequence, comprising the 5p-UTR 5' UTR (SEQ ID NO: 46), D10A Cas9 (SEQ ID NO: 53), and the 3p-UTR 3' UTR (SEQ ID NO: 47).

SEQ ID NO: 32 corresponds to a nucleic acid sequence, such as a DNA sequence, comprising the Minimal 5' UTR (SEQ ID NO: 55), wildtype Cas9 (SEQ ID NO: 48), and the sequence 5'-GAATT-3' 3' UTR.

SEQ ID NO: 36 corresponds to a nucleic acid sequence, such as a DNA sequence, comprising the Minimal 5' UTR (SEQ ID NO: 55), D10A Cas9 (SEQ ID NO: 49), and the sequence 5'-GAATT-3' 3' UTR.

SEQ ID NO: 33 corresponds to a nucleic acid sequence, such as a DNA sequence, comprising the hAg 5' UTR (SEQ ID NO: 56), wildtype Cas9 (SEQ ID NO: 48), and the sequence 5'-GAATT-3' 3' UTR.

SEQ ID NO: 37 corresponds to a nucleic acid sequence, such as a DNA sequence, comprising the hAg 5' UTR (SEQ ID NO: 56), D10A Cas9 (SEQ ID NO: 49), and the sequence 5'-GAATT-3' 3' UTR.

SEQ ID NO: 34 corresponds to a nucleic acid sequence, such as a DNA sequence, comprising the TISU+T 5' UTR (SEQ ID NO: 58), wildtype Cas9 (SEQ ID NO: 48), and the sequence 5'-GAATT-3' 3' UTR.

SEQ ID NO: 38 corresponds to a nucleic acid sequence, such as a DNA sequence, comprising the TISU+T 5' UTR (SEQ ID NO: 58), D10A Cas9 (SEQ ID NO: 49), and the sequence 5'-GAATT-3' 3' UTR.

Modified polyribonucleotides were generated using the plasmids listed in Table 10 and in vitro transcription methods known in the art and those described in US 2012/0195936 A1. Briefly, linearized plasmid DNA of the appropriate DNA construct listed in Table 10 was generated. The mMessage mMachine T7 Ultra Transcription Kit (Ambion, Thermofisher) and a mixture of canonical ribonucleotides and nucleotide analogs (i.e. modified nucleotides; analogs of or non-naturally occurring uridine, adenosine, cytidine, and/or guanosine) were utilized. Several different combinations and ratios of ribonucleotide analogs were tested. A summary of the modified polyribonucleotides created and their characteristics is listed in Table 11. Information regarding the primary sequences of the modified polyribonucleotides created follows after the Table.

TABLE 11

| Modified Polyribonucleotide Name and/or SEQ ID for primary nucleotide sequence | Plasmid Used | Analog Ribonucleotide I Name | Analog Ribonucleotide I Percentage | Analog Ribonucleotide II Name | Analog Ribonucleotide II Percentage |
|---|---|---|---|---|---|
| 015-T01 | pVAXA120-Cas9 | 2-thiouridine triphosphate (also referred to as 2-thiouridine) | 25% | 5-methylcytidine triphosphate (also referred to as 5-methylcytidine) | 25% |
| 015-T02 | pVAXA120-Cas9_D10A | 2-thiouridine triphosphate (also referred to as 2-thiouridine) | 25% | 5-methylcytidine triphosphate (also referred to as 5-methylcytidine) | 25% |
| 015-T03 | pVAXA120-Cas9 | — | — | — | — |
| 015-T04 | pVAXA120-Cas9_D10A | — | — | — | — |

TABLE 11-continued

| Modified Polyribonucleotide Name and/or SEQ ID for primary nucleotide sequence | Plasmid Used | Analog Ribonucleotide I Name | Analog Ribonucleotide I Percentage | Analog Ribonucleotide II Name | Analog Ribonucleotide II Percentage |
|---|---|---|---|---|---|
| 015-T05 (SEQ ID NO: 11) | pVAXA120-Cas9 | 5-iodouridine triphosphate (also referred to as 5-iodouridine) | 35% | 5-iodocytidine triphosphate (also referred to as 5-iodocytidine) | 7.5% |
| 015-T06 (SEQ ID NO: 12) | p128 | 5-iodouridine triphosphate (also referred to as 5-iodouridine) | 35% | 5-iodocytidine triphosphate (also referred to as 5-iodocytidine) | 7.5% |
| 015-T07 (SEQ ID NO: 13) | p129 | 5-iodouridine triphosphate (also referred to as 5-iodouridine) | 35% | 5-iodocytidine triphosphate (also referred to as 5-iodocytidine) | 7.5% |
| 015-T08 (SEQ ID NO: 14) | p130 | 5-iodouridine triphosphate (also referred to as 5-iodouridine) | 35% | 5-iodocytidine triphosphate (also referred to as 5-iodocytidine) | 7.5% |
| COMP | Purchased from Trilink, Cat# L-6125 | Pseudouridine | 100% | 5-methylcytidine | 100% |

SEQ ID NO: 11 corresponds to an RNA sequence comprising ribonucleotide versions of the 5p-UTR 5' UTR (SEQ ID NO: 59), FLAG-tagged wildtype Cas9 (SEQ ID NO: 61), and the 3p-UTR 3' UTR (SEQ ID NO: 60). Note that the primary polyribonucleotide sequence is the same in 015-T05, 015-T03, and 015-T01.

SEQ ID NO: 15 corresponds to an RNA sequence comprising ribonucleotide versions of the 5p-UTR 5' UTR (SEQ ID NO: 59), FLAG-tagged D10A Cas9 (SEQ ID NO: 62), and the 3p-UTR 3' UTR (SEQ ID NO: 60).

SEQ ID NO: 12 corresponds to an RNA sequence comprising a ribonucleotide version of the Minimal 5' UTR (SEQ ID NO: 7), wildtype Cas9 (SEQ ID NO: 1), and the sequence 5'-GAATT-3' 3' UTR.

SEQ ID NO: 16 corresponds to an RNA sequence comprising a ribonucleotide version of the Minimal 5' UTR (SEQ ID NO: 7), D10A Cas9 (SEQ ID NO: 2), and the sequence 5'-GAATT-3' 3' UTR.

SEQ ID NO: 13 corresponds to an RNA sequence comprising a ribonucleotide version of the hAg 5' UTR (SEQ ID NO: 8), wildtype Cas9 (SEQ ID NO: 1), and the sequence 5'-GAATT-3' 3' UTR.

SEQ ID NO: 17 corresponds to an RNA sequence comprising a ribonucleotide version of the hAg 5' UTR (SEQ ID NO: 8), D10A Cas9 (SEQ ID NO: 2), and the sequence 5'-GAATT-3' 3' UTR.

SEQ ID NO: 14 corresponds to an RNA sequence comprising a ribonucleotide version of the TISU+T 5' UTR (SEQ ID NO: 10), wildtype Cas9 (SEQ ID NO: 1), and the sequence 5'-GAATT-3' 3' UTR.

SEQ ID NO: 18 corresponds to an RNA sequence comprising a ribonucleotide version of the TISU+T 5' UTR (SEQ ID NO: 10), D10A Cas9 (SEQ ID NO: 2), and the sequence 5'-GAATT-3' 3' UTR.

Example 2: Cas9 Expression in HEK293 Cells

The expression of wildtype Cas9 in HEK293 cells was tested after transfection with modified polyribonucleotide 015-T05 preparations from two different production days (FIG. 1). Cells expressed Cas9 protein in a consistent manner following transfection, regardless of which RNA preparation cells were transfected with. As expected, transfecting cells with higher quantities of modified polyribonucleotide resulted in greater quantities of Cas9 recovered after lysis, demonstrating dose dependence of Cas9 expression in a population of cells. GAPDH levels, monitored as a control, remained consistent regardless of the quantity or production day of modified polyribonucleotide transfected.

$1\times10^6$HEK293 cells were seeded in 6 well plates and 24 hours later cells were transfected with 5, 1, or 0.5 μg of modified polyribonucleotide 015-T05. Cells were transfected using Lipofectamine MessengerMax, from ThermoFisher Scientific, using the manufacturer's instructions. Briefly, a 1:3 ratio of RNA:Messenger Max was used (e.g. 1 ug of total RNA: 3 uL of MessengerMax). For each transfection, Lipofectamine MesengerMax was diluted in medium without supplements and incubated for 10 minutes at room temperature. During incubation, Cas9 mRNA was diluted in water. After incubation, diluted RNA was mixed with Lipofectamine Messenger Max solution and incubated for an additional 5 minutes at room temperature. For transfection, lipolexes were transferred to each well.

24 hours after transfection, cells were lysed in 150 μl. SDS-PAGE and Western blotting were performed using 30 μl total cell lysate. For Western blot analysis, the following antibodies were used: anti-Cas9 (C15200203; Diagenode; 1:1000); anti-GAPDH (#5174; Cell Signalling; 1:5000); goat anti-mouse IgG-HRP (sc-2005; Santa Cruz; 1:10000); goat anti-rabbit-HRP (sc-2004; Santa Cruz; 1:10000).

Example 3: Cas9 Expression Over Time in HepG2 Cells

Figure 2:
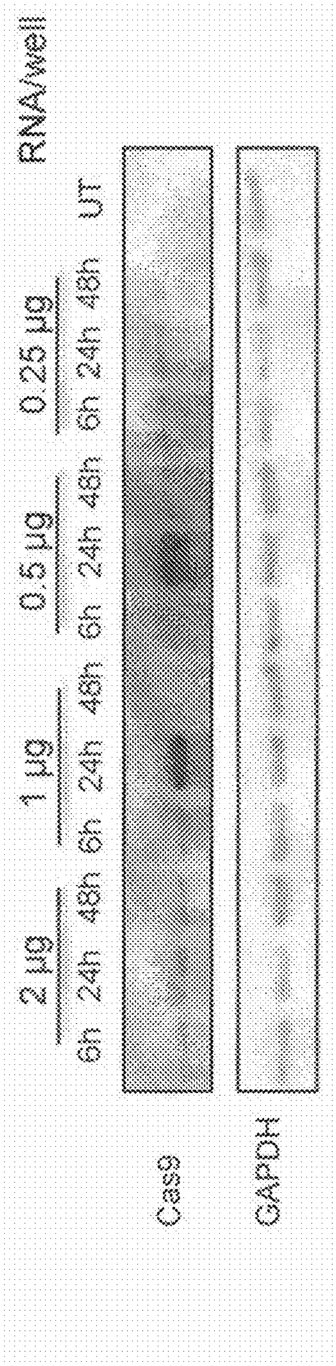
FIG. 2 shows a Western blot against Cas9 protein (top), and GAPDH (control, bottom) obtained from cells transfected with several different quantities of modified polyribonucleotides encoding Cas9, then lysed at varying times after transfection.

The expression of wildtype Cas9 in HepG2 cells was tested after transfection with modified polyribonucleotide 015-T05, measuring Cas9 protein expression at several time points during the first two days after transfection (FIG. 2).

Cas9 expression peaked at 24 hours post-transfection in samples transfected with 1 and 0.5 μg of modified polyribonucleotide and remaining steady over 48 hours in the sample transfected with 2 μg. Cas9 expression declined between 24 hours and 48 hours after transfection in all samples, but was detectable at both 6 and 48 hours post-transfection. GAPDH levels, monitored as a control, were steady in all sample lanes. From Examples 2 and 3, it is clear that 015-T05 transfection was sufficient to supply expression of Cas9 protein in human cells.

$1.5\times10^5$ HepG2 cells were seeded in 6 well plates and 24 hours later cells were transfected with 0.25, 0.5, 1, or 2 μg of modified polyribonucleotide 015-T05. Cells were transfected using Lipofectamine MessengerMax as described above. Cell samples were collected at 6, 24, and 48 hours post-transfection. Cells were lysed and SDS-PAGE and Western blotting were performed using the antibodies described above.

Example 4: Modified Polyribonucleotide-Expressed Cas9 Targeting Mutation of PCSK9 in HepG2 Cells Having determined that Cas9 can be expressed from a modified polyribonucleotide in several human cell lines, whether a modified polyribonucleotide based Cas9 system could specifically target double-stranded breaks (DSBs) to a desired location in the chromosomal DNA of HepG2 cells (derived from human liver cells) was investigated. For this experiment, PCSK9 was chosen as a target gene. PCSK9, proprotein convertase subtilisin/kexin type 9, binds to LDL receptor, which is responsible for removing LDL cholesterol from the blood. PCSK9 causes LDL receptor internalization and degradation. Accordingly, disrupting PCSK9 expression with a targeted insertion or deletion may be beneficial in subjects exhibiting higher than desired circulating LDL cholesterol levels.

sgRNAs with complementarity to regions of PCSK9 were designed to target Cas9 activity to the target gene. The sgRNA sequences are listed in Table 12. The PCSK9 complementary sequences are underlined (e.g., guide sequence). CRISPR-gRNA-hPCSK9-ETH1-5 were designed using the Zhang Lab algorithm; CRISPR-gRNA-hPCSK9-ETH6 is from Ding et al. 2014, Circulation Research. sgRNAs were constructed by in vitro transcription techniques known in the art, using T7 RNA polymerase and unmodified, canonical ribonucleotides, and purchased from Life Technologies.

TABLE 12

| Construct Name (For sgRNAs having complementarity sequence shown in right column) | PCSK9-targeting sgRNA Sequence |
|---|---|
| CRISPR-gRNA-hPCSK9-ETH1 | GGGGUGCUAGCCUUGCGUUCCGGUUUUAGA GCUAGAAAUAGCAAGUUAAAAUAAGGCUA GUCCGUUAUCAACUUGAAAAAGUGGCACCG AGUCGGUGC (SEQ ID NO: 21) |
| CRISPR-gRNA-hPCSK9-ETH2 | GGUCUUGGUGAGGUAUCCCCGGGUUUUAGA GCUAGAAAUAGCAAGUUAAAAUAAGGCUA GUCCGUUAUCAACUUGAAAAAGUGGCACCG AGUCGGUGC (SEQ ID NO: 22) |
| CRISPR-gRNA-hPCSK9-ETH3 | GGGUCGUGCUGGUCACCGCUGCGUUUUAGA GCUAGAAAUAGCAAGUUAAAAUAAGGCUA GUCCGUUAUCAACUUGAAAAAGUGGCACCG AGUCGGUGC (SEQ ID NO: 23) |
| CRISPR-gRNA-hPCSK9-ETH4 | GGCACCGACUUCAACAGCGUGCGUUUUAGA GCUAGAAAUAGCAAGUUAAAAUAAGGCUA GUCCGUUAUCAACUUGAAAAAGUGGCACCG AGUCGGUGC (SEQ ID NO: 24) |
| CRISPR-gRNA-hPCSK9-ETH5 | GGAUGCUGGGAUAAUUCGCUCCGUUUUAGA GCUAGAAAUAGCAAGUUAAAAUAAGGCUA GUCCGUUAUCAACUUGAAAAAGUGGCACCG AGUCGGUGC (SEQ ID NO: 25) |
| CRISPR-gRNA-hPCSK9-ETH6 | GGGGCUGAUGAGGCCGCACAUGGUUUUAGA GCUAGAAAUAGCAAGUUAAAAUAAGGCUA GUCCGUUAUCAACUUGAAAAAGUGGCACCG AGUCGGUGC (SEQ ID NO: 26) |

Figures 3A, 3B:
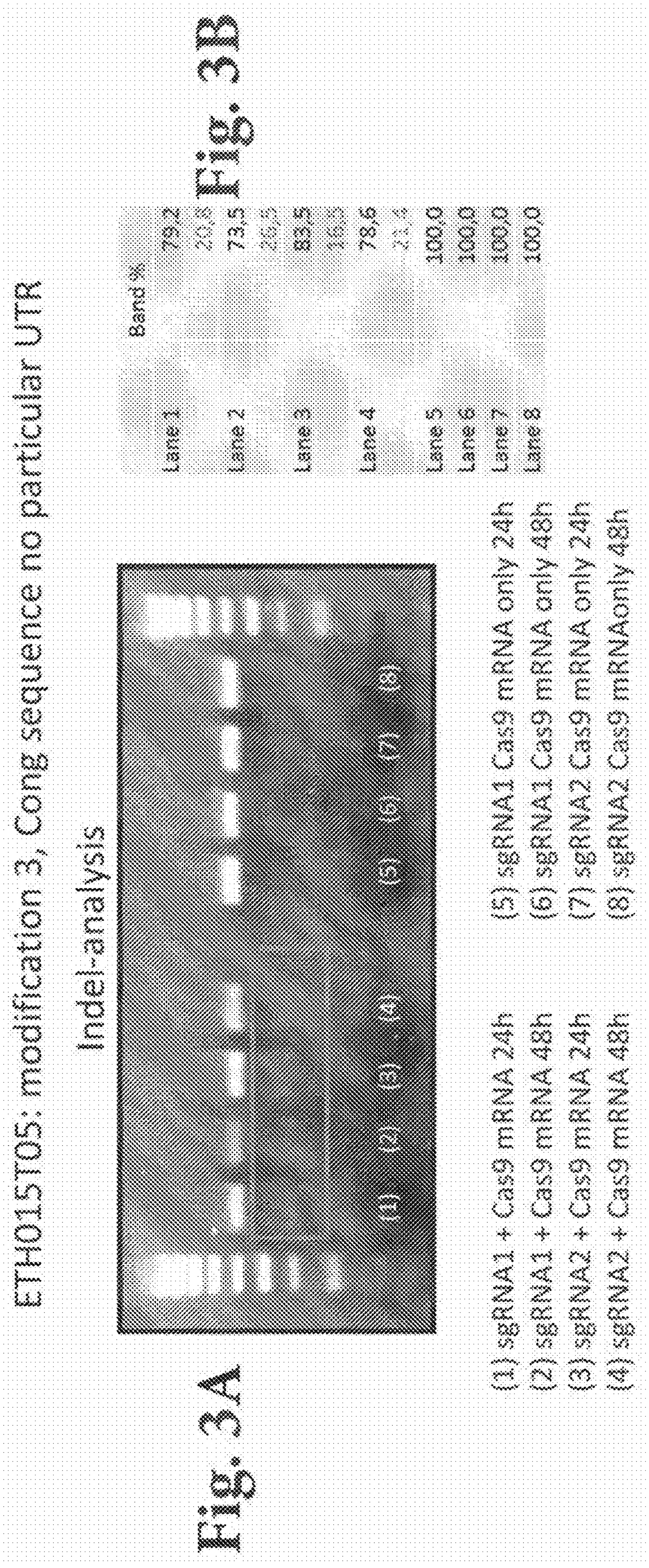
FIGS. 3A and 3B show Cas9 activity in HepG2 cells.

$1.5\times10^5$ HepG2 cells were seeded and transfected 24 hours later with 250 ng of 015-T05 and 25 ng of either sgRNA comprising hPCSK9-ETH1 (sgRNA1 in FIG. 3A) or sgRNA comprising hPCSK9-ETH2 (sgRNA2 in FIG. 3A) using Lipofectamine MessengerMax as described above. During incubation Cas9 modified polyribonucleotide and sgRNA are diluted in water (in a 1:10 ratio, e.g. 250 ng Cas9 modified polyribonucleotide and 25 ng sgRNA) for injection. Control transfections where only 015-T05 was transfected were also performed. 24 and 48 hours after transfection, cells were lysed, chromosomal DNA was isolated, and insertion deletion (Indel) analysis was performed (FIGS. 3A and 3B). Indel analysis techniques are known in the art. For Indel analysis, desired cleavage sites were amplified with PCR. 100 ng of gDNA of each sample was mixed with 5 μL Pfu 10× buffer with Mg2+, 5 μL of 2 mM dNTP mix, and 0.5 μL of Pfu polymerase. The forward and reverse primer pair for each target site were brought to 2 pM and water was added to a total volume of 40 μL. PCR samples were placed in a Mastercycler gradient (Eppendorf) using the following program: 95° C. for 10 min; 40 Cycles with 95° C. 30 sec, 60° C. 30 sec, 72° C. 1 min; 72° C. 5 min and a cooling step at 4° C. 2% Agarose gels were prepared. For detection of PCR products 5 μL of PeqGreen DNA/RNA Dye (PeQlab) was added and the solution was transferred to a gel chamber with 32 pocket ridges. After PCR, 2 μL of each sample was diluted with 10 μL WFI and 2 μL of 6× loading dye. 12 of each sample was loaded and gels were run at 160 V for 45 min. Bands were detected using ChemiDoc XRS+. In the following reannealing was performed. 12 μL of each PCR sample, 2 of NEB2 buffer, and 5 μL WFI were mixed and placed in the PCR cycler using following program: 95° C. 5 min; 95-85° C. (ramp down: 2.0°/s); 85-25° C. (ramp down 0.3°/s); cooling step at 4° C. Subsequently T7 Endonuclease I digestion was performed. For digestion 1 μL of T7 Endonuclease I enzyme was added to each reannealed sample and incubated for 15 min at 37° C. After digestion 2 μL of 0.25 mM EDTA solution was added to inhibit T7 Endonuclease. Again 2% Agarose gels were prepared and 3 μL 6× loading dye was added to each sample. After loading of samples gels were run at 160 V for 45 min. Bands were detected with ChemiDoc XRS+ and analyzed with ImageLab3 software using following formula:

$$Indels\ [\%] = \frac{Intensity_{digested\ band}}{Intensity_{digested\ band} + Intensity_{undigested\ band}} \times 100\%.$$

A lower molecular weight Indel product band appeared on visualized gels when cells were transfected with both modified polyribonucleotide encoding wildtype Cas9 (015-T05) AND sgRNA comprising guide sequences targeting PCSK9, but no Indel product was observed when cells were transfected with only 015-T05 (FIG. 3A). This indicates that a modified polyribonucleotide encoding Cas9, in conjunction with an sgRNA with PCSK9 complementarity, was sufficient to target specific sites in PCSK9 for DSBs in human liver cells. Quantification of the bands by densitometry (FIG. 3B) confirmed that digestion products are only present in lanes of samples where cells were transfected with both modified polyribonucleotide encoding Cas9 and sgRNAs with PCSK9 complementarity. Densitometry further showed that the amount of Indel product increased between 24 hours post-transfection and 48 hours post-transfection, suggesting that modified polyribonucleotide encoded Cas9 activity persists despite the decrease in Cas9 protein levels over the same time interval observed in at least one experiment (Example 3).

Example 5: Modified Polyribonucleotide-Expressed Cas9 Targeting Mutation of PCSK9 in AML12 Cells Whether a modified polyribonucleotide based Cas9 system could specifically target double-stranded breaks (DSBs) to the PCSK9 locus of the chromosomal DNA of AML12 cells (derived from mouse liver cells) was investigated. $5\times10^4$ AML12 cells were seeded in 24 well plates and were transfected 24 hours later with 250 ng of 015-T05 and 25 ng of either sgRNA comprising hPCSK9-ETH4 (sgRNA1 in FIG. 4A) or sgRNA comprising hPCSK9-ETH6 (sgRNA3 in FIG. 4A) using Lipofectamine MessengerMax as described above. Control transfections where only 015-T05 was transfected were also performed. 24 and 48 hours after transfection, cells were lysed, chromosomal DNA was isolated, and insertion deletion (Indel) analysis was performed (FIGS. 4A and 4B) as described in Example 4.

Figures 4A, 4B:
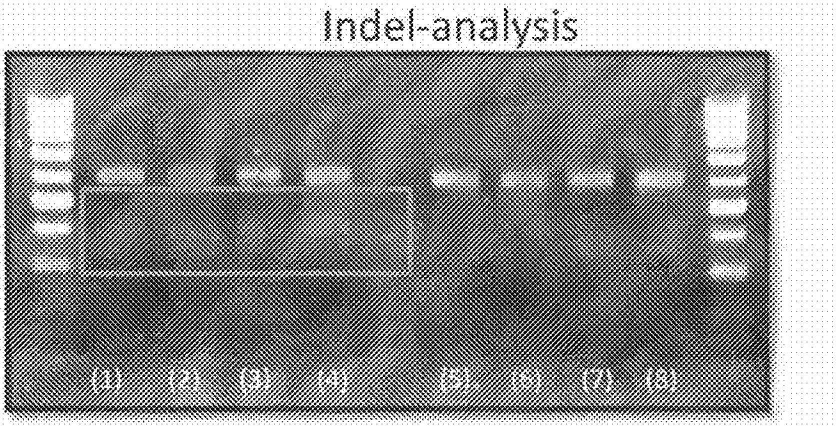
FIGS. 4A and 4B show Cas9 activity in AML12 cells.

A lower molecular weight Indel product band appeared on visualized gels when cells were transfected with both modified polyribonucleotide encoding wildtype Cas9 (015-T05) AND sgRNA comprising guide sequences targeting PCSK9, but no Indel product was observed when cells were transfected with only 015-T05 (FIG. 4A). This indicates that a modified polyribonucleotide encoding Cas9, in conjunction with an sgRNA with PCSK9 complementarity, was sufficient to specifically target sites in PCSK9 for DSBs in mouse liver cells. Quantification of the bands by densitometry (FIG. 4B) confirmed that digestion products are only present in lanes of samples where cells were transfected with both modified polyribonucleotide encoding Cas9 and sgRNAs with PCSK9 complementarity. Densitometry further showed that the amount of Indel product increased between 24 hours post-transfection and 48 hours post-transfection, suggesting that modified polyribonucleotide encoded Cas9 activity persists despite decreases in Cas9 protein levels over the same time interval observed in at least one experiment (Example 3).

Example 6: Modified Polyribonucleotide-Expressed Cas9 Targeting Knockdown of eGFP in HepG2 Cells Having determined that modified polyribonucleotide expressing Cas9 could, in conjunction with appropriate sgRNAs, target insertion/deletions to PCSK9, whether modified polyribonucleotide expressing Cas9 could be used to alter the levels of a marker protein, eGFP, expressed in HepG2 cells was investigated.

sgRNAs with complementarity to regions of eGFP were designed to target Cas9 activity to the target gene. The sgRNA sequences are listed in Table 13. The eGFP complementary sequences are underlined. CRISPR-gRNA-eGFP-ETH1-3 are from Fue et al. 2014, Nature Biotechnology; CRISPR-gRNA-eGFP-ETH1-3 were designed using the Geneart algorithm. sgRNAs were constructed by techniques known in the art, using T7 RNA polymerase and unmodified, canonical ribonucleotides, by Life Technologies.

TABLE 13

| Sequence Name ((For sgRNAs having complementarity sequence shown in right column)) | eGFP-targeting sgRNASequence |
|---|---|
| CRISPR-gRNA-eGFP-ETH1 | GGGGGCACGGGCAGCUUGCCGGGUUUUAGA GCUAGAAAUAGCAAGUUAAAAUAAGGCUA GUCCGUUAUCAACUUGAAAAAGUGGCACCG AGUCGGUGC (SEQ ID NO: 40) |
| CRISPR-gRNA-eGFP-ETH2 | GGGGUGGUGCAGAUGAACUUCAGUUUUAG AGCUAGAAAUAGCAAGUUAAAAUAAGGCU AGUCCGUUAUCAACUUGAAAAAGUGGCACC GAGUCGGUGC (SEQ ID NO: 41) |

TABLE 13-continued

Figures 5A, 5B:
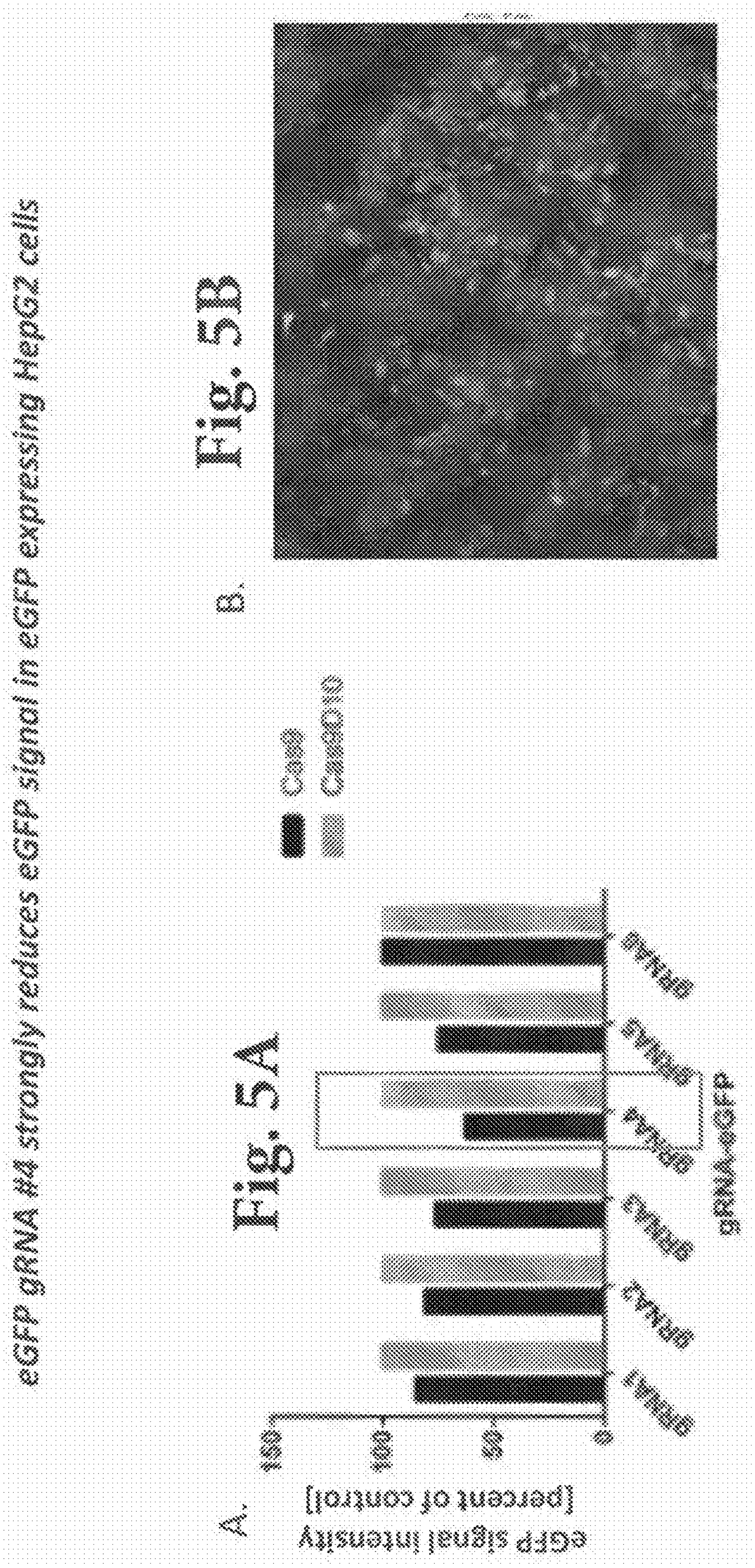
FIGS. 5A and 5B show Cas9 activity in eGFP-expressing HepG2 cells.

| Sequence Name ((For sgRNAs having complementarity sequence shown in right column)) | eGFP-targeting sgRNASequence |
|---|---|
| CRISPR-gRNA-eGFP-ETH3 | GGGGGCGAGGAGCUGUUCACCGGUUUUAGA<br>GCUAGAAAUAGCAAGUUAAAAUAAGGCUA<br>GUCCGUUAUCAACUUGAAAAAGUGGCACCG<br>AGUCGGUGC (SEQ ID NO: 42) |
| CRISPR-gRNA-eGFP-ETH4 | GGCAUGCCCGAAGGCUACGUCCGUUUUAGA<br>GCUAGAAAUAGCAAGUUAAAAUAAGGCUA<br>GUCCGUUAUCAACUUGAAAAAGUGGCACCG<br>AGUCGGUGC (SEQ ID NO: 43) |
| CRISPR-gRNA-eGFP-ETH5 | GGCGGCCAUGAUAUAGACGUUGGUUUUAG<br>AGCUAGAAAUAGCAAGUUAAAAUAAGGCU<br>AGUCCGUUAUCAACUUGAAAAAGUGGCACC<br>GAGUCGGUGC (SEQ ID NO: 44) |
| CRISPR-gRNA-eGFP-ETH6 | GGAGCGUGUCCGGCGAGGGCGAGUUUUAGA<br>GCUAGAAAUAGCAAGUUAAAAUAAGGCUA<br>GUCCGUUAUCAACUUGAAAAAGUGGCACCG<br>AGUCGGUGC (SEQ ID NO: 45) |

eGFP-expressing HepG2 cells were constructed using Lentiviral vectors. The eGFP-expressing HepG2 cells were seeded in 6 well plates. Briefly, these cells were made by transducing HepG2 cells with lentiviral vectors to express eGFP. Cells were transfected at 24 and 48 hours post-seeding with either (i) 015-T05 (encoding wildtype Cas9) and one of the six sgRNAs noted above or (ii) 015-T02 (encoding D10A Cas9) and one of the six sgRNAs noted above, where each of the six sgRNAs comprised an eGFP complementarity sequence as defined in Table 13. 48 hours after the second transfection, eGFP fluorescence was assessed by flow cytometry (FIG. 5).

Lower eGFP signal was observed when eGFP-expressing HepG2 cells were transfected with modified polyribonucleotide encoding wildtype Cas9 (015-T05) and sgRNAs ETH1-5 (gRNAs 1-5 in FIG. 5A), as compared to cells transfected with modified polyribonucleotide encoding Cas9 D10A (015-T02) and sgRNAs ETH1-5. sgRNA ETH4 caused a particularly marked reduction in eGFP signal when transfected with wildtype Cas9 polyribonucleotide, while sgRNA ETH6 (gRNA6 in FIG. 5A) caused no noticeable reduction in eGFP signal when paired with either Cas9 polyribonucleotide. This indicates that a modified polyribonucleotide encoding Cas9, in conjunction with an sgRNA with target gene complementarity, was sufficient to lower target protein levels in human liver cells. The data also demonstrated that D10A Cas9, even with sgRNAs that were proven to specifically target a gene, did not significantly affect target protein levels in a transfected cell. This negative result could be useful, given other applications described in the present disclosure rely on the specificity of Cas9:sgRNA locus targeting but not on the insertion/deletion or expression disruption activities. Each sgRNA, when transfected with polyribonucleotide encoding wildtype Cas9, elicited a different level of eGFP signal reduction, suggesting differing efficacies of different sgRNAs at targeting Cas9 activity to their site of complementarity. The sgRNAs thus also offered an opportunity for tuning Cas9 target binding and/or activity to a particular need.

Example 7: Cas9 Expression in HEK293 and HepG2 Cells

Figures 6A, 6B:
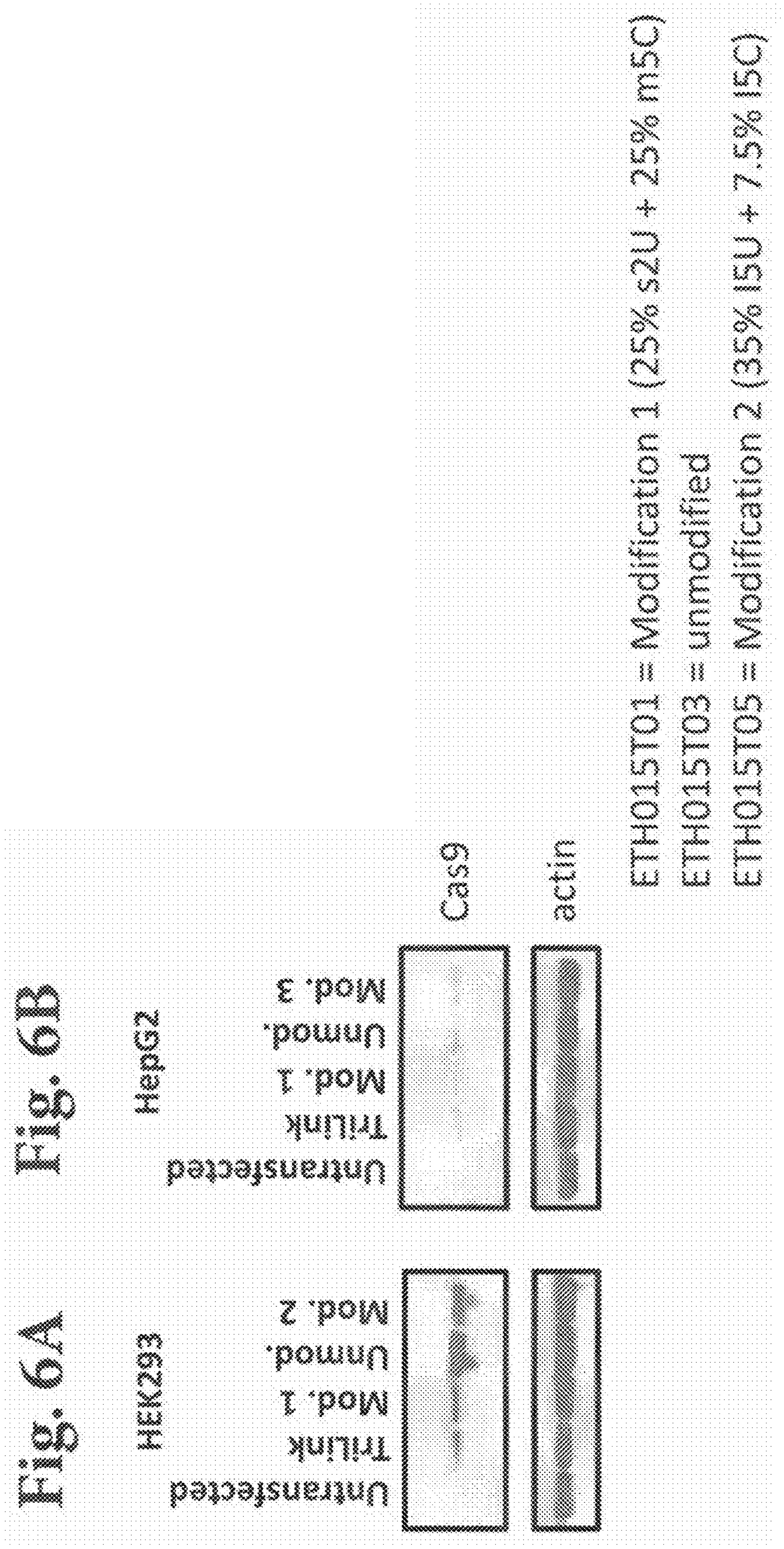
FIGS. 6A and 6B show Western blots against Cas9 (top) and actin (control, bottom) obtained from HEK293 cells or HepG2 cells, respectively, transfected with Cas9-encoding modified polyribonucleotides comprising several different selections and ratios of nucleotide analogs (i.e. modified nucleotides or non-naturally occurring nucleotides).

The levels of expression of different modified polyribonucleotide constructs encoding wildtype Cas9 were investigated in two human cell lines: HEK293 and HepG2. Cells were seeded in 6 well plates. 24 hours after seeding cells were transfected with 5 μg of one of four Cas9-encoding polyribonucleotide variants, each differing in its ribonucleotide analog composition (see Table 11): 015-T01 (Mod. 1 in FIGS. 6A and 6B), 015-T05 (Mod. 2 in FIGS. 6A and 6B), 015-T03 (Unmod. in FIGS. 6A and 6B), and COMP (Tri-Link in FIGS. 6A and 6B). Lipofectamine2000 was used for transfection (ThermoFisher). 24 hours after transfection, cells were lysed and SDS-PAGE and Western blotting were performed to detect the levels of Cas9 protein present in cell lysates (FIGS. 6A and 6B). Actin was used as a control.

At 24 hours after transfection, Cas9 expression was detected by Western blot in this experiment in HEK293 cells transfected with any of the Cas9-encoding polyribonucleotides tested (FIG. 6A). Of the modified polyribonucleotides, 015-T05 showed the highest Cas9 expression. 015-T05 was in vitro transcribed using a nucleotide input mixture containing 35% 5-iodouridine triphosphate (65% uridine triphosphate) and 7.5% 5-iodocytidine triphosphate (92.5% cytidine triphosphate). 015-T01 was in vitro transcribed using a nucleotide input mixture containing 25% 2-thiouridine triphosphate (75% uridine triphosphate) and 25% 5-methylcytidine triphosphate (75% cytidine triphosphate). COMP contains 100% pseudouridine and 100% 5-methylcytidine at all available uridine and cytidine sites, respectively.

At 24 hours after transfection, Cas9 expression was detected by Western blot in this experiment in HepG2 cells transfected with 015-T03 and 015-T05 (FIG. 6B).

Example 8: Impact of UTRs on Cas9 Expression in HEK293 Cells

The effects of several 5' UTR sequences on the expression of Cas9 from modified polyribonucleotides with analog compositions similar to 015-T05 were investigated (see Table 11).

Figure 7:
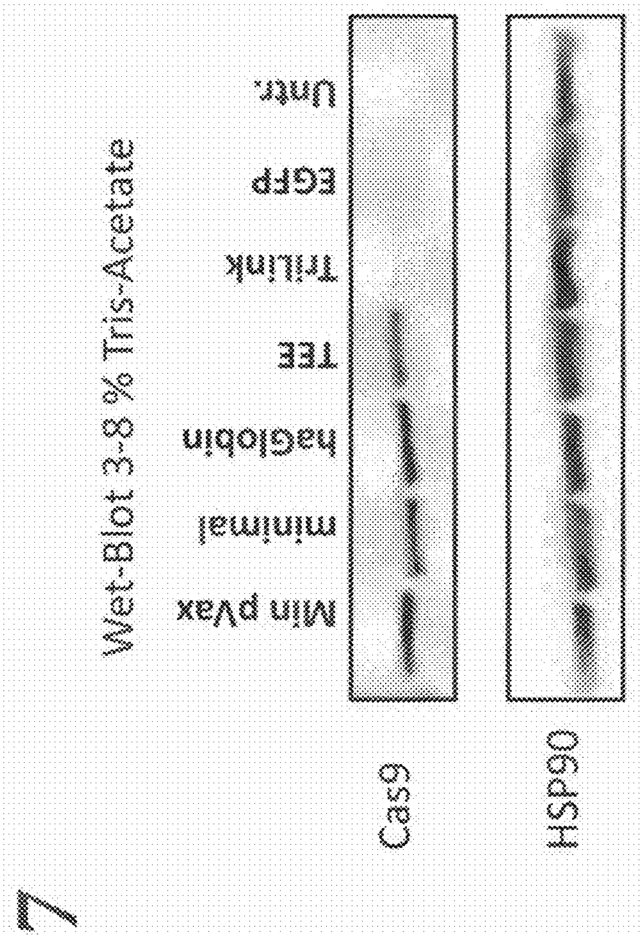
FIG. 7 shows the impact of UTRs on expression of Cas9 in HEK293 cells.

$1\times10^6$HEK293 cells were seeded in 6 well plates. 24 hours after seeding, cells were transfected with 5 μg of one of 015-T05, 015-T06, 015-T07, 015-T08, or COMP. MessengerMax was used for transfection as described above. 24 hours after transfection, cells were lysed and analyzed by SDS-PAGE and Western blot against Cas9 (FIG. 7). Cells were also transfected with eGFP-expressing polyribonucleotides as a mock transfection control. HSP90 served as a control.

The Min pVax lane corresponds to samples transfected with modified polyribonucleotide comprising the 5p-UTR (015-T05), the minimal lane corresponds to samples transfected with modified polyribonucleotide comprising the minimal UTR (015-T06), the haGlobin lane corresponds to samples transfected with modified polyribonucleotide comprising the hAg UTR (015-T07), the TEE lane corresponds to samples transfected with modified polyribonucleotide comprising the TISU+T UTR (015-T08), and the TriLink lane corresponds to samples transfected with COMP polyribonucleotide. The eGFP lane corresponds to samples transfected with eGFP-expressing polyribonucleotide. The Untr. lane corresponds to samples that were not transfected with polyribonucleotide.

Cas9 expression was detected via Western blotting from all samples transfected with 015-T05, 015-T06, 015-T07, and 015-T08, respectively (FIG. 7). Little or no Cas9 expression was detected after transfection of COMP compositions having 100% analogs of uridine and 100% analogs of cytidine.

For Western blot analysis, the following antibodies were used: Anti-Cas9 (C15200203; Diagenode; 1:1000); Anti-Actin (sc-81178; STCBT; 1:500); Anti-Hsp90 (TA500494; Origene; 1:5000); Goat-anti mouse IgG-HRP (sc-2005; Santa Cruz; 1:10000).

Example 9: Impacts of UTRs on Cas9 Expression in AML12 Cells

Figure 8A:
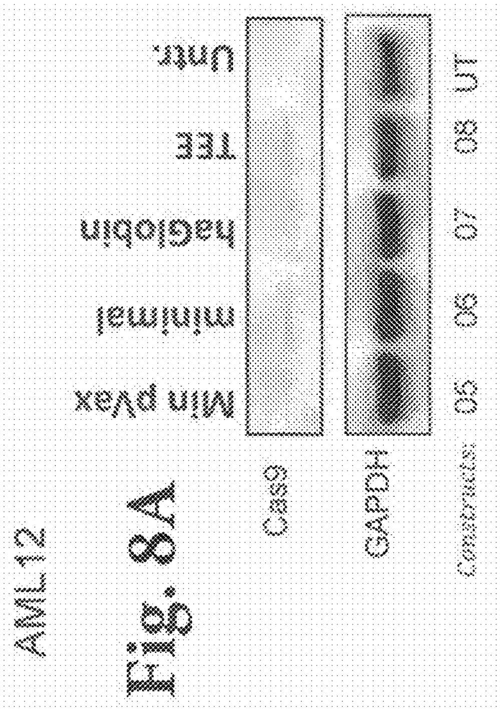
FIGS. 8A and 8B show a Western blot against Cas9 (top) and GAPDH (load control, bottom) obtained from mouse liver-derived AML12 cells and HepG2 cells, respectively, transfected with Cas9-encoding modified polyribonucleotides comprising several different 5' UTR sequences. Labeling nomenclature is as in FIG. 7.
Figure 8B:
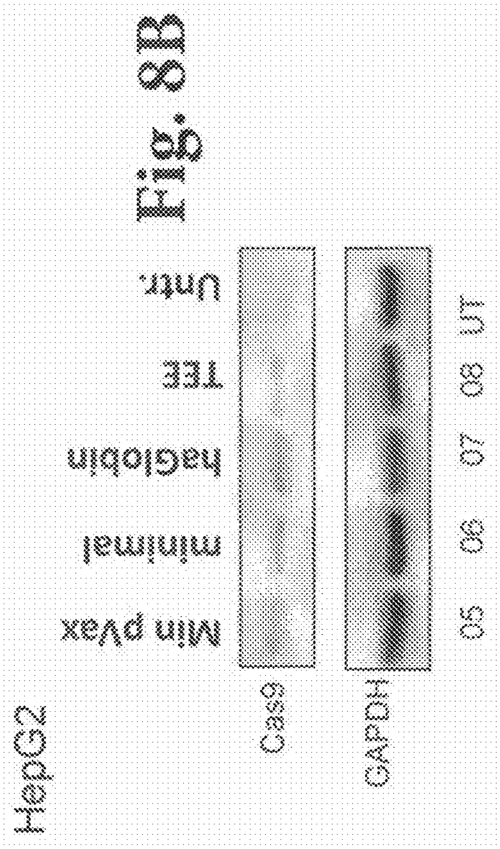

The effects of the 5' UTRs examined in Example 8 on Cas9 expression following transfection of modified polyribonucleotides into AML12 cells (FIG. 8A) and HepG2 cells (FIG. 8B) were investigated. Cells were seeded in 6 well plates. 24 hours after seeding, cells were transfected with 5 μg of one of 015-T05, 015-T06, 015-T07, 015-T08, or COMP. MessengerMax was used for transfection as described above. 24 hours after transfection, cells were lysed and analyzed by Western blot against Cas9. GAPDH was used as a control. Labeling nomenclature in FIGS. 8A and 8B is the same as that used in FIG. 7. Cas9 protein expression was detected via Western blotting from all samples transfected with 015-T05, 015-T06, 015-T07, and 015-T08, respectively (FIGS. 8A and 8B).

Exemplary sequences described in the application are provided below. The disclosure provides, in some embodiments, polynucleotides comprising, for example, the sequence set forth in SEQ ID NO: 1 or 2, or a sequence at least 95%, 96%, 97%, 98%,or 99% identical to such sequences, or a polyribonucleotide sequence, such as an mRNA, corresponding to or encoded by any of the foregoing. In some embodiments, the disclosure provides polynucleotides comprising any of the foregoing sequences, but in the presence or absence of a FLAG and/or HA tag and/or a myc tag. In certain embodiments of any of the foregoing, the polynucleotide or polyribonucleotide is modified (e.g., comprises nucleotide analogues, as described herein).

```
SEQUENCE LISTING
The following polyribonucleotide (e.g., RNA) sequence
(SEQ ID NO: 1) encodes wildtype Cas9.
                                                  (SEQ ID NO: 1)
  1  AUGGCCCCAA AGAAGAAGCG GAAGGUCGGU AUCCACGGAG UCCCAGCAGC

 51  CGACAAGAAG UACAGCAUCG GCCUGGACAU CGGCACCAAC UCUGUGGGCU

101  GGGCCGUGAU CACCGACGAG UACAAGGUGC CCAGCAAGAA AUUCAAGGUG

151  CUGGGCAACA CCGACCGGCA CAGCAUCAAG AAGAACCUGA UCGGAGCCCU

201  GCUGUUCGAC AGCGGCGAAA CAGCCGAGGC CACCCGGCUG AAGAGAACCG

251  CCAGAAGAAG AUACACCAGA CGGAAGAACC GGAUCUGCUA UCUGCAAGAG

301  AUCUUCAGCA ACGAGAUGGC CAAGGUGGAC GACAGCUUCU UCCACAGACU

351  GGAAGAGUCC UUCCUGGUGG AAGAGGAUAA GAAGCACGAG CGGCACCCCA

401  UCUUCGGCAA CAUCGUGGAC GAGGUGGCCU ACCACGAGAA GUACCCCACC

451  AUCUACCACC UGAGAAAGAA ACUGGUGGAC AGCACCGACA AGGCCGACCU

501  GCGGCUGAUC UAUCUGGCCC UGGCCCACAU GAUCAAGUUC CGGGGCCACU

551  UCCUGAUCGA GGGCGACCUG AACCCCGACA ACAGCGACGU GGACAAGCUG

601  UUCAUCCAGC UGGUGCAGAC CUACAACCAG CUGUUCGAGG AAAACCCCAU

651  CAACGCCAGC GGCGUGGACG CCAAGGCCAU CCUGUCUGCC AGACUGAGCA

701  AGAGCAGACG GCUGGAAAAU CUGAUCGCCC AGCUGCCCGG CGAGAAGAAG

751  AAUGGCCUGU UCGGAAACCU GAUUGCCCUG AGCCUGGGCC UGACCCCCAA

801  CUUCAAGAGC AACUUCGACC UGGCCGAGGA UGCCAAACUG CAGCUGAGCA

851  AGGACACCUA CGACGACGAC CUGGACAACC UGCUGGCCCA GAUCGGCGAC

901  CAGUACGCCG ACCUGUUUCU GGCCGCCAAG AACCUGUCCG ACGCCAUCCU

951  GCUGAGCGAC AUCCUGAGAG UGAACACCGA GAUCACCAAG GCCCCCCUGA
```

-continued

1001 GCGCCUCUAU GAUCAAGAGA UACGACGAGC ACCACCAGGA CCUGACCCUG
1051 CUGAAAGCUC UCGUGCGGCA GCAGCUGCCU GAGAAGUACA AAGAGAUUUU
1101 CUUCGACCAG AGCAAGAACG GCUACGCCGG CUACAUUGAC GGCGGAGCCA
1151 GCCAGGAAGA GUUCUACAAG UUCAUCAAGC CCAUCCUGGA AAAGAUGGAC
1201 GGCACCGAGG AACUGCUCGU GAAGCUGAAC AGAGAGGACC UGCUGCGGAA
1251 GCAGCGGACC UUCGACAACG GCAGCAUCCC CCACCAGAUC CACCUGGGAG
1301 AGCUGCACGC CAUUCUGCGG CGGCAGGAAG AUUUUUACCC AUUCCUGAAG
1351 GACAACCGGG AAAAGAUCGA GAAGAUCCUG ACCUUCCGCA UCCCCUACUA
1401 CGUGGGCCCU CUGGCCAGGG GAAACAGCAG AUUCGCCUGG AUGACCAGAA
1451 AGAGCGAGGA AACCAUCACC CCCUGGAACU UCGAGGAAGU GGUGGACAAG
1501 GGCGCUUCCG CCCAGAGCUU CAUCGAGCGG AUGACCAACU UCGAUAAGAA
1551 CCUGCCCAAC GAGAAGGUGC UGCCCAAGCA CAGCCUGCUG UACGAGUACU
1601 UCACCGUGUA UAACGAGCUG ACCAAAGUGA AAUACGUGAC CGAGGGAAUG
1651 AGAAAGCCCG CCUUCCUGAG CGGCGAGCAG AAAAAGGCCA UCGUGGACCU
1701 GCUGUUCAAG ACCAACCGGA AAGUGACCGU GAAGCAGCUG AAAGAGGACU
1751 ACUUCAAGAA AAUCGAGUGC UUCGACUCCG UGGAAAUCUC CGGCGUGGAA
1801 GAUCGGUUCA ACGCCUCCCU GGGCACAUAC CACGAUCUGC UGAAAAUUAU
1851 CAAGGACAAG GACUUCCUGG ACAAUGAGGA AAACGAGGAC AUUCUGGAAG
1901 AUAUCGUGCU GACCCUGACA CUGUUUGAGG ACAGAGAGAU GAUCGAGGAA
1951 CGGCUGAAAA CCUAUGCCCA CCUGUUCGAC GACAAAGUGA UGAAGCAGCU
2001 GAAGCGGCGG AGAUACACCG GCUGGGGCAG GCUGAGCCGG AAGCUGAUCA
2051 ACGGCAUCCG GGACAAGCAG UCCGGCAAGA CAAUCCUGGA UUUCCUGAAG
2101 UCCGACGGCU UCGCCAACAG AAACUUCAUG CAGCUGAUCC ACGACGACAG
2151 CCUGACCUUU AAAGAGGACA UCCAGAAAGC CCAGGUGUCC GGCCAGGGCG
2201 AUAGCCUGCA CGAGCACAUU GCCAAUCUGG CCGGCAGCCC CGCCAUUAAG
2251 AAGGGCAUCC UGCAGACAGU GAAGGUGGUG GACGAGCUCG UGAAAGUGAU
2301 GGGCCGGCAC AAGCCCGAGA ACAUCGUGAU CGAAAUGGCC AGAGAGAACC
2351 AGACCACCCA GAAGGGACAG AAGAACAGCC GCGAGAGAAU GAAGCGGAUC
2401 GAAGAGGGCA UCAAAGAGCU GGGCAGCCAG AUCCUGAAAG AACACCCCGU
2451 GGAAAACACC CAGCUGCAGA ACGAGAAGCU GUACCUGUAC UACCUGCAGA
2501 AUGGGCGGGA UAUGUACGUG GACCAGGAAC UGGACAUCAA CCGGCUGUCC
2551 GACUACGAUG UGGACCAUAU CGUGCCUCAG AGCUUUCUGA AGGACGACUC
2601 CAUCGACAAC AAGGUGCUGA CCAGAAGCGA CAAGAACCGG GGCAAGAGCG
2651 ACAACGUGCC CUCCGAAGAG GUCGUGAAGA AGAUGAAGAA CUACUGGCGG
2701 CAGCUGCUGA ACGCCAAGCU GAUUACCCAG AGAAAGUUCG ACAAUCUGAC
2751 CAAGGCCGAG AGAGGCGGCC UGAGCGAACU GGAUAAGGCC GGCUUCAUCA
2801 AGAGACAGCU GGUGGAAACC CGGCAGAUCA CAAAGCACGU GGCACAGAUC
2851 CUGGACUCCC GGAUGAACAC UAAGUACGAC GAGAAUGACA AGCUGAUCCG
2901 GGAAGUGAAA GUGAUCACCC UGAAGUCCAA GCUGGUGUCC GAUUUCCGGA
2951 AGGAUUUCCA GUUUUACAAA GUGCGCGAGA UCAACAACUA CCACCACGCC

-continued

```
3001 CACGACGCCU ACCUGAACGC CGUCGUGGGA ACCGCCCUGA UCAAAAAGUA

3051 CCCUAAGCUG GAAAGCGAGU UCGUGUACGG CGACUACAAG GUGUACGACG

3101 UGCGGAAGAU GAUCGCCAAG AGCGAGCAGG AAAUCGGCAA GGCUACCGCC

3151 AAGUACUUCU UCUACAGCAA CAUCAUGAAC UUUUUCAAGA CCGAGAUUAC

3201 CCUGGCCAAC GGCGAGAUCC GGAAGCGGCC UCUGAUCGAG ACAAACGGCG

3251 AAACCGGGGA GAUCGUGUGG GAUAAGGGCC GGGAUUUUGC CACCGUGCGG

3301 AAAGUGCUGA GCAUGCCCCA AGUGAAUAUC GUGAAAAAGA CCGAGGUGCA

3351 GACAGGCGGC UUCAGCAAAG AGUCUAUCCU GCCCAAGAGG AACAGCGAUA

3401 AGCUGAUCGC CAGAAAGAAG GACUGGGACC CUAAGAAGUA CGGCGGCUUC

3451 GACAGCCCCA CCGUGGCCUA UUCUGUGCUG GUGGUGGCCA AAGUGGAAAA

3501 GGGCAAGUCC AAGAAACUGA AGAGUGUGAA AGAGCUGCUG GGGAUCACCA

3551 UCAUGGAAAG AAGCAGCUUC GAGAAGAAUC CCAUCGACUU UCUGGAAGCC

3601 AAGGGCUACA AAGAAGUGAA AAAGGACCUG AUCAUCAAGC UGCCUAAGUA

3651 CUCCCUGUUC GAGCUGGAAA ACGGCCGGAA GAGAAUGCUG GCCUCUGCCG

3701 GCGAACUGCA GAAGGGAAAC GAACUGGCCC UGCCCUCCAA AUAUGUGAAC

3751 UUCCUGUACC UGGCCAGCCA CUAUGAGAAG CUGAAGGGCU CCCCCGAGGA

3801 UAAUGAGCAG AAACAGCUGU UUGUGGAACA GCACAAGCAC UACCUGGACG

3851 AGAUCAUCGA GCAGAUCAGC GAGUUCUCCA AGAGAGUGAU CCUGGCCGAC

3901 GCUAAUCUGG ACAAAGUGCU GUCCGCCUAC AACAAGCACC GGGAUAAGCC

3951 CAUCAGAGAG CAGGCCGAGA AUAUCAUCCA CCUGUUUACC CUGACCAAUC

4001 UGGGAGCCCC UGCCGCCUUC AAGUACUUUG ACACCACCAU CGACCGGAAG

4051 AGGUACACCA GCACCAAAGA GGUGCUGGAC GCCACCCUGA UCCACCAGAG

4101 CAUCACCGGC CUGUACGAGA CACGGAUCGA CCUGUCUCAG CUGGGAGGCG

4151 ACAAAAGGCC GGCGGCCACG AAAAAGGCCG GCCAGGCAAA AAAGAAAAAG

4201 UAA
```

The following polyribonucleotide (e.g., RNA) sequence (SEQ ID NO: 2) encodes D10A Cas9.

```
                                                (SEQ ID NO: 2)
   1 AUGGCCCCAA AGAAGAAGCG GAAGGUCGGU AUCCACGGAG UCCCAGCAGC

  51 CGACAAGAAG UACAGCAUCG GCCUGgccAU CGGCACCAAC UCUGUGGGCU

 101 GGGCCGUGAU CACCGACGAG UACAAGGUGC CCAGCAAGAA AUUCAAGGUG

 151 CUGGGCAACA CCGACCGGCA CAGCAUCAAG AAGAACCUGA UCGGAGCCCU

 201 GCUGUUCGAC AGCGGCGAAA CAGCCGAGGC CACCCGGCUG AAGAGAACCG

 251 CCAGAAGAAG AUACACCAGA CGGAAGAACC GGAUCUGCUA UCUGCAAGAG

 301 AUCUUCAGCA ACGAGAUGGC CAAGGUGGAC GACAGCUUCU UCCACAGACU

 351 GGAAGAGUCC UUCCUGGUGG AAGAGGAUAA GAAGCACGAG CGGCACCCCA

 401 UCUUCGGCAA CAUCGUGGAC GAGGUGGCCU ACCACGAGAA GUACCCCACC

 451 AUCUACCACC UGAGAAAGAA ACUGGUGGAC AGCACCGACA AGGCCGACCU

 501 GCGGCUGAUC UAUCUGGCCC UGGCCCACAU GAUCAAGUUC CGGGGCCACU

 551 UCCUGAUCGA GGGCGACCUG AACCCCGACA ACAGCGACGU GGACAAGCUG

 601 UUCAUCCAGC UGGUGCAGAC CUACAACCAG CUGUUCGAGG AAAACCCCAU

 651 CAACGCCAGC GGCGUGGACG CCAAGGCCAU CCUGUCUGCC AGACUGAGCA
```

-continued

701 AGAGCAGACG GCUGGAAAAU CUGAUCGCCC AGCUGCCCGG CGAGAAGAAG

751 AAUGGCCUGU UCGGAAACCU GAUUGCCCUG AGCCUGGGCC UGACCCCCAA

801 CUUCAAGAGC AACUUCGACC UGGCCGAGGA UGCCAAACUG CAGCUGAGCA

851 AGGACACCUA CGACGACGAC CUGGACAACC UGCUGGCCCA GAUCGGCGAC

901 CAGUACGCCG ACCUGUUUCU GGCCGCCAAG AACCUGUCCG ACGCCAUCCU

951 GCUGAGCGAC AUCCUGAGAG UGAACACCGA GAUCACCAAG GCCCCCCUGA

1001 GCGCCUCUAU GAUCAAGAGA UACGACGAGC ACCACCAGGA CCUGACCCUG

1051 CUGAAAGCUC UCGUGCGGCA GCAGCUGCCU GAGAAGUACA AAGAGAUUUU

1101 CUUCGACCAG AGCAAGAACG GCUACGCCGG CUACAUUGAC GGCGGAGCCA

1151 GCCAGGAAGA GUUCUACAAG UUCAUCAAGC CCAUCCUGGA AAAGAUGGAC

1201 GGCACCGAGG AACUGCUCGU GAAGCUGAAC AGAGAGGACC UGCUGCGGAA

1251 GCAGCGGACC UUCGACAACG GCAGCAUCCC CCACCAGAUC CACCUGGGAG

1301 AGCUGCACGC CAUUCUGCGG CGGCAGGAAG AUUUUUACCC AUUCCUGAAG

1351 GACAACCGGG AAAAGAUCGA GAAGAUCCUG ACCUUCCGCA UCCCCUACUA

1401 CGUGGGCCCU CUGGCCAGGG GAAACAGCAG AUUCGCCUGG AUGACCAGAA

1451 AGAGCGAGGA AACCAUCACC CCCUGGAACU UCGAGGAAGU GGUGGACAAG

1501 GGCGCUUCCG CCCAGAGCUU CAUCGAGCGG AUGACCAACU UCGAUAAGAA

1551 CCUGCCCAAC GAGAAGGUGC UGCCCAAGCA CAGCCUGCUG UACGAGUACU

1601 UCACCGUGUA UAACGAGCUG ACCAAAGUGA AAUACGUGAC CGAGGGAAUG

1651 AGAAAGCCCG CCUUCCUGAG CGGCGAGCAG AAAAAGGCCA UCGUGGACCU

1701 GCUGUUCAAG ACCAACCGGA AAGUGACCGU GAAGCAGCUG AAAGAGGACU

1751 ACUUCAAGAA AAUCGAGUGC UUCGACUCCG UGGAAAUCUC CGGCGUGGAA

1801 GAUCGGUUCA ACGCCUCCCU GGGCACAUAC CACGAUCUGC UGAAAAUUAU

1851 CAAGGACAAG GACUUCCUGG ACAAUGAGGA AAACGAGGAC AUUCUGGAAG

1901 AUAUCGUGCU GACCCUGACA CUGUUUGAGG ACAGAGAGAU GAUCGAGGAA

1951 CGGCUGAAAA CCUAUGCCCA CCUGUUCGAC GACAAAGUGA UGAAGCAGCU

2001 GAAGCGGCGG AGAUACACCG GCUGGGGCAG GCUGAGCCGG AAGCUGAUCA

2051 ACGGCAUCCG GGACAAGCAG UCCGGCAAGA CAAUCCUGGA UUUCCUGAAG

2101 UCCGACGGCU UCGCCAACAG AAACUUCAUG CAGCUGAUCC ACGACGACAG

2151 CCUGACCUUU AAAGAGGACA UCCAGAAAGC CCAGGUGUCC GGCCAGGGCG

2201 AUAGCCUGCA CGAGCACAUU GCCAAUCUGG CCGGCAGCCC CGCCAUUAAG

2251 AAGGGCAUCC UGCAGACAGU GAAGGUGGUG GACGAGCUCG UGAAAGUGAU

2301 GGGCCGGCAC AAGCCCGAGA ACAUCGUGAU CGAAAUGGCC AGAGAGAACC

2351 AGACCACCCA GAAGGGACAG AAGAACAGCC GCGAGAGAAU GAAGCGGAUC

2401 GAAGAGGGCA UCAAAGAGCU GGGCAGCCAG AUCCUGAAAG AACACCCCGU

2451 GGAAAACACC CAGCUGCAGA ACGAGAAGCU GUACCUGUAC UACCUGCAGA

2501 AUGGGCGGGA UAUGUACGUG GACCAGGAAC UGGACAUCAA CCGGCUGUCC

2551 GACUACGAUG UGGACCAUAU CGUGCCUCAG AGCUUUCUGA AGGACGACUC

2601 CAUCGACAAC AAGGUGCUGA CCAGAAGCGA CAAGAACCGG GGCAAGAGCG

2651 ACAACGUGCC CUCCGAAGAG GUCGUGAAGA AGAUGAAGAA CUACUGGCGG

2701 CAGCUGCUGA ACGCCAAGCU GAUUACCCAG AGAAAGUUCG ACAAUCUGAC

-continued

```
2751 CAAGGCCGAG AGAGGCGGCC UGAGCGAACU GGAUAAGGCC GGCUUCAUCA

2801 AGAGACAGCU GGUGGAAACC CGGCAGAUCA CAAAGCACGU GGCACAGAUC

2851 CUGGACUCCC GGAUGAACAC UAAGUACGAC GAGAAUGACA AGCUGAUCCG

2901 GGAAGUGAAA GUGAUCACCC UGAAGUCCAA GCUGGUGUCC GAUUUCCGGA

2951 AGGAUUUCCA GUUUUACAAA GUGCGCGAGA UCAACAACUA CCACCACGCC

3001 CACGACGCCU ACCUGAACGC CGUCGUGGGA ACCGCCCUGA UCAAAAAGUA

3051 CCCUAAGCUG GAAAGCGAGU UCGUGUACGG CGACUACAAG GUGUACGACG

3101 UGCGGAAGAU GAUCGCCAAG AGCGAGCAGG AAAUCGGCAA GGCUACCGCC

3151 AAGUACUUCU UCUACAGCAA CAUCAUGAAC UUUUUCAAGA CCGAGAUUAC

3201 CCUGGCCAAC GGCGAGAUCC GGAAGCGGCC UCUGAUCGAG ACAAACGGCG

3251 AAACCGGGGA GAUCGUGUGG GAUAAGGGCC GGGAUUUUGC CACCGUGCGG

3301 AAAGUGCUGA GCAUGCCCCA AGUGAAUAUC GUGAAAAAGA CCGAGGUGCA

3351 GACAGGCGGC UUCAGCAAAG AGUCUAUCCU GCCCAAGAGG AACAGCGAUA

3401 AGCUGAUCGC CAGAAAGAAG GACUGGGACC CUAAGAAGUA CGGCGGCUUC

3451 GACAGCCCCA CCGUGGCCUA UUCUGUGCUG GUGGUGGCCA AAGUGGAAAA

3501 GGGCAAGUCC AAGAAACUGA AGAGUGUGAA AGAGCUGCUG GGGAUCACCA

3551 UCAUGGAAAG AAGCAGCUUC GAGAAGAAUC CCAUCGACUU UCUGGAAGCC

3601 AAGGGCUACA AAGAAGUGAA AAAGGACCUG AUCAUCAAGC UGCCUAAGUA

3651 CUCCCUGUUC GAGCUGGAAA ACGGCCGGAA GAGAAUGCUG GCCUCUGCCG

3701 GCGAACUGCA GAAGGGAAAC GAACUGGCCC UGCCCUCCAA AUAUGUGAAC

3751 UUCCUGUACC UGGCCAGCCA CUAUGAGAAG CUGAAGGGCU CCCCCGAGGA

3801 UAAUGAGCAG AAACAGCUGU UUGUGGAACA GCACAAGCAC UACCUGGACG

3851 AGAUCAUCGA GCAGAUCAGC GAGUUCUCCA AGAGAGUGAU CCUGGCCGAC

3901 GCUAAUCUGG ACAAAGUGCU GUCCGCCUAC AACAAGCACC GGGAUAAGCC

3951 CAUCAGAGAG CAGGCCGAGA AUAUCAUCCA CCUGUUUACC CUGACCAAUC

4001 UGGGAGCCCC UGCCGCCUUC AAGUACUUUG ACACCACCAU CGACCGGAAG

4051 AGGUACACCA GCACCAAAGA GGUGCUGGAC GCCACCCUGA UCCACCAGAG

4101 CAUCACCGGC CUGUACGAGA CACGGAUCGA CCUGUCUCAG CUGGGAGGCG

4151 ACAAAAGGCC GGCGGCCACG AAAAAGGCCG GCCAGGCAAA AAAGAAAAAG

4201 UAA
```

The following polyribonucleotide (e.g., RNA) sequence (SEQ ID NO: 3) corresponds to a T7 promoter sequence. The final underlined g denotes the transcription start site.

```
                                      (SEQ ID NO: 3)
1            UAAUACGACU CACUAUAG
```

The following polyribonucleotide (e.g., RNA) sequence (SEQ ID NO: 4) corresponds to a T3 promoter sequence. The final underlined g denotes the transcription start site.

```
                                      (SEQ ID NO: 4)
1            AAUUAACCCU CACUAAAG
```

The following polyribonucleotide (e.g., RNA) sequence (SEQ ID NO: 5) corresponds to a SP6 promoter sequence. The final underlined g denotes the transcription start site.

```
                                      (SEQ ID NO: 5)
1            AUUUAGGUGA CACUAUAG
```

The following polyribonucleotide (e.g., RNA) sequence (SEQ ID NO: 6) corresponds to a K11 promoter sequence. The underlined g denotes the transcription start site.

```
                                      (SEQ ID NO: 6)
1          AAUUAGGGCA CACUAUAGGG A
```

The following polyribonucleotide (e.g., RNA) sequence (SEQ ID NO: 7) corresponds to a 5' UTR referred to as Minimal.

```
                                       (SEQ ID NO: 7)
    1              GGGAGACGCC ACC
```

The following polyribonucleotide (e.g., RNA) sequence (SEQ ID NO: 8) corresponds to a 5' UTR referred to as hAg, a 5' UTR derived from human alpha globin.

```
                                       (SEQ ID NO: 8)
1 GGGAGACUCU UCUGGUCCCC ACAGACUCAG AGAGAACGCC ACC
```

The following polyribonucleotide (e.g., RNA) sequence (SEQ ID NO: 9) corresponds to a 5' UTR referred to as TISU.

```
                                       (SEQ ID NO: 9)
    1              GGGAGACGCC AAG
```

The following polyribonucleotide (e.g., RNA) sequence (SEQ ID NO: 10) corresponds to a 5' UTR referred to as TISU+T.

```
                                       (SEQ ID NO: 10)
    1              GGGAGACUGC CAAG
```

The following sequence (SEQ ID NO: 11) corresponds to a polyribonucleotide (e.g., RNA) sequence comprising 5p-UTR 5' UTR (SEQ ID NO: 59), FLAG-tagged wildtype Cas9 (SEQ ID NO: 61), and the 3p-UTR 3' UTR (SEQ ID NO: 60).

```
                                                        (SEQ ID NO: 11)
   1 GGGAGACCCA AGCUGGCUAG CGUUUAAACU UAAGCUUGCC ACCAUGGACU

  51 AUAAGGACCA CGACGGAGAC UACAAGGAUC AUGAUAUUGA UUACAAAGAC

 101 GAUGACGAUA AGAUGGCCCC AAAGAAGAAG CGGAAGGUCG GUAUCCACGG

 151 AGUCCCAGCA GCCGACAAGA AGUACAGCAU CGGCCUGGAC AUCGGCACCA

 201 ACUCUGUGGG CUGGGCCGUG AUCACCGACG AGUACAAGGU GCCCAGCAAG

 251 AAAUUCAAGG UGCUGGGCAA CACCGACCGG CACAGCAUCA AGAAGAACCU

 301 GAUCGGAGCC CUGCUGUUCG ACAGCGGCGA AACAGCCGAG GCCACCCGGC

 351 UGAAGAGAAC CGCCAGAAGA AGAUACACCA GACGGAAGAA CCGGAUCUGC

 401 UAUCUGCAAG AGAUCUUCAG CAACGAGAUG GCCAAGGUGG ACGACAGCUU

 451 CUUCCACAGA CUGGAAGAGU CCUUCCUGGU GGAAGAGGAU AAGAAGCACG

 501 AGCGGCACCC CAUCUUCGGC AACAUCGUGG ACGAGGUGGC CUACCACGAG

 551 AAGUACCCCA CCAUCUACCA CCUGAGAAAG AAACUGGUGG ACAGCACCGA

 601 CAAGGCCGAC CUGCGGCUGA UCUAUCUGGC CCUGGCCCAC AUGAUCAAGU

 651 UCCGGGGCCA CUUCCUGAUC GAGGGCGACC UGAACCCCGA CAACAGCGAC

 701 GUGGACAAGC UGUUCAUCCA GCUGGUGCAG ACCUACAACC AGCUGUUCGA

 751 GGAAAACCCC AUCAACGCCA GCGGCGUGGA CGCCAAGGCC AUCCUGUCUG

 801 CCAGACUGAG CAAGAGCAGA CGGCUGGAAA AUCUGAUCGC CCAGCUGCCC

 851 GGCGAGAAGA AGAAUGGCCU GUUCGGAAAC CUGAUUGCCC UGAGCCUGGG

 901 CCUGACCCCC AACUUCAAGA GCAACUUCGA CCUGGCCGAG GAUGCCAAAC

 951 UGCAGCUGAG CAAGGACACC UACGACGACG ACCUGGACAA CCUGCUGGCC

1001 CAGAUCGGCG ACCAGUACGC CGACCUGUUU CUGGCCGCCA AGAACCUGUC

1051 CGACGCCAUC CUGCUGAGCG ACAUCCUGAG AGUGAACACC GAGAUCACCA

1101 AGGCCCCCCU GAGCGCCUCU AUGAUCAAGA GAUACGACGA GCACCACCAG

1151 GACCUGACCC UGCUGAAAGC UCUCGUGCGG CAGCAGCUGC CUGAGAAGUA

1201 CAAAGAGAUU UUCUUCGACC AGAGCAAGAA CGGCUACGCC GGCUACAUUG

1251 ACGGCGGAGC CAGCCAGGAA GAGUUCUACA AGUUCAUCAA GCCCAUCCUG

1301 GAAAAGAUGG ACGGCACCGA GGAACUGCUC GUGAAGCUGA ACAGAGAGGA

1351 CCUGCUGCGG AAGCAGCGGA CCUUCGACAA CGGCAGCAUC CCCCACCAGA

1401 UCCACCUGGG AGAGCUGCAC GCCAUUCUGC GGCGGCAGGA AGAUUUUUAC
```

-continued

1451 CCAUUCCUGA AGGACAACCG GGAAAAGAUC GAGAAGAUCC UGACCUUCCG

1501 CAUCCCCUAC UACGUGGGCC CUCUGGCCAG GGGAAACAGC AGAUUCGCCU

1551 GGAUGACCAG AAAGAGCGAG GAAACCAUCA CCCCCUGGAA CUUCGAGGAA

1601 GUGGUGGACA AGGGCGCUUC CGCCCAGAGC UUCAUCGAGC GGAUGACCAA

1651 CUUCGAUAAG AACCUGCCCA ACGAGAAGGU GCUGCCCAAG CACAGCCUGC

1701 UGUACGAGUA CUUCACCGUG UAUAACGAGC UGACCAAAGU GAAAUACGUG

1751 ACCGAGGGAA UGAGAAAGCC CGCCUUCCUG AGCGGCGAGC AGAAAAAGGC

1801 CAUCGUGGAC CUGCUGUUCA AGACCAACCG GAAAGUGACC GUGAAGCAGC

1851 UGAAAGAGGA CUACUUCAAG AAAAUCGAGU GCUUCGACUC CGUGGAAAUC

1901 UCCGGCGUGG AAGAUCGGUU CAACGCCUCC CUGGGCACAU ACCACGAUCU

1951 GCUGAAAAUU AUCAAGGACA AGGACUUCCU GGACAAUGAG GAAAACGAGG

2001 ACAUUCUGGA AGAUAUCGUG CUGACCCUGA CACUGUUUGA GGACAGAGAG

2051 AUGAUCGAGG AACGGCUGAA AACCUAUGCC CACCUGUUCG ACGACAAAGU

2101 GAUGAAGCAG CUGAAGCGGC GGAGAUACAC CGGCUGGGGC AGGCUGAGCC

2151 GGAAGCUGAU CAACGGCAUC CGGGACAAGC AGUCCGGCAA GACAAUCCUG

2201 GAUUUCCUGA AGUCCGACGG CUUCGCCAAC AGAAACUUCA UGCAGCUGAU

2251 CCACGACGAC AGCCUGACCU UUAAAGAGGA CAUCCAGAAA GCCCAGGUGU

2301 CCGGCCAGGG CGAUAGCCUG CACGAGCACA UUGCCAAUCU GGCCGGCAGC

2351 CCCGCCAUUA AGAAGGGCAU CCUGCAGACA GUGAAGGUGG UGGACGAGCU

2401 CGUGAAAGUG AUGGGCCGGC ACAAGCCCGA GAACAUCGUG AUCGAAAUGG

2451 CCAGAGAGAA CCAGACCACC CAGAAGGGAC AGAAGAACAG CCGCGAGAGA

2501 AUGAAGCGGA UCGAAGAGGG CAUCAAAGAG CUGGGCAGCC AGAUCCUGAA

2551 AGAACACCCC GUGGAAAACA CCCAGCUGCA GAACGAGAAG CUGUACCUGU

2601 ACUACCUGCA GAAUGGGCGG GAUAUGUACG UGGACCAGGA ACUGGACAUC

2651 AACCGGCUGU CCGACUACGA UGUGGACCAU AUCGUGCCUC AGAGCUUUCU

2701 GAAGGACGAC UCCAUCGACA ACAAGGUGCU GACCAGAAGC GACAAGAACC

2751 GGGGCAAGAG CGACAACGUG CCCUCCGAAG AGGUCGUGAA GAAGAUGAAG

2801 AACUACUGGC GGCAGCUGCU GAACGCCAAG CUGAUUACCC AGAGAAAGUU

2851 CGACAAUCUG ACCAAGGCCG AGAGAGGCGG CCUGAGCGAA CUGGAUAAGG

2901 CCGGCUUCAU CAAGAGACAG CUGGUGGAAA CCCGGCAGAU CACAAAGCAC

2951 GUGGCACAGA UCCUGGACUC CCGGAUGAAC ACUAAGUACG ACGAGAAUGA

3001 CAAGCUGAUC CGGGAAGUGA AAGUGAUCAC CCUGAAGUCC AAGCUGGUGU

3051 CCGAUUUCCG GAAGGAUUUC CAGUUUUACA AAGUGCGCGA GAUCAACAAC

3101 UACCACCACG CCCACGACGC CUACCUGAAC GCCGUCGUGG GAACCGCCCU

3151 GAUCAAAAAG UACCCUAAGC UGGAAAGCGA GUUCGUGUAC GGCGACUACA

3201 AGGUGUACGA CGUGCGGAAG AUGAUCGCCA AGAGCGAGCA GGAAAUCGGC

3251 AAGGCUACCG CCAAGUACUU CUUCUACAGC AACAUCAUGA ACUUUUUCAA

3301 GACCGAGAUU ACCCUGGCCA ACGGCGAGAU CCGGAAGCGG CCUCUGAUCG

3351 AGACAAACGG CGAAACCGGG GAGAUCGUGU GGGAUAAGGG CCGGGAUUUU

3401 GCCACCGUGC GGAAAGUGCU GAGCAUGCCC CAAGUGAAUA UCGUGAAAAA

3451 GACCGAGGUG CAGACAGGCG GCUUCAGCAA AGAGUCUAUC CUGCCCAAGA

-continued

```
3501 GGAACAGCGA UAAGCUGAUC GCCAGAAAGA AGGACUGGGA CCCUAAGAAG
3551 UACGGCGGCU UCGACAGCCC CACCGUGGCC UAUUCUGUGC UGGUGGUGGC
3601 CAAAGUGGAA AAGGGCAAGU CCAAGAAACU GAAGAGUGUG AAAGAGCUGC
3651 UGGGGAUCAC CAUCAUGGAA AGAAGCAGCU UCGAGAAGAA UCCCAUCGAC
3701 UUUCUGGAAG CCAAGGGCUA CAAAGAAGUG AAAAAGGACC UGAUCAUCAA
3751 GCUGCCUAAG UACUCCCUGU UCGAGCUGGA AAACGGCCGG AAGAGAAUGC
3801 UGGCCUCUGC CGGCGAACUG CAGAAGGGAA ACGAACUGGC CCUGCCCUCC
3851 AAAUAUGUGA ACUUCCUGUA CCUGGCCAGC CACUAUGAGA AGCUGAAGGG
3901 CUCCCCCGAG GAUAAUGAGC AGAAACAGCU GUUUGUGGAA CAGCACAAGC
3951 ACUACCUGGA CGAGAUCAUC GAGCAGAUCA GCGAGUUCUC CAAGAGAGUG
4001 AUCCUGGCCG ACGCUAAUCU GGACAAAGUG CUGUCCGCCU ACAACAAGCA
4051 CCGGGAUAAG CCCAUCAGAG AGCAGGCCGA GAAUAUCAUC CACCUGUUUA
4101 CCCUGACCAA UCUGGGAGCC CCUGCCGCCU UCAAGUACUU UGACACCACC
4151 AUCGACCGGA AGAGGUACAC CAGCACCAAA GAGGUGCUGG ACGCCACCCU
4201 GAUCCACCAG AGCAUCACCG GCCUGUACGA GACACGGAUC GACCUGUCUC
4251 AGCUGGGAGG CGACAAAAGG CCGGCGGCCA CGAAAAAGGC CGGCCAGGCA
4301 AAAAAGAAAA AGUAAGAAUU CCUAggaUcc ACUAGUCCAG UGUGGUGGAA
4351 UUCUGCAGAA AAAAAAAAAA AAAAAAAAAA AAAAAAAAAA AAAAAAAAAA
4401 AAAAAAAAAA AAAAAAAAAA AAAAAAAAAA AAAAAAAAAA AAAAAAAAAA
4451 AAAAAAAAAA AAAAAAAAAA AAAAAAAAGC GGCC
```

The following sequence (SEQ ID NO: 12) corresponds to a polyribonucleotide (e.g., RNA) sequence comprising Minimal 5' UTR (SEQ ID NO: 7), wildtype Cas9 (SEQ ID NO: 1), and the sequence 5'-GAATT-3' 3' UTR.

```
                                                    (SEQ ID NO: 12)
  1 GGGAGACGCC ACCAUGGCCC CAAAGAAGAA GCGGAAGGUC GGUAUCCACG
 51 GAGUCCCAGC AGCCGACAAG AAGUACAGCA UCGGCCUGGA CAUCGGCACC
101 AACUCUGUGG GCUGGGCCGU GAUCACCGAC GAGUACAAGG UGCCCAGCAA
151 GAAAUUCAAG GUGCUGGGCA ACACCGACCG GCACAGCAUC AAGAAGAACC
201 UGAUCGGAGC CCUGCUGUUC GACAGCGGCG AAACAGCCGA GGCCACCCGG
251 CUGAAGAGAA CCGCCAGAAG AAGAUACACC AGACGGAAGA ACCGGAUCUG
301 CUAUCUGCAA GAGAUCUUCA GCAACGAGAU GGCCAAGGUG GACGACAGCU
351 UCUUCCACAG ACUGGAAGAG UCCUUCCUGG UGGAAGAGGA UAAGAAGCAC
401 GAGCGGCACC CCAUCUUCGG CAACAUCGUG GACGAGGUGG CCUACCACGA
451 GAAGUACCCC ACCAUCUACC ACCUGAGAAA GAAACUGGUG GACAGCACCG
501 ACAAGGCCGA CCUGCGGCUG AUCUAUCUGG CCCUGGCCCA CAUGAUCAAG
551 UUCCGGGGCC ACUUCCUGAU CGAGGGCGAC CUGAACCCCG ACAACAGCGA
601 CGUGGACAAG CUGUUCAUCC AGCUGGUGCA GACCUACAAC CAGCUGUUCG
651 AGGAAAACCC CAUCAACGCC AGCGGCGUGG ACGCCAAGGC CAUCCUGUCU
701 GCCAGACUGA GCAAGAGCAG ACGGCUGGAA AAUCUGAUCG CCCAGCUGCC
751 CGGCGAGAAG AAGAAUGGCC UGUUCGGAAA CCUGAUUGCC CUGAGCCUGG
801 GCCUGACCCC CAACUUCAAG AGCAACUUCG ACCUGGCCGA GGAUGCCAAA
```

-continued

```
851  CUGCAGCUGA GCAAGGACAC CUACGACGAC GACCUGGACA ACCUGCUGGC
901  CCAGAUCGGC GACCAGUACG CCGACCUGUU UCUGGCCGCC AAGAACCUGU
951  CCGACGCCAU CCUGCUGAGC GACAUCCUGA GAGUGAACAC CGAGAUCACC
1001 AAGGCCCCCC UGAGCGCCUC UAUGAUCAAG AGAUACGACG AGCACCACCA
1051 GGACCUGACC CUGCUGAAAG CUCUCGUGCG GCAGCAGCUG CCUGAGAAGU
1101 ACAAAGAGAU UUUCUUCGAC CAGAGCAAGA ACGGCUACGC CGGCUACAUU
1151 GACGGCGGAG CCAGCCAGGA AGAGUUCUAC AAGUUCAUCA AGCCCAUCCU
1201 GGAAAAGAUG GACGGCACCG AGGAACUGCU CGUGAAGCUG AACAGAGAGG
1251 ACCUGCUGCG GAAGCAGCGG ACCUUCGACA ACGGCAGCAU CCCCCACCAG
1301 AUCCACCUGG GAGAGCUGCA CGCCAUUCUG CGGCGGCAGG AAGAUUUUUA
1351 CCCAUUCCUG AAGGACAACC GGGAAAAGAU CGAGAAGAUC CUGACCUUCC
1401 GCAUCCCCUA CUACGUGGGC CCUCUGGCCA GGGGAAACAG CAGAUUCGCC
1451 UGGAUGACCA GAAAGAGCGA GGAAACCAUC ACCCCCUGGA ACUUCGAGGA
1501 AGUGGUGGAC AAGGGCGCUU CCGCCCAGAG CUUCAUCGAG CGGAUGACCA
1551 ACUUCGAUAA GAACCUGCCC AACGAGAAGG UGCUGCCCAA GCACAGCCUG
1601 CUGUACGAGU ACUUCACCGU GUAUAACGAG CUGACCAAAG UGAAAUACGU
1651 GACCGAGGGA AUGAGAAAGC CCGCCUUCCU GAGCGGCGAG CAGAAAAAGG
1701 CCAUCGUGGA CCUGCUGUUC AAGACCAACC GGAAAGUGAC CGUGAAGCAG
1751 CUGAAAGAGG ACUACUUCAA GAAAAUCGAG UGCUUCGACU CCGUGGAAAU
1801 CUCCGGCGUG GAAGAUCGGU UCAACGCCUC CCUGGGCACA UACCACGAUC
1851 UGCUGAAAAU UAUCAAGGAC AAGGACUUCC UGGACAAUGA GGAAAACGAG
1901 GACAUUCUGG AAGAUAUCGU GCUGACCCUG ACACUGUUUG AGGACAGAGA
1951 GAUGAUCGAG GAACGGCUGA AAACCUAUGC CCACCUGUUC GACGACAAAG
2001 UGAUGAAGCA GCUGAAGCGG CGGAGAUACA CCGGCUGGGG CAGGCUGAGC
2051 CGGAAGCUGA UCAACGGCAU CCGGGACAAG CAGUCCGGCA AGACAAUCCU
2101 GGAUUUCCUG AAGUCCGACG GCUUCGCCAA CAGAAACUUC AUGCAGCUGA
2151 UCCACGACGA CAGCCUGACC UUUAAAGAGG ACAUCCAGAA AGCCCAGGUG
2201 UCCGGCCAGG GCGAUAGCCU GCACGAGCAC AUUGCCAAUC UGGCCGGCAG
2251 CCCCGCCAUU AAGAAGGGCA UCCUGCAGAC AGUGAAGGUG GUGGACGAGC
2301 UCGUGAAAGU GAUGGGCCGG CACAAGCCCG AGAACAUCGU GAUCGAAAUG
2351 GCCAGAGAGA ACCAGACCAC CCAGAAGGGA CAGAAGAACA GCCGCGAGAG
2401 AAUGAAGCGG AUCGAAGAGG GCAUCAAAGA GCUGGGCAGC CAGAUCCUGA
2451 AAGAACACCC CGUGGAAAAC ACCCAGCUGC AGAACGAGAA GCUGUACCUG
2501 UACUACCUGC AGAAUGGGCG GGAUAUGUAC GUGGACCAGG AACUGGACAU
2551 CAACCGGCUG UCCGACUACG AUGUGGACCA UAUCGUGCCU CAGAGCUUUC
2601 UGAAGGACGA CUCCAUCGAC AACAAGGUGC UGACCAGAAG CGACAAGAAC
2651 CGGGGCAAGA GCGACAACGU GCCCUCCGAA GAGGUCGUGA AGAAGAUGAA
2701 GAACUACUGG CGGCAGCUGC UGAACGCCAA GCUGAUUACC CAGAGAAAGU
2751 UCGACAAUCU GACCAAGGCC GAGAGAGGCG GCCUGAGCGA ACUGGAUAAG
2801 GCCGGCUUCA UCAAGAGACA GCUGGUGGAA ACCCGGCAGA UCACAAAGCA
```

-continued

2851 CGUGGCACAG AUCCUGGACU CCCGGAUGAA CACUAAGUAC GACGAGAAUG

2901 ACAAGCUGAU CCGGGAAGUG AAAGUGAUCA CCCUGAAGUC CAAGCUGGUG

2951 UCCGAUUUCC GGAAGGAUUU CCAGUUUUAC AAAGUGCGCG AGAUCAACAA

3001 CUACCACCAC GCCCACGACG CCUACCUGAA CGCCGUCGUG GGAACCGCCC

3051 UGAUCAAAAA GUACCCUAAG CUGGAAAGCG AGUUCGUGUA CGGCGACUAC

3101 AAGGUGUACG ACGUGCGGAA GAUGAUCGCC AAGAGCGAGC AGGAAAUCGG

3151 CAAGGCUACC GCCAAGUACU UCUUCUACAG CAACAUCAUG AACUUUUUCA

3201 AGACCGAGAU UACCCUGGCC AACGGCGAGA UCCGGAAGCG GCCUCUGAUC

3251 GAGACAAACG GCGAAACCGG GGAGAUCGUG UGGGAUAAGG GCCGGGAUUU

3301 UGCCACCGUG CGGAAAGUGC UGAGCAUGCC CCAAGUGAAU AUCGUGAAAA

3351 AGACCGAGGU GCAGACAGGC GGCUUCAGCA AAGAGUCUAU CCUGCCCAAG

3401 AGGAACAGCG AUAAGCUGAU CGCCAGAAAG AAGGACUGGG ACCCUAAGAA

3451 GUACGGCGGC UUCGACAGCC CCACCGUGGC CUAUUCUGUG CUGGUGGUGG

3501 CCAAAGUGGA AAAGGGCAAG UCCAAGAAAC UGAAGAGUGU GAAAGAGCUG

3551 CUGGGGAUCA CCAUCAUGGA AAGAAGCAGC UUCGAGAAGA AUCCCAUCGA

3601 CUUUCUGGAA GCCAAGGGCU ACAAAGAAGU GAAAAAGGAC CUGAUCAUCA

3651 AGCUGCCUAA GUACUCCCUG UUCGAGCUGG AAAACGGCCG GAAGAGAAUG

3701 CUGGCCUCUG CCGGCGAACU GCAGAAGGGA AACGAACUGG CCCUGCCCUC

3751 CAAAUAUGUG AACUUCCUGU ACCUGGCCAG CCACUAUGAG AAGCUGAAGG

3801 GCUCCCCCGA GGAUAAUGAG CAGAAACAGC UGUUUGUGGA ACAGCACAAG

3851 CACUACCUGG ACGAGAUCAU CGAGCAGAUC AGCGAGUUCU CCAAGAGAGU

3901 GAUCCUGGCC GACGCUAAUC UGGACAAAGU GCUGUCCGCC UACAACAAGC

3951 ACCGGGAUAA GCCCAUCAGA GAGCAGGCCG AGAAUAUCAU CCACCUGUUU

4001 ACCCUGACCA AUCUGGGAGC CCCUGCCGCC UUCAAGUACU UUGACACCAC

4051 CAUCGACCGG AAGAGGUACA CCAGCACCAA AGAGGUGCUG GACGCCACCC

4101 UGAUCCACCA GAGCAUCACC GGCCUGUACG AGACACGGAU CGACCUGUCU

4151 CAGCUGGGAG GCGACAAAAG GCCGGCGGCC ACGAAAAAGG CCGGCCAGGC

4201 AAAAAAGAAA AAGUAAGAAU U

The following sequence (SEQ ID NO: 13) corresponds to a polyribonucleotide (e.g., RNA) sequence comprising a hAg 5' UTR (SEQ ID NO: 8), wildtype Cas9 (SEQ ID NO: 1), and the sequence 5'-GAATT-3' 3' UTR.

(SEQ ID NO: 13)

1 GGGAGACUCU UCUGGUCCCC ACAGACUCAG AGAGAACGCC ACCAUGGCCC

51 CAAAGAAGAA GCGGAAGGUC GGUAUCCACG GAGUCCCAGC AGCCGACAAG

101 AAGUACAGCA UCGGCCUGGA CAUCGGCACC AACUCUGUGG GCUGGGCCGU

151 GAUCACCGAC GAGUACAAGG UGCCCAGCAA GAAAUUCAAG GUGCUGGGCA

201 ACACCGACCG GCACAGCAUC AAGAAGAACC UGAUCGGAGC CCUGCUGUUC

251 GACAGCGGCG AAACAGCCGA GGCCACCCGG CUGAAGAGAA CCGCCAGAAG

301 AAGAUACACC AGACGGAAGA ACCGGAUCUG CUAUCUGCAA GAGAUCUUCA

351 GCAACGAGAU GGCCAAGGUG GACGACAGCU UCUUCCACAG ACUGGAAGAG

401 UCCUUCCUGG UGGAAGAGGA UAAGAAGCAC GAGCGGCACC CCAUCUUCGG

-continued

451 CAACAUCGUG GACGAGGUGG CCUACCACGA GAAGUACCCC ACCAUCUACC

501 ACCUGAGAAA GAAACUGGUG GACAGCACCG ACAAGGCCGA CCUGCGGCUG

551 AUCUAUCUGG CCCUGGCCCA CAUGAUCAAG UUCCGGGGCC ACUUCCUGAU

601 CGAGGGCGAC CUGAACCCCG ACAACAGCGA CGUGGACAAG CUGUUCAUCC

651 AGCUGGUGCA GACCUACAAC CAGCUGUUCG AGGAAAACCC CAUCAACGCC

701 AGCGGCGUGG ACGCCAAGGC CAUCCUGUCU GCCAGACUGA GCAAGAGCAG

751 ACGGCUGGAA AAUCUGAUCG CCCAGCUGCC CGGCGAGAAG AAGAAUGGCC

801 UGUUCGGAAA CCUGAUUGCC CUGAGCCUGG GCCUGACCCC CAACUUCAAG

851 AGCAACUUCG ACCUGGCCGA GGAUGCCAAA CUGCAGCUGA GCAAGGACAC

901 CUACGACGAC GACCUGGACA ACCUGCUGGC CCAGAUCGGC GACCAGUACG

951 CCGACCUGUU UCUGGCCGCC AAGAACCUGU CCGACGCCAU CCUGCUGAGC

1001 GACAUCCUGA GAGUGAACAC CGAGAUCACC AAGGCCCCCC UGAGCGCCUC

1051 UAUGAUCAAG AGAUACGACG AGCACCACCA GGACCUGACC CUGCUGAAAG

1101 CUCUCGUGCG GCAGCAGCUG CCUGAGAAGU ACAAAGAGAU UUUCUUCGAC

1151 CAGAGCAAGA ACGGCUACGC CGGCUACAUU GACGGCGGAG CCAGCCAGGA

1201 AGAGUUCUAC AAGUUCAUCA AGCCCAUCCU GGAAAAGAUG GACGGCACCG

1251 AGGAACUGCU CGUGAAGCUG AACAGAGAGG ACCUGCUGCG GAAGCAGCGG

1301 ACCUUCGACA ACGGCAGCAU CCCCCACCAG AUCCACCUGG GAGAGCUGCA

1351 CGCCAUUCUG CGGCGGCAGG AAGAUUUUUA CCCAUUCCUG AAGGACAACC

1401 GGGAAAAGAU CGAGAAGAUC CUGACCUUCC GCAUCCCCUA CUACGUGGGC

1451 CCUCUGGCCA GGGGAAACAG CAGAUUCGCC UGGAUGACCA GAAAGAGCGA

1501 GGAAACCAUC ACCCCCUGGA ACUUCGAGGA AGUGGUGGAC AAGGGCGCUU

1551 CCGCCCAGAG CUUCAUCGAG CGGAUGACCA ACUUCGAUAA GAACCUGCCC

1601 AACGAGAAGG UGCUGCCCAA GCACAGCCUG CUGUACGAGU ACUUCACCGU

1651 GUAUAACGAG CUGACCAAAG UGAAAUACGU GACCGAGGGA AUGAGAAAGC

1701 CCGCCUUCCU GAGCGGCGAG CAGAAAAAGG CCAUCGUGGA CCUGCUGUUC

1751 AAGACCAACC GGAAAGUGAC CGUGAAGCAG CUGAAAGAGG ACUACUUCAA

1801 GAAAAUCGAG UGCUUCGACU CCGUGGAAAU CUCCGGCGUG GAAGAUCGGU

1851 UCAACGCCUC CCUGGGCACA UACCACGAUC UGCUGAAAAU UAUCAAGGAC

1901 AAGGACUUCC UGGACAAUGA GGAAAACGAG GACAUUCUGG AAGAUAUCGU

1951 GCUGACCCUG ACACUGUUUG AGGACAGAGA GAUGAUCGAG GAACGGCUGA

2001 AAACCUAUGC CCACCUGUUC GACGACAAAG UGAUGAAGCA GCUGAAGCGG

2051 CGGAGAUACA CCGGCUGGGG CAGGCUGAGC CGGAAGCUGA UCAACGGCAU

2101 CCGGGACAAG CAGUCCGGCA AGACAAUCCU GGAUUUCCUG AAGUCCGACG

2151 GCUUCGCCAA CAGAAACUUC AUGCAGCUGA UCCACGACGA CAGCCUGACC

2201 UUUAAAGAGG ACAUCCAGAA AGCCCAGGUG UCCGGCCAGG GCGAUAGCCU

2251 GCACGAGCAC AUUGCCAAUC UGGCCGGCAG CCCCGCCAUU AAGAAGGGCA

2301 UCCUGCAGAC AGUGAAGGUG GUGGACGAGC UCGUGAAAGU GAUGGGCCGG

2351 CACAAGCCCG AGAACAUCGU GAUCGAAAUG GCCAGAGAGA ACCAGACCAC

2401 CCAGAAGGGA CAGAAGAACA GCCGCGAGAG AAUGAAGCGG AUCGAAGAGG

2451 GCAUCAAAGA GCUGGGCAGC CAGAUCCUGA AAGAACACCC CGUGGAAAAC

-continued

```
2501 ACCCAGCUGC AGAACGAGAA GCUGUACCUG UACUACCUGC AGAAUGGGCG
2551 GGAUAUGUAC GUGGACCAGG AACUGGACAU CAACCGGCUG UCCGACUACG
2601 AUGUGGACCA UAUCGUGCCU CAGAGCUUUC UGAAGGACGA CUCCAUCGAC
2651 AACAAGGUGC UGACCAGAAG CGACAAGAAC CGGGGCAAGA GCGACAACGU
2701 GCCCUCCGAA GAGGUCGUGA AGAAGAUGAA GAACUACUGG CGGCAGCUGC
2751 UGAACGCCAA GCUGAUUACC CAGAGAAAGU UCGACAAUCU GACCAAGGCC
2801 GAGAGAGGCG GCCUGAGCGA ACUGGAUAAG GCCGGCUUCA UCAAGAGACA
2851 GCUGGUGGAA ACCCGGCAGA UCACAAAGCA CGUGGCACAG AUCCUGGACU
2901 CCCGGAUGAA CACUAAGUAC GACGAGAAUG ACAAGCUGAU CCGGGAAGUG
2951 AAAGUGAUCA CCCUGAAGUC CAAGCUGGUG UCCGAUUUCC GGAAGGAUUU
3001 CCAGUUUUAC AAAGUGCGCG AGAUCAACAA CUACCACCAC GCCCACGACG
3051 CCUACCUGAA CGCCGUCGUG GGAACCGCCC UGAUCAAAAA GUACCCUAAG
3101 CUGGAAAGCG AGUUCGUGUA CGGCGACUAC AAGGUGUACG ACGUGCGGAA
3151 GAUGAUCGCC AAGAGCGAGC AGGAAAUCGG CAAGGCUACC GCCAAGUACU
3201 UCUUCUACAG CAACAUCAUG AACUUUUUCA AGACCGAGAU UACCCUGGCC
3251 AACGGCGAGA UCCGGAAGCG GCCUCUGAUC GAGACAAACG GCGAAACCGG
3301 GGAGAUCGUG UGGGAUAAGG GCCGGGAUUU UGCCACCGUG CGGAAAGUGC
3351 UGAGCAUGCC CCAAGUGAAU AUCGUGAAAA AGACCGAGGU GCAGACAGGC
3401 GGCUUCAGCA AAGAGUCUAU CCUGCCCAAG AGGAACAGCG AUAAGCUGAU
3451 CGCCAGAAAG AAGGACUGGG ACCCUAAGAA GUACGGCGGC UUCGACAGCC
3501 CCACCGUGGC CUAUUCUGUG CUGGUGGUGG CCAAAGUGGA AAAGGGCAAG
3551 UCCAAGAAAC UGAAGAGUGU GAAAGAGCUG CUGGGGAUCA CCAUCAUGGA
3601 AAGAAGCAGC UUCGAGAAGA AUCCCAUCGA CUUUCUGGAA GCCAAGGGCU
3651 ACAAAGAAGU GAAAAAGGAC CUGAUCAUCA AGCUGCCUAA GUACUCCCUG
3701 UUCGAGCUGG AAAACGGCCG GAAGAGAAUG CUGGCCUCUG CCGGCGAACU
3751 GCAGAAGGGA AACGAACUGG CCCUGCCCUC CAAAUAUGUG AACUUCCUGU
3801 ACCUGGCCAG CCACUAUGAG AAGCUGAAGG GCUCCCCCGA GGAUAAUGAG
3851 CAGAAACAGC UGUUUGUGGA ACAGCACAAG CACUACCUGG ACGAGAUCAU
3901 CGAGCAGAUC AGCGAGUUCU CCAAGAGAGU GAUCCUGGCC GACGCUAAUC
3951 UGGACAAAGU GCUGUCCGCC UACAACAAGC ACCGGGAUAA GCCCAUCAGA
4001 GAGCAGGCCG AGAAUAUCAU CCACCUGUUU ACCCUGACCA AUCUGGGAGC
4051 CCCUGCCGCC UUCAAGUACU UUGACACCAC CAUCGACCGG AAGAGGUACA
4101 CCAGCACCAA AGAGGUGCUG GACGCCACCC UGAUCCACCA GAGCAUCACC
4151 GGCCUGUACG AGACACGGAU CGACCUGUCU CAGCUGGGAG GCGACAAAAG
4201 GCCGGCGGCC ACGAAAAAGG CCGGCCAGGC AAAAAAGAAA AAGUAAGAAU
4251 U
```

The following sequence (SEQ ID NO: 14) corresponds to a polyribonucleotide (e.g., RNA) sequence comprising a ribonucleotide version of the TISU+T 5' UTR (SEQ ID NO: 10), wildtype Cas9 (SEQ ID NO: 1), and the sequence 5'-GAATT-3' 3' UTR.

(SEQ ID NO: 14)

1 GGGAGACUGC CAAGAUGGCC CCAAAGAAGA AGCGGAAGGU CGGUAUCCAC

51 GGAGUCCCAG CAGCCGACAA GAAGUACAGC AUCGGCCUGG ACAUCGGCAC

101 CAACUCUGUG GGCUGGGCCG UGAUCACCGA CGAGUACAAG GUGCCCAGCA

151 AGAAAUUCAA GGUGCUGGGC AACACCGACC GGCACAGCAU CAAGAAGAAC

201 CUGAUCGGAG CCCUGCUGUU CGACAGCGGC GAAACAGCCG AGGCCACCCG

251 GCUGAAGAGA ACCGCCAGAA GAAGAUACAC CAGACGGAAG AACCGGAUCU

301 GCUAUCUGCA AGAGAUCUUC AGCAACGAGA UGGCCAAGGU GGACGACAGC

351 UUCUUCCACA GACUGGAAGA GUCCUUCCUG GUGGAAGAGG AUAAGAAGCA

401 CGAGCGGCAC CCCAUCUUCG GCAACAUCGU GGACGAGGUG GCCUACCACG

451 AGAAGUACCC CACCAUCUAC CACCUGAGAA AGAAACUGGU GGACAGCACC

501 GACAAGGCCG ACCUGCGGCU GAUCUAUCUG GCCCUGGCCC ACAUGAUCAA

551 GUUCCGGGGC CACUUCCUGA UCGAGGGCGA CCUGAACCCC GACAACAGCG

601 ACGUGGACAA GCUGUUCAUC CAGCUGGUGC AGACCUACAA CCAGCUGUUC

651 GAGGAAAACC CCAUCAACGC CAGCGGCGUG GACGCCAAGG CCAUCCUGUC

701 UGCCAGACUG AGCAAGAGCA GACGGCUGGA AAAUCUGAUC GCCCAGCUGC

751 CCGGCGAGAA GAAGAAUGGC CUGUUCGGAA ACCUGAUUGC CCUGAGCCUG

801 GGCCUGACCC CCAACUUCAA GAGCAACUUC GACCUGGCCG AGGAUGCCAA

851 ACUGCAGCUG AGCAAGGACA CCUACGACGA CGACCUGGAC AACCUGCUGG

901 CCCAGAUCGG CGACCAGUAC GCCGACCUGU UUCUGGCCGC CAAGAACCUG

951 UCCGACGCCA UCCUGCUGAG CGACAUCCUG AGAGUGAACA CCGAGAUCAC

1001 CAAGGCCCCC CUGAGCGCCU CUAUGAUCAA GAGAUACGAC GAGCACCACC

1051 AGGACCUGAC CCUGCUGAAA GCUCUCGUGC GGCAGCAGCU GCCUGAGAAG

1101 UACAAAGAGA UUUUCUUCGA CCAGAGCAAG AACGGCUACG CCGGCUACAU

1151 UGACGGCGGA GCCAGCCAGG AAGAGUUCUA CAAGUUCAUC AAGCCCAUCC

1201 UGGAAAAGAU GGACGGCACC GAGGAACUGC UCGUGAAGCU GAACAGAGAG

1251 GACCUGCUGC GGAAGCAGCG GACCUUCGAC AACGGCAGCA UCCCCCACCA

1301 GAUCCACCUG GGAGAGCUGC ACGCCAUUCU GCGGCGGCAG GAAGAUUUUU

1351 ACCCAUUCCU GAAGGACAAC CGGGAAAAGA UCGAGAAGAU CCUGACCUUC

1401 CGCAUCCCCU ACUACGUGGG CCCUCUGGCC AGGGGAAACA GCAGAUUCGC

1451 CUGGAUGACC AGAAAGAGCG AGGAAACCAU CACCCCCUGG AACUUCGAGG

1501 AAGUGGUGGA CAAGGGCGCU UCCGCCCAGA GCUUCAUCGA GCGGAUGACC

1551 AACUUCGAUA AGAACCUGCC CAACGAGAAG GUGCUGCCCA AGCACAGCCU

1601 GCUGUACGAG UACUUCACCG UGUAUAACGA GCUGACCAAA GUGAAAUACG

1651 UGACCGAGGG AAUGAGAAAG CCCGCCUUCC UGAGCGGCGA GCAGAAAAAG

1701 GCCAUCGUGG ACCUGCUGUU CAAGACCAAC CGGAAAGUGA CCGUGAAGCA

1751 GCUGAAAGAG GACUACUUCA AGAAAAUCGA GUGCUUCGAC UCCGUGGAAA

1801 UCUCCGGCGU GGAAGAUCGG UUCAACGCCU CCCUGGGCAC AUACCACGAU

1851 CUGCUGAAAA UUAUCAAGGA CAAGGACUUC CUGGACAAUG AGGAAAACGA

1901 GGACAUUCUG GAAGAUAUCG UGCUGACCCU GACACUGUUU GAGGACAGAG

1951 AGAUGAUCGA GGAACGGCUG AAAACCUAUG CCCACCUGUU CGACGACAAA

-continued

2001 GUGAUGAAGC AGCUGAAGCG GCGGAGAUAC ACCGGCUGGG GCAGGCUGAG

2051 CCGGAAGCUG AUCAACGGCA UCCGGGACAA GCAGUCCGGC AAGACAAUCC

2101 UGGAUUUCCU GAAGUCCGAC GGCUUCGCCA ACAGAAACUU CAUGCAGCUG

2151 AUCCACGACG ACAGCCUGAC CUUUAAAGAG GACAUCCAGA AAGCCCAGGU

2201 GUCCGGCCAG GGCGAUAGCC UGCACGAGCA CAUUGCCAAU CUGGCCGGCA

2251 GCCCCGCCAU UAAGAAGGGC AUCCUGCAGA CAGUGAAGGU GGUGGACGAG

2301 CUCGUGAAAG UGAUGGGCCG GCACAAGCCC GAGAACAUCG UGAUCGAAAU

2351 GGCCAGAGAG AACCAGACCA CCCAGAAGGG ACAGAAGAAC AGCCGCGAGA

2401 GAAUGAAGCG GAUCGAAGAG GGCAUCAAAG AGCUGGGCAG CCAGAUCCUG

2451 AAAGAACACC CCGUGGAAAA CACCCAGCUG CAGAACGAGA AGCUGUACCU

2501 GUACUACCUG CAGAAUGGGC GGGAUAUGUA CGUGGACCAG GAACUGGACA

2551 UCAACCGGCU GUCCGACUAC GAUGUGGACC AUAUCGUGCC UCAGAGCUUU

2601 CUGAAGGACG ACUCCAUCGA CAACAAGGUG CUGACCAGAA GCGACAAGAA

2651 CCGGGGCAAG AGCGACAACG UGCCCUCCGA AGAGGUCGUG AAGAAGAUGA

2701 AGAACUACUG GCGGCAGCUG CUGAACGCCA AGCUGAUUAC CCAGAGAAAG

2751 UUCGACAAUC UGACCAAGGC CGAGAGAGGC GGCCUGAGCG AACUGGAUAA

2801 GGCCGGCUUC AUCAAGAGAC AGCUGGUGGA AACCCGGCAG AUCACAAAGC

2851 ACGUGGCACA GAUCCUGGAC UCCCGGAUGA ACACUAAGUA CGACGAGAAU

2901 GACAAGCUGA UCCGGGAAGU GAAAGUGAUC ACCCUGAAGU CCAAGCUGGU

2951 GUCCGAUUUC CGGAAGGAUU UCCAGUUUUA CAAAGUGCGC GAGAUCAACA

3001 ACUACCACCA CGCCCACGAC GCCUACCUGA ACGCCGUCGU GGGAACCGCC

3051 CUGAUCAAAA AGUACCCUAA GCUGGAAAGC GAGUUCGUGU ACGGCGACUA

3101 CAAGGUGUAC GACGUGCGGA AGAUGAUCGC CAAGAGCGAG CAGGAAAUCG

3151 GCAAGGCUAC CGCCAAGUAC UUCUUCUACA GCAACAUCAU GAACUUUUUC

3201 AAGACCGAGA UUACCCUGGC CAACGGCGAG AUCCGGAAGC GGCCUCUGAU

3251 CGAGACAAAC GGCGAAACCG GGGAGAUCGU GUGGGAUAAG GGCCGGGAUU

3301 UUGCCACCGU GCGGAAAGUG CUGAGCAUGC CCCAAGUGAA UAUCGUGAAA

3351 AAGACCGAGG UGCAGACAGG CGGCUUCAGC AAAGAGUCUA UCCUGCCCAA

3401 GAGGAACAGC GAUAAGCUGA UCGCCAGAAA GAAGGACUGG GACCCUAAGA

3451 AGUACGGCGG CUUCGACAGC CCCACCGUGG CCUAUUCUGU GCUGGUGGUG

3501 GCCAAAGUGG AAAAGGGCAA GUCCAAGAAA CUGAAGAGUG UGAAAGAGCU

3551 GCUGGGGAUC ACCAUCAUGG AAAGAAGCAG CUUCGAGAAG AAUCCCAUCG

3601 ACUUUCUGGA AGCCAAGGGC UACAAAGAAG UGAAAAAGGA CCUGAUCAUC

3651 AAGCUGCCUA AGUACUCCCU GUUCGAGCUG GAAAACGGCC GGAAGAGAAU

3701 GCUGGCCUCU GCCGGCGAAC UGCAGAAGGG AAACGAACUG GCCCUGCCCU

3751 CCAAAUAUGU GAACUUCCUG UACCUGGCCA GCCACUAUGA GAAGCUGAAG

3801 GGCUCCCCCG AGGAUAAUGA GCAGAAACAG CUGUUUGUGG AACAGCACAA

3851 GCACUACCUG GACGAGAUCA UCGAGCAGAU CAGCGAGUUC UCCAAGAGAG

3901 UGAUCCUGGC CGACGCUAAU CUGGACAAAG UGCUGUCCGC CUACAACAAG

3951 CACCGGGAUA AGCCCAUCAG AGAGCAGGCC GAGAAUAUCA UCCACCUGUU

4001 UACCCUGACC AAUCUGGGAG CCCCUGCCGC CUUCAAGUAC UUUGACACCA

-continued

```
4051 CCAUCGACCG GAAGAGGUAC ACCAGCACCA AAGAGGUGCU GGACGCCACC

4101 CUGAUCCACC AGAGCAUCAC CGGCCUGUAC GAGACACGGA UCGACCUGUC

4151 UCAGCUGGGA GGCGACAAAA GGCCGGCGGC CACGAAAAAG GCCGGCCAGG

4201 CAAAAAAGAA AAAGUAAGAA UU
```

The following polyribonucleotide (e.g., RNA) sequence (SEQ ID NO: 15) comprises a 5p-UTR 5' UTR (SEQ ID NO: 59), HA-tagged D10A Cas9 (SEQ ID NO: 62), and a 3p-UTR 3' UTR (SEQ ID NO: 60).

```
                                                    (SEQ ID NO: 15)
   1 GGGAGACCCA AGCUGGCUAG CGUUUAAACU UAAGCUUGCC ACCAUGUACC

  51 CAUACGAUGU UCCAGAUUAC GCUAUGGCCC CAAAGAAGAA GCGGAAGGUC

 101 GGUAUCCACG GAGUCCCAGC AGCCGACAAG AAGUACAGCA UCGGCCUGgc

 151 cAUCGGCACC AACUCUGUGG GCUGGGCCGU GAUCACCGAC GAGUACAAGG

 201 UGCCCAGCAA GAAAUUCAAG GUGCUGGGCA ACACCGACCG GCACAGCAUC

 251 AAGAAGAACC UGAUCGGAGC CCUGCUGUUC GACAGCGGCG AAACAGCCGA

 301 GGCCACCCGG CUGAAGAGAA CCGCCAGAAG AAGAUACACC AGACGGAAGA

 351 ACCGGAUCUG CUAUCUGCAA GAGAUCUUCA GCAACGAGAU GGCCAAGGUG

 401 GACGACAGCU UCUUCCACAG ACUGGAAGAG UCCUUCCUGG UGGAAGAGGA

 451 UAAGAAGCAC GAGCGGCACC CCAUCUUCGG CAACAUCGUG GACGAGGUGG

 501 CCUACCACGA GAAGUACCCC ACCAUCUACC ACCUGAGAAA GAAACUGGUG

 551 GACAGCACCG ACAAGGCCGA CCUGCGGCUG AUCUAUCUGG CCCUGGCCCA

 601 CAUGAUCAAG UUCCGGGGCC ACUUCCUGAU CGAGGGCGAC CUGAACCCCG

 651 ACAACAGCGA CGUGGACAAG CUGUUCAUCC AGCUGGUGCA GACCUACAAC

 701 CAGCUGUUCG AGGAAAACCC CAUCAACGCC AGCGGCGUGG ACGCCAAGGC

 751 CAUCCUGUCU GCCAGACUGA GCAAGAGCAG ACGGCUGGAA AAUCUGAUCG

 801 CCCAGCUGCC CGGCGAGAAG AAGAAUGGCC UGUUCGGAAA CCUGAUUGCC

 851 CUGAGCCUGG GCCUGACCCC CAACUUCAAG AGCAACUUCG ACCUGGCCGA

 901 GGAUGCCAAA CUGCAGCUGA GCAAGGACAC CUACGACGAC GACCUGGACA

 951 ACCUGCUGGC CCAGAUCGGC GACCAGUACG CCGACCUGUU UCUGGCCGCC

1001 AAGAACCUGU CCGACGCCAU CCUGCUGAGC GACAUCCUGA GAGUGAACAC

1051 CGAGAUCACC AAGGCCCCCC UGAGCGCCUC UAUGAUCAAG AGAUACGACG

1101 AGCACCACCA GGACCUGACC CUGCUGAAAG CUCUCGUGCG GCAGCAGCUG

1151 CCUGAGAAGU ACAAAGAGAU UUUCUUCGAC CAGAGCAAGA ACGGCUACGC

1201 CGGCUACAUU GACGGCGGAG CCAGCCAGGA AGAGUUCUAC AAGUUCAUCA

1251 AGCCCAUCCU GGAAAAGAUG GACGGCACCG AGGAACUGCU CGUGAAGCUG

1301 AACAGAGAGG ACCUGCUGCG GAAGCAGCGG ACCUUCGACA ACGGCAGCAU

1351 CCCCCACCAG AUCCACCUGG GAGAGCUGCA CGCCAUUCUG CGGCGGCAGG

1401 AAGAUUUUUA CCCAUUCCUG AAGGACAACC GGGAAAAGAU CGAGAAGAUC

1451 CUGACCUUCC GCAUCCCCUA CUACGUGGGC CCUCUGGCCA GGGGAAACAG

1501 CAGAUUCGCC UGGAUGACCA GAAAGAGCGA GGAAACCAUC ACCCCCUGGA

1551 ACUUCGAGGA AGUGGUGGAC AAGGGCGCUU CCGCCCAGAG CUUCAUCGAG

1601 CGGAUGACCA ACUUCGAUAA GAACCUGCCC AACGAGAAGG UGCUGCCCAA
```

-continued

1651 GCACAGCCUG CUGUACGAGU ACUUCACCGU GUAUAACGAG CUGACCAAAG

1701 UGAAAUACGU GACCGAGGGA AUGAGAAAGC CCGCCUUCCU GAGCGGCGAG

1751 CAGAAAAAGG CCAUCGUGGA CCUGCUGUUC AAGACCAACC GGAAAGUGAC

1801 CGUGAAGCAG CUGAAAGAGG ACUACUUCAA GAAAAUCGAG UGCUUCGACU

1851 CCGUGGAAAU CUCCGGCGUG GAAGAUCGGU UCAACGCCUC CCUGGGCACA

1901 UACCACGAUC UGCUGAAAAU UAUCAAGGAC AAGGACUUCC UGGACAAUGA

1951 GGAAAACGAG GACAUUCUGG AAGAUAUCGU GCUGACCCUG ACACUGUUUG

2001 AGGACAGAGA GAUGAUCGAG GAACGGCUGA AAACCUAUGC CCACCUGUUC

2051 GACGACAAAG UGAUGAAGCA GCUGAAGCGG CGGAGAUACA CCGGCUGGGG

2101 CAGGCUGAGC CGGAAGCUGA UCAACGGCAU CCGGGACAAG CAGUCCGGCA

2151 AGACAAUCCU GGAUUUCCUG AAGUCCGACG GCUUCGCCAA CAGAAACUUC

2201 AUGCAGCUGA UCCACGACGA CAGCCUGACC UUUAAAGAGG ACAUCCAGAA

2251 AGCCCAGGUG UCCGGCCAGG GCGAUAGCCU GCACGAGCAC AUUGCCAAUC

2301 UGGCCGGCAG CCCCGCCAUU AAGAAGGGCA UCCUGCAGAC AGUGAAGGUG

2351 GUGGACGAGC UCGUGAAAGU GAUGGGCCGG CACAAGCCCG AGAACAUCGU

2401 GAUCGAAAUG GCCAGAGAGA ACCAGACCAC CCAGAAGGGA CAGAAGAACA

2451 GCCGCGAGAG AAUGAAGCGG AUCGAAGAGG GCAUCAAAGA GCUGGGCAGC

2501 CAGAUCCUGA AAGAACACCC CGUGGAAAAC ACCCAGCUGC AGAACGAGAA

2551 GCUGUACCUG UACUACCUGC AGAAUGGGCG GGAUAUGUAC GUGGACCAGG

2601 AACUGGACAU CAACCGGCUG UCCGACUACG AUGUGGACCA UAUCGUGCCU

2651 CAGAGCUUUC UGAAGGACGA CUCCAUCGAC AACAAGGUGC UGACCAGAAG

2701 CGACAAGAAC CGGGGCAAGA GCGACAACGU GCCCUCCGAA GAGGUCGUGA

2751 AGAAGAUGAA GAACUACUGG CGGCAGCUGC UGAACGCCAA GCUGAUUACC

2801 CAGAGAAAGU UCGACAAUCU GACCAAGGCC GAGAGAGGCG GCCUGAGCGA

2851 ACUGGAUAAG GCCGGCUUCA UCAAGAGACA GCUGGUGGAA ACCCGGCAGA

2901 UCACAAAGCA CGUGGCACAG AUCCUGGACU CCCGGAUGAA CACUAAGUAC

2951 GACGAGAAUG ACAAGCUGAU CCGGGAAGUG AAAGUGAUCA CCCUGAAGUC

3001 CAAGCUGGUG UCCGAUUUCC GGAAGGAUUU CCAGUUUUAC AAAGUGCGCG

3051 AGAUCAACAA CUACCACCAC GCCCACGACG CCUACCUGAA CGCCGUCGUG

3101 GGAACCGCCC UGAUCAAAAA GUACCCUAAG CUGGAAAGCG AGUUCGUGUA

3151 CGGCGACUAC AAGGUGUACG ACGUGCGGAA GAUGAUCGCC AAGAGCGAGC

3201 AGGAAAUCGG CAAGGCUACC GCCAAGUACU UCUUCUACAG CAACAUCAUG

3251 AACUUUUUCA AGACCGAGAU UACCCUGGCC AACGGCGAGA UCCGGAAGCG

3301 GCCUCUGAUC GAGACAAACG GCGAAACCGG GGAGAUCGUG UGGGAUAAGG

3351 GCCGGGAUUU UGCCACCGUG CGGAAAGUGC UGAGCAUGCC CCAAGUGAAU

3401 AUCGUGAAAA AGACCGAGGU GCAGACAGGC GGCUUCAGCA AAGAGUCUAU

3451 CCUGCCCAAG AGGAACAGCG AUAAGCUGAU CGCCAGAAAG AAGGACUGGG

3501 ACCCUAAGAA GUACGGCGGC UUCGACAGCC CCACCGUGGC CUAUUCUGUG

3551 CUGGUGGUGG CCAAAGUGGA AAAGGGCAAG UCCAAGAAAC UGAAGAGUGU

3601 GAAAGAGCUG CUGGGGAUCA CCAUCAUGGA AAGAAGCAGC UUCGAGAAGA

-continued

```
3651 AUCCCAUCGA CUUUCUGGAA GCCAAGGGCU ACAAAGAAGU GAAAAAGGAC
3701 CUGAUCAUCA AGCUGCCUAA GUACUCCCUG UUCGAGCUGG AAAACGGCCG
3751 GAAGAGAAUG CUGGCCUCUG CCGGCGAACU GCAGAAGGGA AACGAACUGG
3801 CCCUGCCCUC CAAAUAUGUG AACUUCCUGU ACCUGGCCAG CCACUAUGAG
3851 AAGCUGAAGG GCUCCCCCGA GGAUAAUGAG CAGAAACAGC UGUUUGUGGA
3901 ACAGCACAAG CACUACCUGG ACGAGAUCAU CGAGCAGAUC AGCGAGUUCU
3951 CCAAGAGAGU GAUCCUGGCC GACGCUAAUC UGGACAAAGU GCUGUCCGCC
4001 UACAACAAGC ACCGGGAUAA GCCCAUCAGA GAGCAGGCCG AGAAUAUCAU
4051 CCACCUGUUU ACCCUGACCA AUCUGGGAGC CCCUGCCGCC UUCAAGUACU
4101 UUGACACCAC CAUCGACCGG AAGAGGUACA CCAGCACCAA AGAGGUGCUG
4151 GACGCCACCC UGAUCCACCA GAGCAUCACC GGCCUGUACG AGACACGGAU
4201 CGACCUGUCU CAGCUGGGAG GCGACAAAAG GCCGGCGGCC ACGAAAAAGG
4251 CCGGCCAGGC AAAAAAGAAA AAGUAAGAAU UCCUAggaUc cACUAGUCCA
4301 GUGUGGUGGA AUUCUGCAGA AAAAAAAAAA AAAAAAAAAA AAAAAAAAAA
4351 AAAAAAAAAA AAAAAAAAAA AAAAAAAAAA AAAAAAAAAA AAAAAAAAAA
4401 AAAAAAAAAA AAAAAAAAAA AAAAAAAAAA AAAAAAAAAG CGGCC
```

The following sequence (SEQ ID NO: 16) corresponds to a polyribonucleotide (e.g., RNA) sequence comprising Minimal 5' UTR (SEQ ID NO: 7), D10A Cas9 (SEQ ID NO: 2), and the sequence 5'-GAATT-3' 3' UTR.

```
                                                      (SEQ ID NO: 16)
   1 GGGAGACGCC ACCAUGGCCC CAAAGAAGAA GCGGAAGGUC GGUAUCCACG
  51 GAGUCCCAGC AGCCGACAAG AAGUACAGCA UCGGCCUGgc cAUCGGCACC
 101 AACUCUGUGG GCUGGGCCGU GAUCACCGAC GAGUACAAGG UGCCCAGCAA
 151 GAAAUUCAAG GUGCUGGGCA ACACCGACCG GCACAGCAUC AAGAAGAACC
 201 UGAUCGGAGC CCUGCUGUUC GACAGCGGCG AAACAGCCGA GGCCACCCGG
 251 CUGAAGAGAA CCGCCAGAAG AAGAUACACC AGACGGAAGA ACCGGAUCUG
 301 CUAUCUGCAA GAGAUCUUCA GCAACGAGAU GGCCAAGGUG GACGACAGCU
 351 UCUUCCACAG ACUGGAAGAG UCCUUCCUGG UGGAAGAGGA UAAGAAGCAC
 401 GAGCGGCACC CCAUCUUCGG CAACAUCGUG GACGAGGUGG CCUACCACGA
 451 GAAGUACCCC ACCAUCUACC ACCUGAGAAA GAAACUGGUG GACAGCACCG
 501 ACAAGGCCGA CCUGCGGCUG AUCUAUCUGG CCCUGGCCCA CAUGAUCAAG
 551 UUCCGGGGCC ACUUCCUGAU CGAGGGCGAC CUGAACCCCG ACAACAGCGA
 601 CGUGGACAAG CUGUUCAUCC AGCUGGUGCA GACCUACAAC CAGCUGUUCG
 651 AGGAAAACCC CAUCAACGCC AGCGGCGUGG ACGCCAAGGC CAUCCUGUCU
 701 GCCAGACUGA GCAAGAGCAG ACGGCUGGAA AAUCUGAUCG CCCAGCUGCC
 751 CGGCGAGAAG AAGAAUGGCC UGUUCGGAAA CCUGAUUGCC CUGAGCCUGG
 801 GCCUGACCCC CAACUUCAAG AGCAACUUCG ACCUGGCCGA GGAUGCCAAA
 851 CUGCAGCUGA GCAAGGACAC CUACGACGAC GACCUGGACA ACCUGCUGGC
 901 CCAGAUCGGC GACCAGUACG CCGACCUGUU UCUGGCCGCC AAGAACCUGU
 951 CCGACGCCAU CCUGCUGAGC GACAUCCUGA GAGUGAACAC CGAGAUCACC
1001 AAGGCCCCCC UGAGCGCCUC UAUGAUCAAG AGAUACGACG AGCACCACCA
```

-continued

1051 GGACCUGACC CUGCUGAAAG CUCUCGUGCG GCAGCAGCUG CCUGAGAAGU

1101 ACAAAGAGAU UUUCUUCGAC CAGAGCAAGA ACGGCUACGC CGGCUACAUU

1151 GACGGCGGAG CCAGCCAGGA AGAGUUCUAC AAGUUCAUCA AGCCCAUCCU

1201 GGAAAAGAUG GACGGCACCG AGGAACUGCU CGUGAAGCUG AACAGAGAGG

1251 ACCUGCUGCG GAAGCAGCGG ACCUUCGACA ACGGCAGCAU CCCCCACCAG

1301 AUCCACCUGG GAGAGCUGCA CGCCAUUCUG CGGCGGCAGG AAGAUUUUUA

1351 CCCAUUCCUG AAGGACAACC GGGAAAAGAU CGAGAAGAUC CUGACCUUCC

1401 GCAUCCCCUA CUACGUGGGC CCUCUGGCCA GGGGAAACAG CAGAUUCGCC

1451 UGGAUGACCA GAAAGAGCGA GGAAACCAUC ACCCCCUGGA ACUUCGAGGA

1501 AGUGGUGGAC AAGGGCGCUU CCGCCCAGAG CUUCAUCGAG CGGAUGACCA

1551 ACUUCGAUAA GAACCUGCCC AACGAGAAGG UGCUGCCCAA GCACAGCCUG

1601 CUGUACGAGU ACUUCACCGU GUAUAACGAG CUGACCAAAG UGAAAUACGU

1651 GACCGAGGGA AUGAGAAAGC CCGCCUUCCU GAGCGGCGAG CAGAAAAAGG

1701 CCAUCGUGGA CCUGCUGUUC AAGACCAACC GGAAAGUGAC CGUGAAGCAG

1751 CUGAAAGAGG ACUACUUCAA GAAAAUCGAG UGCUUCGACU CCGUGGAAAU

1801 CUCCGGCGUG GAAGAUCGGU UCAACGCCUC CCUGGGCACA UACCACGAUC

1851 UGCUGAAAAU UAUCAAGGAC AAGGACUUCC UGGACAAUGA GGAAAACGAG

1901 GACAUUCUGG AAGAUAUCGU GCUGACCCUG ACACUGUUUG AGGACAGAGA

1951 GAUGAUCGAG GAACGGCUGA AAACCUAUGC CCACCUGUUC GACGACAAAG

2001 UGAUGAAGCA GCUGAAGCGG CGGAGAUACA CCGGCUGGGG CAGGCUGAGC

2051 CGGAAGCUGA UCAACGGCAU CCGGGACAAG CAGUCCGGCA AGACAAUCCU

2101 GGAUUUCCUG AAGUCCGACG GCUUCGCCAA CAGAAACUUC AUGCAGCUGA

2151 UCCACGACGA CAGCCUGACC UUUAAAGAGG ACAUCCAGAA AGCCCAGGUG

2201 UCCGGCCAGG GCGAUAGCCU GCACGAGCAC AUUGCCAAUC UGGCCGGCAG

2251 CCCCGCCAUU AAGAAGGGCA UCCUGCAGAC AGUGAAGGUG GUGGACGAGC

2301 UCGUGAAAGU GAUGGGCCGG CACAAGCCCG AGAACAUCGU GAUCGAAAUG

2351 GCCAGAGAGA ACCAGACCAC CCAGAAGGGA CAGAAGAACA GCCGCGAGAG

2401 AAUGAAGCGG AUCGAAGAGG GCAUCAAAGA GCUGGGCAGC CAGAUCCUGA

2451 AAGAACACCC CGUGGAAAAC ACCCAGCUGC AGAACGAGAA GCUGUACCUG

2501 UACUACCUGC AGAAUGGGCG GGAUAUGUAC GUGGACCAGG AACUGGACAU

2551 CAACCGGCUG UCCGACUACG AUGUGGACCA UAUCGUGCCU CAGAGCUUUC

2601 UGAAGGACGA CUCCAUCGAC AACAAGGUGC UGACCAGAAG CGACAAGAAC

2651 CGGGGCAAGA GCGACAACGU GCCCUCCGAA GAGGUCGUGA AGAAGAUGAA

2701 GAACUACUGG CGGCAGCUGC UGAACGCCAA GCUGAUUACC CAGAGAAAGU

2751 UCGACAAUCU GACCAAGGCC GAGAGAGGCG GCCUGAGCGA ACUGGAUAAG

2801 GCCGGCUUCA UCAAGAGACA GCUGGUGGAA ACCCGGCAGA UCACAAAGCA

2851 CGUGGCACAG AUCCUGGACU CCCGGAUGAA CACUAAGUAC GACGAGAAUG

2901 ACAAGCUGAU CCGGGAAGUG AAAGUGAUCA CCCUGAAGUC CAAGCUGGUG

2951 UCCGAUUUCC GGAAGGAUUU CCAGUUUUAC AAAGUGCGCG AGAUCAACAA

3001 CUACCACCAC GCCCACGACG CCUACCUGAA CGCCGUCGUG GGAACCGCCC

3051 UGAUCAAAAA GUACCCUAAG CUGGAAAGCG AGUUCGUGUA CGGCGACUAC

-continued

```
3101 AAGGUGUACG ACGUGCGGAA GAUGAUCGCC AAGAGCGAGC AGGAAAUCGG
3151 CAAGGCUACC GCCAAGUACU UCUUCUACAG CAACAUCAUG AACUUUUUCA
3201 AGACCGAGAU UACCCUGGCC AACGGCGAGA UCCGGAAGCG GCCUCUGAUC
3251 GAGACAAACG GCGAAACCGG GGAGAUCGUG UGGGAUAAGG GCCGGGAUUU
3301 UGCCACCGUG CGGAAAGUGC UGAGCAUGCC CCAAGUGAAU AUCGUGAAAA
3351 AGACCGAGGU GCAGACAGGC GGCUUCAGCA AAGAGUCUAU CCUGCCCAAG
3401 AGGAACAGCG AUAAGCUGAU CGCCAGAAAG AAGGACUGGG ACCCUAAGAA
3451 GUACGGCGGC UUCGACAGCC CCACCGUGGC CUAUUCUGUG CUGGUGGUGG
3501 CCAAAGUGGA AAAGGGCAAG UCCAAGAAAC UGAAGAGUGU GAAAGAGCUG
3551 CUGGGGAUCA CCAUCAUGGA AAGAAGCAGC UUCGAGAAGA AUCCCAUCGA
3601 CUUUCUGGAA GCCAAGGGCU ACAAAGAAGU GAAAAAGGAC CUGAUCAUCA
3651 AGCUGCCUAA GUACUCCCUG UUCGAGCUGG AAAACGGCCG GAAGAGAAUG
3701 CUGGCCUCUG CCGGCGAACU GCAGAAGGGA AACGAACUGG CCCUGCCCUC
3751 CAAAUAUGUG AACUUCCUGU ACCUGGCCAG CCACUAUGAG AAGCUGAAGG
3801 GCUCCCCCGA GGAUAAUGAG CAGAAACAGC UGUUUGUGGA ACAGCACAAG
3851 CACUACCUGG ACGAGAUCAU CGAGCAGAUC AGCGAGUUCU CCAAGAGAGU
3901 GAUCCUGGCC GACGCUAAUC UGGACAAAGU GCUGUCCGCC UACAACAAGC
3951 ACCGGGAUAA GCCCAUCAGA GAGCAGGCCG AGAAUAUCAU CCACCUGUUU
4001 ACCCUGACCA AUCUGGGAGC CCCUGCCGCC UUCAAGUACU UUGACACCAC
4051 CAUCGACCGG AAGAGGUACA CCAGCACCAA AGAGGUGCUG GACGCCACCC
4101 UGAUCCACCA GAGCAUCACC GGCCUGUACG AGACACGGAU CGACCUGUCU
4151 CAGCUGGGAG GCGACAAAAG GCCGGCGGCC ACGAAAAAGG CCGGCCAGGC
4201 AAAAAAGAAA AAGUAAGAAU U
```

The following sequence (SEQ ID NO: 17) corresponds to a polyribonucleotide (e.g., RNA) sequence comprising a hAg 5' UTR (SEQ ID NO: 8), D10A Cas9 (SEQ ID NO: 2), and the sequence 5'-GAATT-3' 3' UTR.

```
                                                    (SEQ ID NO: 17)
  1 GGGAGACUCU UCUGGUCCCC ACAGACUCAG AGAGAACGCC ACCAUGGCCC
 51 CAAAGAAGAA GCGGAAGGUC GGUAUCCACG GAGUCCCAGC AGCCGACAAG
101 AAGUACAGCA UCGGCCUGgc cAUCGGCACC AACUCUGUGG GCUGGGCCGU
151 GAUCACCGAC GAGUACAAGG UGCCCAGCAA GAAAUUCAAG GUGCUGGGCA
201 ACACCGACCG GCACAGCAUC AAGAAGAACC UGAUCGGAGC CCUGCUGUUC
251 GACAGCGGCG AAACAGCCGA GGCCACCCGG CUGAAGAGAA CCGCCAGAAG
301 AAGAUACACC AGACGGAAGA ACCGGAUCUG CUAUCUGCAA GAGAUCUUCA
351 GCAACGAGAU GGCCAAGGUG GACGACAGCU UCUUCCACAG ACUGGAAGAG
401 UCCUUCCUGG UGGAAGAGGA UAAGAAGCAC GAGCGGCACC CCAUCUUCGG
451 CAACAUCGUG GACGAGGUGG CCUACCACGA GAAGUACCCC ACCAUCUACC
501 ACCUGAGAAA GAAACUGGUG GACAGCACCG ACAAGGCCGA CCUGCGGCUG
551 AUCUAUCUGG CCCUGGCCCA CAUGAUCAAG UUCCGGGGCC ACUUCCUGAU
601 CGAGGGCGAC CUGAACCCCG ACAACAGCGA CGUGGACAAG CUGUUCAUCC
651 AGCUGGUGCA GACCUACAAC CAGCUGUUCG AGGAAAACCC CAUCAACGCC
```

-continued

```
 701 AGCGGCGUGG ACGCCAAGGC CAUCCUGUCU GCCAGACUGA GCAAGAGCAG
 751 ACGGCUGGAA AAUCUGAUCG CCCAGCUGCC CGGCGAGAAG AAGAAUGGCC
 801 UGUUCGGAAA CCUGAUUGCC CUGAGCCUGG GCCUGACCCC CAACUUCAAG
 851 AGCAACUUCG ACCUGGCCGA GGAUGCCAAA CUGCAGCUGA GCAAGGACAC
 901 CUACGACGAC GACCUGGACA ACCUGCUGGC CCAGAUCGGC GACCAGUACG
 951 CCGACCUGUU UCUGGCCGCC AAGAACCUGU CCGACGCCAU CCUGCUGAGC
1001 GACAUCCUGA GAGUGAACAC CGAGAUCACC AAGGCCCCCC UGAGCGCCUC
1051 UAUGAUCAAG AGAUACGACG AGCACCACCA GGACCUGACC CUGCUGAAAG
1101 CUCUCGUGCG GCAGCAGCUG CCUGAGAAGU ACAAAGAGAU UUUCUUCGAC
1151 CAGAGCAAGA ACGGCUACGC CGGCUACAUU GACGGCGGAG CCAGCCAGGA
1201 AGAGUUCUAC AAGUUCAUCA AGCCCAUCCU GGAAAAGAUG GACGGCACCG
1251 AGGAACUGCU CGUGAAGCUG AACAGAGAGG ACCUGCUGCG GAAGCAGCGG
1301 ACCUUCGACA ACGGCAGCAU CCCCCACCAG AUCCACCUGG GAGAGCUGCA
1351 CGCCAUUCUG CGGCGGCAGG AAGAUUUUUA CCCAUUCCUG AAGGACAACC
1401 GGGAAAAGAU CGAGAAGAUC CUGACCUUCC GCAUCCCCUA CUACGUGGGC
1451 CCUCUGGCCA GGGGAAACAG CAGAUUCGCC UGGAUGACCA GAAAGAGCGA
1501 GGAAACCAUC ACCCCCUGGA ACUUCGAGGA AGUGGUGGAC AAGGGCGCUU
1551 CCGCCCAGAG CUUCAUCGAG CGGAUGACCA ACUUCGAUAA GAACCUGCCC
1601 AACGAGAAGG UGCUGCCCAA GCACAGCCUG CUGUACGAGU ACUUCACCGU
1651 GUAUAACGAG CUGACCAAAG UGAAAUACGU GACCGAGGGA AUGAGAAAGC
1701 CCGCCUUCCU GAGCGGCGAG CAGAAAAAGG CCAUCGUGGA CCUGCUGUUC
1751 AAGACCAACC GGAAAGUGAC CGUGAAGCAG CUGAAAGAGG ACUACUUCAA
1801 GAAAAUCGAG UGCUUCGACU CCGUGGAAAU CUCCGGCGUG GAAGAUCGGU
1851 UCAACGCCUC CCUGGGCACA UACCACGAUC UGCUGAAAAU UAUCAAGGAC
1901 AAGGACUUCC UGGACAAUGA GGAAAACGAG GACAUUCUGG AAGAUAUCGU
1951 GCUGACCCUG ACACUGUUUG AGGACAGAGA GAUGAUCGAG GAACGGCUGA
2001 AAACCUAUGC CCACCUGUUC GACGACAAAG UGAUGAAGCA GCUGAAGCGG
2051 CGGAGAUACA CCGGCUGGGG CAGGCUGAGC CGGAAGCUGA UCAACGGCAU
2101 CCGGGACAAG CAGUCCGGCA AGACAAUCCU GGAUUUCCUG AAGUCCGACG
2151 GCUUCGCCAA CAGAAACUUC AUGCAGCUGA UCCACGACGA CAGCCUGACC
2201 UUUAAAGAGG ACAUCCAGAA AGCCCAGGUG UCCGGCCAGG GCGAUAGCCU
2251 GCACGAGCAC AUUGCCAAUC UGGCCGGCAG CCCCGCCAUU AAGAAGGGCA
2301 UCCUGCAGAC AGUGAAGGUG GUGGACGAGC UCGUGAAAGU GAUGGGCCGG
2351 CACAAGCCCG AGAACAUCGU GAUCGAAAUG GCCAGAGAGA ACCAGACCAC
2401 CCAGAAGGGA CAGAAGAACA GCCGCGAGAG AAUGAAGCGG AUCGAAGAGG
2451 GCAUCAAAGA GCUGGGCAGC CAGAUCCUGA AAGAACACCC CGUGGAAAAC
2501 ACCCAGCUGC AGAACGAGAA GCUGUACCUG UACUACCUGC AGAAUGGGCG
2551 GGAUAUGUAC GUGGACCAGG AACUGGACAU CAACCGGCUG UCCGACUACG
2601 AUGUGGACCA UAUCGUGCCU CAGAGCUUUC UGAAGGACGA CUCCAUCGAC
2651 AACAAGGUGC UGACCAGAAG CGACAAGAAC CGGGGCAAGA GCGACAACGU
```

-continued

2701 GCCCUCCGAA GAGGUCGUGA AGAAGAUGAA GAACUACUGG CGGCAGCUGC

2751 UGAACGCCAA GCUGAUUACC CAGAGAAAGU UCGACAAUCU GACCAAGGCC

2801 GAGAGAGGCG GCCUGAGCGA ACUGGAUAAG GCCGGCUUCA UCAAGAGACA

2851 GCUGGUGGAA ACCCGGCAGA UCACAAAGCA CGUGGCACAG AUCCUGGACU

2901 CCCGGAUGAA CACUAAGUAC GACGAGAAUG ACAAGCUGAU CCGGGAAGUG

2951 AAAGUGAUCA CCCUGAAGUC CAAGCUGGUG UCCGAUUUCC GGAAGGAUUU

3001 CCAGUUUUAC AAAGUGCGCG AGAUCAACAA CUACCACCAC GCCCACGACG

3051 CCUACCUGAA CGCCGUCGUG GGAACCGCCC UGAUCAAAAA GUACCCUAAG

3101 CUGGAAAGCG AGUUCGUGUA CGGCGACUAC AAGGUGUACG ACGUGCGGAA

3151 GAUGAUCGCC AAGAGCGAGC AGGAAAUCGG CAAGGCUACC GCCAAGUACU

3201 UCUUCUACAG CAACAUCAUG AACUUUUUCA AGACCGAGAU UACCCUGGCC

3251 AACGGCGAGA UCCGGAAGCG GCCUCUGAUC GAGACAAACG GCGAAACCGG

3301 GGAGAUCGUG UGGGAUAAGG GCCGGGAUUU UGCCACCGUG CGGAAAGUGC

3351 UGAGCAUGCC CCAAGUGAAU AUCGUGAAAA AGACCGAGGU GCAGACAGGC

3401 GGCUUCAGCA AAGAGUCUAU CCUGCCCAAG AGGAACAGCG AUAAGCUGAU

3451 CGCCAGAAAG AAGGACUGGG ACCCUAAGAA GUACGGCGGC UUCGACAGCC

3501 CCACCGUGGC CUAUUCUGUG CUGGUGGUGG CCAAAGUGGA AAAGGGCAAG

3551 UCCAAGAAAC UGAAGAGUGU GAAAGAGCUG CUGGGGAUCA CCAUCAUGGA

3601 AAGAAGCAGC UUCGAGAAGA AUCCCAUCGA CUUUCUGGAA GCCAAGGGCU

3651 ACAAAGAAGU GAAAAAGGAC CUGAUCAUCA AGCUGCCUAA GUACUCCCUG

3701 UUCGAGCUGG AAAACGGCCG GAAGAGAAUG CUGGCCUCUG CCGGCGAACU

3751 GCAGAAGGGA AACGAACUGG CCCUGCCCUC CAAAUAUGUG AACUUCCUGU

3801 ACCUGGCCAG CCACUAUGAG AAGCUGAAGG GCUCCCCCGA GGAUAAUGAG

3851 CAGAAACAGC UGUUUGUGGA ACAGCACAAG CACUACCUGG ACGAGAUCAU

3901 CGAGCAGAUC AGCGAGUUCU CCAAGAGAGU GAUCCUGGCC GACGCUAAUC

3951 UGGACAAAGU GCUGUCCGCC UACAACAAGC ACCGGGAUAA GCCCAUCAGA

4001 GAGCAGGCCG AGAAUAUCAU CCACCUGUUU ACCCUGACCA AUCUGGGAGC

4051 CCCUGCCGCC UUCAAGUACU UUGACACCAC CAUCGACCGG AAGAGGUACA

4101 CCAGCACCAA AGAGGUGCUG GACGCCACCC UGAUCCACCA GAGCAUCACC

4151 GGCCUGUACG AGACACGGAU CGACCUGUCU CAGCUGGGAG GCGACAAAAG

4201 GCCGGCGGCC ACGAAAAAGG CCGGCCAGGC AAAAAAGAAA AAGUAAGAAU

4251 U

The following sequence (SEQ ID NO: 18) corresponds to a polyribonucleotide (e.g., RNA) sequence comprising TISU+T 5' UTR (SEQ ID NO: 10), D10A Cas9 (SEQ ID NO: 2), and the sequence 5'-GAATT-3' 3' UTR.

(SEQ ID NO: 18)

1 GGGAGACUGC CAAGAUGGCC CCAAAGAAGA AGCGGAAGGU CGGUAUCCAC

51 GGAGUCCCAG CAGCCGACAA GAAGUACAGC AUCGGCCUGg ccAUCGGCAC

101 CAACUCUGUG GGCUGGGCCG UGAUCACCGA CGAGUACAAG GUGCCCAGCA

151 AGAAAUUCAA GGUGCUGGGC AACACCGACC GGCACAGCAU CAAGAAGAAC

201 CUGAUCGGAG CCCUGCUGUU CGACAGCGGC GAAACAGCCG AGGCCACCCG

-continued

251 GCUGAAGAGA ACCGCCAGAA GAAGAUACAC CAGACGGAAG AACCGGAUCU

301 GCUAUCUGCA AGAGAUCUUC AGCAACGAGA UGGCCAAGGU GGACGACAGC

351 UUCUUCCACA GACUGGAAGA GUCCUUCCUG GUGGAAGAGG AUAAGAAGCA

401 CGAGCGGCAC CCCAUCUUCG GCAACAUCGU GGACGAGGUG GCCUACCACG

451 AGAAGUACCC CACCAUCUAC CACCUGAGAA AGAAACUGGU GGACAGCACC

501 GACAAGGCCG ACCUGCGGCU GAUCUAUCUG GCCCUGGCCC ACAUGAUCAA

551 GUUCCGGGGC CACUUCCUGA UCGAGGGCGA CCUGAACCCC GACAACAGCG

601 ACGUGGACAA GCUGUUCAUC CAGCUGGUGC AGACCUACAA CCAGCUGUUC

651 GAGGAAAACC CCAUCAACGC CAGCGGCGUG GACGCCAAGG CCAUCCUGUC

701 UGCCAGACUG AGCAAGAGCA GACGGCUGGA AAAUCUGAUC GCCCAGCUGC

751 CCGGCGAGAA GAAGAAUGGC CUGUUCGGAA ACCUGAUUGC CCUGAGCCUG

801 GGCCUGACCC CCAACUUCAA GAGCAACUUC GACCUGGCCG AGGAUGCCAA

851 ACUGCAGCUG AGCAAGGACA CCUACGACGA CGACCUGGAC AACCUGCUGG

901 CCCAGAUCGG CGACCAGUAC GCCGACCUGU UUCUGGCCGC CAAGAACCUG

951 UCCGACGCCA UCCUGCUGAG CGACAUCCUG AGAGUGAACA CCGAGAUCAC

1001 CAAGGCCCCC CUGAGCGCCU CUAUGAUCAA GAGAUACGAC GAGCACCACC

1051 AGGACCUGAC CCUGCUGAAA GCUCUCGUGC GGCAGCAGCU GCCUGAGAAG

1101 UACAAAGAGA UUUUCUUCGA CCAGAGCAAG AACGGCUACG CCGGCUACAU

1151 UGACGGCGGA GCCAGCCAGG AAGAGUUCUA CAAGUUCAUC AAGCCCAUCC

1201 UGGAAAAGAU GGACGGCACC GAGGAACUGC UCGUGAAGCU GAACAGAGAG

1251 GACCUGCUGC GGAAGCAGCG GACCUUCGAC AACGGCAGCA UCCCCCACCA

1301 GAUCCACCUG GGAGAGCUGC ACGCCAUUCU GCGGCGGCAG GAAGAUUUUU

1351 ACCCAUUCCU GAAGGACAAC CGGGAAAAGA UCGAGAAGAU CCUGACCUUC

1401 CGCAUCCCCU ACUACGUGGG CCCUCUGGCC AGGGGAAACA GCAGAUUCGC

1451 CUGGAUGACC AGAAAGAGCG AGGAAACCAU CACCCCCUGG AACUUCGAGG

1501 AAGUGGUGGA CAAGGGCGCU UCCGCCCAGA GCUUCAUCGA GCGGAUGACC

1551 AACUUCGAUA AGAACCUGCC CAACGAGAAG GUGCUGCCCA AGCACAGCCU

1601 GCUGUACGAG UACUUCACCG UGUAUAACGA GCUGACCAAA GUGAAAUACG

1651 UGACCGAGGG AAUGAGAAAG CCCGCCUUCC UGAGCGGCGA GCAGAAAAAG

1701 GCCAUCGUGG ACCUGCUGUU CAAGACCAAC CGGAAAGUGA CCGUGAAGCA

1751 GCUGAAAGAG GACUACUUCA AGAAAAUCGA GUGCUUCGAC UCCGUGGAAA

1801 UCUCCGGCGU GGAAGAUCGG UUCAACGCCU CCCUGGGCAC AUACCACGAU

1851 CUGCUGAAAA UUAUCAAGGA CAAGGACUUC CUGGACAAUG AGGAAAACGA

1901 GGACAUUCUG GAAGAUAUCG UGCUGACCCU GACACUGUUU GAGGACAGAG

1951 AGAUGAUCGA GGAACGGCUG AAAACCUAUG CCCACCUGUU CGACGACAAA

2001 GUGAUGAAGC AGCUGAAGCG GCGGAGAUAC ACCGGCUGGG GCAGGCUGAG

2051 CCGGAAGCUG AUCAACGGCA UCCGGGACAA GCAGUCCGGC AAGACAAUCC

2101 UGGAUUUCCU GAAGUCCGAC GGCUUCGCCA ACAGAAACUU CAUGCAGCUG

2151 AUCCACGACG ACAGCCUGAC CUUUAAAGAG GACAUCCAGA AAGCCCAGGU

2201 GUCCGGCCAG GGCGAUAGCC UGCACGAGCA CAUUGCCAAU CUGGCCGGCA

2251 GCCCCGCCAU UAAGAAGGGC AUCCUGCAGA CAGUGAAGGU GGUGGACGAG

-continued

2301 CUCGUGAAAG UGAUGGGCCG GCACAAGCCC GAGAACAUCG UGAUCGAAAU

2351 GGCCAGAGAG AACCAGACCA CCCAGAAGGG ACAGAAGAAC AGCCGCGAGA

2401 GAAUGAAGCG GAUCGAAGAG GGCAUCAAAG AGCUGGGCAG CCAGAUCCUG

2451 AAAGAACACC CCGUGGAAAA CACCCAGCUG CAGAACGAGA AGCUGUACCU

2501 GUACUACCUG CAGAAUGGGC GGGAUAUGUA CGUGGACCAG GAACUGGACA

2551 UCAACCGGCU GUCCGACUAC GAUGUGGACC AUAUCGUGCC UCAGAGCUUU

2601 CUGAAGGACG ACUCCAUCGA CAACAAGGUG CUGACCAGAA GCGACAAGAA

2651 CCGGGGCAAG AGCGACAACG UGCCCUCCGA AGAGGUCGUG AAGAAGAUGA

2701 AGAACUACUG GCGGCAGCUG CUGAACGCCA AGCUGAUUAC CCAGAGAAAG

2751 UUCGACAAUC UGACCAAGGC CGAGAGAGGC GGCCUGAGCG AACUGGAUAA

2801 GGCCGGCUUC AUCAAGAGAC AGCUGGUGGA AACCCGGCAG AUCACAAAGC

2851 ACGUGGCACA GAUCCUGGAC UCCCGGAUGA ACACUAAGUA CGACGAGAAU

2901 GACAAGCUGA UCCGGGAAGU GAAAGUGAUC ACCCUGAAGU CCAAGCUGGU

2951 GUCCGAUUUC CGGAAGGAUU UCCAGUUUUA CAAAGUGCGC GAGAUCAACA

3001 ACUACCACCA CGCCCACGAC GCCUACCUGA ACGCCGUCGU GGGAACCGCC

3051 CUGAUCAAAA AGUACCCUAA GCUGGAAAGC GAGUUCGUGU ACGGCGACUA

3101 CAAGGUGUAC GACGUGCGGA AGAUGAUCGC CAAGAGCGAG CAGGAAAUCG

3151 GCAAGGCUAC CGCCAAGUAC UUCUUCUACA GCAACAUCAU GAACUUUUUC

3201 AAGACCGAGA UUACCCUGGC CAACGGCGAG AUCCGGAAGC GGCCUCUGAU

3251 CGAGACAAAC GGCGAAACCG GGGAGAUCGU GUGGGAUAAG GGCCGGGAUU

3301 UUGCCACCGU GCGGAAAGUG CUGAGCAUGC CCCAAGUGAA UAUCGUGAAA

3351 AAGACCGAGG UGCAGACAGG CGGCUUCAGC AAAGAGUCUA UCCUGCCCAA

3401 GAGGAACAGC GAUAAGCUGA UCGCCAGAAA GAAGGACUGG GACCCUAAGA

3451 AGUACGGCGG CUUCGACAGC CCCACCGUGG CCUAUUCUGU GCUGGUGGUG

3501 GCCAAAGUGG AAAAGGGCAA GUCCAAGAAA CUGAAGAGUG UGAAAGAGCU

3551 GCUGGGGAUC ACCAUCAUGG AAAGAAGCAG CUUCGAGAAG AAUCCCAUCG

3601 ACUUUCUGGA AGCCAAGGGC UACAAAGAAG UGAAAAAGGA CCUGAUCAUC

3651 AAGCUGCCUA AGUACUCCCU GUUCGAGCUG GAAAACGGCC GGAAGAGAAU

3701 GCUGGCCUCU GCCGGCGAAC UGCAGAAGGG AAACGAACUG GCCCUGCCCU

3751 CCAAAUAUGU GAACUUCCUG UACCUGGCCA GCCACUAUGA GAAGCUGAAG

3801 GGCUCCCCCG AGGAUAAUGA GCAGAAACAG CUGUUUGUGG AACAGCACAA

3851 GCACUACCUG GACGAGAUCA UCGAGCAGAU CAGCGAGUUC UCCAAGAGAG

3901 UGAUCCUGGC CGACGCUAAU CUGGACAAAG UGCUGUCCGC CUACAACAAG

3951 CACCGGGAUA AGCCCAUCAG AGAGCAGGCC GAGAAUAUCA UCCACCUGUU

4001 UACCCUGACC AAUCUGGGAG CCCCUGCCGC CUUCAAGUAC UUUGACACCA

4051 CCAUCGACCG GAAGAGGUAC ACCAGCACCA AAGAGGUGCU GGACGCCACC

4101 CUGAUCCACC AGAGCAUCAC CGGCCUGUAC GAGACACGGA UCGACCUGUC

4151 UCAGCUGGGA GGCGACAAAA GGCCGGCGGC CACGAAAAAG GCCGGCCAGG

4201 CAAAAAAGAA AAAGUAAGAA UU

The following amino acid sequence (SEQ ID NO: 19) corresponds to a wildtype Cas9, as can be encoded by SEQ ID NO: 1.

```
                                              (SEQ ID NO: 19)
   1 MAPKKKRKVG IHGVPAADKK YSIGLDIGTN SVGWAVITDE YKVPSKKFKV

  51 LGNTDRHSIK KNLIGALLFD SGETAEATRL KRTARRRYTR RKNRICYLQE

 101 IFSNEMAKVD DSFFHRLEES FLVEEDKKHE RHPIFGNIVD EVAYHEKYPT

 151 IYHLRKKLVD STDKADLRLI YLALAHMIKF RGHFLIEGDL NPDNSDVDKL

 201 FIQLVQTYNQ LFEENPINAS GVDAKAILSA RLSKSRRLEN LIAQLPGEKK

 251 NGLFGNLIAL SLGLTPNFKS NFDLAEDAKL QLSKDTYDDD LDNLLAQIGD

 301 QYADLFLAAK NLSDAILLSD ILRVNTEITK APLSASMIKR YDEHHQDLTL

 351 LKALVRQQLP EKYKEIFFDQ SKNGYAGYID GGASQEEFYK FIKPILEKMD

 401 GTEELLVKLN REDLLRKQRT FDNGSIPHQI HLGELHAILR RQEDFYPFLK

 451 DNREKIEKIL TFRIPYYVGP LARGNSRFAW MTRKSEETIT PWNFEEVVDK

 501 GASAQSFIER MTNFDKNLPN EKVLPKHSLL YEYFTVYNEL TKVKYVTEGM

 551 RKPAFLSGEQ KKAIVDLLFK TNRKVTVKQL KEDYFKKIEC FDSVEISGVE

 601 DRFNASLGTY HDLLKIIKDK DFLDNEENED ILEDIVLTLT LFEDREMIEE

 651 RLKTYAHLFD DKVMKQLKRR RYTGWGRLSR KLINGIRDKQ SGKTILDFLK

 701 SDGFANRNFM QLIHDDSLTF KEDIQKAQVS GQGDSLHEHI ANLAGSPAIK

 751 KGILQTVKVV DELVKVMGRH KPENIVIEMA RENQTTQKGQ KNSRERMKRI

 801 EEGIKELGSQ ILKEHPVENT QLQNEKLYLY YLQNGRDMYV DQELDINRLS

 851 DYDVDHIVPQ SFLKDDSIDN KVLTRSDKNR GKSDNVPSEE VVKKMKNYWR

 901 QLLNAKLITQ RKFDNLTKAE RGGLSELDKA GFIKRQLVET RQITKHVAQI

 951 LDSRMNTKYD ENDKLIREVK VITLKSKLVS DFRKDFQFYK VREINNYHHA

1001 HDAYLNAVVG TALIKKYPKL ESEFVYGDYK VYDVRKMIAK SEQEIGKATA

1051 KYFFYSNIMN FFKTEITLAN GEIRKRPLIE TNGETGEIVW DKGRDFATVR

1101 KVLSMPQVNI VKKTEVQTGG FSKESILPKR NSDKLIARKK DWDPKKYGGF

1151 DSPTVAYSVL VVAKVEKGKS KKLKVKELLG ITIMERSSFE KNPIDFLEAK

1201 GYKEVKKDLI IKLPKYSLFE LENGRKRMLA SAGELQKGNE LALPSKYVNF

1251 LYLASHYEKL KGSPEDNEQK QLFVEQHKHY LDEIIEQISE FSKRVILADA

1301 NLDKVLSAYN KHRDKPIREQ AENIIHLFTL TNLGAPAAFK YFDTTIDRKR

1351 YTSTKEVLDA TLIHQSITGL YETRIDLSQL GGDKRPAATK KAGQAKKKK
```

The following amino acid sequence (SEQ ID NO: 20) corresponds to a D10A Cas9, as can be encoded by SEQ ID NO: 2.

```
                                              (SEQ ID NO: 20)
   1 MAPKKKRKVG IHGVPAADKK YSIGLAIGTN SVGWAVITDE YKVPSKKFKV

  51 LGNTDRHSIK KNLIGALLFD SGETAEATRL KRTARRRYTR RKNRICYLQE

 101 IFSNEMAKVD DSFFHRLEES FLVEEDKKHE RHPIFGNIVD EVAYHEKYPT

 151 IYHLRKKLVD STDKADLRLI YLALAHMIKF RGHFLIEGDL NPDNSDVDKL

 201 FIQLVQTYNQ LFEENPINAS GVDAKAILSA RLSKSRRLEN LIAQLPGEKK

 251 NGLFGNLIAL SLGLTPNFKS NFDLAEDAKL QLSKDTYDDD LDNLLAQIGD
```

-continued

```
 301 QYADLFLAAK NLSDAILLSD ILRVNTEITK APLSASMIKR YDEHHQDLTL

 351 LKALVRQQLP EKYKEIFFDQ SKNGYAGYID GGASQEEFYK FIKPILEKMD

 401 GTEELLVKLN REDLLRKQRT FDNGSIPHQI HLGELHAILR RQEDFYPFLK

 451 DNREKIEKIL TFRIPYYVGP LARGNSRFAW MTRKSEETIT PWNFEEVVDK

 501 GASAQSFIER MTNFDKNLPN EKVLPKHSLL YEYFTVYNEL TKVKYVTEGM

 551 RKPAFLSGEQ KKAIVDLLFK TNRKVTVKQL KEDYFKKIEC FDSVEISGVE

 601 DRFNASLGTY HDLLKIIKDK DFLDNEENED ILEDIVLTLT LFEDREMIEE

 651 RLKTYAHLFD DKVMKQLKRR RYTGWGRLSR KLINGIRDKQ SGKTILDFLK

 701 SDGFANRNFM QLIHDDSLTF KEDIQKAQVS GQGDSLHEHI ANLAGSPAIK

 751 KGILQTVKVV DELVKVMGRH KPENIVIEMA RENQTTQKGQ KNSRERMKRI

 801 EEGIKELGSQ ILKEHPVENT QLQNEKLYLY YLQNGRDMYV DQELDINRLS

 851 DYDVDHIVPQ SFLKDDSIDN KVLTRSDKNR GKSDNVPSEE VVKKMKNYWR

 901 QLLNAKLITQ RKFDNLTKAE RGGLSELDKA GFIKRQLVET RQITKHVAQI

 951 LDSRMNTKYD ENDKLIREVK VITLKSKLVS DFRKDFQFYK VREINNYHHA

1001 HDAYLNAVVG TALIKKYPKL ESEFVYGDYK VYDVRKMIAK SEQEIGKATA

1051 KYFFYSNIMN FFKTEITLAN GEIRKRPLIE TNGETGEIVW DKGRDFATVR

1101 KVLSMPQVNI VKKTEVQTGG FSKESILPKR NSDKLIARKK DWDPKKYGGF

1151 DSPTVAYSVL VVAKVEKGKS KKLKVKELLG ITIMERSSFE KNPIDFLEAK

1201 GYKEVKKDLI IKLPKYSLFE LENGRKRMLA SAGELQKGNE LALPSKYVNF

1251 LYLASHYEKL KGSPEDNEQK QLFVEQHKHY LDEIIEQISE FSKRVILADA

1301 NLDKVLSAYN KHRDKPIREQ AENIIHLFTL TNLGAPAAFK YFDTTIDRKR

1351 YTSTKEVLDA TLIHQSITGL YETRIDLSQL GGDKRPAATK KAGQAKKKK
```

The following polyribonucleotide (e.g., RNA) sequence (SEQ ID NO: 21) corresponds to CRISPR-gRNA-hPCSK9-ETH1.

```
                                               (SEQ ID NO: 21)
  1  GGGGUGCUAG CCUUGCGUUC CGGUUUUAGA GCUAGAAAUA GCAAGUUAAA

 51  AUAAGGCUAG UCCGUUAUCA ACUUGAAAAA GUGGCACCGA GUCGGUGCUU

101  UUUU
```

The following polyribonucleotide (e.g., RNA) sequence (SEQ ID NO: 22) corresponds to CRISPR-gRNA-hPCSK9-ETH2.

```
                                              (SEQ ID NO: 22)
  1 GGUCUUGGUG AGGUAUCCCC GGGUUUUAGA GCUAGAAAUA GCAAGUUAAA

 51 AUAAGGCUAG UCCGUUAUCA ACUUGAAAAA GUGGCACCGA GUCGGUGCUU

101 UUUU
```

The following polyribonucleotide (e.g., RNA) sequence (SEQ ID NO: 23) corresponds to CRISPR-gRNA-hPCSK9-ETH3.

(SEQ ID NO: 23)
1 GGGUCGUGCU GGUCACCGCU GCGUUUUAGA GCUAGAAAUA GCAAGUUAAA

51 AUAAGGCUAG UCCGUUAUCA ACUUGAAAAA GUGGCACCGA GUCGGUGCUU

101 UUUU

The following polyribonucleotide (e.g., RNA) sequence (SEQ ID NO: 24) corresponds to CRISPR-gRNA-hPCSK9-ETH4.

(SEQ ID NO: 24)
1 GGCACCGACU UCAACAGCGU GCGUUUUAGA GCUAGAAAUA GCAAGUUAAA

51 AUAAGGCUAG UCCGUUAUCA ACUUGAAAAA GUGGCACCGA GUCGGUGCUU

101 UUUU

The following polyribonucleotide (e.g., RNA) sequence (SEQ ID NO: 25) corresponds to CRISPR-gRNA-hPCSK9-ETH5.

(SEQ ID NO: 25)
1 GGAUGCUGGG AUAAUUCGCU CCGUUUUAGA GCUAGAAAUA GCAAGUUAAA

51 AUAAGGCUAG UCCGUUAUCA ACUUGAAAAA GUGGCACCGA GUCGGUGCUU

101 UUUU

The following polyribonucleotide (e.g., RNA) sequence (SEQ ID NO: 26) corresponds to CRISPR-gRNA-hPCSK9-ETH6.

(SEQ ID NO: 26)
1 GGGGCUGAUG AGGCCGCACA UGGUUUUAGA GCUAGAAAUA GCAAGUUAAA

51 AUAAGGCUAG UCCGUUAUCA ACUUGAAAAA GUGGCACCGA GUCGGUGCUU

101 UUUU

The following polynucleotide (e.g., DNA) sequence (SEQ ID NO: 27) encodes for a start codon and a FLAG tag.

(SEQ ID NO: 27)
1 ATGGACTATA AGGACCACGA CGGAGACTAC AAGGATCATG ATATTGATTA

51 CAAAGACGAT GACGATAAG

The following polyribonucleotide (e.g., RNA) sequence (SEQ ID NO: 28) encodes for a start codon and a FLAG tag.

(SEQ ID NO: 28)
1 AUGGACUAUA AGGACCACGA CGGAGACUAC AAGGAUCAUG AUAUUGAUUA

51 CAAAGACGAU GACGAUAAG

The following polyribonucleotide (e.g., RNA) sequence (SEQ ID NO: 29) corresponds to a 5' UTR referred to as CYBA 5' UTR.

(SEQ ID NO: 29)
1 CGCGCCUAGC AGUGUCCCAG CCGGGUUCGU GUCGCC

The following polyribonucleotide (e.g., RNA) sequence (SEQ ID NO: 30) corresponds to a 3' UTR referred to as CYBA 3' UTR.

```
                                          (SEQ ID NO: 30)
  1  CCUCGCCCCG GACCUGCCCU CCCGCCAGGU GCACCCACCU GCAAUAAAUG

 51  CAGCGAAGCC GGGA
```

The following polynucleotide (e.g., DNA) sequence (SEQ ID NO: 31) comprises 5p-UTR 5' UTR (SEQ ID NO: 46), wildtype Cas9 (SEQ ID NO: 52), and 3p-UTR 3' UTR (SEQ ID NO: 47).

```
                                            (SEQ ID NO: 31)
   1  GGGAGACCCA AGCTGGCTAG CGTTTAAACT TAAGCTTGCC ACCATGGACT

  51  ATAAGGACCA CGACGGAGAC TACAAGGATC ATGATATTGA TTACAAAGAC

 101  GATGACGATA AGATGGCCCC AAAGAAGAAG CGGAAGGTCG GTATCCACGG

 151  AGTCCCAGCA GCCGACAAGA AGTACAGCAT CGGCCTGGAC ATCGGCACCA

 201  ACTCTGTGGG CTGGGCCGTG ATCACCGACG AGTACAAGGT GCCCAGCAAG

 251  AAATTCAAGG TGCTGGGCAA CACCGACCGG CACAGCATCA AGAAGAACCT

 301  GATCGGAGCC CTGCTGTTCG ACAGCGGCGA AACAGCCGAG GCCACCCGGC

 351  TGAAGAGAAC CGCCAGAAGA AGATACACCA GACGGAAGAA CCGGATCTGC

 401  TATCTGCAAG AGATCTTCAG CAACGAGATG GCCAAGGTGG ACGACAGCTT

 451  CTTCCACAGA CTGGAAGAGT CCTTCCTGGT GGAAGAGGAT AAGAAGCACG

 501  AGCGGCACCC CATCTTCGGC AACATCGTGG ACGAGGTGGC CTACCACGAG

 551  AAGTACCCCA CCATCTACCA CCTGAGAAAG AAACTGGTGG ACAGCACCGA

 601  CAAGGCCGAC CTGCGGCTGA TCTATCTGGC CCTGGCCCAC ATGATCAAGT

 651  TCCGGGGCCA CTTCCTGATC GAGGGCGACC TGAACCCCGA CAACAGCGAC

 701  GTGGACAAGC TGTTCATCCA GCTGGTGCAG ACCTACAACC AGCTGTTCGA

 751  GGAAAACCCC ATCAACGCCA GCGGCGTGGA CGCCAAGGCC ATCCTGTCTG

 801  CCAGACTGAG CAAGAGCAGA CGGCTGGAAA ATCTGATCGC CCAGCTGCCC

 851  GGCGAGAAGA AGAATGGCCT GTTCGGAAAC CTGATTGCCC TGAGCCTGGG

 901  CCTGACCCCC AACTTCAAGA GCAACTTCGA CCTGGCCGAG GATGCCAAAC

 951  TGCAGCTGAG CAAGGACACC TACGACGACG ACCTGGACAA CCTGCTGGCC

1001  CAGATCGGCG ACCAGTACGC CGACCTGTTT CTGGCCGCCA AGAACCTGTC

1051  CGACGCCATC CTGCTGAGCG ACATCCTGAG AGTGAACACC GAGATCACCA

1101  AGGCCCCCCT GAGCGCCTCT ATGATCAAGA GATACGACGA GCACCACCAG

1151  GACCTGACCC TGCTGAAAGC TCTCGTGCGG CAGCAGCTGC CTGAGAAGTA

1201  CAAAGAGATT TTCTTCGACC AGAGCAAGAA CGGCTACGCC GGCTACATTG

1251  ACGGCGGAGC CAGCCAGGAA GAGTTCTACA AGTTCATCAA GCCCATCCTG

1301  GAAAAGATGG ACGGCACCGA GGAACTGCTC GTGAAGCTGA ACAGAGAGGA

1351  CCTGCTGCGG AAGCAGCGGA CCTTCGACAA CGGCAGCATC CCCCACCAGA

1401  TCCACCTGGG AGAGCTGCAC GCCATTCTGC GGCGGCAGGA AGATTTTTAC

1451  CCATTCCTGA AGGACAACCG GGAAAAGATC GAGAAGATCC TGACCTTCCG

1501  CATCCCCTAC TACGTGGGCC CTCTGGCCAG GGGAAACAGC AGATTCGCCT

1551  GGATGACCAG AAAGAGCGAG GAAACCATCA CCCCCTGGAA CTTCGAGGAA
```

-continued

1601 GTGGTGGACA AGGGCGCTTC CGCCCAGAGC TTCATCGAGC GGATGACCAA
1651 CTTCGATAAG AACCTGCCCA ACGAGAAGGT GCTGCCCAAG CACAGCCTGC
1701 TGTACGAGTA CTTCACCGTG TATAACGAGC TGACCAAAGT GAAATACGTG
1751 ACCGAGGGAA TGAGAAAGCC CGCCTTCCTG AGCGGCGAGC AGAAAAAGGC
1801 CATCGTGGAC CTGCTGTTCA AGACCAACCG GAAAGTGACC GTGAAGCAGC
1851 TGAAAGAGGA CTACTTCAAG AAAATCGAGT GCTTCGACTC CGTGGAAATC
1901 TCCGGCGTGG AAGATCGGTT CAACGCCTCC CTGGGCACAT ACCACGATCT
1951 GCTGAAAATT ATCAAGGACA AGGACTTCCT GGACAATGAG GAAAACGAGG
2001 ACATTCTGGA AGATATCGTG CTGACCCTGA CACTGTTTGA GGACAGAGAG
2051 ATGATCGAGG AACGGCTGAA AACCTATGCC CACCTGTTCG ACGACAAAGT
2101 GATGAAGCAG CTGAAGCGGC GGAGATACAC CGGCTGGGGC AGGCTGAGCC
2151 GGAAGCTGAT CAACGGCATC CGGGACAAGC AGTCCGGCAA GACAATCCTG
2201 GATTTCCTGA AGTCCGACGG CTTCGCCAAC AGAAACTTCA TGCAGCTGAT
2251 CCACGACGAC AGCCTGACCT TTAAAGAGGA CATCCAGAAA GCCCAGGTGT
2301 CCGGCCAGGG CGATAGCCTG CACGAGCACA TTGCCAATCT GGCCGGCAGC
2351 CCCGCCATTA AGAAGGGCAT CCTGCAGACA GTGAAGGTGG TGGACGAGCT
2401 CGTGAAAGTG ATGGGCCGGC ACAAGCCCGA GAACATCGTG ATCGAAATGG
2451 CCAGAGAGAA CCAGACCACC CAGAAGGGAC AGAAGAACAG CCGCGAGAGA
2501 ATGAAGCGGA TCGAAGAGGG CATCAAAGAG CTGGGCAGCC AGATCCTGAA
2551 AGAACACCCC GTGGAAAACA CCCAGCTGCA GAACGAGAAG CTGTACCTGT
2601 ACTACCTGCA GAATGGGCGG GATATGTACG TGGACCAGGA ACTGGACATC
2651 AACCGGCTGT CCGACTACGA TGTGGACCAT ATCGTGCCTC AGAGCTTTCT
2701 GAAGGACGAC TCCATCGACA ACAAGGTGCT GACCAGAAGC GACAAGAACC
2751 GGGGCAAGAG CGACAACGTG CCCTCCGAAG AGGTCGTGAA GAAGATGAAG
2801 AACTACTGGC GGCAGCTGCT GAACGCCAAG CTGATTACCC AGAGAAAGTT
2851 CGACAATCTG ACCAAGGCCG AGAGAGGCGG CCTGAGCGAA CTGGATAAGG
2901 CCGGCTTCAT CAAGAGACAG CTGGTGGAAA CCCGGCAGAT CACAAAGCAC
2951 GTGGCACAGA TCCTGGACTC CCGGATGAAC ACTAAGTACG ACGAGAATGA
3001 CAAGCTGATC CGGGAAGTGA AAGTGATCAC CCTGAAGTCC AAGCTGGTGT
3051 CCGATTTCCG GAAGGATTTC CAGTTTTACA AAGTGCGCGA GATCAACAAC
3101 TACCACCACG CCCACGACGC CTACCTGAAC GCCGTCGTGG GAACCGCCCT
3151 GATCAAAAAG TACCCTAAGC TGGAAAGCGA GTTCGTGTAC GGCGACTACA
3201 AGGTGTACGA CGTGCGGAAG ATGATCGCCA AGAGCGAGCA GGAAATCGGC
3251 AAGGCTACCG CCAAGTACTT CTTCTACAGC AACATCATGA ACTTTTTCAA
3301 GACCGAGATT ACCCTGGCCA ACGGCGAGAT CCGGAAGCGG CCTCTGATCG
3351 AGACAAACGG CGAAACCGGG GAGATCGTGT GGGATAAGGG CCGGGATTTT
3401 GCCACCGTGC GGAAAGTGCT GAGCATGCCC CAAGTGAATA TCGTGAAAAA
3451 GACCGAGGTG CAGACAGGCG GCTTCAGCAA AGAGTCTATC CTGCCCAAGA
3501 GGAACAGCGA TAAGCTGATC GCCAGAAAGA AGGACTGGGA CCCTAAGAAG
3551 TACGGCGGCT TCGACAGCCC CACCGTGGCC TATTCTGTGC TGGTGGTGGC

-continued

```
3601 CAAAGTGGAA AAGGGCAAGT CCAAGAAACT GAAGAGTGTG AAAGAGCTGC
3651 TGGGGATCAC CATCATGGAA AGAAGCAGCT TCGAGAAGAA TCCCATCGAC
3701 TTTCTGGAAG CCAAGGGCTA CAAAGAAGTG AAAAAGGACC TGATCATCAA
3751 GCTGCCTAAG TACTCCCTGT TCGAGCTGGA AAACGGCCGG AAGAGAATGC
3801 TGGCCTCTGC CGGCGAACTG CAGAAGGGAA ACGAACTGGC CCTGCCCTCC
3851 AAATATGTGA ACTTCCTGTA CCTGGCCAGC CACTATGAGA AGCTGAAGGG
3901 CTCCCCCGAG GATAATGAGC AGAAACAGCT GTTTGTGGAA CAGCACAAGC
3951 ACTACCTGGA CGAGATCATC GAGCAGATCA GCGAGTTCTC CAAGAGAGTG
4001 ATCCTGGCCG ACGCTAATCT GGACAAAGTG CTGTCCGCCT ACAACAAGCA
4051 CCGGGATAAG CCCATCAGAG AGCAGGCCGA GAATATCATC CACCTGTTTA
4101 CCCTGACCAA TCTGGGAGCC CCTGCCGCCT TCAAGTACTT TGACACCACC
4151 ATCGACCGGA AGAGGTACAC CAGCACCAAA GAGGTGCTGG ACGCCACCCT
4201 GATCCACCAG AGCATCACCG GCCTGTACGA GACACGGATC GACCTGTCTC
4251 AGCTGGGAGG CGACAAAAGG CCGGCGGCCA CGAAAAAGGC CGGCCAGGCA
4301 AAAAAGAAAA AGTAAGAATT CCTAggatcc ACTAGTCCAG TGTGGTGGAA
4351 TTCTGCAGAA AAAAAAAAAA AAAAAAAAAA AAAAAAAAAA AAAAAAAAAA
4401 AAAAAAAAAA AAAAAAAAAA AAAAAAAAAA AAAAAAAAAA AAAAAAAAAA
4451 AAAAAAAAAA AAAAAAAAAA AAAAAAAAGC GGCC
```

The following polynucleotide (e.g., DNA) sequence (SEQ ID NO: 32) comprises Minimal 5' UTR (SEQ ID NO: 55), wildtype Cas9 (SEQ ID NO: 48), and the sequence 5'-GAATT-3' 3' UTR.

```
                                                 (SEQ ID NO: 32)
  1 GGGAGACGCC ACCATGGCCC CAAAGAAGAA GCGGAAGGTC GGTATCCACG
 51 GAGTCCCAGC AGCCGACAAG AAGTACAGCA TCGGCCTGGA CATCGGCACC
101 AACTCTGTGG GCTGGGCCGT GATCACCGAC GAGTACAAGG TGCCCAGCAA
151 GAAATTCAAG GTGCTGGGCA ACACCGACCG GCACAGCATC AAGAAGAACC
201 TGATCGGAGC CCTGCTGTTC GACAGCGGCG AAACAGCCGA GGCCACCCGG
251 CTGAAGAGAA CCGCCAGAAG AAGATACACC AGACGGAAGA ACCGGATCTG
301 CTATCTGCAA GAGATCTTCA GCAACGAGAT GGCCAAGGTG GACGACAGCT
351 TCTTCCACAG ACTGGAAGAG TCCTTCCTGG TGGAAGAGGA TAAGAAGCAC
401 GAGCGGCACC CCATCTTCGG CAACATCGTG GACGAGGTGG CCTACCACGA
451 GAAGTACCCC ACCATCTACC ACCTGAGAAA GAAACTGGTG GACAGCACCG
501 ACAAGGCCGA CCTGCGGCTG ATCTATCTGG CCCTGGCCCA CATGATCAAG
551 TTCCGGGGCC ACTTCCTGAT CGAGGGCGAC CTGAACCCCG ACAACAGCGA
601 CGTGGACAAG CTGTTCATCC AGCTGGTGCA GACCTACAAC CAGCTGTTCG
651 AGGAAAACCC CATCAACGCC AGCGGCGTGG ACGCCAAGGC CATCCTGTCT
701 GCCAGACTGA GCAAGAGCAG ACGGCTGGAA AATCTGATCG CCCAGCTGCC
751 CGGCGAGAAG AAGAATGGCC TGTTCGGAAA CCTGATTGCC CTGAGCCTGG
801 GCCTGACCCC CAACTTCAAG AGCAACTTCG ACCTGGCCGA GGATGCCAAA
851 CTGCAGCTGA GCAAGGACAC CTACGACGAC GACCTGGACA ACCTGCTGGC
```

-continued

```
 901 CCAGATCGGC GACCAGTACG CCGACCTGTT TCTGGCCGCC AAGAACCTGT
 951 CCGACGCCAT CCTGCTGAGC GACATCCTGA GAGTGAACAC CGAGATCACC
1001 AAGGCCCCCC TGAGCGCCTC TATGATCAAG AGATACGACG AGCACCACCA
1051 GGACCTGACC CTGCTGAAAG CTCTCGTGCG GCAGCAGCTG CCTGAGAAGT
1101 ACAAAGAGAT TTTCTTCGAC CAGAGCAAGA ACGGCTACGC CGGCTACATT
1151 GACGGCGGAG CCAGCCAGGA AGAGTTCTAC AAGTTCATCA AGCCCATCCT
1201 GGAAAAGATG GACGGCACCG AGGAACTGCT CGTGAAGCTG AACAGAGAGG
1251 ACCTGCTGCG GAAGCAGCGG ACCTTCGACA ACGGCAGCAT CCCCCACCAG
1301 ATCCACCTGG GAGAGCTGCA CGCCATTCTG CGGCGGCAGG AAGATTTTTA
1351 CCCATTCCTG AAGGACAACC GGGAAAAGAT CGAGAAGATC CTGACCTTCC
1401 GCATCCCCTA CTACGTGGGC CCTCTGGCCA GGGGAAACAG CAGATTCGCC
1451 TGGATGACCA GAAAGAGCGA GGAAACCATC ACCCCCTGGA ACTTCGAGGA
1501 AGTGGTGGAC AAGGGCGCTT CCGCCCAGAG CTTCATCGAG CGGATGACCA
1551 ACTTCGATAA GAACCTGCCC AACGAGAAGG TGCTGCCCAA GCACAGCCTG
1601 CTGTACGAGT ACTTCACCGT GTATAACGAG CTGACCAAAG TGAAATACGT
1651 GACCGAGGGA ATGAGAAAGC CCGCCTTCCT GAGCGGCGAG CAGAAAAAGG
1701 CCATCGTGGA CCTGCTGTTC AAGACCAACC GGAAAGTGAC CGTGAAGCAG
1751 CTGAAAGAGG ACTACTTCAA GAAAATCGAG TGCTTCGACT CCGTGGAAAT
1801 CTCCGGCGTG GAAGATCGGT TCAACGCCTC CCTGGGCACA TACCACGATC
1851 TGCTGAAAAT TATCAAGGAC AAGGACTTCC TGGACAATGA GGAAAACGAG
1901 GACATTCTGG AAGATATCGT GCTGACCCTG ACACTGTTTG AGGACAGAGA
1951 GATGATCGAG GAACGGCTGA AAACCTATGC CCACCTGTTC GACGACAAAG
2001 TGATGAAGCA GCTGAAGCGG CGGAGATACA CCGGCTGGGG CAGGCTGAGC
2051 CGGAAGCTGA TCAACGGCAT CCGGGACAAG CAGTCCGGCA AGACAATCCT
2101 GGATTTCCTG AAGTCCGACG GCTTCGCCAA CAGAAACTTC ATGCAGCTGA
2151 TCCACGACGA CAGCCTGACC TTTAAAGAGG ACATCCAGAA AGCCCAGGTG
2201 TCCGGCCAGG GCGATAGCCT GCACGAGCAC ATTGCCAATC TGGCCGGCAG
2251 CCCCGCCATT AAGAAGGGCA TCCTGCAGAC AGTGAAGGTG GTGGACGAGC
2301 TCGTGAAAGT GATGGGCCGG CACAAGCCCG AGAACATCGT GATCGAAATG
2351 GCCAGAGAGA ACCAGACCAC CCAGAAGGGA CAGAAGAACA GCCGCGAGAG
2401 AATGAAGCGG ATCGAAGAGG GCATCAAAGA GCTGGGCAGC CAGATCCTGA
2451 AAGAACACCC CGTGGAAAAC ACCCAGCTGC AGAACGAGAA GCTGTACCTG
2501 TACTACCTGC AGAATGGGCG GGATATGTAC GTGGACCAGG AACTGGACAT
2551 CAACCGGCTG TCCGACTACG ATGTGGACCA TATCGTGCCT CAGAGCTTTC
2601 TGAAGGACGA CTCCATCGAC AACAAGGTGC TGACCAGAAG CGACAAGAAC
2651 CGGGGCAAGA GCGACAACGT GCCCTCCGAA GAGGTCGTGA AGAAGATGAA
2701 GAACTACTGG CGGCAGCTGC TGAACGCCAA GCTGATTACC CAGAGAAAGT
2751 TCGACAATCT GACCAAGGCC GAGAGAGGCG GCCTGAGCGA ACTGGATAAG
2801 GCCGGCTTCA TCAAGAGACA GCTGGTGGAA ACCCGGCAGA TCACAAAGCA
2851 CGTGGCACAG ATCCTGGACT CCCGGATGAA CACTAAGTAC GACGAGAATG
2901 ACAAGCTGAT CCGGGAAGTG AAAGTGATCA CCCTGAAGTC CAAGCTGGTG
```

-continued

```
2951 TCCGATTTCC GGAAGGATTT CCAGTTTTAC AAAGTGCGCG AGATCAACAA
3001 CTACCACCAC GCCCACGACG CCTACCTGAA CGCCGTCGTG GGAACCGCCC
3051 TGATCAAAAA GTACCCTAAG CTGGAAAGCG AGTTCGTGTA CGGCGACTAC
3101 AAGGTGTACG ACGTGCGGAA GATGATCGCC AAGAGCGAGC AGGAAATCGG
3151 CAAGGCTACC GCCAAGTACT TCTTCTACAG CAACATCATG AACTTTTTCA
3201 AGACCGAGAT TACCCTGGCC AACGGCGAGA TCCGGAAGCG GCCTCTGATC
3251 GAGACAAACG GCGAAACCGG GGAGATCGTG TGGGATAAGG GCCGGGATTT
3301 TGCCACCGTG CGGAAAGTGC TGAGCATGCC CCAAGTGAAT ATCGTGAAAA
3351 AGACCGAGGT GCAGACAGGC GGCTTCAGCA AAGAGTCTAT CCTGCCCAAG
3401 AGGAACAGCG ATAAGCTGAT CGCCAGAAAG AAGGACTGGG ACCCTAAGAA
3451 GTACGGCGGC TTCGACAGCC CCACCGTGGC CTATTCTGTG CTGGTGGTGG
3501 CCAAAGTGGA AAAGGGCAAG TCCAAGAAAC TGAAGAGTGT GAAAGAGCTG
3551 CTGGGGATCA CCATCATGGA AAGAAGCAGC TTCGAGAAGA ATCCCATCGA
3601 CTTTCTGGAA GCCAAGGGCT ACAAAGAAGT GAAAAAGGAC CTGATCATCA
3651 AGCTGCCTAA GTACTCCCTG TTCGAGCTGG AAAACGGCCG GAAGAGAATG
3701 CTGGCCTCTG CCGGCGAACT GCAGAAGGGA AACGAACTGG CCCTGCCCTC
3751 CAAATATGTG AACTTCCTGT ACCTGGCCAG CCACTATGAG AAGCTGAAGG
3801 GCTCCCCCGA GGATAATGAG CAGAAACAGC TGTTTGTGGA ACAGCACAAG
3851 CACTACCTGG ACGAGATCAT CGAGCAGATC AGCGAGTTCT CCAAGAGAGT
3901 GATCCTGGCC GACGCTAATC TGGACAAAGT GCTGTCCGCC TACAACAAGC
3951 ACCGGGATAA GCCCATCAGA GAGCAGGCCG AGAATATCAT CCACCTGTTT
4001 ACCCTGACCA ATCTGGGAGC CCCTGCCGCC TTCAAGTACT TTGACACCAC
4051 CATCGACCGG AAGAGGTACA CCAGCACCAA AGAGGTGCTG GACGCCACCC
4101 TGATCCACCA GAGCATCACC GGCCTGTACG AGACACGGAT CGACCTGTCT
4151 CAGCTGGGAG GCGACAAAAG GCCGGCGGCC ACGAAAAAGG CCGGCCAGGC
4201 AAAAAAGAAA AAGTAAGAAT T
```

The following polynucleotide (e.g., DNA) sequence (SEQ ID NO: 33) comprises hAg 5' UTR (SEQ ID NO: 56), wildtype Cas9 (SEQ ID NO: 48), and the sequence 5'-GAATT-3' 3' UTR.

```
                                              (SEQ ID NO: 33)
   1 GGGAGACTCT TCTGGTCCCC ACAGACTCAG AGAGAACGCC ACCATGGCCC
  51 CAAAGAAGAA GCGGAAGGTC GGTATCCACG GAGTCCCAGC AGCCGACAAG
 101 AAGTACAGCA TCGGCCTGGA CATCGGCACC AACTCTGTGG GCTGGGCCGT
 151 GATCACCGAC GAGTACAAGG TGCCCAGCAA GAAATTCAAG GTGCTGGGCA
 201 ACACCGACCG GCACAGCATC AAGAAGAACC TGATCGGAGC CCTGCTGTTC
 251 GACAGCGGCG AAACAGCCGA GGCCACCCGG CTGAAGAGAA CCGCCAGAAG
 301 AAGATACACC AGACGGAAGA ACCGGATCTG CTATCTGCAA GAGATCTTCA
 351 GCAACGAGAT GGCCAAGGTG GACGACAGCT TCTTCCACAG ACTGGAAGAG
 401 TCCTTCCTGG TGGAAGAGGA TAAGAAGCAC GAGCGGCACC CCATCTTCGG
 451 CAACATCGTG GACGAGGTGG CCTACCACGA GAAGTACCCC ACCATCTACC
```

-continued

```
 501 ACCTGAGAAA GAAACTGGTG GACAGCACCG ACAAGGCCGA CCTGCGGCTG
 551 ATCTATCTGG CCCTGGCCCA CATGATCAAG TTCCGGGGCC ACTTCCTGAT
 601 CGAGGGCGAC CTGAACCCCG ACAACAGCGA CGTGGACAAG CTGTTCATCC
 651 AGCTGGTGCA GACCTACAAC CAGCTGTTCG AGGAAAACCC CATCAACGCC
 701 AGCGGCGTGG ACGCCAAGGC CATCCTGTCT GCCAGACTGA GCAAGAGCAG
 751 ACGGCTGGAA AATCTGATCG CCCAGCTGCC CGGCGAGAAG AAGAATGGCC
 801 TGTTCGGAAA CCTGATTGCC CTGAGCCTGG GCCTGACCCC CAACTTCAAG
 851 AGCAACTTCG ACCTGGCCGA GGATGCCAAA CTGCAGCTGA GCAAGGACAC
 901 CTACGACGAC GACCTGGACA ACCTGCTGGC CCAGATCGGC GACCAGTACG
 951 CCGACCTGTT TCTGGCCGCC AAGAACCTGT CCGACGCCAT CCTGCTGAGC
1001 GACATCCTGA GAGTGAACAC CGAGATCACC AAGGCCCCCC TGAGCGCCTC
1051 TATGATCAAG AGATACGACG AGCACCACCA GGACCTGACC CTGCTGAAAG
1101 CTCTCGTGCG GCAGCAGCTG CCTGAGAAGT ACAAAGAGAT TTTCTTCGAC
1151 CAGAGCAAGA ACGGCTACGC CGGCTACATT GACGGCGGAG CCAGCCAGGA
1201 AGAGTTCTAC AAGTTCATCA AGCCCATCCT GGAAAAGATG GACGGCACCG
1251 AGGAACTGCT CGTGAAGCTG AACAGAGAGG ACCTGCTGCG GAAGCAGCGG
1301 ACCTTCGACA ACGGCAGCAT CCCCCACCAG ATCCACCTGG GAGAGCTGCA
1351 CGCCATTCTG CGGCGGCAGG AAGATTTTTA CCCATTCCTG AAGGACAACC
1401 GGGAAAAGAT CGAGAAGATC CTGACCTTCC GCATCCCCTA CTACGTGGGC
1451 CCTCTGGCCA GGGGAAACAG CAGATTCGCC TGGATGACCA GAAAGAGCGA
1501 GGAAACCATC ACCCCCTGGA ACTTCGAGGA AGTGGTGGAC AAGGGCGCTT
1551 CCGCCCAGAG CTTCATCGAG CGGATGACCA ACTTCGATAA GAACCTGCCC
1601 AACGAGAAGG TGCTGCCCAA GCACAGCCTG CTGTACGAGT ACTTCACCGT
1651 GTATAACGAG CTGACCAAAG TGAAATACGT GACCGAGGGA ATGAGAAAGC
1701 CCGCCTTCCT GAGCGGCGAG CAGAAAAAGG CCATCGTGGA CCTGCTGTTC
1751 AAGACCAACC GGAAAGTGAC CGTGAAGCAG CTGAAAGAGG ACTACTTCAA
1801 GAAAATCGAG TGCTTCGACT CCGTGGAAAT CTCCGGCGTG GAAGATCGGT
1851 TCAACGCCTC CCTGGGCACA TACCACGATC TGCTGAAAAT TATCAAGGAC
1901 AAGGACTTCC TGGACAATGA GGAAAACGAG GACATTCTGG AAGATATCGT
1951 GCTGACCCTG ACACTGTTTG AGGACAGAGA GATGATCGAG GAACGGCTGA
2001 AAACCTATGC CCACCTGTTC GACGACAAAG TGATGAAGCA GCTGAAGCGG
2051 CGGAGATACA CCGGCTGGGG CAGGCTGAGC CGGAAGCTGA TCAACGGCAT
2101 CCGGGACAAG CAGTCCGGCA AGACAATCCT GGATTTCCTG AAGTCCGACG
2151 GCTTCGCCAA CAGAAACTTC ATGCAGCTGA TCCACGACGA CAGCCTGACC
2201 TTTAAAGAGG ACATCCAGAA AGCCCAGGTG TCCGGCCAGG GCGATAGCCT
2251 GCACGAGCAC ATTGCCAATC TGGCCGGCAG CCCCGCCATT AAGAAGGGCA
2301 TCCTGCAGAC AGTGAAGGTG GTGGACGAGC TCGTGAAAGT GATGGGCCGG
2351 CACAAGCCCG AGAACATCGT GATCGAAATG GCCAGAGAGA ACCAGACCAC
2401 CCAGAAGGGA CAGAAGAACA GCCGCGAGAG AATGAAGCGG ATCGAAGAGG
2451 GCATCAAAGA GCTGGGCAGC CAGATCCTGA AAGAACACCC CGTGGAAAAC
```

-continued

```
2501 ACCCAGCTGC AGAACGAGAA GCTGTACCTG TACTACCTGC AGAATGGGCG
2551 GGATATGTAC GTGGACCAGG AACTGGACAT CAACCGGCTG TCCGACTACG
2601 ATGTGGACCA TATCGTGCCT CAGAGCTTTC TGAAGGACGA CTCCATCGAC
2651 AACAAGGTGC TGACCAGAAG CGACAAGAAC CGGGGCAAGA GCGACAACGT
2701 GCCCTCCGAA GAGGTCGTGA AGAAGATGAA GAACTACTGG CGGCAGCTGC
2751 TGAACGCCAA GCTGATTACC CAGAGAAAGT TCGACAATCT GACCAAGGCC
2801 GAGAGAGGCG GCCTGAGCGA ACTGGATAAG GCCGGCTTCA TCAAGAGACA
2851 GCTGGTGGAA ACCCGGCAGA TCACAAAGCA CGTGGCACAG ATCCTGGACT
2901 CCCGGATGAA CACTAAGTAC GACGAGAATG ACAAGCTGAT CCGGGAAGTG
2951 AAAGTGATCA CCCTGAAGTC CAAGCTGGTG TCCGATTTCC GGAAGGATTT
3001 CCAGTTTTAC AAAGTGCGCG AGATCAACAA CTACCACCAC GCCCACGACG
3051 CCTACCTGAA CGCCGTCGTG GGAACCGCCC TGATCAAAAA GTACCCTAAG
3101 CTGGAAAGCG AGTTCGTGTA CGGCGACTAC AAGGTGTACG ACGTGCGGAA
3151 GATGATCGCC AAGAGCGAGC AGGAAATCGG CAAGGCTACC GCCAAGTACT
3201 TCTTCTACAG CAACATCATG AACTTTTTCA AGACCGAGAT TACCCTGGCC
3251 AACGGCGAGA TCCGGAAGCG GCCTCTGATC GAGACAAACG GCGAAACCGG
3301 GGAGATCGTG TGGGATAAGG GCCGGGATTT TGCCACCGTG CGGAAAGTGC
3351 TGAGCATGCC CCAAGTGAAT ATCGTGAAAA AGACCGAGGT GCAGACAGGC
3401 GGCTTCAGCA AAGAGTCTAT CCTGCCCAAG AGGAACAGCG ATAAGCTGAT
3451 CGCCAGAAAG AAGGACTGGG ACCCTAAGAA GTACGGCGGC TTCGACAGCC
3501 CCACCGTGGC CTATTCTGTG CTGGTGGTGG CCAAAGTGGA AAAGGGCAAG
3551 TCCAAGAAAC TGAAGAGTGT GAAAGAGCTG CTGGGGATCA CCATCATGGA
3601 AAGAAGCAGC TTCGAGAAGA ATCCCATCGA CTTTCTGGAA GCCAAGGGCT
3651 ACAAAGAAGT GAAAAAGGAC CTGATCATCA AGCTGCCTAA GTACTCCCTG
3701 TTCGAGCTGG AAAACGGCCG GAAGAGAATG CTGGCCTCTG CCGGCGAACT
3751 GCAGAAGGGA AACGAACTGG CCCTGCCCTC CAAATATGTG AACTTCCTGT
3801 ACCTGGCCAG CCACTATGAG AAGCTGAAGG GCTCCCCCGA GGATAATGAG
3851 CAGAAACAGC TGTTTGTGGA ACAGCACAAG CACTACCTGG ACGAGATCAT
3901 CGAGCAGATC AGCGAGTTCT CCAAGAGAGT GATCCTGGCC GACGCTAATC
3951 TGGACAAAGT GCTGTCCGCC TACAACAAGC ACCGGGATAA GCCCATCAGA
4001 GAGCAGGCCG AGAATATCAT CCACCTGTTT ACCCTGACCA ATCTGGGAGC
4051 CCCTGCCGCC TTCAAGTACT TTGACACCAC CATCGACCGG AAGAGGTACA
4101 CCAGCACCAA AGAGGTGCTG GACGCCACCC TGATCCACCA GAGCATCACC
4151 GGCCTGTACG AGACACGGAT CGACCTGTCT CAGCTGGGAG GCGACAAAAG
4201 GCCGGCGGCC ACGAAAAAGG CCGGCCAGGC AAAAAAGAAA AAGTAAGAAT
4251 T
```

The following polynucleotide (e.g., DNA) sequence (SEQ ID NO: 34) comprises TISU+T 5' UTR (SEQ ID NO: 58), wildtype Cas9 (SEQ ID NO: 48), and the sequence 5'-GAATT-3' 3' UTR.

(SEQ ID NO: 34)

1 GGGAGACTGC CAAGATGGCC CCAAAGAAGA AGCGGAAGGT CGGTATCCAC

51 GGAGTCCCAG CAGCCGACAA GAAGTACAGC ATCGGCCTGG ACATCGGCAC

101 CAACTCTGTG GGCTGGGCCG TGATCACCGA CGAGTACAAG GTGCCCAGCA

151 AGAAATTCAA GGTGCTGGGC AACACCGACC GGCACAGCAT CAAGAAGAAC

201 CTGATCGGAG CCCTGCTGTT CGACAGCGGC GAAACAGCCG AGGCCACCCG

251 GCTGAAGAGA ACCGCCAGAA GAAGATACAC CAGACGGAAG AACCGGATCT

301 GCTATCTGCA AGAGATCTTC AGCAACGAGA TGGCCAAGGT GGACGACAGC

351 TTCTTCCACA GACTGGAAGA GTCCTTCCTG GTGGAAGAGG ATAAGAAGCA

401 CGAGCGGCAC CCCATCTTCG GCAACATCGT GGACGAGGTG GCCTACCACG

451 AGAAGTACCC CACCATCTAC CACCTGAGAA AGAAACTGGT GGACAGCACC

501 GACAAGGCCG ACCTGCGGCT GATCTATCTG GCCCTGGCCC ACATGATCAA

551 GTTCCGGGGC CACTTCCTGA TCGAGGGCGA CCTGAACCCC GACAACAGCG

601 ACGTGGACAA GCTGTTCATC CAGCTGGTGC AGACCTACAA CCAGCTGTTC

651 GAGGAAAACC CCATCAACGC CAGCGGCGTG GACGCCAAGG CCATCCTGTC

701 TGCCAGACTG AGCAAGAGCA GACGGCTGGA AAATCTGATC GCCCAGCTGC

751 CCGGCGAGAA GAAGAATGGC CTGTTCGGAA ACCTGATTGC CCTGAGCCTG

801 GGCCTGACCC CCAACTTCAA GAGCAACTTC GACCTGGCCG AGGATGCCAA

851 ACTGCAGCTG AGCAAGGACA CCTACGACGA CGACCTGGAC AACCTGCTGG

901 CCCAGATCGG CGACCAGTAC GCCGACCTGT TTCTGGCCGC CAAGAACCTG

951 TCCGACGCCA TCCTGCTGAG CGACATCCTG AGAGTGAACA CCGAGATCAC

1001 CAAGGCCCCC CTGAGCGCCT CTATGATCAA GAGATACGAC GAGCACCACC

1051 AGGACCTGAC CCTGCTGAAA GCTCTCGTGC GGCAGCAGCT GCCTGAGAAG

1101 TACAAAGAGA TTTTCTTCGA CCAGAGCAAG AACGGCTACG CCGGCTACAT

1151 TGACGGCGGA GCCAGCCAGG AAGAGTTCTA CAAGTTCATC AAGCCCATCC

1201 TGGAAAAGAT GGACGGCACC GAGGAACTGC TCGTGAAGCT GAACAGAGAG

1251 GACCTGCTGC GGAAGCAGCG GACCTTCGAC AACGGCAGCA TCCCCCACCA

1301 GATCCACCTG GGAGAGCTGC ACGCCATTCT GCGGCGGCAG GAAGATTTTT

1351 ACCCATTCCT GAAGGACAAC CGGGAAAAGA TCGAGAAGAT CCTGACCTTC

1401 CGCATCCCCT ACTACGTGGG CCCTCTGGCC AGGGGAAACA GCAGATTCGC

1451 CTGGATGACC AGAAAGAGCG AGGAAACCAT CACCCCCTGG AACTTCGAGG

1501 AAGTGGTGGA CAAGGGCGCT TCCGCCCAGA GCTTCATCGA GCGGATGACC

1551 AACTTCGATA AGAACCTGCC CAACGAGAAG GTGCTGCCCA AGCACAGCCT

1601 GCTGTACGAG TACTTCACCG TGTATAACGA GCTGACCAAA GTGAAATACG

1651 TGACCGAGGG AATGAGAAAG CCCGCCTTCC TGAGCGGCGA GCAGAAAAAG

1701 GCCATCGTGG ACCTGCTGTT CAAGACCAAC CGGAAAGTGA CCGTGAAGCA

1751 GCTGAAAGAG GACTACTTCA AGAAAATCGA GTGCTTCGAC TCCGTGGAAA

1801 TCTCCGGCGT GGAAGATCGG TTCAACGCCT CCCTGGGCAC ATACCACGAT

1851 CTGCTGAAAA TTATCAAGGA CAAGGACTTC CTGGACAATG AGGAAAACGA

1901 GGACATTCTG GAAGATATCG TGCTGACCCT GACACTGTTT GAGGACAGAG

1951 AGATGATCGA GGAACGGCTG AAAACCTATG CCCACCTGTT CGACGACAAA

-continued

```
2001 GTGATGAAGC AGCTGAAGCG GCGGAGATAC ACCGGCTGGG GCAGGCTGAG
2051 CCGGAAGCTG ATCAACGGCA TCCGGGACAA GCAGTCCGGC AAGACAATCC
2101 TGGATTTCCT GAAGTCCGAC GGCTTCGCCA ACAGAAACTT CATGCAGCTG
2151 ATCCACGACG ACAGCCTGAC CTTTAAAGAG GACATCCAGA AAGCCCAGGT
2201 GTCCGGCCAG GGCGATAGCC TGCACGAGCA CATTGCCAAT CTGGCCGGCA
2251 GCCCCGCCAT TAAGAAGGGC ATCCTGCAGA CAGTGAAGGT GGTGGACGAG
2301 CTCGTGAAAG TGATGGGCCG GCACAAGCCC GAGAACATCG TGATCGAAAT
2351 GGCCAGAGAG AACCAGACCA CCCAGAAGGG ACAGAAGAAC AGCCGCGAGA
2401 GAATGAAGCG GATCGAAGAG GGCATCAAAG AGCTGGGCAG CCAGATCCTG
2451 AAAGAACACC CCGTGGAAAA CACCCAGCTG CAGAACGAGA AGCTGTACCT
2501 GTACTACCTG CAGAATGGGC GGGATATGTA CGTGGACCAG GAACTGGACA
2551 TCAACCGGCT GTCCGACTAC GATGTGGACC ATATCGTGCC TCAGAGCTTT
2601 CTGAAGGACG ACTCCATCGA CAACAAGGTG CTGACCAGAA GCGACAAGAA
2651 CCGGGGCAAG AGCGACAACG TGCCCTCCGA AGAGGTCGTG AAGAAGATGA
2701 AGAACTACTG GCGGCAGCTG CTGAACGCCA AGCTGATTAC CCAGAGAAAG
2751 TTCGACAATC TGACCAAGGC CGAGAGAGGC GGCCTGAGCG AACTGGATAA
2801 GGCCGGCTTC ATCAAGAGAC AGCTGGTGGA AACCCGGCAG ATCACAAAGC
2851 ACGTGGCACA GATCCTGGAC TCCCGGATGA ACACTAAGTA CGACGAGAAT
2901 GACAAGCTGA TCCGGGAAGT GAAAGTGATC ACCCTGAAGT CCAAGCTGGT
2951 GTCCGATTTC CGGAAGGATT TCCAGTTTTA CAAAGTGCGC GAGATCAACA
3001 ACTACCACCA CGCCCACGAC GCCTACCTGA ACGCCGTCGT GGGAACCGCC
3051 CTGATCAAAA AGTACCCTAA GCTGGAAAGC GAGTTCGTGT ACGGCGACTA
3101 CAAGGTGTAC GACGTGCGGA AGATGATCGC CAAGAGCGAG CAGGAAATCG
3151 GCAAGGCTAC CGCCAAGTAC TTCTTCTACA GCAACATCAT GAACTTTTTC
3201 AAGACCGAGA TTACCCTGGC CAACGGCGAG ATCCGGAAGC GGCCTCTGAT
3251 CGAGACAAAC GGCGAAACCG GGGAGATCGT GTGGGATAAG GGCCGGGATT
3301 TTGCCACCGT GCGGAAAGTG CTGAGCATGC CCCAAGTGAA TATCGTGAAA
3351 AAGACCGAGG TGCAGACAGG CGGCTTCAGC AAAGAGTCTA TCCTGCCCAA
3401 GAGGAACAGC GATAAGCTGA TCGCCAGAAA GAAGGACTGG GACCCTAAGA
3451 AGTACGGCGG CTTCGACAGC CCCACCGTGG CCTATTCTGT GCTGGTGGTG
3501 GCCAAAGTGG AAAAGGGCAA GTCCAAGAAA CTGAAGAGTG TGAAAGAGCT
3551 GCTGGGGATC ACCATCATGG AAAGAAGCAG CTTCGAGAAG AATCCCATCG
3601 ACTTTCTGGA AGCCAAGGGC TACAAAGAAG TGAAAAAGGA CCTGATCATC
3651 AAGCTGCCTA AGTACTCCCT GTTCGAGCTG GAAAACGGCC GGAAGAGAAT
3701 GCTGGCCTCT GCCGGCGAAC TGCAGAAGGG AAACGAACTG GCCCTGCCCT
3751 CCAAATATGT GAACTTCCTG TACCTGGCCA GCCACTATGA GAAGCTGAAG
3801 GGCTCCCCCG AGGATAATGA GCAGAAACAG CTGTTTGTGG AACAGCACAA
3851 GCACTACCTG GACGAGATCA TCGAGCAGAT CAGCGAGTTC TCCAAGAGAG
3901 TGATCCTGGC CGACGCTAAT CTGGACAAAG TGCTGTCCGC CTACAACAAG
3951 CACCGGGATA AGCCCATCAG AGAGCAGGCC GAGAATATCA TCCACCTGTT
4001 TACCCTGACC AATCTGGGAG CCCCTGCCGC CTTCAAGTAC TTTGACACCA
```

-continued

```
4051 CCATCGACCG GAAGAGGTAC ACCAGCACCA AAGAGGTGCT GGACGCCACC

4101 CTGATCCACC AGAGCATCAC CGGCCTGTAC GAGACACGGA TCGACCTGTC

4151 TCAGCTGGGA GGCGACAAAA GGCCGGCGGC CACGAAAAAG GCCGGCCAGG

4201 CAAAAAAGAA AAAGTAAGAA TT
```

The following polynucleotide (e.g., DNA) sequence (SEQ ID NO: 35) comprises 5p-UTR 5' UTR (SEQ ID NO: 46), D10A Cas9 (SEQ ID NO: 53), and 3p-UTR 3' UTR (SEQ ID NO: 47).

(SEQ ID NO: 35)

```
   1 GGGAGACCCA AGCTGGCTAG CGTTTAAACT TAAGCTTGCC ACCATGGACT

  51 ATAAGGACCA CGACGGAGAC TACAAGGATC ATGATATTGA TTACAAAGAC

 101 GATGACGATA AGATGGCCCC AAAGAAGAAG CGGAAGGTCG GTATCCACGG

 151 AGTCCCAGCA GCCGACAAGA AGTACAGCAT CGGCCTGgcc ATCGGCACCA

 201 ACTCTGTGGG CTGGGCCGTG ATCACCGACG AGTACAAGGT GCCCAGCAAG

 251 AAATTCAAGG TGCTGGGCAA CACCGACCGG CACAGCATCA AGAAGAACCT

 301 GATCGGAGCC CTGCTGTTCG ACAGCGGCGA AACAGCCGAG GCCACCCGGC

 351 TGAAGAGAAC CGCCAGAAGA AGATACACCA GACGGAAGAA CCGGATCTGC

 401 TATCTGCAAG AGATCTTCAG CAACGAGATG GCCAAGGTGG ACGACAGCTT

 451 CTTCCACAGA CTGGAAGAGT CCTTCCTGGT GGAAGAGGAT AAGAAGCACG

 501 AGCGGCACCC CATCTTCGGC AACATCGTGG ACGAGGTGGC CTACCACGAG

 551 AAGTACCCCA CCATCTACCA CCTGAGAAAG AAACTGGTGG ACAGCACCGA

 601 CAAGGCCGAC CTGCGGCTGA TCTATCTGGC CCTGGCCCAC ATGATCAAGT

 651 TCCGGGGCCA CTTCCTGATC GAGGGCGACC TGAACCCCGA CAACAGCGAC

 701 GTGGACAAGC TGTTCATCCA GCTGGTGCAG ACCTACAACC AGCTGTTCGA

 751 GGAAAACCCC ATCAACGCCA GCGGCGTGGA CGCCAAGGCC ATCCTGTCTG

 801 CCAGACTGAG CAAGAGCAGA CGGCTGGAAA ATCTGATCGC CCAGCTGCCC

 851 GGCGAGAAGA AGAATGGCCT GTTCGGAAAC CTGATTGCCC TGAGCCTGGG

 901 CCTGACCCCC AACTTCAAGA GCAACTTCGA CCTGGCCGAG GATGCCAAAC

 951 TGCAGCTGAG CAAGGACACC TACGACGACG ACCTGGACAA CCTGCTGGCC

1001 CAGATCGGCG ACCAGTACGC CGACCTGTTT CTGGCCGCCA AGAACCTGTC

1051 CGACGCCATC CTGCTGAGCG ACATCCTGAG AGTGAACACC GAGATCACCA

1101 AGGCCCCCCT GAGCGCCTCT ATGATCAAGA GATACGACGA GCACCACCAG

1151 GACCTGACCC TGCTGAAAGC TCTCGTGCGG CAGCAGCTGC CTGAGAAGTA

1201 CAAAGAGATT TTCTTCGACC AGAGCAAGAA CGGCTACGCC GGCTACATTG

1251 ACGGCGGAGC CAGCCAGGAA GAGTTCTACA AGTTCATCAA GCCCATCCTG

1301 GAAAAGATGG ACGGCACCGA GGAACTGCTC GTGAAGCTGA ACAGAGAGGA

1351 CCTGCTGCGG AAGCAGCGGA CCTTCGACAA CGGCAGCATC CCCCACCAGA

1401 TCCACCTGGG AGAGCTGCAC GCCATTCTGC GGCGGCAGGA AGATTTTTAC

1451 CCATTCCTGA AGGACAACCG GGAAAAGATC GAGAAGATCC TGACCTTCCG

1501 CATCCCCTAC TACGTGGGCC CTCTGGCCAG GGGAAACAGC AGATTCGCCT

1551 GGATGACCAG AAAGAGCGAG GAAACCATCA CCCCCTGGAA CTTCGAGGAA
```

-continued

```
1601 GTGGTGGACA AGGGCGCTTC CGCCCAGAGC TTCATCGAGC GGATGACCAA

1651 CTTCGATAAG AACCTGCCCA ACGAGAAGGT GCTGCCCAAG CACAGCCTGC

1701 TGTACGAGTA CTTCACCGTG TATAACGAGC TGACCAAAGT GAAATACGTG

1751 ACCGAGGGAA TGAGAAAGCC CGCCTTCCTG AGCGGCGAGC AGAAAAAGGC

1801 CATCGTGGAC CTGCTGTTCA AGACCAACCG GAAAGTGACC GTGAAGCAGC

1851 TGAAAGAGGA CTACTTCAAG AAAATCGAGT GCTTCGACTC CGTGGAAATC

1901 TCCGGCGTGG AAGATCGGTT CAACGCCTCC CTGGGCACAT ACCACGATCT

1951 GCTGAAAATT ATCAAGGACA AGGACTTCCT GGACAATGAG GAAAACGAGG

2001 ACATTCTGGA AGATATCGTG CTGACCCTGA CACTGTTTGA GGACAGAGAG

2051 ATGATCGAGG AACGGCTGAA AACCTATGCC CACCTGTTCG ACGACAAAGT

2101 GATGAAGCAG CTGAAGCGGC GGAGATACAC CGGCTGGGGC AGGCTGAGCC

2151 GGAAGCTGAT CAACGGCATC CGGGACAAGC AGTCCGGCAA GACAATCCTG

2201 GATTTCCTGA AGTCCGACGG CTTCGCCAAC AGAAACTTCA TGCAGCTGAT

2251 CCACGACGAC AGCCTGACCT TTAAAGAGGA CATCCAGAAA GCCCAGGTGT

2301 CCGGCCAGGG CGATAGCCTG CACGAGCACA TTGCCAATCT GGCCGGCAGC

2351 CCCGCCATTA AGAAGGGCAT CCTGCAGACA GTGAAGGTGG TGGACGAGCT

2401 CGTGAAAGTG ATGGGCCGGC ACAAGCCCGA GAACATCGTG ATCGAAATGG

2451 CCAGAGAGAA CCAGACCACC CAGAAGGGAC AGAAGAACAG CCGCGAGAGA

2501 ATGAAGCGGA TCGAAGAGGG CATCAAAGAG CTGGGCAGCC AGATCCTGAA

2551 AGAACACCCC GTGGAAAACA CCCAGCTGCA GAACGAGAAG CTGTACCTGT

2601 ACTACCTGCA GAATGGGCGG GATATGTACG TGGACCAGGA ACTGGACATC

2651 AACCGGCTGT CCGACTACGA TGTGGACCAT ATCGTGCCTC AGAGCTTTCT

2701 GAAGGACGAC TCCATCGACA ACAAGGTGCT GACCAGAAGC GACAAGAACC

2751 GGGGCAAGAG CGACAACGTG CCCTCCGAAG AGGTCGTGAA GAAGATGAAG

2801 AACTACTGGC GGCAGCTGCT GAACGCCAAG CTGATTACCC AGAGAAAGTT

2851 CGACAATCTG ACCAAGGCCG AGAGAGGCGG CCTGAGCGAA CTGGATAAGG

2901 CCGGCTTCAT CAAGAGACAG CTGGTGGAAA CCCGGCAGAT CACAAAGCAC

2951 GTGGCACAGA TCCTGGACTC CCGGATGAAC ACTAAGTACG ACGAGAATGA

3001 CAAGCTGATC CGGGAAGTGA AAGTGATCAC CCTGAAGTCC AAGCTGGTGT

3051 CCGATTTCCG GAAGGATTTC CAGTTTTACA AAGTGCGCGA GATCAACAAC

3101 TACCACCACG CCCACGACGC CTACCTGAAC GCCGTCGTGG GAACCGCCCT

3151 GATCAAAAAG TACCCTAAGC TGGAAAGCGA GTTCGTGTAC GGCGACTACA

3201 AGGTGTACGA CGTGCGGAAG ATGATCGCCA AGAGCGAGCA GGAAATCGGC

3251 AAGGCTACCG CCAAGTACTT CTTCTACAGC AACATCATGA ACTTTTTCAA

3301 GACCGAGATT ACCCTGGCCA ACGGCGAGAT CCGGAAGCGG CCTCTGATCG

3351 AGACAAACGG CGAAACCGGG GAGATCGTGT GGGATAAGGG CCGGGATTTT

3401 GCCACCGTGC GGAAAGTGCT GAGCATGCCC CAAGTGAATA TCGTGAAAAA

3451 GACCGAGGTG CAGACAGGCG GCTTCAGCAA AGAGTCTATC CTGCCCAAGA

3501 GGAACAGCGA TAAGCTGATC GCCAGAAAGA AGGACTGGGA CCCTAAGAAG

3551 TACGGCGGCT TCGACAGCCC CACCGTGGCC TATTCTGTGC TGGTGGTGGC

3601 CAAAGTGGAA AAGGGCAAGT CCAAGAAACT GAAGAGTGTG AAAGAGCTGC
```

-continued

```
3651  TGGGGATCAC CATCATGGAA AGAAGCAGCT TCGAGAAGAA TCCCATCGAC

3701  TTTCTGGAAG CCAAGGGCTA CAAAGAAGTG AAAAAGGACC TGATCATCAA

3751  GCTGCCTAAG TACTCCCTGT TCGAGCTGGA AAACGGCCGG AAGAGAATGC

3801  TGGCCTCTGC CGGCGAACTG CAGAAGGGAA ACGAACTGGC CCTGCCCTCC

3851  AAATATGTGA ACTTCCTGTA CCTGGCCAGC CACTATGAGA AGCTGAAGGG

3901  CTCCCCCGAG GATAATGAGC AGAAACAGCT GTTTGTGGAA CAGCACAAGC

3951  ACTACCTGGA CGAGATCATC GAGCAGATCA GCGAGTTCTC CAAGAGAGTG

4001  ATCCTGGCCG ACGCTAATCT GGACAAAGTG CTGTCCGCCT ACAACAAGCA

4051  CCGGGATAAG CCCATCAGAG AGCAGGCCGA GAATATCATC CACCTGTTTA

4101  CCCTGACCAA TCTGGGAGCC CCTGCCGCCT TCAAGTACTT TGACACCACC

4151  ATCGACCGGA AGAGGTACAC CAGCACCAAA GAGGTGCTGG ACGCCACCCT

4201  GATCCACCAG AGCATCACCG GCCTGTACGA GACACGGATC GACCTGTCTC

4251  AGCTGGGAGG CGACAAAAGG CCGGCGGCCA CGAAAAAGGC CGGCCAGGCA

4301  AAAAAGAAAA AGTAAGAATT CCTAggatcc ACTAGTCCAG TGTGGTGGAA

4351  TTCTGCAGAA AAAAAAAAAA AAAAAAAAAA AAAAAAAAAA AAAAAAAAAA

4401  AAAAAAAAAA AAAAAAAAAA AAAAAAAAAA AAAAAAAAAA AAAAAAAAAA

4451  AAAAAAAAAA AAAAAAAAAA AAAAAAAAGC GGCC
```

The following polynucleotide (e.g., DNA) sequence (SEQ ID NO: 36) comprises Minimal 5' UTR (SEQ ID NO: 55), D10A Cas9 (SEQ ID NO: 49), and the sequence 5'-GAATT-3' 3' UTR.

```
                                                 (SEQ ID NO: 36)
   1  GGGAGACGCC ACCATGGCCC CAAAGAAGAA GCGGAAGGTC GGTATCCACG

  51  GAGTCCCAGC AGCCGACAAG AAGTACAGCA TCGGCCTGgc cATCGGCACC

 101  AACTCTGTGG GCTGGGCCGT GATCACCGAC GAGTACAAGG TGCCCAGCAA

 151  GAAATTCAAG GTGCTGGGCA ACACCGACCG GCACAGCATC AAGAAGAACC

 201  TGATCGGAGC CCTGCTGTTC GACAGCGGCG AAACAGCCGA GGCCACCCGG

 251  CTGAAGAGAA CCGCCAGAAG AAGATACACC AGACGGAAGA ACCGGATCTG

 301  CTATCTGCAA GAGATCTTCA GCAACGAGAT GGCCAAGGTG GACGACAGCT

 351  TCTTCCACAG ACTGGAAGAG TCCTTCCTGG TGGAAGAGGA TAAGAAGCAC

 401  GAGCGGCACC CCATCTTCGG CAACATCGTG GACGAGGTGG CCTACCACGA

 451  GAAGTACCCC ACCATCTACC ACCTGAGAAA GAAACTGGTG GACAGCACCG

 501  ACAAGGCCGA CCTGCGGCTG ATCTATCTGG CCCTGGCCCA CATGATCAAG

 551  TTCCGGGGCC ACTTCCTGAT CGAGGGCGAC CTGAACCCCG ACAACAGCGA

 601  CGTGGACAAG CTGTTCATCC AGCTGGTGCA GACCTACAAC CAGCTGTTCG

 651  AGGAAAACCC CATCAACGCC AGCGGCGTGG ACGCCAAGGC CATCCTGTCT

 701  GCCAGACTGA GCAAGAGCAG ACGGCTGGAA AATCTGATCG CCCAGCTGCC

 751  CGGCGAGAAG AAGAATGGCC TGTTCGGAAA CCTGATTGCC CTGAGCCTGG

 801  GCCTGACCCC CAACTTCAAG AGCAACTTCG ACCTGGCCGA GGATGCCAAA

 851  CTGCAGCTGA GCAAGGACAC CTACGACGAC GACCTGGACA ACCTGCTGGC

 901  CCAGATCGGC GACCAGTACG CCGACCTGTT TCTGGCCGCC AAGAACCTGT
```

-continued

951 CCGACGCCAT CCTGCTGAGC GACATCCTGA GAGTGAACAC CGAGATCACC

1001 AAGGCCCCCC TGAGCGCCTC TATGATCAAG AGATACGACG AGCACCACCA

1051 GGACCTGACC CTGCTGAAAG CTCTCGTGCG GCAGCAGCTG CCTGAGAAGT

1101 ACAAAGAGAT TTTCTTCGAC CAGAGCAAGA ACGGCTACGC CGGCTACATT

1151 GACGGCGGAG CCAGCCAGGA AGAGTTCTAC AAGTTCATCA AGCCCATCCT

1201 GGAAAAGATG GACGGCACCG AGGAACTGCT CGTGAAGCTG AACAGAGAGG

1251 ACCTGCTGCG GAAGCAGCGG ACCTTCGACA ACGGCAGCAT CCCCCACCAG

1301 ATCCACCTGG GAGAGCTGCA CGCCATTCTG CGGCGGCAGG AAGATTTTTA

1351 CCCATTCCTG AAGGACAACC GGGAAAAGAT CGAGAAGATC CTGACCTTCC

1401 GCATCCCCTA CTACGTGGGC CCTCTGGCCA GGGGAAACAG CAGATTCGCC

1451 TGGATGACCA GAAAGAGCGA GGAAACCATC ACCCCCTGGA ACTTCGAGGA

1501 AGTGGTGGAC AAGGGCGCTT CCGCCCAGAG CTTCATCGAG CGGATGACCA

1551 ACTTCGATAA GAACCTGCCC AACGAGAAGG TGCTGCCCAA GCACAGCCTG

1601 CTGTACGAGT ACTTCACCGT GTATAACGAG CTGACCAAAG TGAAATACGT

1651 GACCGAGGGA ATGAGAAAGC CCGCCTTCCT GAGCGGCGAG CAGAAAAAGG

1701 CCATCGTGGA CCTGCTGTTC AAGACCAACC GGAAAGTGAC CGTGAAGCAG

1751 CTGAAAGAGG ACTACTTCAA GAAAATCGAG TGCTTCGACT CCGTGGAAAT

1801 CTCCGGCGTG GAAGATCGGT TCAACGCCTC CCTGGGCACA TACCACGATC

1851 TGCTGAAAAT TATCAAGGAC AAGGACTTCC TGGACAATGA GGAAAACGAG

1901 GACATTCTGG AAGATATCGT GCTGACCCTG ACACTGTTTG AGGACAGAGA

1951 GATGATCGAG GAACGGCTGA AAACCTATGC CCACCTGTTC GACGACAAAG

2001 TGATGAAGCA GCTGAAGCGG CGGAGATACA CCGGCTGGGG CAGGCTGAGC

2051 CGGAAGCTGA TCAACGGCAT CCGGGACAAG CAGTCCGGCA AGACAATCCT

2101 GGATTTCCTG AAGTCCGACG GCTTCGCCAA CAGAAACTTC ATGCAGCTGA

2151 TCCACGACGA CAGCCTGACC TTTAAAGAGG ACATCCAGAA AGCCCAGGTG

2201 TCCGGCCAGG GCGATAGCCT GCACGAGCAC ATTGCCAATC TGGCCGGCAG

2251 CCCCGCCATT AAGAAGGGCA TCCTGCAGAC AGTGAAGGTG GTGGACGAGC

2301 TCGTGAAAGT GATGGGCCGG CACAAGCCCG AGAACATCGT GATCGAAATG

2351 GCCAGAGAGA ACCAGACCAC CCAGAAGGGA CAGAAGAACA GCCGCGAGAG

2401 AATGAAGCGG ATCGAAGAGG GCATCAAAGA GCTGGGCAGC CAGATCCTGA

2451 AAGAACACCC CGTGGAAAAC ACCCAGCTGC AGAACGAGAA GCTGTACCTG

2501 TACTACCTGC AGAATGGGCG GGATATGTAC GTGGACCAGG AACTGGACAT

2551 CAACCGGCTG TCCGACTACG ATGTGGACCA TATCGTGCCT CAGAGCTTTC

2601 TGAAGGACGA CTCCATCGAC AACAAGGTGC TGACCAGAAG CGACAAGAAC

2651 CGGGGCAAGA GCGACAACGT GCCCTCCGAA GAGGTCGTGA AGAAGATGAA

2701 GAACTACTGG CGGCAGCTGC TGAACGCCAA GCTGATTACC CAGAGAAAGT

2751 TCGACAATCT GACCAAGGCC GAGAGAGGCG GCCTGAGCGA ACTGGATAAG

2801 GCCGGCTTCA TCAAGAGACA GCTGGTGGAA ACCCGGCAGA TCACAAAGCA

2851 CGTGGCACAG ATCCTGGACT CCCGGATGAA CACTAAGTAC GACGAGAATG

2901 ACAAGCTGAT CCGGGAAGTG AAAGTGATCA CCCTGAAGTC CAAGCTGGTG

-continued

```
2951 TCCGATTTCC GGAAGGATTT CCAGTTTTAC AAAGTGCGCG AGATCAACAA
3001 CTACCACCAC GCCCACGACG CCTACCTGAA CGCCGTCGTG GGAACCGCCC
3051 TGATCAAAAA GTACCCTAAG CTGGAAAGCG AGTTCGTGTA CGGCGACTAC
3101 AAGGTGTACG ACGTGCGGAA GATGATCGCC AAGAGCGAGC AGGAAATCGG
3151 CAAGGCTACC GCCAAGTACT TCTTCTACAG CAACATCATG AACTTTTTCA
3201 AGACCGAGAT TACCCTGGCC AACGGCGAGA TCCGGAAGCG GCCTCTGATC
3251 GAGACAAACG GCGAAACCGG GGAGATCGTG TGGGATAAGG GCCGGGATTT
3301 TGCCACCGTG CGGAAAGTGC TGAGCATGCC CCAAGTGAAT ATCGTGAAAA
3351 AGACCGAGGT GCAGACAGGC GGCTTCAGCA AAGAGTCTAT CCTGCCCAAG
3401 AGGAACAGCG ATAAGCTGAT CGCCAGAAAG AAGGACTGGG ACCCTAAGAA
3451 GTACGGCGGC TTCGACAGCC CCACCGTGGC CTATTCTGTG CTGGTGGTGG
3501 CCAAAGTGGA AAAGGGCAAG TCCAAGAAAC TGAAGAGTGT GAAAGAGCTG
3551 CTGGGGATCA CCATCATGGA AAGAAGCAGC TTCGAGAAGA ATCCCATCGA
3601 CTTTCTGGAA GCCAAGGGCT ACAAAGAAGT GAAAAAGGAC CTGATCATCA
3651 AGCTGCCTAA GTACTCCCTG TTCGAGCTGG AAAACGGCCG GAAGAGAATG
3701 CTGGCCTCTG CCGGCGAACT GCAGAAGGGA AACGAACTGG CCCTGCCCTC
3751 CAAATATGTG AACTTCCTGT ACCTGGCCAG CCACTATGAG AAGCTGAAGG
3801 GCTCCCCCGA GGATAATGAG CAGAAACAGC TGTTTGTGGA ACAGCACAAG
3851 CACTACCTGG ACGAGATCAT CGAGCAGATC AGCGAGTTCT CCAAGAGAGT
3901 GATCCTGGCC GACGCTAATC TGGACAAAGT GCTGTCCGCC TACAACAAGC
3951 ACCGGGATAA GCCCATCAGA GAGCAGGCCG AGAATATCAT CCACCTGTTT
4001 ACCCTGACCA ATCTGGGAGC CCCTGCCGCC TTCAAGTACT TTGACACCAC
4051 CATCGACCGG AAGAGGTACA CCAGCACCAA AGAGGTGCTG GACGCCACCC
4101 TGATCCACCA GAGCATCACC GGCCTGTACG AGACACGGAT CGACCTGTCT
4151 CAGCTGGGAG GCGACAAAAG GCCGGCGGCC ACGAAAAAGG CCGGCCAGGC
4201 AAAAAAGAAA AAGTAAGAAT T
```

The following polynucleotide (e.g., DNA) sequence (SEQ ID NO: 37) comprises hAg 5' UTR (SEQ ID NO: 56), D10A Cas9 (SEQ ID NO: 49), and the sequence 5'-GAATT-3' 3' UTR.

(SEQ ID NO: 37)

```
  1 GGGAGACTCT TCTGGTCCCC ACAGACTCAG AGAGAACGCC ACCATGGCCC
 51 CAAAGAAGAA GCGGAAGGTC GGTATCCACG GAGTCCCAGC AGCCGACAAG
101 AAGTACAGCA TCGGCCTGgc cATCGGCACC AACTCTGTGG GCTGGGCCGT
151 GATCACCGAC GAGTACAAGG TGCCCAGCAA GAAATTCAAG GTGCTGGGCA
201 ACACCGACCG GCACAGCATC AAGAAGAACC TGATCGGAGC CCTGCTGTTC
251 GACAGCGGCG AAACAGCCGA GGCCACCCGG CTGAAGAGAA CCGCCAGAAG
301 AAGATACACC AGACGGAAGA ACCGGATCTG CTATCTGCAA GAGATCTTCA
351 GCAACGAGAT GGCCAAGGTG GACGACAGCT TCTTCCACAG ACTGGAAGAG
401 TCCTTCCTGG TGGAAGAGGA TAAGAAGCAC GAGCGGCACC CCATCTTCGG
451 CAACATCGTG GACGAGGTGG CCTACCACGA GAAGTACCCC ACCATCTACC
```

-continued

501 ACCTGAGAAA GAAACTGGTG GACAGCACCG ACAAGGCCGA CCTGCGGCTG

551 ATCTATCTGG CCCTGGCCCA CATGATCAAG TTCCGGGGCC ACTTCCTGAT

601 CGAGGGCGAC CTGAACCCCG ACAACAGCGA CGTGGACAAG CTGTTCATCC

651 AGCTGGTGCA GACCTACAAC CAGCTGTTCG AGGAAAACCC CATCAACGCC

701 AGCGGCGTGG ACGCCAAGGC CATCCTGTCT GCCAGACTGA GCAAGAGCAG

751 ACGGCTGGAA AATCTGATCG CCCAGCTGCC CGGCGAGAAG AAGAATGGCC

801 TGTTCGGAAA CCTGATTGCC CTGAGCCTGG GCCTGACCCC CAACTTCAAG

851 AGCAACTTCG ACCTGGCCGA GGATGCCAAA CTGCAGCTGA GCAAGGACAC

901 CTACGACGAC GACCTGGACA ACCTGCTGGC CCAGATCGGC GACCAGTACG

951 CCGACCTGTT TCTGGCCGCC AAGAACCTGT CCGACGCCAT CCTGCTGAGC

1001 GACATCCTGA GAGTGAACAC CGAGATCACC AAGGCCCCCC TGAGCGCCTC

1051 TATGATCAAG AGATACGACG AGCACCACCA GGACCTGACC CTGCTGAAAG

1101 CTCTCGTGCG GCAGCAGCTG CCTGAGAAGT ACAAAGAGAT TTTCTTCGAC

1151 CAGAGCAAGA ACGGCTACGC CGGCTACATT GACGGCGGAG CCAGCCAGGA

1201 AGAGTTCTAC AAGTTCATCA AGCCCATCCT GGAAAAGATG GACGGCACCG

1251 AGGAACTGCT CGTGAAGCTG AACAGAGAGG ACCTGCTGCG GAAGCAGCGG

1301 ACCTTCGACA ACGGCAGCAT CCCCCACCAG ATCCACCTGG GAGAGCTGCA

1351 CGCCATTCTG CGGCGGCAGG AAGATTTTTA CCCATTCCTG AAGGACAACC

1401 GGGAAAAGAT CGAGAAGATC CTGACCTTCC GCATCCCCTA CTACGTGGGC

1451 CCTCTGGCCA GGGGAAACAG CAGATTCGCC TGGATGACCA GAAAGAGCGA

1501 GGAAACCATC ACCCCCTGGA ACTTCGAGGA AGTGGTGGAC AAGGGCGCTT

1551 CCGCCCAGAG CTTCATCGAG CGGATGACCA ACTTCGATAA GAACCTGCCC

1601 AACGAGAAGG TGCTGCCCAA GCACAGCCTG CTGTACGAGT ACTTCACCGT

1651 GTATAACGAG CTGACCAAAG TGAAATACGT GACCGAGGGA ATGAGAAAGC

1701 CCGCCTTCCT GAGCGGCGAG CAGAAAAAGG CCATCGTGGA CCTGCTGTTC

1751 AAGACCAACC GGAAAGTGAC CGTGAAGCAG CTGAAAGAGG ACTACTTCAA

1801 GAAAATCGAG TGCTTCGACT CCGTGGAAAT CTCCGGCGTG GAAGATCGGT

1851 TCAACGCCTC CCTGGGCACA TACCACGATC TGCTGAAAAT TATCAAGGAC

1901 AAGGACTTCC TGGACAATGA GGAAAACGAG GACATTCTGG AAGATATCGT

1951 GCTGACCCTG ACACTGTTTG AGGACAGAGA GATGATCGAG GAACGGCTGA

2001 AAACCTATGC CCACCTGTTC GACGACAAAG TGATGAAGCA GCTGAAGCGG

2051 CGGAGATACA CCGGCTGGGG CAGGCTGAGC CGGAAGCTGA TCAACGGCAT

2101 CCGGGACAAG CAGTCCGGCA AGACAATCCT GGATTTCCTG AAGTCCGACG

2151 GCTTCGCCAA CAGAAACTTC ATGCAGCTGA TCCACGACGA CAGCCTGACC

2201 TTTAAAGAGG ACATCCAGAA AGCCCAGGTG TCCGGCCAGG GCGATAGCCT

2251 GCACGAGCAC ATTGCCAATC TGGCCGGCAG CCCCGCCATT AAGAAGGGCA

2301 TCCTGCAGAC AGTGAAGGTG GTGGACGAGC TCGTGAAAGT GATGGGCCGG

2351 CACAAGCCCG AGAACATCGT GATCGAAATG GCCAGAGAGA ACCAGACCAC

2401 CCAGAAGGGA CAGAAGAACA GCCGCGAGAG AATGAAGCGG ATCGAAGAGG

2451 GCATCAAAGA GCTGGGCAGC CAGATCCTGA AAGAACACCC CGTGGAAAAC

-continued

2501 ACCCAGCTGC AGAACGAGAA GCTGTACCTG TACTACCTGC AGAATGGGCG
2551 GGATATGTAC GTGGACCAGG AACTGGACAT CAACCGGCTG TCCGACTACG
2601 ATGTGGACCA TATCGTGCCT CAGAGCTTTC TGAAGGACGA CTCCATCGAC
2651 AACAAGGTGC TGACCAGAAG CGACAAGAAC CGGGGCAAGA GCGACAACGT
2701 GCCCTCCGAA GAGGTCGTGA AGAAGATGAA GAACTACTGG CGGCAGCTGC
2751 TGAACGCCAA GCTGATTACC CAGAGAAAGT TCGACAATCT GACCAAGGCC
2801 GAGAGAGGCG GCCTGAGCGA ACTGGATAAG GCCGGCTTCA TCAAGAGACA
2851 GCTGGTGGAA ACCCGGCAGA TCACAAAGCA CGTGGCACAG ATCCTGGACT
2901 CCCGGATGAA CACTAAGTAC GACGAGAATG ACAAGCTGAT CCGGGAAGTG
2951 AAAGTGATCA CCCTGAAGTC CAAGCTGGTG TCCGATTTCC GGAAGGATTT
3001 CCAGTTTTAC AAAGTGCGCG AGATCAACAA CTACCACCAC GCCCACGACG
3051 CCTACCTGAA CGCCGTCGTG GGAACCGCCC TGATCAAAAA GTACCCTAAG
3101 CTGGAAAGCG AGTTCGTGTA CGGCGACTAC AAGGTGTACG ACGTGCGGAA
3151 GATGATCGCC AAGAGCGAGC AGGAAATCGG CAAGGCTACC GCCAAGTACT
3201 TCTTCTACAG CAACATCATG AACTTTTTCA AGACCGAGAT TACCCTGGCC
3251 AACGGCGAGA TCCGGAAGCG GCCTCTGATC GAGACAAACG GCGAAACCGG
3301 GGAGATCGTG TGGGATAAGG GCCGGGATTT TGCCACCGTG CGGAAAGTGC
3351 TGAGCATGCC CCAAGTGAAT ATCGTGAAAA AGACCGAGGT GCAGACAGGC
3401 GGCTTCAGCA AAGAGTCTAT CCTGCCCAAG AGGAACAGCG ATAAGCTGAT
3451 CGCCAGAAAG AAGGACTGGG ACCCTAAGAA GTACGGCGGC TTCGACAGCC
3501 CCACCGTGGC CTATTCTGTG CTGGTGGTGG CCAAAGTGGA AAAGGGCAAG
3551 TCCAAGAAAC TGAAGAGTGT GAAAGAGCTG CTGGGGATCA CCATCATGGA
3601 AAGAAGCAGC TTCGAGAAGA ATCCCATCGA CTTTCTGGAA GCCAAGGGCT
3651 ACAAAGAAGT GAAAAAGGAC CTGATCATCA AGCTGCCTAA GTACTCCCTG
3701 TTCGAGCTGG AAAACGGCCG GAAGAGAATG CTGGCCTCTG CCGGCGAACT
3751 GCAGAAGGGA AACGAACTGG CCCTGCCCTC CAAATATGTG AACTTCCTGT
3801 ACCTGGCCAG CCACTATGAG AAGCTGAAGG GCTCCCCCGA GGATAATGAG
3851 CAGAAACAGC TGTTTGTGGA ACAGCACAAG CACTACCTGG ACGAGATCAT
3901 CGAGCAGATC AGCGAGTTCT CCAAGAGAGT GATCCTGGCC GACGCTAATC
3951 TGGACAAAGT GCTGTCCGCC TACAACAAGC ACCGGGATAA GCCCATCAGA
4001 GAGCAGGCCG AGAATATCAT CCACCTGTTT ACCCTGACCA ATCTGGGAGC
4051 CCCTGCCGCC TTCAAGTACT TTGACACCAC CATCGACCGG AAGAGGTACA
4101 CCAGCACCAA AGAGGTGCTG GACGCCACCC TGATCCACCA GAGCATCACC
4151 GGCCTGTACG AGACACGGAT CGACCTGTCT CAGCTGGGAG GCGACAAAAG
4201 GCCGGCGGCC ACGAAAAAGG CCGGCCAGGC AAAAAAGAAA AAGTAAGAAT
4251 T

The following polynucleotide (e.g., DNA) sequence (SEQ ID NO: 38) comprises TISU+T 5' UTR (SEQ ID NO: 58), D10A Cas9 (SEQ ID NO: 49), and the sequence 5'-GAATT-3' 3' UTR.

(SEQ ID NO: 38)

```
   1 GGGAGACTGC CAAGATGGCC CCAAAGAAGA AGCGGAAGGT CGGTATCCAC
  51 GGAGTCCCAG CAGCCGACAA GAAGTACAGC ATCGGCCTGg ccATCGGCAC
 101 CAACTCTGTG GGCTGGGCCG TGATCACCGA CGAGTACAAG GTGCCCAGCA
 151 AGAAATTCAA GGTGCTGGGC AACACCGACC GGCACAGCAT CAAGAAGAAC
 201 CTGATCGGAG CCCTGCTGTT CGACAGCGGC GAAACAGCCG AGGCCACCCG
 251 GCTGAAGAGA ACCGCCAGAA GAAGATACAC CAGACGGAAG AACCGGATCT
 301 GCTATCTGCA AGAGATCTTC AGCAACGAGA TGGCCAAGGT GGACGACAGC
 351 TTCTTCCACA GACTGGAAGA GTCCTTCCTG GTGGAAGAGG ATAAGAAGCA
 401 CGAGCGGCAC CCCATCTTCG GCAACATCGT GGACGAGGTG GCCTACCACG
 451 AGAAGTACCC CACCATCTAC CACCTGAGAA AGAAACTGGT GGACAGCACC
 501 GACAAGGCCG ACCTGCGGCT GATCTATCTG GCCCTGGCCC ACATGATCAA
 551 GTTCCGGGGC CACTTCCTGA TCGAGGGCGA CCTGAACCCC GACAACAGCG
 601 ACGTGGACAA GCTGTTCATC CAGCTGGTGC AGACCTACAA CCAGCTGTTC
 651 GAGGAAAACC CCATCAACGC CAGCGGCGTG GACGCCAAGG CCATCCTGTC
 701 TGCCAGACTG AGCAAGAGCA GACGGCTGGA AAATCTGATC GCCCAGCTGC
 751 CCGGCGAGAA GAAGAATGGC CTGTTCGGAA ACCTGATTGC CCTGAGCCTG
 801 GGCCTGACCC CCAACTTCAA GAGCAACTTC GACCTGGCCG AGGATGCCAA
 851 ACTGCAGCTG AGCAAGGACA CCTACGACGA CGACCTGGAC AACCTGCTGG
 901 CCCAGATCGG CGACCAGTAC GCCGACCTGT TTCTGGCCGC CAAGAACCTG
 951 TCCGACGCCA TCCTGCTGAG CGACATCCTG AGAGTGAACA CCGAGATCAC
1001 CAAGGCCCCC CTGAGCGCCT CTATGATCAA GAGATACGAC GAGCACCACC
1051 AGGACCTGAC CCTGCTGAAA GCTCTCGTGC GGCAGCAGCT GCCTGAGAAG
1101 TACAAAGAGA TTTTCTTCGA CCAGAGCAAG AACGGCTACG CCGGCTACAT
1151 TGACGGCGGA GCCAGCCAGG AAGAGTTCTA CAAGTTCATC AAGCCCATCC
1201 TGGAAAAGAT GGACGGCACC GAGGAACTGC TCGTGAAGCT GAACAGAGAG
1251 GACCTGCTGC GGAAGCAGCG GACCTTCGAC AACGGCAGCA TCCCCCACCA
1301 GATCCACCTG GGAGAGCTGC ACGCCATTCT GCGGCGGCAG GAAGATTTTT
1351 ACCCATTCCT GAAGGACAAC CGGGAAAAGA TCGAGAAGAT CCTGACCTTC
1401 CGCATCCCCT ACTACGTGGG CCCTCTGGCC AGGGGAAACA GCAGATTCGC
1451 CTGGATGACC AGAAAGAGCG AGGAAACCAT CACCCCCTGG AACTTCGAGG
1501 AAGTGGTGGA CAAGGGCGCT TCCGCCCAGA GCTTCATCGA GCGGATGACC
1551 AACTTCGATA AGAACCTGCC CAACGAGAAG GTGCTGCCCA AGCACAGCCT
1601 GCTGTACGAG TACTTCACCG TGTATAACGA GCTGACCAAA GTGAAATACG
1651 TGACCGAGGG AATGAGAAAG CCCGCCTTCC TGAGCGGCGA GCAGAAAAAG
1701 GCCATCGTGG ACCTGCTGTT CAAGACCAAC CGGAAAGTGA CCGTGAAGCA
1751 GCTGAAAGAG GACTACTTCA AGAAAATCGA GTGCTTCGAC TCCGTGGAAA
1801 TCTCCGGCGT GGAAGATCGG TTCAACGCCT CCCTGGGCAC ATACCACGAT
1851 CTGCTGAAAA TTATCAAGGA CAAGGACTTC CTGGACAATG AGGAAAACGA
1901 GGACATTCTG GAAGATATCG TGCTGACCCT GACACTGTTT GAGGACAGAG
1951 AGATGATCGA GGAACGGCTG AAAACCTATG CCCACCTGTT CGACGACAAA
```

-continued

```
2001 GTGATGAAGC AGCTGAAGCG GCGGAGATAC ACCGGCTGGG GCAGGCTGAG
2051 CCGGAAGCTG ATCAACGGCA TCCGGGACAA GCAGTCCGGC AAGACAATCC
2101 TGGATTTCCT GAAGTCCGAC GGCTTCGCCA ACAGAAACTT CATGCAGCTG
2151 ATCCACGACG ACAGCCTGAC CTTTAAAGAG GACATCCAGA AAGCCCAGGT
2201 GTCCGGCCAG GGCGATAGCC TGCACGAGCA CATTGCCAAT CTGGCCGGCA
2251 GCCCCGCCAT TAAGAAGGGC ATCCTGCAGA CAGTGAAGGT GGTGGACGAG
2301 CTCGTGAAAG TGATGGGCCG GCACAAGCCC GAGAACATCG TGATCGAAAT
2351 GGCCAGAGAG AACCAGACCA CCCAGAAGGG ACAGAAGAAC AGCCGCGAGA
2401 GAATGAAGCG GATCGAAGAG GGCATCAAAG AGCTGGGCAG CCAGATCCTG
2451 AAAGAACACC CCGTGGAAAA CACCCAGCTG CAGAACGAGA AGCTGTACCT
2501 GTACTACCTG CAGAATGGGC GGGATATGTA CGTGGACCAG GAACTGGACA
2551 TCAACCGGCT GTCCGACTAC GATGTGGACC ATATCGTGCC TCAGAGCTTT
2601 CTGAAGGACG ACTCCATCGA CAACAAGGTG CTGACCAGAA GCGACAAGAA
2651 CCGGGGCAAG AGCGACAACG TGCCCTCCGA AGAGGTCGTG AAGAAGATGA
2701 AGAACTACTG GCGGCAGCTG CTGAACGCCA AGCTGATTAC CCAGAGAAAG
2751 TTCGACAATC TGACCAAGGC CGAGAGAGGC GGCCTGAGCG AACTGGATAA
2801 GGCCGGCTTC ATCAAGAGAC AGCTGGTGGA AACCCGGCAG ATCACAAAGC
2851 ACGTGGCACA GATCCTGGAC TCCCGGATGA ACACTAAGTA CGACGAGAAT
2901 GACAAGCTGA TCCGGGAAGT GAAAGTGATC ACCCTGAAGT CCAAGCTGGT
2951 GTCCGATTTC CGGAAGGATT TCCAGTTTTA CAAAGTGCGC GAGATCAACA
3001 ACTACCACCA CGCCCACGAC GCCTACCTGA ACGCCGTCGT GGGAACCGCC
3051 CTGATCAAAA AGTACCCTAA GCTGGAAAGC GAGTTCGTGT ACGGCGACTA
3101 CAAGGTGTAC GACGTGCGGA AGATGATCGC CAAGAGCGAG CAGGAAATCG
3151 GCAAGGCTAC CGCCAAGTAC TTCTTCTACA GCAACATCAT GAACTTTTTC
3201 AAGACCGAGA TTACCCTGGC CAACGGCGAG ATCCGGAAGC GGCCTCTGAT
3251 CGAGACAAAC GGCGAAACCG GGGAGATCGT GTGGGATAAG GGCCGGGATT
3301 TTGCCACCGT GCGGAAAGTG CTGAGCATGC CCCAAGTGAA TATCGTGAAA
3351 AAGACCGAGG TGCAGACAGG CGGCTTCAGC AAAGAGTCTA TCCTGCCCAA
3401 GAGGAACAGC GATAAGCTGA TCGCCAGAAA GAAGGACTGG GACCCTAAGA
3451 AGTACGGCGG CTTCGACAGC CCCACCGTGG CCTATTCTGT GCTGGTGGTG
3501 GCCAAAGTGG AAAAGGGCAA GTCCAAGAAA CTGAAGAGTG TGAAAGAGCT
3551 GCTGGGGATC ACCATCATGG AAAGAAGCAG CTTCGAGAAG AATCCCATCG
3601 ACTTTCTGGA AGCCAAGGGC TACAAAGAAG TGAAAAAGGA CCTGATCATC
3651 AAGCTGCCTA AGTACTCCCT GTTCGAGCTG GAAAACGGCC GGAAGAGAAT
3701 GCTGGCCTCT GCCGGCGAAC TGCAGAAGGG AAACGAACTG GCCCTGCCCT
3751 CCAAATATGT GAACTTCCTG TACCTGGCCA GCCACTATGA GAAGCTGAAG
3801 GGCTCCCCCG AGGATAATGA GCAGAAACAG CTGTTTGTGG AACAGCACAA
3851 GCACTACCTG GACGAGATCA TCGAGCAGAT CAGCGAGTTC TCCAAGAGAG
3901 TGATCCTGGC CGACGCTAAT CTGGACAAAG TGCTGTCCGC CTACAACAAG
3951 CACCGGGATA AGCCCATCAG AGAGCAGGCC GAGAATATCA TCCACCTGTT
4001 TACCCTGACC AATCTGGGAG CCCCTGCCGC CTTCAAGTAC TTTGACACCA
```

-continued

```
4051 CCATCGACCG GAAGAGGTAC ACCAGCACCA AAGAGGTGCT GGACGCCACC

4101 CTGATCCACC AGAGCATCAC CGGCCTGTAC GAGACACGGA TCGACCTGTC

4151 TCAGCTGGGA GGCGACAAAA GGCCGGCGGC CACGAAAAAG GCCGGCCAGG

4201 CAAAAAAGAA AAAGTAAGAA TT
```

The following polyribonucleotide (e.g., RNA) sequence (SEQ ID NO: 39) corresponds to hGH 3' UTR, as disclosed in WO 2012/170930.

```
                                                    (SEQ ID NO: 39)
 1  CGGGUGGCAU CCCUGUGACC CCUCCCCAGU GCCUCUCCUG GCCCUGGAAG

51  UUGCCACUCC AGUGCCCACC AGCCUUGUCC UAAUAAAAUU AAGUUGCAUC
```

The following polyribonucleotide (e.g., RNA) sequence (SEQ ID NO: 40) corresponds to CRISPR-gRNA-eGFP-ETH1.

```
                                                    (SEQ ID NO: 40)
  1  GGGGGCACGG GCAGCUUGCC GGGUUUUAGA GCUAGAAAUA GCAAGUUAAA

 51  AUAAGGCUAG UCCGUUAUCA ACUUGAAAAA GUGGCACCGA GUCGGUGCUU

101  UUUU
```

The following polyribonucleotide (e.g., RNA) sequence (SEQ ID NO: 41) corresponds to CRISPR-gRNA-eGFP-ETH2.

```
                                                    (SEQ ID NO: 41)
  1  GGGGUGGUGC AGAUGAACUU CAGUUUUAGA GCUAGAAAUA GCAAGUUAAA

 51  AUAAGGCUAG UCCGUUAUCA ACUUGAAAAA GUGGCACCGA GUCGGUGCUU

101  UUUU
```

The following polyribonucleotide (e.g., RNA) sequence (SEQ ID NO: 42) corresponds to CRISPR-gRNA-eGFP-ETH3.

```
                                                    (SEQ ID NO: 42)
  1  GGGGGCGAGG AGCUGUUCAC CGGUUUUAGA GCUAGAAAUA GCAAGUUAAA

 51  AUAAGGCUAG UCCGUUAUCA ACUUGAAAAA GUGGCACCGA GUCGGUGCUU

101  UUUU
```

The following polyribonucleotide (e.g., RNA) sequence (SEQ ID NO: 43) corresponds to CRISPR-gRNA-eGFP-ETH4.

```
                                                    (SEQ ID NO: 43)
  1  GGCAUGCCCG AAGGCUACGU CCGUUUUAGA GCUAGAAAUA GCAAGUUAAA

 51  AUAAGGCUAG UCCGUUAUCA ACUUGAAAAA GUGGCACCGA GUCGGUGCUU

101  UUUU
```

The following polyribonucleotide (e.g., RNA) sequence (SEQ ID NO: 44) corresponds to CRISPR-sRNA-eGFP-ETH5.

(SEQ ID NO: 44)
```
  1  GGCGGCCAUG AUAUAGACGU UGGUUUUAGA GCUAGAAAUA GCAAGUUAAA

 51  AUAAGGCUAG UCCGUUAUCA ACUUGAAAAA GUGGCACCGA GUCGGUGCUU

101  UUUU
```

The following polyribonucleotide (e.g., RNA) sequence (SEQ ID NO: 45) corresponds to CRISPR-gRNA-eGFP-ETH6.

(SEQ ID NO: 45)
```
  1  GGAGCGUGUC CGGCGAGGGC GAGUUUUAGA GCUAGAAAUA GCAAGUUAAA

 51  AUAAGGCUAG UCCGUUAUCA ACUUGAAAAA GUGGCACCGA GUCGGUGCUU

101  UUUU
```

The following polynucleotide (e.g., DNA) sequence (SEQ ID NO: 46) corresponds to a 5' UTR referred to as 5p-UTR.

(SEQ ID NO: 46)
```
1 GGGAGACCCA AGCTGGCTAG CGTTTAAACT TAAGCTTGCC ACC
```

The following polynucleotide (e.g., DNA) sequence (SEQ ID NO: 47) corresponds to a 3' UTR referred to as 3p-UTR.

(SEQ ID NO: 47)
```
  1  GAATTCCTAg gatccACTAG TCCAGTGTGG TGGAATTCTG CAGAAAAAAA

 51  AAAAAAAAAA AAAAAAAAAA AAAAAAAAAA AAAAAAAAAA AAAAAAAAAA

101  AAAAAAAAAA AAAAAAAAAA AAAAAAAAAA AAAAAAAAAA AAAAAAAAAA

151  AAAAAAAAAA AAAGCGGCC
```

The following polynucleotide (e.g., DNA) sequence (SEQ ID NO: 48) corresponds to codon optimized wildtype Cas9.

(SEQ ID NO: 48)
```
  1  ATGGCCCCAA AGAAGAAGCG GAAGGTCGGT ATCCACGGAG TCCCAGCAGC

 51  CGACAAGAAG TACAGCATCG GCCTGGACAT CGGCACCAAC TCTGTGGGCT

101  GGGCCGTGAT CACCGACGAG TACAAGGTGC CCAGCAAGAA ATTCAAGGTG

151  CTGGGCAACA CCGACCGGCA CAGCATCAAG AAGAACCTGA TCGGAGCCCT

201  GCTGTTCGAC AGCGGCGAAA CAGCCGAGGC CACCCGGCTG AAGAGAACCG

251  CCAGAAGAAG ATACACCAGA CGGAAGAACC GGATCTGCTA TCTGCAAGAG

301  ATCTTCAGCA ACGAGATGGC CAAGGTGGAC GACAGCTTCT TCCACAGACT

351  GGAAGAGTCC TTCCTGGTGG AAGAGGATAA GAAGCACGAG CGGCACCCCA

401  TCTTCGGCAA CATCGTGGAC GAGGTGGCCT ACCACGAGAA GTACCCCACC

451  ATCTACCACC TGAGAAAGAA ACTGGTGGAC AGCACCGACA AGGCCGACCT

501  GCGGCTGATC TATCTGGCCC TGGCCCACAT GATCAAGTTC CGGGGCCACT

551  TCCTGATCGA GGGCGACCTG AACCCCGACA ACAGCGACGT GGACAAGCTG

601  TTCATCCAGC TGGTGCAGAC CTACAACCAG CTGTTCGAGG AAAACCCCAT

651  CAACGCCAGC GGCGTGGACG CCAAGGCCAT CCTGTCTGCC AGACTGAGCA

701  AGAGCAGACG GCTGGAAAAT CTGATCGCCC AGCTGCCCGG CGAGAAGAAG

751  AATGGCCTGT TCGGAAACCT GATTGCCCTG AGCCTGGGCC TGACCCCCAA
```

-continued

801 CTTCAAGAGC AACTTCGACC TGGCCGAGGA TGCCAAACTG CAGCTGAGCA

851 AGGACACCTA CGACGACGAC CTGGACAACC TGCTGGCCCA GATCGGCGAC

901 CAGTACGCCG ACCTGTTTCT GGCCGCCAAG AACCTGTCCG ACGCCATCCT

951 GCTGAGCGAC ATCCTGAGAG TGAACACCGA GATCACCAAG GCCCCCCTGA

1001 GCGCCTCTAT GATCAAGAGA TACGACGAGC ACCACCAGGA CCTGACCCTG

1051 CTGAAAGCTC TCGTGCGGCA GCAGCTGCCT GAGAAGTACA AAGAGATTTT

1101 CTTCGACCAG AGCAAGAACG GCTACGCCGG CTACATTGAC GGCGGAGCCA

1151 GCCAGGAAGA GTTCTACAAG TTCATCAAGC CCATCCTGGA AAAGATGGAC

1201 GGCACCGAGG AACTGCTCGT GAAGCTGAAC AGAGAGGACC TGCTGCGGAA

1251 GCAGCGGACC TTCGACAACG GCAGCATCCC CCACCAGATC CACCTGGGAG

1301 AGCTGCACGC CATTCTGCGG CGGCAGGAAG ATTTTTACCC ATTCCTGAAG

1351 GACAACCGGG AAAAGATCGA GAAGATCCTG ACCTTCCGCA TCCCCTACTA

1401 CGTGGGCCCT CTGGCCAGGG GAAACAGCAG ATTCGCCTGG ATGACCAGAA

1451 AGAGCGAGGA AACCATCACC CCCTGGAACT TCGAGGAAGT GGTGGACAAG

1501 GGCGCTTCCG CCCAGAGCTT CATCGAGCGG ATGACCAACT TCGATAAGAA

1551 CCTGCCCAAC GAGAAGGTGC TGCCCAAGCA CAGCCTGCTG TACGAGTACT

1601 TCACCGTGTA TAACGAGCTG ACCAAAGTGA AATACGTGAC CGAGGGAATG

1651 AGAAAGCCCG CCTTCCTGAG CGGCGAGCAG AAAAAGGCCA TCGTGGACCT

1701 GCTGTTCAAG ACCAACCGGA AAGTGACCGT GAAGCAGCTG AAAGAGGACT

1751 ACTTCAAGAA AATCGAGTGC TTCGACTCCG TGGAAATCTC CGGCGTGGAA

1801 GATCGGTTCA ACGCCTCCCT GGGCACATAC CACGATCTGC TGAAAATTAT

1851 CAAGGACAAG GACTTCCTGG ACAATGAGGA AAACGAGGAC ATTCTGGAAG

1901 ATATCGTGCT GACCCTGACA CTGTTTGAGG ACAGAGAGAT GATCGAGGAA

1951 CGGCTGAAAA CCTATGCCCA CCTGTTCGAC GACAAAGTGA TGAAGCAGCT

2001 GAAGCGGCGG AGATACACCG GCTGGGGCAG GCTGAGCCGG AAGCTGATCA

2051 ACGGCATCCG GGACAAGCAG TCCGGCAAGA CAATCCTGGA TTTCCTGAAG

2101 TCCGACGGCT TCGCCAACAG AAACTTCATG CAGCTGATCC ACGACGACAG

2151 CCTGACCTTT AAAGAGGACA TCCAGAAAGC CCAGGTGTCC GGCCAGGGCG

2201 ATAGCCTGCA CGAGCACATT GCCAATCTGG CCGGCAGCCC CGCCATTAAG

2251 AAGGGCATCC TGCAGACAGT GAAGGTGGTG GACGAGCTCG TGAAAGTGAT

2301 GGGCCGGCAC AAGCCCGAGA ACATCGTGAT CGAAATGGCC AGAGAGAACC

2351 AGACCACCCA GAAGGGACAG AAGAACAGCC GCGAGAGAAT GAAGCGGATC

2401 GAAGAGGGCA TCAAAGAGCT GGGCAGCCAG ATCCTGAAAG AACACCCCGT

2451 GGAAAACACC CAGCTGCAGA ACGAGAAGCT GTACCTGTAC TACCTGCAGA

2501 ATGGGCGGGA TATGTACGTG GACCAGGAAC TGGACATCAA CCGGCTGTCC

2551 GACTACGATG TGGACCATAT CGTGCCTCAG AGCTTTCTGA AGGACGACTC

2601 CATCGACAAC AAGGTGCTGA CCAGAAGCGA CAAGAACCGG GGCAAGAGCG

2651 ACAACGTGCC CTCCGAAGAG GTCGTGAAGA AGATGAAGAA CTACTGGCGG

2701 CAGCTGCTGA ACGCCAAGCT GATTACCCAG AGAAAGTTCG ACAATCTGAC

2751 CAAGGCCGAG AGAGGCGGCC TGAGCGAACT GGATAAGGCC GGCTTCATCA

2801 AGAGACAGCT GGTGGAAACC CGGCAGATCA CAAAGCACGT GGCACAGATC

-continued

```
2851 CTGGACTCCC GGATGAACAC TAAGTACGAC GAGAATGACA AGCTGATCCG
2901 GGAAGTGAAA GTGATCACCC TGAAGTCCAA GCTGGTGTCC GATTTCCGGA
2951 AGGATTTCCA GTTTTACAAA GTGCGCGAGA TCAACAACTA CCACCACGCC
3001 CACGACGCCT ACCTGAACGC CGTCGTGGGA ACCGCCCTGA TCAAAAAGTA
3051 CCCTAAGCTG GAAAGCGAGT TCGTGTACGG CGACTACAAG GTGTACGACG
3101 TGCGGAAGAT GATCGCCAAG AGCGAGCAGG AAATCGGCAA GGCTACCGCC
3151 AAGTACTTCT TCTACAGCAA CATCATGAAC TTTTTCAAGA CCGAGATTAC
3201 CCTGGCCAAC GGCGAGATCC GGAAGCGGCC TCTGATCGAG ACAAACGGCG
3251 AAACCGGGGA GATCGTGTGG GATAAGGGCC GGGATTTTGC CACCGTGCGG
3301 AAAGTGCTGA GCATGCCCCA AGTGAATATC GTGAAAAAGA CCGAGGTGCA
3351 GACAGGCGGC TTCAGCAAAG AGTCTATCCT GCCCAAGAGG AACAGCGATA
3401 AGCTGATCGC CAGAAAGAAG GACTGGGACC CTAAGAAGTA CGGCGGCTTC
3451 GACAGCCCCA CCGTGGCCTA TTCTGTGCTG GTGGTGGCCA AAGTGGAAAA
3501 GGGCAAGTCC AAGAAACTGA AGAGTGTGAA AGAGCTGCTG GGGATCACCA
3551 TCATGGAAAG AAGCAGCTTC GAGAAGAATC CCATCGACTT TCTGGAAGCC
3601 AAGGGCTACA AAGAAGTGAA AAAGGACCTG ATCATCAAGC TGCCTAAGTA
3651 CTCCCTGTTC GAGCTGGAAA ACGGCCGGAA GAGAATGCTG GCCTCTGCCG
3701 GCGAACTGCA GAAGGGAAAC GAACTGGCCC TGCCCTCCAA ATATGTGAAC
3751 TTCCTGTACC TGGCCAGCCA CTATGAGAAG CTGAAGGGCT CCCCCGAGGA
3801 TAATGAGCAG AAACAGCTGT TTGTGGAACA GCACAAGCAC TACCTGGACG
3851 AGATCATCGA GCAGATCAGC GAGTTCTCCA AGAGAGTGAT CCTGGCCGAC
3901 GCTAATCTGG ACAAAGTGCT GTCCGCCTAC AACAAGCACC GGGATAAGCC
3951 CATCAGAGAG CAGGCCGAGA ATATCATCCA CCTGTTTACC CTGACCAATC
4001 TGGGAGCCCC TGCCGCCTTC AAGTACTTTG ACACCACCAT CGACCGGAAG
4051 AGGTACACCA GCACCAAAGA GGTGCTGGAC GCCACCCTGA TCCACCAGAG
4101 CATCACCGGC CTGTACGAGA CACGGATCGA CCTGTCTCAG CTGGGAGGCG
4151 ACAAAAGGCC GGCGGCCACG AAAAAGGCCG GCCAGGCAAA AAAGAAAAAG
4201 TAA
```

The following polynucleotide (e.g., DNA) sequence (SEQ ID NO: 49) corresponds to codon optimized D10A Cas9.

```
                                              (SEQ ID NO: 49)
  1 ATGGCCCCAA AGAAGAAGCG GAAGGTCGGT ATCCACGGAG TCCCAGCAGC
 51 CGACAAGAAG TACAGCATCG GCCTGgccAT CGGCACCAAC TCTGTGGGCT
101 GGGCCGTGAT CACCGACGAG TACAAGGTGC CCAGCAAGAA ATTCAAGGTG
151 CTGGGCAACA CCGACCGGCA CAGCATCAAG AAGAACCTGA TCGGAGCCCT
201 GCTGTTCGAC AGCGGCGAAA CAGCCGAGGC CACCCGGCTG AAGAGAACCG
251 CCAGAAGAAG ATACACCAGA CGGAAGAACC GGATCTGCTA TCTGCAAGAG
301 ATCTTCAGCA ACGAGATGGC CAAGGTGGAC GACAGCTTCT TCCACAGACT
351 GGAAGAGTCC TTCCTGGTGG AAGAGGATAA GAAGCACGAG CGGCACCCCA
401 TCTTCGGCAA CATCGTGGAC GAGGTGGCCT ACCACGAGAA GTACCCCACC
```

-continued

451 ATCTACCACC TGAGAAAGAA ACTGGTGGAC AGCACCGACA AGGCCGACCT

501 GCGGCTGATC TATCTGGCCC TGGCCCACAT GATCAAGTTC CGGGGCCACT

551 TCCTGATCGA GGGCGACCTG AACCCCGACA ACAGCGACGT GGACAAGCTG

601 TTCATCCAGC TGGTGCAGAC CTACAACCAG CTGTTCGAGG AAAACCCCAT

651 CAACGCCAGC GGCGTGGACG CCAAGGCCAT CCTGTCTGCC AGACTGAGCA

701 AGAGCAGACG GCTGGAAAAT CTGATCGCCC AGCTGCCCGG CGAGAAGAAG

751 AATGGCCTGT TCGGAAACCT GATTGCCCTG AGCCTGGGCC TGACCCCCAA

801 CTTCAAGAGC AACTTCGACC TGGCCGAGGA TGCCAAACTG CAGCTGAGCA

851 AGGACACCTA CGACGACGAC CTGGACAACC TGCTGGCCCA GATCGGCGAC

901 CAGTACGCCG ACCTGTTTCT GGCCGCCAAG AACCTGTCCG ACGCCATCCT

951 GCTGAGCGAC ATCCTGAGAG TGAACACCGA GATCACCAAG GCCCCCCTGA

1001 GCGCCTCTAT GATCAAGAGA TACGACGAGC ACCACCAGGA CCTGACCCTG

1051 CTGAAAGCTC TCGTGCGGCA GCAGCTGCCT GAGAAGTACA AAGAGATTTT

1101 CTTCGACCAG AGCAAGAACG GCTACGCCGG CTACATTGAC GGCGGAGCCA

1151 GCCAGGAAGA GTTCTACAAG TTCATCAAGC CCATCCTGGA AAAGATGGAC

1201 GGCACCGAGG AACTGCTCGT GAAGCTGAAC AGAGAGGACC TGCTGCGGAA

1251 GCAGCGGACC TTCGACAACG GCAGCATCCC CCACCAGATC CACCTGGGAG

1301 AGCTGCACGC CATTCTGCGG CGGCAGGAAG ATTTTTACCC ATTCCTGAAG

1351 GACAACCGGG AAAAGATCGA GAAGATCCTG ACCTTCCGCA TCCCCTACTA

1401 CGTGGGCCCT CTGGCCAGGG GAAACAGCAG ATTCGCCTGG ATGACCAGAA

1451 AGAGCGAGGA AACCATCACC CCCTGGAACT TCGAGGAAGT GGTGGACAAG

1501 GGCGCTTCCG CCCAGAGCTT CATCGAGCGG ATGACCAACT TCGATAAGAA

1551 CCTGCCCAAC GAGAAGGTGC TGCCCAAGCA CAGCCTGCTG TACGAGTACT

1601 TCACCGTGTA TAACGAGCTG ACCAAAGTGA AATACGTGAC CGAGGGAATG

1651 AGAAAGCCCG CCTTCCTGAG CGGCGAGCAG AAAAAGGCCA TCGTGGACCT

1701 GCTGTTCAAG ACCAACCGGA AAGTGACCGT GAAGCAGCTG AAAGAGGACT

1751 ACTTCAAGAA AATCGAGTGC TTCGACTCCG TGGAAATCTC CGGCGTGGAA

1801 GATCGGTTCA ACGCCTCCCT GGGCACATAC CACGATCTGC TGAAAATTAT

1851 CAAGGACAAG GACTTCCTGG ACAATGAGGA AAACGAGGAC ATTCTGGAAG

1901 ATATCGTGCT GACCCTGACA CTGTTTGAGG ACAGAGAGAT GATCGAGGAA

1951 CGGCTGAAAA CCTATGCCCA CCTGTTCGAC GACAAAGTGA TGAAGCAGCT

2001 GAAGCGGCGG AGATACACCG GCTGGGGCAG GCTGAGCCGG AAGCTGATCA

2051 ACGGCATCCG GGACAAGCAG TCCGGCAAGA CAATCCTGGA TTTCCTGAAG

2101 TCCGACGGCT TCGCCAACAG AAACTTCATG CAGCTGATCC ACGACGACAG

2151 CCTGACCTTT AAAGAGGACA TCCAGAAAGC CCAGGTGTCC GGCCAGGGCG

2201 ATAGCCTGCA CGAGCACATT GCCAATCTGG CCGGCAGCCC CGCCATTAAG

2251 AAGGGCATCC TGCAGACAGT GAAGGTGGTG GACGAGCTCG TGAAAGTGAT

2301 GGGCCGGCAC AAGCCCGAGA ACATCGTGAT CGAAATGGCC AGAGAGAACC

2351 AGACCACCCA GAAGGGACAG AAGAACAGCC GCGAGAGAAT GAAGCGGATC

2401 GAAGAGGGCA TCAAAGAGCT GGGCAGCCAG ATCCTGAAAG AACACCCCGT

-continued

```
2451 GGAAAACACC CAGCTGCAGA ACGAGAAGCT GTACCTGTAC TACCTGCAGA

2501 ATGGGCGGGA TATGTACGTG GACCAGGAAC TGGACATCAA CCGGCTGTCC

2551 GACTACGATG TGGACCATAT CGTGCCTCAG AGCTTTCTGA AGGACGACTC

2601 CATCGACAAC AAGGTGCTGA CCAGAAGCGA CAAGAACCGG GGCAAGAGCG

2651 ACAACGTGCC CTCCGAAGAG GTCGTGAAGA AGATGAAGAA CTACTGGCGG

2701 CAGCTGCTGA ACGCCAAGCT GATTACCCAG AGAAAGTTCG ACAATCTGAC

2751 CAAGGCCGAG AGAGGCGGCC TGAGCGAACT GGATAAGGCC GGCTTCATCA

2801 AGAGACAGCT GGTGGAAACC CGGCAGATCA CAAAGCACGT GGCACAGATC

2851 CTGGACTCCC GGATGAACAC TAAGTACGAC GAGAATGACA AGCTGATCCG

2901 GGAAGTGAAA GTGATCACCC TGAAGTCCAA GCTGGTGTCC GATTTCCGGA

2951 AGGATTTCCA GTTTTACAAA GTGCGCGAGA TCAACAACTA CCACCACGCC

3001 CACGACGCCT ACCTGAACGC CGTCGTGGGA ACCGCCCTGA TCAAAAAGTA

3051 CCCTAAGCTG GAAAGCGAGT TCGTGTACGG CGACTACAAG GTGTACGACG

3101 TGCGGAAGAT GATCGCCAAG AGCGAGCAGG AAATCGGCAA GGCTACCGCC

3151 AAGTACTTCT TCTACAGCAA CATCATGAAC TTTTTCAAGA CCGAGATTAC

3201 CCTGGCCAAC GGCGAGATCC GGAAGCGGCC TCTGATCGAG ACAAACGGCG

3251 AAACCGGGGA GATCGTGTGG GATAAGGGCC GGGATTTTGC CACCGTGCGG

3301 AAAGTGCTGA GCATGCCCCA AGTGAATATC GTGAAAAAGA CCGAGGTGCA

3351 GACAGGCGGC TTCAGCAAAG AGTCTATCCT GCCCAAGAGG AACAGCGATA

3401 AGCTGATCGC CAGAAAGAAG GACTGGGACC CTAAGAAGTA CGGCGGCTTC

3451 GACAGCCCCA CCGTGGCCTA TTCTGTGCTG GTGGTGGCCA AAGTGGAAAA

3501 GGGCAAGTCC AAGAAACTGA AGAGTGTGAA AGAGCTGCTG GGGATCACCA

3551 TCATGGAAAG AAGCAGCTTC GAGAAGAATC CCATCGACTT TCTGGAAGCC

3601 AAGGGCTACA AAGAAGTGAA AAAGGACCTG ATCATCAAGC TGCCTAAGTA

3651 CTCCCTGTTC GAGCTGGAAA ACGGCCGGAA GAGAATGCTG GCCTCTGCCG

3701 GCGAACTGCA GAAGGGAAAC GAACTGGCCC TGCCCTCCAA ATATGTGAAC

3751 TTCCTGTACC TGGCCAGCCA CTATGAGAAG CTGAAGGGCT CCCCCGAGGA

3801 TAATGAGCAG AAACAGCTGT TTGTGGAACA GCACAAGCAC TACCTGGACG

3851 AGATCATCGA GCAGATCAGC GAGTTCTCCA AGAGAGTGAT CCTGGCCGAC

3901 GCTAATCTGG ACAAAGTGCT GTCCGCCTAC AACAAGCACC GGGATAAGCC

3951 CATCAGAGAG CAGGCCGAGA ATATCATCCA CCTGTTTACC CTGACCAATC

4001 TGGGAGCCCC TGCCGCCTTC AAGTACTTTG ACACCACCAT CGACCGGAAG

4051 AGGTACACCA GCACCAAAGA GGTGCTGGAC GCCACCCTGA TCCACCAGAG

4101 CATCACCGGC CTGTACGAGA CACGGATCGA CCTGTCTCAG CTGGGAGGCG

4151 ACAAAAGGCC GGCGGCCACG AAAAAGGCCG GCCAGGCAAA AAAGAAAAAG

4201 TAA
```

The following polynucleotide (e.g., DNA) sequence (SEQ ID NO: 50) corresponds to D10A H841A Cas9 (referred to as dCas9) as disclosed by Jinek et al.

(SEQ ID NO: 50)

1 ATGGCCCCAA AGAAGAAGCG GAAGGTCGGT ATCCACGGAG TCCCAGCAGC

51 CGACAAGAAG TACAGCATCG GCCTGgccAT CGGCACCAAC TCTGTGGGCT

101 GGGCCGTGAT CACCGACGAG TACAAGGTGC CCAGCAAGAA ATTCAAGGTG

151 CTGGGCAACA CCGACCGGCA CAGCATCAAG AAGAACCTGA TCGGAGCCCT

201 GCTGTTCGAC AGCGGCGAAA CAGCCGAGGC CACCCGGCTG AAGAGAACCG

251 CCAGAAGAAG ATACACCAGA CGGAAGAACC GGATCTGCTA TCTGCAAGAG

301 ATCTTCAGCA ACGAGATGGC CAAGGTGGAC GACAGCTTCT TCCACAGACT

351 GGAAGAGTCC TTCCTGGTGG AAGAGGATAA GAAGCACGAG CGGCACCCCA

401 TCTTCGGCAA CATCGTGGAC GAGGTGGCCT ACCACGAGAA GTACCCCACC

451 ATCTACCACC TGAGAAAGAA ACTGGTGGAC AGCACCGACA AGGCCGACCT

501 GCGGCTGATC TATCTGGCCC TGGCCCACAT GATCAAGTTC CGGGGCCACT

551 TCCTGATCGA GGGCGACCTG AACCCCGACA ACAGCGACGT GGACAAGCTG

601 TTCATCCAGC TGGTGCAGAC CTACAACCAG CTGTTCGAGG AAAACCCCAT

651 CAACGCCAGC GGCGTGGACG CCAAGGCCAT CCTGTCTGCC AGACTGAGCA

701 AGAGCAGACG GCTGGAAAAT CTGATCGCCC AGCTGCCCGG CGAGAAGAAG

751 AATGGCCTGT TCGGAAACCT GATTGCCCTG AGCCTGGGCC TGACCCCCAA

801 CTTCAAGAGC AACTTCGACC TGGCCGAGGA TGCCAAACTG CAGCTGAGCA

851 AGGACACCTA CGACGACGAC CTGGACAACC TGCTGGCCCA GATCGGCGAC

901 CAGTACGCCG ACCTGTTTCT GGCCGCCAAG AACCTGTCCG ACGCCATCCT

951 GCTGAGCGAC ATCCTGAGAG TGAACACCGA GATCACCAAG GCCCCCCTGA

1001 GCGCCTCTAT GATCAAGAGA TACGACGAGC ACCACCAGGA CCTGACCCTG

1051 CTGAAAGCTC TCGTGCGGCA GCAGCTGCCT GAGAAGTACA AAGAGATTTT

1101 CTTCGACCAG AGCAAGAACG GCTACGCCGG CTACATTGAC GGCGGAGCCA

1151 GCCAGGAAGA GTTCTACAAG TTCATCAAGC CCATCCTGGA AAAGATGGAC

1201 GGCACCGAGG AACTGCTCGT GAAGCTGAAC AGAGAGGACC TGCTGCGGAA

1251 GCAGCGGACC TTCGACAACG GCAGCATCCC CCACCAGATC CACCTGGGAG

1301 AGCTGCACGC CATTCTGCGG CGGCAGGAAG ATTTTTACCC ATTCCTGAAG

1351 GACAACCGGG AAAAGATCGA GAAGATCCTG ACCTTCCGCA TCCCCTACTA

1401 CGTGGGCCCT CTGGCCAGGG GAAACAGCAG ATTCGCCTGG ATGACCAGAA

1451 AGAGCGAGGA AACCATCACC CCCTGGAACT TCGAGGAAGT GGTGGACAAG

1501 GGCGCTTCCG CCCAGAGCTT CATCGAGCGG ATGACCAACT TCGATAAGAA

1551 CCTGCCCAAC GAGAAGGTGC TGCCCAAGCA CAGCCTGCTG TACGAGTACT

1601 TCACCGTGTA TAACGAGCTG ACCAAAGTGA AATACGTGAC CGAGGGAATG

1651 AGAAAGCCCG CCTTCCTGAG CGGCGAGCAG AAAAAGGCCA TCGTGGACCT

1701 GCTGTTCAAG ACCAACCGGA AAGTGACCGT GAAGCAGCTG AAAGAGGACT

1751 ACTTCAAGAA AATCGAGTGC TTCGACTCCG TGGAAATCTC CGGCGTGGAA

1801 GATCGGTTCA ACGCCTCCCT GGGCACATAC CACGATCTGC TGAAAATTAT

1851 CAAGGACAAG GACTTCCTGG ACAATGAGGA AAACGAGGAC ATTCTGGAAG

1901 ATATCGTGCT GACCCTGACA CTGTTTGAGG ACAGAGAGAT GATCGAGGAA

1951 CGGCTGAAAA CCTATGCCCA CCTGTTCGAC GACAAAGTGA TGAAGCAGCT

-continued

```
2001 GAAGCGGCGG AGATACACCG GCTGGGGCAG GCTGAGCCGG AAGCTGATCA

2051 ACGGCATCCG GGACAAGCAG TCCGGCAAGA CAATCCTGGA TTTCCTGAAG

2101 TCCGACGGCT TCGCCAACAG AAACTTCATG CAGCTGATCC ACGACGACAG

2151 CCTGACCTTT AAAGAGGACA TCCAGAAAGC CCAGGTGTCC GGCCAGGGCG

2201 ATAGCCTGCA CGAGCACATT GCCAATCTGG CCGGCAGCCC CGCCATTAAG

2251 AAGGGCATCC TGCAGACAGT GAAGGTGGTG GACGAGCTCG TGAAAGTGAT

2301 GGGCCGGCAC AAGCCCGAGA ACATCGTGAT CGAAATGGCC AGAGAGAACC

2351 AGACCACCCA GAAGGGACAG AAGAACAGCC GCGAGAGAAT GAAGCGGATC

2401 GAAGAGGGCA TCAAAGAGCT GGGCAGCCAG ATCCTGAAAG AACACCCCGT

2451 GGAAAACACC CAGCTGCAGA ACGAGAAGCT GTACCTGTAC TACCTGCAGA

2501 ATGGGCGGGA TATGTACGTG GACCAGGAAC TGGACATCAA CCGGCTGTCC

2551 GACTACGATG TGGACgccAT CGTGCCTCAG AGCTTTCTGA AGGACGACTC

2601 CATCGACAAC AAGGTGCTGA CCAGAAGCGA CAAGAACCGG GGCAAGAGCG

2651 ACAACGTGCC CTCCGAAGAG GTCGTGAAGA AGATGAAGAA CTACTGGCGG

2701 CAGCTGCTGA ACGCCAAGCT GATTACCCAG AGAAAGTTCG ACAATCTGAC

2751 CAAGGCCGAG AGAGGCGGCC TGAGCGAACT GGATAAGGCC GGCTTCATCA

2801 AGAGACAGCT GGTGGAAACC CGGCAGATCA CAAAGCACGT GGCACAGATC

2851 CTGGACTCCC GGATGAACAC TAAGTACGAC GAGAATGACA AGCTGATCCG

2901 GGAAGTGAAA GTGATCACCC TGAAGTCCAA GCTGGTGTCC GATTTCCGGA

2951 AGGATTTCCA GTTTTACAAA GTGCGCGAGA TCAACAACTA CCACCACGCC

3001 CACGACGCCT ACCTGAACGC CGTCGTGGGA ACCGCCCTGA TCAAAAAGTA

3051 CCCTAAGCTG GAAAGCGAGT TCGTGTACGG CGACTACAAG GTGTACGACG

3101 TGCGGAAGAT GATCGCCAAG AGCGAGCAGG AAATCGGCAA GGCTACCGCC

3151 AAGTACTTCT TCTACAGCAA CATCATGAAC TTTTTCAAGA CCGAGATTAC

3201 CCTGGCCAAC GGCGAGATCC GGAAGCGGCC TCTGATCGAG ACAAACGGCG

3251 AAACCGGGGA GATCGTGTGG GATAAGGGCC GGGATTTTGC CACCGTGCGG

3301 AAAGTGCTGA GCATGCCCCA AGTGAATATC GTGAAAAAGA CCGAGGTGCA

3351 GACAGGCGGC TTCAGCAAAG AGTCTATCCT GCCCAAGAGG AACAGCGATA

3401 AGCTGATCGC CAGAAAGAAG GACTGGGACC CTAAGAAGTA CGGCGGCTTC

3451 GACAGCCCCA CCGTGGCCTA TTCTGTGCTG GTGGTGGCCA AAGTGGAAAA

3501 GGGCAAGTCC AAGAAACTGA AGAGTGTGAA AGAGCTGCTG GGGATCACCA

3551 TCATGGAAAG AAGCAGCTTC GAGAAGAATC CCATCGACTT TCTGGAAGCC

3601 AAGGGCTACA AAGAAGTGAA AAAGGACCTG ATCATCAAGC TGCCTAAGTA

3651 CTCCCTGTTC GAGCTGGAAA ACGGCCGGAA GAGAATGCTG GCCTCTGCCG

3701 GCGAACTGCA GAAGGGAAAC GAACTGGCCC TGCCCTCCAA ATATGTGAAC

3751 TTCCTGTACC TGGCCAGCCA CTATGAGAAG CTGAAGGGCT CCCCCGAGGA

3801 TAATGAGCAG AAACAGCTGT TTGTGGAACA GCACAAGCAC TACCTGGACG

3851 AGATCATCGA GCAGATCAGC GAGTTCTCCA AGAGAGTGAT CCTGGCCGAC

3901 GCTAATCTGG ACAAAGTGCT GTCCGCCTAC AACAAGCACC GGGATAAGCC

3951 CATCAGAGAG CAGGCCGAGA ATATCATCCA CCTGTTTACC CTGACCAATC

4001 TGGGAGCCCC TGCCGCCTTC AAGTACTTTG ACACCACCAT CGACCGGAAG
```

-continued

```
4051 AGGTACACCA GCACCAAAGA GGTGCTGGAC GCCACCCTGA TCCACCAGAG
4101 CATCACCGGC CTGTACGAGA CACGGATCGA CCTGTCTCAG CTGGGAGGCG
4151 ACAAAAGGCC GGCGGCCACG AAAAAGGCCG GCCAGGCAAA AAAGAAAAAG
4201 TAA
```

The following polyribonucleotide (e.g., RNA) sequence (SEQ ID NO: 51) encodes D10A H841A Cas9 (referred to as dCas9) as disclosed by Jinek et al.

```
                                           (SEQ ID NO: 51)
   1 AUGGCCCCAA AGAAGAAGCG GAAGGUCGGU AUCCACGGAG UCCCAGCAGC
  51 CGACAAGAAG UACAGCAUCG GCCUGgccAU CGGCACCAAC UCUGUGGGCU
 101 GGGCCGUGAU CACCGACGAG UACAAGGUGC CCAGCAAGAA AUUCAAGGUG
 151 CUGGGCAACA CCGACCGGCA CAGCAUCAAG AAGAACCUGA UCGGAGCCCU
 201 GCUGUUCGAC AGCGGCGAAA CAGCCGAGGC CACCCGGCUG AAGAGAACCG
 251 CCAGAAGAAG AUACACCAGA CGGAAGAACC GGAUCUGCUA UCUGCAAGAG
 301 AUCUUCAGCA ACGAGAUGGC CAAGGUGGAC GACAGCUUCU UCCACAGACU
 351 GGAAGAGUCC UUCCUGGUGG AAGAGGAUAA GAAGCACGAG CGGCACCCCA
 401 UCUUCGGCAA CAUCGUGGAC GAGGUGGCCU ACCACGAGAA GUACCCCACC
 451 AUCUACCACC UGAGAAAGAA ACUGGUGGAC AGCACCGACA AGGCCGACCU
 501 GCGGCUGAUC UAUCUGGCCC UGGCCCACAU GAUCAAGUUC CGGGGCCACU
 551 UCCUGAUCGA GGGCGACCUG AACCCCGACA ACAGCGACGU GGACAAGCUG
 601 UUCAUCCAGC UGGUGCAGAC CUACAACCAG CUGUUCGAGG AAAACCCCAU
 651 CAACGCCAGC GGCGUGGACG CCAAGGCCAU CCUGUCUGCC AGACUGAGCA
 701 AGAGCAGACG GCUGGAAAAU CUGAUCGCCC AGCUGCCCGG CGAGAAGAAG
 751 AAUGGCCUGU UCGGAAACCU GAUUGCCCUG AGCCUGGGCC UGACCCCCAA
 801 CUUCAAGAGC AACUUCGACC UGGCCGAGGA UGCCAAACUG CAGCUGAGCA
 851 AGGACACCUA CGACGACGAC CUGGACAACC UGCUGGCCCA GAUCGGCGAC
 901 CAGUACGCCG ACCUGUUUCU GGCCGCCAAG AACCUGUCCG ACGCCAUCCU
 951 GCUGAGCGAC AUCCUGAGAG UGAACACCGA GAUCACCAAG GCCCCCCUGA
1001 GCGCCUCUAU GAUCAAGAGA UACGACGAGC ACCACCAGGA CCUGACCCUG
1051 CUGAAAGCUC UCGUGCGGCA GCAGCUGCCU GAGAAGUACA AAGAGAUUUU
1101 CUUCGACCAG AGCAAGAACG GCUACGCCGG CUACAUUGAC GGCGGAGCCA
1151 GCCAGGAAGA GUUCUACAAG UUCAUCAAGC CCAUCCUGGA AAAGAUGGAC
1201 GGCACCGAGG AACUGCUCGU GAAGCUGAAC AGAGAGGACC UGCUGCGGAA
1251 GCAGCGGACC UUCGACAACG GCAGCAUCCC CCACCAGAUC CACCUGGGAG
1301 AGCUGCACGC CAUUCUGCGG CGGCAGGAAG AUUUUUACCC AUUCCUGAAG
1351 GACAACCGGG AAAAGAUCGA GAAGAUCCUG ACCUUCCGCA UCCCCUACUA
1401 CGUGGGCCCU CUGGCCAGGG GAAACAGCAG AUUCGCCUGG AUGACCAGAA
1451 AGAGCGAGGA AACCAUCACC CCCUGGAACU UCGAGGAAGU GGUGGACAAG
1501 GGCGCUUCCG CCCAGAGCUU CAUCGAGCGG AUGACCAACU UCGAUAAGAA
1551 CCUGCCCAAC GAGAAGGUGC UGCCCAAGCA CAGCCUGCUG UACGAGUACU
```

-continued

1601 UCACCGUGUA UAACGAGCUG ACCAAAGUGA AAUACGUGAC CGAGGGAAUG

1651 AGAAAGCCCG CCUUCCUGAG CGGCGAGCAG AAAAAGGCCA UCGUGGACCU

1701 GCUGUUCAAG ACCAACCGGA AAGUGACCGU GAAGCAGCUG AAAGAGGACU

1751 ACUUCAAGAA AAUCGAGUGC UUCGACUCCG UGGAAAUCUC CGGCGUGGAA

1801 GAUCGGUUCA ACGCCUCCCU GGGCACAUAC CACGAUCUGC UGAAAAUUAU

1851 CAAGGACAAG GACUUCCUGG ACAAUGAGGA AAACGAGGAC AUUCUGGAAG

1901 AUAUCGUGCU GACCCUGACA CUGUUUGAGG ACAGAGAGAU GAUCGAGGAA

1951 CGGCUGAAAA CCUAUGCCCA CCUGUUCGAC GACAAAGUGA UGAAGCAGCU

2001 GAAGCGGCGG AGAUACACCG GCUGGGGCAG GCUGAGCCGG AAGCUGAUCA

2051 ACGGCAUCCG GGACAAGCAG UCCGGCAAGA CAAUCCUGGA UUUCCUGAAG

2101 UCCGACGGCU UCGCCAACAG AAACUUCAUG CAGCUGAUCC ACGACGACAG

2151 CCUGACCUUU AAAGAGGACA UCCAGAAAGC CCAGGUGUCC GGCCAGGGCG

2201 AUAGCCUGCA CGAGCACAUU GCCAAUCUGG CCGGCAGCCC CGCCAUUAAG

2251 AAGGGCAUCC UGCAGACAGU GAAGGUGGUG GACGAGCUCG UGAAAGUGAU

2301 GGGCCGGCAC AAGCCCGAGA ACAUCGUGAU CGAAAUGGCC AGAGAGAACC

2351 AGACCACCCA GAAGGGACAG AAGAACAGCC GCGAGAGAAU GAAGCGGAUC

2401 GAAGAGGGCA UCAAAGAGCU GGGCAGCCAG AUCCUGAAAG AACACCCCGU

2451 GGAAAACACC CAGCUGCAGA ACGAGAAGCU GUACCUGUAC UACCUGCAGA

2501 AUGGGCGGGA UAUGUACGUG GACCAGGAAC UGGACAUCAA CCGGCUGUCC

2551 GACUACGAUG UGGACgccAU CGUGCCUCAG AGCUUUCUGA AGGACGACUC

2601 CAUCGACAAC AAGGUGCUGA CCAGAAGCGA CAAGAACCGG GGCAAGAGCG

2651 ACAACGUGCC CUCCGAAGAG GUCGUGAAGA AGAUGAAGAA CUACUGGCGG

2701 CAGCUGCUGA ACGCCAAGCU GAUUACCCAG AGAAAGUUCG ACAAUCUGAC

2751 CAAGGCCGAG AGAGGCGGCC UGAGCGAACU GGAUAAGGCC GGCUUCAUCA

2801 AGAGACAGCU GGUGGAAACC CGGCAGAUCA CAAAGCACGU GGCACAGAUC

2851 CUGGACUCCC GGAUGAACAC UAAGUACGAC GAGAAUGACA AGCUGAUCCG

2901 GGAAGUGAAA GUGAUCACCC UGAAGUCCAA GCUGGUGUCC GAUUUCCGGA

2951 AGGAUUUCCA GUUUUACAAA GUGCGCGAGA UCAACAACUA CCACCACGCC

3001 CACGACGCCU ACCUGAACGC CGUCGUGGGA ACCGCCCUGA UCAAAAAGUA

3051 CCCUAAGCUG GAAAGCGAGU UCGUGUACGG CGACUACAAG GUGUACGACG

3101 UGCGGAAGAU GAUCGCCAAG AGCGAGCAGG AAAUCGGCAA GGCUACCGCC

3151 AAGUACUUCU UCUACAGCAA CAUCAUGAAC UUUUUCAAGA CCGAGAUUAC

3201 CCUGGCCAAC GGCGAGAUCC GGAAGCGGCC UCUGAUCGAG ACAAACGGCG

3251 AAACCGGGGA GAUCGUGUGG GAUAAGGGCC GGGAUUUUGC CACCGUGCGG

3301 AAAGUGCUGA GCAUGCCCCA AGUGAAUAUC GUGAAAAAGA CCGAGGUGCA

3351 GACAGGCGGC UUCAGCAAAG AGUCUAUCCU GCCCAAGAGG AACAGCGAUA

3401 AGCUGAUCGC CAGAAAGAAG GACUGGGACC CUAAGAAGUA CGGCGGCUUC

3451 GACAGCCCCA CCGUGGCCUA UUCUGUGCUG GUGGUGGCCA AAGUGGAAAA

3501 GGGCAAGUCC AAGAAACUGA AGAGUGUGAA AGAGCUGCUG GGGAUCACCA

3551 UCAUGGAAAG AAGCAGCUUC GAGAAGAAUC CCAUCGACUU UCUGGAAGCC

3601 AAGGGCUACA AAGAAGUGAA AAAGGACCUG AUCAUCAAGC UGCCUAAGUA

-continued

3651 CUCCCUGUUC GAGCUGGAAA ACGGCCGGAA GAGAAUGCUG GCCUCUGCCG

3701 GCGAACUGCA GAAGGGAAAC GAACUGGCCC UGCCCUCCAA AUAUGUGAAC

3751 UUCCUGUACC UGGCCAGCCA CUAUGAGAAG CUGAAGGGCU CCCCCGAGGA

3801 UAAUGAGCAG AAACAGCUGU UUGUGGAACA GCACAAGCAC UACCUGGACG

3851 AGAUCAUCGA GCAGAUCAGC GAGUUCUCCA AGAGAGUGAU CCUGGCCGAC

3901 GCUAAUCUGG ACAAAGUGCU GUCCGCCUAC AACAAGCACC GGGAUAAGCC

3951 CAUCAGAGAG CAGGCCGAGA AUAUCAUCCA CCUGUUUACC CUGACCAAUC

4001 UGGGAGCCCC UGCCGCCUUC AAGUACUUUG ACACCACCAU CGACCGGAAG

4051 AGGUACACCA GCACCAAAGA GGUGCUGGAC GCCACCCUGA UCCACCAGAG

4101 CAUCACCGGC CUGUACGAGA CACGGAUCGA CCUGUCUCAG CUGGGAGGCG

4151 ACAAAAGGCC GGCGGCCACG AAAAAGGCCG GCCAGGCAAA AAAGAAAAAG

4201 UAA

The following polynucleotide (e.g., DNA) sequence (SEQ ID NO: 52) corresponds to FLAG-tagged wildtype Cas9.

(SEQ ID NO: 52)

1 ATGGACTATA AGGACCACGA CGGAGACTAC AAGGATCATG ATATTGATTA

51 CAAAGACGAT GACGATAAGA TGGCCCCAAA GAAGAAGCGG AAGGTCGGTA

101 TCCACGGAGT CCCAGCAGCC GACAAGAAGT ACAGCATCGG CCTGGACATC

151 GGCACCAACT CTGTGGGCTG GGCCGTGATC ACCGACGAGT ACAAGGTGCC

201 CAGCAAGAAA TTCAAGGTGC TGGGCAACAC CGACCGGCAC AGCATCAAGA

251 AGAACCTGAT CGGAGCCCTG CTGTTCGACA GCGGCGAAAC AGCCGAGGCC

301 ACCCGGCTGA AGAGAACCGC CAGAAGAAGA TACACCAGAC GGAAGAACCG

351 GATCTGCTAT CTGCAAGAGA TCTTCAGCAA CGAGATGGCC AAGGTGGACG

401 ACAGCTTCTT CCACAGACTG GAAGAGTCCT TCCTGGTGGA AGAGGATAAG

451 AAGCACGAGC GGCACCCCAT CTTCGGCAAC ATCGTGGACG AGGTGGCCTA

501 CCACGAGAAG TACCCCACCA TCTACCACCT GAGAAAGAAA CTGGTGGACA

551 GCACCGACAA GGCCGACCTG CGGCTGATCT ATCTGGCCCT GGCCCACATG

601 ATCAAGTTCC GGGGCCACTT CCTGATCGAG GGCGACCTGA ACCCCGACAA

651 CAGCGACGTG GACAAGCTGT TCATCCAGCT GGTGCAGACC TACAACCAGC

701 TGTTCGAGGA AAACCCCATC AACGCCAGCG GCGTGGACGC CAAGGCCATC

751 CTGTCTGCCA GACTGAGCAA GAGCAGACGG CTGGAAAATC TGATCGCCCA

801 GCTGCCCGGC GAGAAGAAGA ATGGCCTGTT CGGAAACCTG ATTGCCCTGA

851 GCCTGGGCCT GACCCCCAAC TTCAAGAGCA ACTTCGACCT GGCCGAGGAT

901 GCCAAACTGC AGCTGAGCAA GGACACCTAC GACGACGACC TGGACAACCT

951 GCTGGCCCAG ATCGGCGACC AGTACGCCGA CCTGTTTCTG GCCGCCAAGA

1001 ACCTGTCCGA CGCCATCCTG CTGAGCGACA TCCTGAGAGT GAACACCGAG

1051 ATCACCAAGG CCCCCCTGAG CGCCTCTATG ATCAAGAGAT ACGACGAGCA

1101 CCACCAGGAC CTGACCCTGC TGAAAGCTCT CGTGCGGCAG CAGCTGCCTG

1151 AGAAGTACAA AGAGATTTTC TTCGACCAGA GCAAGAACGG CTACGCCGGC

1201 TACATTGACG GCGGAGCCAG CCAGGAAGAG TTCTACAAGT TCATCAAGCC

-continued

1251 CATCCTGGAA AAGATGGACG GCACCGAGGA ACTGCTCGTG AAGCTGAACA

1301 GAGAGGACCT GCTGCGGAAG CAGCGGACCT TCGACAACGG CAGCATCCCC

1351 CACCAGATCC ACCTGGGAGA GCTGCACGCC ATTCTGCGGC GGCAGGAAGA

1401 TTTTTACCCA TTCCTGAAGG ACAACCGGGA AAAGATCGAG AAGATCCTGA

1451 CCTTCCGCAT CCCCTACTAC GTGGGCCCTC TGGCCAGGGG AAACAGCAGA

1501 TTCGCCTGGA TGACCAGAAA GAGCGAGGAA ACCATCACCC CCTGGAACTT

1551 CGAGGAAGTG GTGGACAAGG GCGCTTCCGC CCAGAGCTTC ATCGAGCGGA

1601 TGACCAACTT CGATAAGAAC CTGCCCAACG AGAAGGTGCT GCCCAAGCAC

1651 AGCCTGCTGT ACGAGTACTT CACCGTGTAT AACGAGCTGA CCAAAGTGAA

1701 ATACGTGACC GAGGGAATGA GAAAGCCCGC CTTCCTGAGC GGCGAGCAGA

1751 AAAAGGCCAT CGTGGACCTG CTGTTCAAGA CCAACCGGAA AGTGACCGTG

1801 AAGCAGCTGA AAGAGGACTA CTTCAAGAAA ATCGAGTGCT TCGACTCCGT

1851 GGAAATCTCC GGCGTGGAAG ATCGGTTCAA CGCCTCCCTG GGCACATACC

1901 ACGATCTGCT GAAAATTATC AAGGACAAGG ACTTCCTGGA CAATGAGGAA

1951 AACGAGGACA TTCTGGAAGA TATCGTGCTG ACCCTGACAC TGTTTGAGGA

2001 CAGAGAGATG ATCGAGGAAC GGCTGAAAAC CTATGCCCAC CTGTTCGACG

2051 ACAAAGTGAT GAAGCAGCTG AAGCGGCGGA GATACACCGG CTGGGGCAGG

2101 CTGAGCCGGA AGCTGATCAA CGGCATCCGG GACAAGCAGT CCGGCAAGAC

2151 AATCCTGGAT TTCCTGAAGT CCGACGGCTT CGCCAACAGA AACTTCATGC

2201 AGCTGATCCA CGACGACAGC CTGACCTTTA AAGAGGACAT CCAGAAAGCC

2251 CAGGTGTCCG GCCAGGGCGA TAGCCTGCAC GAGCACATTG CCAATCTGGC

2301 CGGCAGCCCC GCCATTAAGA AGGGCATCCT GCAGACAGTG AAGGTGGTGG

2351 ACGAGCTCGT GAAAGTGATG GGCCGGCACA AGCCCGAGAA CATCGTGATC

2401 GAAATGGCCA GAGAGAACCA GACCACCCAG AAGGGACAGA AGAACAGCCG

2451 CGAGAGAATG AAGCGGATCG AAGAGGGCAT CAAAGAGCTG GGCAGCCAGA

2501 TCCTGAAAGA ACACCCCGTG GAAAACACCC AGCTGCAGAA CGAGAAGCTG

2551 TACCTGTACT ACCTGCAGAA TGGGCGGGAT ATGTACGTGG ACCAGGAACT

2601 GGACATCAAC CGGCTGTCCG ACTACGATGT GGACCATATC GTGCCTCAGA

2651 GCTTTCTGAA GGACGACTCC ATCGACAACA AGGTGCTGAC CAGAAGCGAC

2701 AAGAACCGGG GCAAGAGCGA CAACGTGCCC TCCGAAGAGG TCGTGAAGAA

2751 GATGAAGAAC TACTGGCGGC AGCTGCTGAA CGCCAAGCTG ATTACCCAGA

2801 GAAAGTTCGA CAATCTGACC AAGGCCGAGA GAGGCGGCCT GAGCGAACTG

2851 GATAAGGCCG GCTTCATCAA GAGACAGCTG GTGGAAACCC GGCAGATCAC

2901 AAAGCACGTG GCACAGATCC TGGACTCCCG GATGAACACT AAGTACGACG

2951 AGAATGACAA GCTGATCCGG GAAGTGAAAG TGATCACCCT GAAGTCCAAG

3001 CTGGTGTCCG ATTTCCGGAA GGATTTCCAG TTTTACAAAG TGCGCGAGAT

3051 CAACAACTAC CACCACGCCC ACGACGCCTA CCTGAACGCC GTCGTGGGAA

3101 CCGCCCTGAT CAAAAAGTAC CCTAAGCTGG AAAGCGAGTT CGTGTACGGC

3151 GACTACAAGG TGTACGACGT GCGGAAGATG ATCGCCAAGA GCGAGCAGGA

3201 AATCGGCAAG GCTACCGCCA AGTACTTCTT CTACAGCAAC ATCATGAACT

-continued

```
3251  TTTTCAAGAC CGAGATTACC CTGGCCAACG GCGAGATCCG GAAGCGGCCT

3301  CTGATCGAGA CAAACGGCGA AACCGGGGAG ATCGTGTGGG ATAAGGGCCG

3351  GGATTTTGCC ACCGTGCGGA AAGTGCTGAG CATGCCCCAA GTGAATATCG

3401  TGAAAAAGAC CGAGGTGCAG ACAGGCGGCT TCAGCAAAGA GTCTATCCTG

3451  CCCAAGAGGA ACAGCGATAA GCTGATCGCC AGAAAGAAGG ACTGGGACCC

3501  TAAGAAGTAC GGCGGCTTCG ACAGCCCCAC CGTGGCCTAT TCTGTGCTGG

3551  TGGTGGCCAA AGTGGAAAAG GGCAAGTCCA AGAAACTGAA GAGTGTGAAA

3601  GAGCTGCTGG GGATCACCAT CATGGAAAGA AGCAGCTTCG AGAAGAATCC

3651  CATCGACTTT CTGGAAGCCA AGGGCTACAA AGAAGTGAAA AAGGACCTGA

3701  TCATCAAGCT GCCTAAGTAC TCCCTGTTCG AGCTGGAAAA CGGCCGGAAG

3751  AGAATGCTGG CCTCTGCCGG CGAACTGCAG AAGGGAAACG AACTGGCCCT

3801  GCCCTCCAAA TATGTGAACT TCCTGTACCT GGCCAGCCAC TATGAGAAGC

3851  TGAAGGGCTC CCCCGAGGAT AATGAGCAGA AACAGCTGTT TGTGGAACAG

3901  CACAAGCACT ACCTGGACGA GATCATCGAG CAGATCAGCG AGTTCTCCAA

3951  GAGAGTGATC CTGGCCGACG CTAATCTGGA CAAAGTGCTG TCCGCCTACA

4001  ACAAGCACCG GGATAAGCCC ATCAGAGAGC AGGCCGAGAA TATCATCCAC

4051  CTGTTTACCC TGACCAATCT GGGAGCCCCT GCCGCCTTCA AGTACTTTGA

4101  CACCACCATC GACCGGAAGA GGTACACCAG CACCAAAGAG GTGCTGGACG

4151  CCACCCTGAT CCACCAGAGC ATCACCGGCC TGTACGAGAC ACGGATCGAC

4201  CTGTCTCAGC TGGGAGGCGA CAAAAGGCCG GCGGCCACGA AAAAGGCCGG

4251  CCAGGCAAAA AAGAAAAAGT AA
```

The following polynucleotide (e.g., DNA) sequence (SEQ ID NO: 53) corresponds to HA-tagged D10A Cas9 (the mutated codon corresponding to D10A is indicated with lower case letters).

```
                                                (SEQ ID NO: 53)
   1  ATGTACCCAT ACGATGTTCC AGATTACGCT ATGGCCCCAA AGAAGAAGCG

  51  GAAGGTCGGT ATCCACGGAG TCCCAGCAGC CGACAAGAAG TACAGCATCG

 101  GCCTGgccAT CGGCACCAAC TCTGTGGGCT GGGCCGTGAT CACCGACGAG

 151  TACAAGGTGC CCAGCAAGAA ATTCAAGGTG CTGGGCAACA CCGACCGGCA

 201  CAGCATCAAG AAGAACCTGA TCGGAGCCCT GCTGTTCGAC AGCGGCGAAA

 251  CAGCCGAGGC CACCCGGCTG AAGAGAACCG CCAGAAGAAG ATACACCAGA

 301  CGGAAGAACC GGATCTGCTA TCTGCAAGAG ATCTTCAGCA ACGAGATGGC

 351  CAAGGTGGAC GACAGCTTCT TCCACAGACT GGAAGAGTCC TTCCTGGTGG

 401  AAGAGGATAA GAAGCACGAG CGGCACCCCA TCTTCGGCAA CATCGTGGAC

 451  GAGGTGGCCT ACCACGAGAA GTACCCCACC ATCTACCACC TGAGAAAGAA

 501  ACTGGTGGAC AGCACCGACA AGGCCGACCT GCGGCTGATC TATCTGGCCC

 551  TGGCCCACAT GATCAAGTTC CGGGGCCACT TCCTGATCGA GGGCGACCTG

 601  AACCCCGACA ACAGCGACGT GGACAAGCTG TTCATCCAGC TGGTGCAGAC

 651  CTACAACCAG CTGTTCGAGG AAAACCCCAT CAACGCCAGC GGCGTGGACG

 701  CCAAGGCCAT CCTGTCTGCC AGACTGAGCA AGAGCAGACG GCTGGAAAAT
```

-continued

751 CTGATCGCCC AGCTGCCCGG CGAGAAGAAG AATGGCCTGT TCGGAAACCT

801 GATTGCCCTG AGCCTGGGCC TGACCCCCAA CTTCAAGAGC AACTTCGACC

851 TGGCCGAGGA TGCCAAACTG CAGCTGAGCA AGGACACCTA CGACGACGAC

901 CTGGACAACC TGCTGGCCCA GATCGGCGAC CAGTACGCCG ACCTGTTTCT

951 GGCCGCCAAG AACCTGTCCG ACGCCATCCT GCTGAGCGAC ATCCTGAGAG

1001 TGAACACCGA GATCACCAAG GCCCCCCTGA GCGCCTCTAT GATCAAGAGA

1051 TACGACGAGC ACCACCAGGA CCTGACCCTG CTGAAAGCTC TCGTGCGGCA

1101 GCAGCTGCCT GAGAAGTACA AAGAGATTTT CTTCGACCAG AGCAAGAACG

1151 GCTACGCCGG CTACATTGAC GGCGGAGCCA GCCAGGAAGA GTTCTACAAG

1201 TTCATCAAGC CCATCCTGGA AAAGATGGAC GGCACCGAGG AACTGCTCGT

1251 GAAGCTGAAC AGAGAGGACC TGCTGCGGAA GCAGCGGACC TTCGACAACG

1301 GCAGCATCCC CCACCAGATC CACCTGGGAG AGCTGCACGC CATTCTGCGG

1351 CGGCAGGAAG ATTTTTACCC ATTCCTGAAG GACAACCGGG AAAAGATCGA

1401 GAAGATCCTG ACCTTCCGCA TCCCCTACTA CGTGGGCCCT CTGGCCAGGG

1451 GAAACAGCAG ATTCGCCTGG ATGACCAGAA AGAGCGAGGA AACCATCACC

1501 CCCTGGAACT TCGAGGAAGT GGTGGACAAG GGCGCTTCCG CCCAGAGCTT

1551 CATCGAGCGG ATGACCAACT TCGATAAGAA CCTGCCCAAC GAGAAGGTGC

1601 TGCCCAAGCA CAGCCTGCTG TACGAGTACT TCACCGTGTA TAACGAGCTG

1651 ACCAAAGTGA AATACGTGAC CGAGGGAATG AGAAAGCCCG CCTTCCTGAG

1701 CGGCGAGCAG AAAAAGGCCA TCGTGGACCT GCTGTTCAAG ACCAACCGGA

1751 AAGTGACCGT GAAGCAGCTG AAAGAGGACT ACTTCAAGAA AATCGAGTGC

1801 TTCGACTCCG TGGAAATCTC CGGCGTGGAA GATCGGTTCA ACGCCTCCCT

1851 GGGCACATAC CACGATCTGC TGAAAATTAT CAAGGACAAG GACTTCCTGG

1901 ACAATGAGGA AAACGAGGAC ATTCTGGAAG ATATCGTGCT GACCCTGACA

1951 CTGTTTGAGG ACAGAGAGAT GATCGAGGAA CGGCTGAAAA CCTATGCCCA

2001 CCTGTTCGAC GACAAAGTGA TGAAGCAGCT GAAGCGGCGG AGATACACCG

2051 GCTGGGGCAG GCTGAGCCGG AAGCTGATCA ACGGCATCCG GGACAAGCAG

2101 TCCGGCAAGA CAATCCTGGA TTTCCTGAAG TCCGACGGCT TCGCCAACAG

2151 AAACTTCATG CAGCTGATCC ACGACGACAG CCTGACCTTT AAAGAGGACA

2201 TCCAGAAAGC CCAGGTGTCC GGCCAGGGCG ATAGCCTGCA CGAGCACATT

2251 GCCAATCTGG CCGGCAGCCC CGCCATTAAG AAGGGCATCC TGCAGACAGT

2301 GAAGGTGGTG GACGAGCTCG TGAAAGTGAT GGGCCGGCAC AAGCCCGAGA

2351 ACATCGTGAT CGAAATGGCC AGAGAGAACC AGACCACCCA GAAGGGACAG

2401 AAGAACAGCC GCGAGAGAAT GAAGCGGATC GAAGAGGGCA TCAAAGAGCT

2451 GGGCAGCCAG ATCCTGAAAG AACACCCCGT GGAAAACACC CAGCTGCAGA

2501 ACGAGAAGCT GTACCTGTAC TACCTGCAGA ATGGGCGGGA TATGTACGTG

2551 GACCAGGAAC TGGACATCAA CCGGCTGTCC GACTACGATG TGGACCATAT

2601 CGTGCCTCAG AGCTTTCTGA AGGACGACTC CATCGACAAC AAGGTGCTGA

2651 CCAGAAGCGA CAAGAACCGG GGCAAGAGCG ACAACGTGCC CTCCGAAGAG

2701 GTCGTGAAGA AGATGAAGAA CTACTGGCGG CAGCTGCTGA ACGCCAAGCT

2751 GATTACCCAG AGAAAGTTCG ACAATCTGAC CAAGGCCGAG AGAGGCGGCC

-continued

```
2801 TGAGCGAACT GGATAAGGCC GGCTTCATCA AGAGACAGCT GGTGGAAACC

2851 CGGCAGATCA CAAAGCACGT GGCACAGATC CTGGACTCCC GGATGAACAC

2901 TAAGTACGAC GAGAATGACA AGCTGATCCG GGAAGTGAAA GTGATCACCC

2951 TGAAGTCCAA GCTGGTGTCC GATTTCCGGA AGGATTTCCA GTTTTACAAA

3001 GTGCGCGAGA TCAACAACTA CCACCACGCC CACGACGCCT ACCTGAACGC

3051 CGTCGTGGGA ACCGCCCTGA TCAAAAAGTA CCCTAAGCTG GAAAGCGAGT

3101 TCGTGTACGG CGACTACAAG GTGTACGACG TGCGGAAGAT GATCGCCAAG

3151 AGCGAGCAGG AAATCGGCAA GGCTACCGCC AAGTACTTCT TCTACAGCAA

3201 CATCATGAAC TTTTTCAAGA CCGAGATTAC CCTGGCCAAC GGCGAGATCC

3251 GGAAGCGGCC TCTGATCGAG ACAAACGGCG AAACCGGGGA GATCGTGTGG

3301 GATAAGGGCC GGGATTTTGC CACCGTGCGG AAAGTGCTGA GCATGCCCCA

3351 AGTGAATATC GTGAAAAAGA CCGAGGTGCA GACAGGCGGC TTCAGCAAAG

3401 AGTCTATCCT GCCCAAGAGG AACAGCGATA AGCTGATCGC CAGAAAGAAG

3451 GACTGGGACC CTAAGAAGTA CGGCGGCTTC GACAGCCCCA CCGTGGCCTA

3501 TTCTGTGCTG GTGGTGGCCA AAGTGGAAAA GGGCAAGTCC AAGAAACTGA

3551 AGAGTGTGAA AGAGCTGCTG GGGATCACCA TCATGGAAAG AAGCAGCTTC

3601 GAGAAGAATC CCATCGACTT TCTGGAAGCC AAGGGCTACA AAGAAGTGAA

3651 AAAGGACCTG ATCATCAAGC TGCCTAAGTA CTCCCTGTTC GAGCTGGAAA

3701 ACGGCCGGAA GAGAATGCTG GCCTCTGCCG GCGAACTGCA GAAGGGAAAC

3751 GAACTGGCCC TGCCCTCCAA ATATGTGAAC TTCCTGTACC TGGCCAGCCA

3801 CTATGAGAAG CTGAAGGGCT CCCCCGAGGA TAATGAGCAG AAACAGCTGT

3851 TTGTGGAACA GCACAAGCAC TACCTGGACG AGATCATCGA GCAGATCAGC

3901 GAGTTCTCCA AGAGAGTGAT CCTGGCCGAC GCTAATCTGG ACAAAGTGCT

3951 GTCCGCCTAC AACAAGCACC GGGATAAGCC CATCAGAGAG CAGGCCGAGA

4001 ATATCATCCA CCTGTTTACC CTGACCAATC TGGGAGCCCC TGCCGCCTTC

4051 AAGTACTTTG ACACCACCAT CGACCGGAAG AGGTACACCA GCACCAAAGA

4101 GGTGCTGGAC GCCACCCTGA TCCACCAGAG CATCACCGGC CTGTACGAGA

4151 CACGGATCGA CCTGTCTCAG CTGGGAGGCG ACAAAAGGCC GGCGGCCACG

4201 AAAAAGGCCG GCCAGGCAAA AAAGAAAAAG TAA
```

The following polynucleotide (e.g., DNA) sequence (SEQ ID NO: 54) corresponds to FLAG-tagged D10A H841A Cas9 (referred to as dCas9) as disclosed by Jinek et al. (the mutated codons corresponding to D10A and H841A are indicated with lower case letters).

```
                                              (SEQ ID NO: 54)
  1 ATGGACTATA AGGACCACGA CGGAGACTAC AAGGATCATG ATATTGATTA

 51 CAAAGACGAT GACGATAAGA TGGCCCCAAA GAAGAAGCGG AAGGTCGGTA

101 TCCACGGAGT CCCAGCAGCC GACAAGAAGT ACAGCATCGG CCTGgccATC

151 GGCACCAACT CTGTGGGCTG GGCCGTGATC ACCGACGAGT ACAAGGTGCC

201 CAGCAAGAAA TTCAAGGTGC TGGGCAACAC CGACCGGCAC AGCATCAAGA

251 AGAACCTGAT CGGAGCCCTG CTGTTCGACA GCGGCGAAAC AGCCGAGGCC
```

-continued

```
301   ACCCGGCTGA AGAGAACCGC CAGAAGAAGA TACACCAGAC GGAAGAACCG
351   GATCTGCTAT CTGCAAGAGA TCTTCAGCAA CGAGATGGCC AAGGTGGACG
401   ACAGCTTCTT CCACAGACTG GAAGAGTCCT TCCTGGTGGA AGAGGATAAG
451   AAGCACGAGC GGCACCCCAT CTTCGGCAAC ATCGTGGACG AGGTGGCCTA
501   CCACGAGAAG TACCCCACCA TCTACCACCT GAGAAAGAAA CTGGTGGACA
551   GCACCGACAA GGCCGACCTG CGGCTGATCT ATCTGGCCCT GGCCCACATG
601   ATCAAGTTCC GGGGCCACTT CCTGATCGAG GGCGACCTGA ACCCCGACAA
651   CAGCGACGTG GACAAGCTGT TCATCCAGCT GGTGCAGACC TACAACCAGC
701   TGTTCGAGGA AAACCCCATC AACGCCAGCG GCGTGGACGC CAAGGCCATC
751   CTGTCTGCCA GACTGAGCAA GAGCAGACGG CTGGAAAATC TGATCGCCCA
801   GCTGCCCGGC GAGAAGAAGA ATGGCCTGTT CGGAAACCTG ATTGCCCTGA
851   GCCTGGGCCT GACCCCCAAC TTCAAGAGCA ACTTCGACCT GGCCGAGGAT
901   GCCAAACTGC AGCTGAGCAA GGACACCTAC GACGACGACC TGGACAACCT
951   GCTGGCCCAG ATCGGCGACC AGTACGCCGA CCTGTTTCTG GCCGCCAAGA
1001  ACCTGTCCGA CGCCATCCTG CTGAGCGACA TCCTGAGAGT GAACACCGAG
1051  ATCACCAAGG CCCCCCTGAG CGCCTCTATG ATCAAGAGAT ACGACGAGCA
1101  CCACCAGGAC CTGACCCTGC TGAAAGCTCT CGTGCGGCAG CAGCTGCCTG
1151  AGAAGTACAA AGAGATTTTC TTCGACCAGA GCAAGAACGG CTACGCCGGC
1201  TACATTGACG GCGGAGCCAG CCAGGAAGAG TTCTACAAGT TCATCAAGCC
1251  CATCCTGGAA AAGATGGACG GCACCGAGGA ACTGCTCGTG AAGCTGAACA
1301  GAGAGGACCT GCTGCGGAAG CAGCGGACCT TCGACAACGG CAGCATCCCC
1351  CACCAGATCC ACCTGGGAGA GCTGCACGCC ATTCTGCGGC GGCAGGAAGA
1401  TTTTTACCCA TTCCTGAAGG ACAACCGGGA AAAGATCGAG AAGATCCTGA
1451  CCTTCCGCAT CCCCTACTAC GTGGGCCCTC TGGCCAGGGG AAACAGCAGA
1501  TTCGCCTGGA TGACCAGAAA GAGCGAGGAA ACCATCACCC CCTGGAACTT
1551  CGAGGAAGTG GTGGACAAGG GCGCTTCCGC CCAGAGCTTC ATCGAGCGGA
1601  TGACCAACTT CGATAAGAAC CTGCCCAACG AGAAGGTGCT GCCCAAGCAC
1651  AGCCTGCTGT ACGAGTACTT CACCGTGTAT AACGAGCTGA CCAAAGTGAA
1701  ATACGTGACC GAGGGAATGA GAAAGCCCGC CTTCCTGAGC GGCGAGCAGA
1751  AAAAGGCCAT CGTGGACCTG CTGTTCAAGA CCAACCGGAA AGTGACCGTG
1801  AAGCAGCTGA AAGAGGACTA CTTCAAGAAA ATCGAGTGCT TCGACTCCGT
1851  GGAAATCTCC GGCGTGGAAG ATCGGTTCAA CGCCTCCCTG GGCACATACC
1901  ACGATCTGCT GAAAATTATC AAGGACAAGG ACTTCCTGGA CAATGAGGAA
1951  AACGAGGACA TTCTGGAAGA TATCGTGCTG ACCCTGACAC TGTTTGAGGA
2001  CAGAGAGATG ATCGAGGAAC GGCTGAAAAC CTATGCCCAC CTGTTCGACG
2051  ACAAAGTGAT GAAGCAGCTG AAGCGGCGGA GATACACCGG CTGGGGCAGG
2101  CTGAGCCGGA AGCTGATCAA CGGCATCCGG GACAAGCAGT CCGGCAAGAC
2151  AATCCTGGAT TTCCTGAAGT CCGACGGCTT CGCCAACAGA AACTTCATGC
2201  AGCTGATCCA CGACGACAGC CTGACCTTTA AAGAGGACAT CCAGAAAGCC
2251  CAGGTGTCCG GCCAGGGCGA TAGCCTGCAC GAGCACATTG CCAATCTGGC
```

-continued

```
2301  CGGCAGCCCC GCCATTAAGA AGGGCATCCT GCAGACAGTG AAGGTGGTGG
2351  ACGAGCTCGT GAAAGTGATG GGCCGGCACA AGCCCGAGAA CATCGTGATC
2401  GAAATGGCCA GAGAGAACCA GACCACCCAG AAGGGACAGA AGAACAGCCG
2451  CGAGAGAATG AAGCGGATCG AAGAGGGCAT CAAAGAGCTG GGCAGCCAGA
2501  TCCTGAAAGA ACACCCCGTG GAAAACACCC AGCTGCAGAA CGAGAAGCTG
2551  TACCTGTACT ACCTGCAGAA TGGGCGGGAT ATGTACGTGG ACCAGGAACT
2601  GGACATCAAC CGGCTGTCCG ACTACGATGT GGACgccATC GTGCCTCAGA
2651  GCTTTCTGAA GGACGACTCC ATCGACAACA AGGTGCTGAC CAGAAGCGAC
2701  AAGAACCGGG GCAAGAGCGA CAACGTGCCC TCCGAAGAGG TCGTGAAGAA
2751  GATGAAGAAC TACTGGCGGC AGCTGCTGAA CGCCAAGCTG ATTACCCAGA
2801  GAAAGTTCGA CAATCTGACC AAGGCCGAGA GAGGCGGCCT GAGCGAACTG
2851  GATAAGGCCG GCTTCATCAA GAGACAGCTG GTGGAAACCC GGCAGATCAC
2901  AAAGCACGTG GCACAGATCC TGGACTCCCG GATGAACACT AAGTACGACG
2951  AGAATGACAA GCTGATCCGG GAAGTGAAAG TGATCACCCT GAAGTCCAAG
3001  CTGGTGTCCG ATTTCCGGAA GGATTTCCAG TTTTACAAAG TGCGCGAGAT
3051  CAACAACTAC CACCACGCCC ACGACGCCTA CCTGAACGCC GTCGTGGGAA
3101  CCGCCCTGAT CAAAAAGTAC CCTAAGCTGG AAAGCGAGTT CGTGTACGGC
3151  GACTACAAGG TGTACGACGT GCGGAAGATG ATCGCCAAGA GCGAGCAGGA
3201  AATCGGCAAG GCTACCGCCA AGTACTTCTT CTACAGCAAC ATCATGAACT
3251  TTTTCAAGAC CGAGATTACC CTGGCCAACG GCGAGATCCG GAAGCGGCCT
3301  CTGATCGAGA CAAACGGCGA AACCGGGGAG ATCGTGTGGG ATAAGGGCCG
3351  GGATTTTGCC ACCGTGCGGA AAGTGCTGAG CATGCCCCAA GTGAATATCG
3401  TGAAAAAGAC CGAGGTGCAG ACAGGCGGCT TCAGCAAAGA GTCTATCCTG
3451  CCCAAGAGGA ACAGCGATAA GCTGATCGCC AGAAAGAAGG ACTGGGACCC
3501  TAAGAAGTAC GGCGGCTTCG ACAGCCCCAC CGTGGCCTAT TCTGTGCTGG
3551  TGGTGGCCAA AGTGGAAAAG GGCAAGTCCA AGAAACTGAA GAGTGTGAAA
3601  GAGCTGCTGG GGATCACCAT CATGGAAAGA AGCAGCTTCG AGAAGAATCC
3651  CATCGACTTT CTGGAAGCCA AGGGCTACAA AGAAGTGAAA AAGGACCTGA
3701  TCATCAAGCT GCCTAAGTAC TCCCTGTTCG AGCTGGAAAA CGGCCGGAAG
3751  AGAATGCTGG CCTCTGCCGG CGAACTGCAG AAGGGAAACG AACTGGCCCT
3801  GCCCTCCAAA TATGTGAACT TCCTGTACCT GGCCAGCCAC TATGAGAAGC
3851  TGAAGGGCTC CCCCGAGGAT AATGAGCAGA AACAGCTGTT TGTGGAACAG
3901  CACAAGCACT ACCTGGACGA GATCATCGAG CAGATCAGCG AGTTCTCCAA
3951  GAGAGTGATC CTGGCCGACG CTAATCTGGA CAAAGTGCTG TCCGCCTACA
4001  ACAAGCACCG GGATAAGCCC ATCAGAGAGC AGGCCGAGAA TATCATCCAC
4051  CTGTTTACCC TGACCAATCT GGGAGCCCCT GCCGCCTTCA AGTACTTTGA
4101  CACCACCATC GACCGGAAGA GGTACACCAG CACCAAAGAG GTGCTGGACG
4151  CCACCCTGAT CCACCAGAGC ATCACCGGCC TGTACGAGAC ACGGATCGAC
4201  CTGTCTCAGC TGGGAGGCGA CAAAAGGCCG GCGGCCACGA AAAAGGCCGG
4251  CCAGGCAAAA AAGAAAAAGT AA
```

The following polynucleotide (e.g., DNA) sequence (SEQ ID NO: 55) corresponds to a 5' UTR referred to as Minimal.

(SEQ ID NO: 55)
1 GGGAGACGCC ACC

The following polynucleotide (e.g., DNA) sequence (SEQ ID NO: 56) corresponds to a 5' UTR referred to as hAg, a 5' UTR derived from human alpha globin.

(SEQ ID NO: 56)
1 GGGAGACTCT TCTGGTCCCC ACAGACTCAG AGAGAACGCC ACC

The following polynucleotide (e.g., DNA) sequence (SEQ ID NO: 57) corresponds to a 5' UTR referred to as TISU.

(SEQ ID NO: 57)
1 GGGAGACGCC AAG

The following polynucleotide (e.g., DNA) sequence (SEQ ID NO: 58) corresponds to a 5' UTR referred to as TISU+T.

(SEQ ID NO: 58)
1 GGGAGACTGC CAAG

The following polyribonucleotide (e.g., RNA) sequence (SEQ ID NO: 59) corresponds to a 5' UTR referred to as 5p-UTR.

(SEQ ID NO: 59)
1 GGGAGACCCA AGCUGGCUAG CGUUUAAACU UAAGCUUGCC ACC

The following polyribonucleotide (e.g., RNA) sequence (SEQ ID NO: 60) corresponds to a 3' UTR referred to as 3p-UTR.

(SEQ ID NO: 60)
1 GAAUUCCUAg gaUccACUAG UCCAGUGUGG UGGAAUUCUG CAGAAAAAAA
51 AAAAAAAAAA AAAAAAAAAA AAAAAAAAAA AAAAAAAAAA AAAAAAAAAA
101 AAAAAAAAAA AAAAAAAAAA AAAAAAAAAA AAAAAAAAAA AAAAAAAAAA
151 AAAAAAAAAA AAAGCGGCC

The following polyribonucleotide (e.g., RNA) sequence (SEQ ID NO: 61) encodes FLAG-tagged wildtype Cas9.

(SEQ ID NO: 61)
1 AUGGACUAUA AGGACCACGA CGGAGACUAC AAGGAUCAUG AUAUUGAUUA
51 CAAAGACGAU GACGAUAAGA UGGCCCCAAA GAAGAAGCGG AAGGUCGGUA
101 UCCACGGAGU CCCAGCAGCC GACAAGAAGU ACAGCAUCGG CCUGGACAUC
151 GGCACCAACU CUGUGGGCUG GGCCGUGAUC ACCGACGAGU ACAAGGUGCC
201 CAGCAAGAAA UUCAAGGUGC UGGGCAACAC CGACCGGCAC AGCAUCAAGA
251 AGAACCUGAU CGGAGCCCUG CUGUUCGACA GCGGCGAAAC AGCCGAGGCC
301 ACCCGGCUGA AGAGAACCGC CAGAAGAAGA UACACCAGAC GGAAGAACCG
351 GAUCUGCUAU CUGCAAGAGA UCUUCAGCAA CGAGAUGGCC AAGGUGGACG
401 ACAGCUUCUU CCACAGACUG GAAGAGUCCU UCCUGGUGGA AGAGGAUAAG
451 AAGCACGAGC GGCACCCCAU CUUCGGCAAC AUCGUGGACG AGGUGGCCUA
501 CCACGAGAAG UACCCCACCA UCUACCACCU GAGAAAGAAA CUGGUGGACA
551 GCACCGACAA GGCCGACCUG CGGCUGAUCU AUCUGGCCCU GGCCCACAUG
601 AUCAAGUUCC GGGGCCACUU CCUGAUCGAG GGCGACCUGA ACCCCGACAA
651 CAGCGACGUG GACAAGCUGU UCAUCCAGCU GGUGCAGACC UACAACCAGC
701 UGUUCGAGGA AAACCCCAUC AACGCCAGCG GCGUGGACGC CAAGGCCAUC
751 CUGUCUGCCA GACUGAGCAA GAGCAGACGG CUGGAAAAUC UGAUCGCCCA
801 GCUGCCCGGC GAGAAGAAGA AUGGCCUGUU CGGAAACCUG AUUGCCCUGA
851 GCCUGGGCCU GACCCCCAAC UUCAAGAGCA ACUUCGACCU GGCCGAGGAU
901 GCCAAACUGC AGCUGAGCAA GGACACCUAC GACGACGACC UGGACAACCU
951 GCUGGCCCAG AUCGGCGACC AGUACGCCGA CCUGUUUCUG GCCGCCAAGA
1001 ACCUGUCCGA CGCCAUCCUG CUGAGCGACA UCCUGAGAGU GAACACCGAG

-continued

```
1051  AUCACCAAGG CCCCCCUGAG CGCCUCUAUG AUCAAGAGAU ACGACGAGCA
1101  CCACCAGGAC CUGACCCUGC UGAAAGCUCU CGUGCGGCAG CAGCUGCCUG
1151  AGAAGUACAA AGAGAUUUUC UUCGACCAGA GCAAGAACGG CUACGCCGGC
1201  UACAUUGACG GCGGAGCCAG CCAGGAAGAG UUCUACAAGU UCAUCAAGCC
1251  CAUCCUGGAA AAGAUGGACG GCACCGAGGA ACUGCUCGUG AAGCUGAACA
1301  GAGAGGACCU GCUGCGGAAG CAGCGGACCU UCGACAACGG CAGCAUCCCC
1351  CACCAGAUCC ACCUGGGAGA GCUGCACGCC AUUCUGCGGC GGCAGGAAGA
1401  UUUUUACCCA UUCCUGAAGG ACAACCGGGA AAAGAUCGAG AAGAUCCUGA
1451  CCUUCCGCAU CCCCUACUAC GUGGGCCCUC UGGCCAGGGG AAACAGCAGA
1501  UUCGCCUGGA UGACCAGAAA GAGCGAGGAA ACCAUCACCC CCUGGAACUU
1551  CGAGGAAGUG GUGGACAAGG GCGCUUCCGC CCAGAGCUUC AUCGAGCGGA
1601  UGACCAACUU CGAUAAGAAC CUGCCCAACG AGAAGGUGCU GCCCAAGCAC
1651  AGCCUGCUGU ACGAGUACUU CACCGUGUAU AACGAGCUGA CCAAAGUGAA
1701  AUACGUGACC GAGGGAAUGA GAAAGCCCGC CUUCCUGAGC GGCGAGCAGA
1751  AAAAGGCCAU CGUGGACCUG CUGUUCAAGA CCAACCGGAA AGUGACCGUG
1801  AAGCAGCUGA AAGAGGACUA CUUCAAGAAA AUCGAGUGCU UCGACUCCGU
1851  GGAAAUCUCC GGCGUGGAAG AUCGGUUCAA CGCCUCCCUG GGCACAUACC
1901  ACGAUCUGCU GAAAAUUAUC AAGGACAAGG ACUUCCUGGA CAAUGAGGAA
1951  AACGAGGACA UUCUGGAAGA UAUCGUGCUG ACCCUGACAC UGUUUGAGGA
2001  CAGAGAGAUG AUCGAGGAAC GGCUGAAAAC CUAUGCCCAC CUGUUCGACG
2051  ACAAAGUGAU GAAGCAGCUG AAGCGGCGGA GAUACACCGG CUGGGGCAGG
2101  CUGAGCCGGA AGCUGAUCAA CGGCAUCCGG GACAAGCAGU CCGGCAAGAC
2151  AAUCCUGGAU UUCCUGAAGU CCGACGGCUU CGCCAACAGA AACUUCAUGC
2201  AGCUGAUCCA CGACGACAGC CUGACCUUUA AAGAGGACAU CCAGAAAGCC
2251  CAGGUGUCCG GCCAGGGCGA UAGCCUGCAC GAGCACAUUG CCAAUCUGGC
2301  CGGCAGCCCC GCCAUUAAGA AGGGCAUCCU GCAGACAGUG AAGGUGGUGG
2351  ACGAGCUCGU GAAAGUGAUG GGCCGGCACA AGCCCGAGAA CAUCGUGAUC
2401  GAAAUGGCCA GAGAGAACCA GACCACCCAG AAGGGACAGA AGAACAGCCG
2451  CGAGAGAAUG AAGCGGAUCG AAGAGGGCAU CAAAGAGCUG GGCAGCCAGA
2501  UCCUGAAAGA ACACCCCGUG GAAAACACCC AGCUGCAGAA CGAGAAGCUG
2551  UACCUGUACU ACCUGCAGAA UGGGCGGGAU AUGUACGUGG ACCAGGAACU
2601  GGACAUCAAC CGGCUGUCCG ACUACGAUGU GGACCAUAUC GUGCCUCAGA
2651  GCUUUCUGAA GGACGACUCC AUCGACAACA AGGUGCUGAC CAGAAGCGAC
2701  AAGAACCGGG GCAAGAGCGA CAACGUGCCC UCCGAAGAGG UCGUGAAGAA
2751  GAUGAAGAAC UACUGGCGGC AGCUGCUGAA CGCCAAGCUG AUUACCCAGA
2801  GAAAGUUCGA CAAUCUGACC AAGGCCGAGA GAGGCGGCCU GAGCGAACUG
2851  GAUAAGGCCG GCUUCAUCAA GAGACAGCUG GUGGAAACCC GGCAGAUCAC
2901  AAAGCACGUG GCACAGAUCC UGGACUCCCG GAUGAACACU AAGUACGACG
2951  AGAAUGACAA GCUGAUCCGG GAAGUGAAAG UGAUCACCCU GAAGUCCAAG
3001  CUGGUGUCCG AUUUCCGGAA GGAUUUCCAG UUUUACAAAG UGCGCGAGAU
```

-continued

```
3051   CAACAACUAC CACCACGCCC ACGACGCCUA CCUGAACGCC GUCGUGGGAA

3101   CCGCCCUGAU CAAAAAGUAC CCUAAGCUGG AAAGCGAGUU CGUGUACGGC

3151   GACUACAAGG UGUACGACGU GCGGAAGAUG AUCGCCAAGA GCGAGCAGGA

3201   AAUCGGCAAG GCUACCGCCA AGUACUUCUU CUACAGCAAC AUCAUGAACU

3251   UUUUCAAGAC CGAGAUUACC CUGGCCAACG GCGAGAUCCG GAAGCGGCCU

3301   CUGAUCGAGA CAAACGGCGA AACCGGGGAG AUCGUGUGGG AUAAGGGCCG

3351   GGAUUUUGCC ACCGUGCGGA AAGUGCUGAG CAUGCCCCAA GUGAAUAUCG

3401   UGAAAAAGAC CGAGGUGCAG ACAGGCGGCU UCAGCAAAGA GUCUAUCCUG

3451   CCCAAGAGGA ACAGCGAUAA GCUGAUCGCC AGAAAGAAGG ACUGGGACCC

3501   UAAGAAGUAC GGCGGCUUCG ACAGCCCCAC CGUGGCCUAU UCUGUGCUGG

3551   UGGUGGCCAA AGUGGAAAAG GGCAAGUCCA AGAAACUGAA GAGUGUGAAA

3601   GAGCUGCUGG GGAUCACCAU CAUGGAAAGA AGCAGCUUCG AGAAGAAUCC

3651   CAUCGACUUU CUGGAAGCCA AGGGCUACAA AGAAGUGAAA AAGGACCUGA

3701   UCAUCAAGCU GCCUAAGUAC UCCCUGUUCG AGCUGGAAAA CGGCCGGAAG

3751   AGAAUGCUGG CCUCUGCCGG CGAACUGCAG AAGGGAAACG AACUGGCCCU

3801   GCCCUCCAAA UAUGUGAACU UCCUGUACCU GGCCAGCCAC UAUGAGAAGC

3851   UGAAGGGCUC CCCCGAGGAU AAUGAGCAGA AACAGCUGUU UGUGGAACAG

3901   CACAAGCACU ACCUGGACGA GAUCAUCGAG CAGAUCAGCG AGUUCUCCAA

3951   GAGAGUGAUC CUGGCCGACG CUAAUCUGGA CAAAGUGCUG UCCGCCUACA

4001   ACAAGCACCG GGAUAAGCCC AUCAGAGAGC AGGCCGAGAA UAUCAUCCAC

4051   CUGUUUACCC UGACCAAUCU GGGAGCCCCU GCCGCCUUCA AGUACUUUGA

4101   CACCACCAUC GACCGGAAGA GGUACACCAG CACCAAAGAG GUGCUGGACG

4151   CCACCCUGAU CCACCAGAGC AUCACCGGCC UGUACGAGAC ACGGAUCGAC

4201   CUGUCUCAGC UGGGAGGCGA CAAAAGGCCG GCGGCCACGA AAAAGGCCGG

4251   CCAGGCAAAA AAGAAAAAGU AA
```

The following polyribonucleotide (e.g., RNA) sequence (SEQ ID NO: 62) encodes HA-tagged D10A Cas9.

```
                                              (SEQ ID NO: 62)
   1   AUGUACCCAU ACGAUGUUCC AGAUUACGCU AUGGCCCCAA AGAAGAAGCG

  51   GAAGGUCGGU AUCCACGGAG UCCCAGCAGC CGACAAGAAG UACAGCAUCG

 101   GCCUGgccAU CGGCACCAAC UCUGUGGGCU GGGCCGUGAU CACCGACGAG

 151   UACAAGGUGC CCAGCAAGAA AUUCAAGGUG CUGGGCAACA CCGACCGGCA

 201   CAGCAUCAAG AAGAACCUGA UCGGAGCCCU GCUGUUCGAC AGCGGCGAAA

 251   CAGCCGAGGC CACCCGGCUG AAGAGAACCG CCAGAAGAAG AUACACCAGA

 301   CGGAAGAACC GGAUCUGCUA UCUGCAAGAG AUCUUCAGCA ACGAGAUGGC

 351   CAAGGUGGAC GACAGCUUCU UCCACAGACU GGAAGAGUCC UUCCUGGUGG

 401   AAGAGGAUAA GAAGCACGAG CGGCACCCCA UCUUCGGCAA CAUCGUGGAC

 451   GAGGUGGCCU ACCACGAGAA GUACCCCACC AUCUACCACC UGAGAAAGAA

 501   ACUGGUGGAC AGCACCGACA AGGCCGACCU GCGGCUGAUC UAUCUGGCCC

 551   UGGCCCACAU GAUCAAGUUC CGGGGCCACU UCCUGAUCGA GGGCGACCUG
```

-continued

601 AACCCCGACA ACAGCGACGU GGACAAGCUG UUCAUCCAGC UGGUGCAGAC

651 CUACAACCAG CUGUUCGAGG AAAACCCCAU CAACGCCAGC GGCGUGGACG

701 CCAAGGCCAU CCUGUCUGCC AGACUGAGCA AGAGCAGACG GCUGGAAAAU

751 CUGAUCGCCC AGCUGCCCGG CGAGAAGAAG AAUGGCCUGU UCGGAAACCU

801 GAUUGCCCUG AGCCUGGGCC UGACCCCCAA CUUCAAGAGC AACUUCGACC

851 UGGCCGAGGA UGCCAAACUG CAGCUGAGCA AGGACACCUA CGACGACGAC

901 CUGGACAACC UGCUGGCCCA GAUCGGCGAC CAGUACGCCG ACCUGUUUCU

951 GGCCGCCAAG AACCUGUCCG ACGCCAUCCU GCUGAGCGAC AUCCUGAGAG

1001 UGAACACCGA GAUCACCAAG GCCCCCCUGA GCGCCUCUAU GAUCAAGAGA

1051 UACGACGAGC ACCACCAGGA CCUGACCCUG CUGAAAGCUC UCGUGCGGCA

1101 GCAGCUGCCU GAGAAGUACA AAGAGAUUUU CUUCGACCAG AGCAAGAACG

1151 GCUACGCCGG CUACAUUGAC GGCGGAGCCA GCCAGGAAGA GUUCUACAAG

1201 UUCAUCAAGC CCAUCCUGGA AAAGAUGGAC GGCACCGAGG AACUGCUCGU

1251 GAAGCUGAAC AGAGAGGACC UGCUGCGGAA GCAGCGGACC UUCGACAACG

1301 GCAGCAUCCC CCACCAGAUC CACCUGGGAG AGCUGCACGC CAUUCUGCGG

1351 CGGCAGGAAG AUUUUUACCC AUUCCUGAAG GACAACCGGG AAAAGAUCGA

1401 GAAGAUCCUG ACCUUCCGCA UCCCCUACUA CGUGGGCCCU CUGGCCAGGG

1451 GAAACAGCAG AUUCGCCUGG AUGACCAGAA AGAGCGAGGA AACCAUCACC

1501 CCCUGGAACU UCGAGGAAGU GGUGGACAAG GGCGCUUCCG CCCAGAGCUU

1551 CAUCGAGCGG AUGACCAACU UCGAUAAGAA CCUGCCCAAC GAGAAGGUGC

1601 UGCCCAAGCA CAGCCUGCUG UACGAGUACU UCACCGUGUA UAACGAGCUG

1651 ACCAAAGUGA AAUACGUGAC CGAGGGAAUG AGAAAGCCCG CCUUCCUGAG

1701 CGGCGAGCAG AAAAAGGCCA UCGUGGACCU GCUGUUCAAG ACCAACCGGA

1751 AAGUGACCGU GAAGCAGCUG AAAGAGGACU ACUUCAAGAA AAUCGAGUGC

1801 UUCGACUCCG UGGAAAUCUC CGGCGUGGAA GAUCGGUUCA ACGCCUCCCU

1851 GGGCACAUAC CACGAUCUGC UGAAAAUUAU CAAGGACAAG GACUUCCUGG

1901 ACAAUGAGGA AAACGAGGAC AUUCUGGAAG AUAUCGUGCU GACCCUGACA

1951 CUGUUUGAGG ACAGAGAGAU GAUCGAGGAA CGGCUGAAAA CCUAUGCCCA

2001 CCUGUUCGAC GACAAAGUGA UGAAGCAGCU GAAGCGGCGG AGAUACACCG

2051 GCUGGGGCAG GCUGAGCCGG AAGCUGAUCA ACGGCAUCCG GGACAAGCAG

2101 UCCGGCAAGA CAAUCCUGGA UUUCCUGAAG UCCGACGGCU UCGCCAACAG

2151 AAACUUCAUG CAGCUGAUCC ACGACGACAG CCUGACCUUU AAAGAGGACA

2201 UCCAGAAAGC CCAGGUGUCC GGCCAGGGCG AUAGCCUGCA CGAGCACAUU

2251 GCCAAUCUGG CCGGCAGCCC CGCCAUUAAG AAGGGCAUCC UGCAGACAGU

2301 GAAGGUGGUG GACGAGCUCG UGAAAGUGAU GGGCCGGCAC AAGCCCGAGA

2351 ACAUCGUGAU CGAAAUGGCC AGAGAGAACC AGACCACCCA GAAGGGACAG

2401 AAGAACAGCC GCGAGAGAAU GAAGCGGAUC GAAGAGGGCA UCAAAGAGCU

2451 GGGCAGCCAG AUCCUGAAAG AACACCCCGU GGAAAACACC CAGCUGCAGA

2501 ACGAGAAGCU GUACCUGUAC UACCUGCAGA AUGGGCGGGA UAUGUACGUG

2551 GACCAGGAAC UGGACAUCAA CCGGCUGUCC GACUACGAUG UGGACCAUAU

2601 CGUGCCUCAG AGCUUUCUGA AGGACGACUC CAUCGACAAC AAGGUGCUGA

-continued

2651 CCAGAAGCGA CAAGAACCGG GGCAAGAGCG ACAACGUGCC CUCCGAAGAG

2701 GUCGUGAAGA AGAUGAAGAA CUACUGGCGG CAGCUGCUGA ACGCCAAGCU

2751 GAUUACCCAG AGAAAGUUCG ACAAUCUGAC CAAGGCCGAG AGAGGCGGCC

2801 UGAGCGAACU GGAUAAGGCC GGCUUCAUCA AGAGACAGCU GGUGGAAACC

2851 CGGCAGAUCA CAAAGCACGU GGCACAGAUC CUGGACUCCC GGAUGAACAC

2901 UAAGUACGAC GAGAAUGACA AGCUGAUCCG GGAAGUGAAA GUGAUCACCC

2951 UGAAGUCCAA GCUGGUGUCC GAUUUCCGGA AGGAUUUCCA GUUUUACAAA

3001 GUGCGCGAGA UCAACAACUA CCACCACGCC CACGACGCCU ACCUGAACGC

3051 CGUCGUGGGA ACCGCCCUGA UCAAAAAGUA CCCUAAGCUG GAAAGCGAGU

3101 UCGUGUACGG CGACUACAAG GUGUACGACG UGCGGAAGAU GAUCGCCAAG

3151 AGCGAGCAGG AAAUCGGCAA GGCUACCGCC AAGUACUUCU UCUACAGCAA

3201 CAUCAUGAAC UUUUUCAAGA CCGAGAUUAC CCUGGCCAAC GGCGAGAUCC

3251 GGAAGCGGCC UCUGAUCGAG ACAAACGGCG AAACCGGGGA GAUCGUGUGG

3301 GAUAAGGGCC GGGAUUUUGC CACCGUGCGG AAAGUGCUGA GCAUGCCCCA

3351 AGUGAAUAUC GUGAAAAAGA CCGAGGUGCA GACAGGCGGC UUCAGCAAAG

3401 AGUCUAUCCU GCCCAAGAGG AACAGCGAUA AGCUGAUCGC CAGAAAGAAG

3451 GACUGGGACC CUAAGAAGUA CGGCGGCUUC GACAGCCCCA CCGUGGCCUA

3501 UUCUGUGCUG GUGGUGGCCA AAGUGGAAAA GGGCAAGUCC AAGAAACUGA

3551 AGAGUGUGAA AGAGCUGCUG GGGAUCACCA UCAUGGAAAG AAGCAGCUUC

3601 GAGAAGAAUC CCAUCGACUU UCUGGAAGCC AAGGGCUACA AAGAAGUGAA

3651 AAAGGACCUG AUCAUCAAGC UGCCUAAGUA CUCCCUGUUC GAGCUGGAAA

3701 ACGGCCGGAA GAGAAUGCUG GCCUCUGCCG GCGAACUGCA GAAGGGAAAC

3751 GAACUGGCCC UGCCCUCCAA AUAUGUGAAC UUCCUGUACC UGGCCAGCCA

3801 CUAUGAGAAG CUGAAGGGCU CCCCCGAGGA UAAUGAGCAG AAACAGCUGU

3851 UUGUGGAACA GCACAAGCAC UACCUGGACG AGAUCAUCGA GCAGAUCAGC

3901 GAGUUCUCCA AGAGAGUGAU CCUGGCCGAC GCUAAUCUGG ACAAAGUGCU

3951 GUCCGCCUAC AACAAGCACC GGGAUAAGCC CAUCAGAGAG CAGGCCGAGA

4001 AUAUCAUCCA CCUGUUUACC CUGACCAAUC UGGGAGCCCC UGCCGCCUUC

4051 AAGUACUUUG ACACCACCAU CGACCGGAAG AGGUACACCA GCACCAAAGA

4101 GGUGCUGGAC GCCACCCUGA UCCACCAGAG CAUCACCGGC CUGUACGAGA

4151 CACGGAUCGA CCUGUCUCAG CUGGGAGGCG ACAAAAGGCC GGCGGCCACG

4201 AAAAAGGCCG GCCAGGCAAA AAAGAAAAAG UAA

The following polyribonucleotide (e.g., RNA) sequence (SEQ ID NO: 63) encodes FLAG-tagged D10A H841A Cas9.

(SEQ ID NO: 63)

1 AUGGACUAUA AGGACCACGA CGGAGACUAC AAGGAUCAUG AUAUUGAUUA

51 CAAAGACGAU GACGAUAAGA UGGCCCCAAA GAAGAAGCGG AAGGUCGGUA

101 UCCACGGAGU CCCAGCAGCC GACAAGAAGU ACAGCAUCGG CCUGgccAUC

151 GGCACCAACU CUGUGGGCUG GGCCGUGAUC ACCGACGAGU ACAAGGUGCC

-continued

201 CAGCAAGAAA UUCAAGGUGC UGGGCAACAC CGACCGGCAC AGCAUCAAGA

251 AGAACCUGAU CGGAGCCCUG CUGUUCGACA GCGGCGAAAC AGCCGAGGCC

301 ACCCGGCUGA AGAGAACCGC CAGAAGAAGA UACACCAGAC GGAAGAACCG

351 GAUCUGCUAU CUGCAAGAGA UCUUCAGCAA CGAGAUGGCC AAGGUGGACG

401 ACAGCUUCUU CCACAGACUG GAAGAGUCCU UCCUGGUGGA AGAGGAUAAG

451 AAGCACGAGC GGCACCCCAU CUUCGGCAAC AUCGUGGACG AGGUGGCCUA

501 CCACGAGAAG UACCCCACCA UCUACCACCU GAGAAAGAAA CUGGUGGACA

551 GCACCGACAA GGCCGACCUG CGGCUGAUCU AUCUGGCCCU GGCCCACAUG

601 AUCAAGUUCC GGGGCCACUU CCUGAUCGAG GGCGACCUGA ACCCCGACAA

651 CAGCGACGUG GACAAGCUGU UCAUCCAGCU GGUGCAGACC UACAACCAGC

701 UGUUCGAGGA AAACCCCAUC AACGCCAGCG GCGUGGACGC CAAGGCCAUC

751 CUGUCUGCCA GACUGAGCAA GAGCAGACGG CUGGAAAAUC UGAUCGCCCA

801 GCUGCCCGGC GAGAAGAAGA AUGGCCUGUU CGGAAACCUG AUUGCCCUGA

851 GCCUGGGCCU GACCCCCAAC UUCAAGAGCA ACUUCGACCU GGCCGAGGAU

901 GCCAAACUGC AGCUGAGCAA GGACACCUAC GACGACGACC UGGACAACCU

951 GCUGGCCCAG AUCGGCGACC AGUACGCCGA CCUGUUUCUG GCCGCCAAGA

1001 ACCUGUCCGA CGCCAUCCUG CUGAGCGACA UCCUGAGAGU GAACACCGAG

1051 AUCACCAAGG CCCCCCUGAG CGCCUCUAUG AUCAAGAGAU ACGACGAGCA

1101 CCACCAGGAC CUGACCCUGC UGAAAGCUCU CGUGCGGCAG CAGCUGCCUG

1151 AGAAGUACAA AGAGAUUUUC UUCGACCAGA GCAAGAACGG CUACGCCGGC

1201 UACAUUGACG GCGGAGCCAG CCAGGAAGAG UUCUACAAGU UCAUCAAGCC

1251 CAUCCUGGAA AAGAUGGACG GCACCGAGGA ACUGCUCGUG AAGCUGAACA

1301 GAGAGGACCU GCUGCGGAAG CAGCGGACCU UCGACAACGG CAGCAUCCCC

1351 CACCAGAUCC ACCUGGGAGA GCUGCACGCC AUUCUGCGGC GGCAGGAAGA

1401 UUUUUACCCA UUCCUGAAGG ACAACCGGGA AAAGAUCGAG AAGAUCCUGA

1451 CCUUCCGCAU CCCCUACUAC GUGGGCCCUC UGGCCAGGGG AAACAGCAGA

1501 UUCGCCUGGA UGACCAGAAA GAGCGAGGAA ACCAUCACCC CCUGGAACUU

1551 CGAGGAAGUG GUGGACAAGG GCGCUUCCGC CCAGAGCUUC AUCGAGCGGA

1601 UGACCAACUU CGAUAAGAAC CUGCCCAACG AGAAGGUGCU GCCCAAGCAC

1651 AGCCUGCUGU ACGAGUACUU CACCGUGUAU AACGAGCUGA CCAAAGUGAA

1701 AUACGUGACC GAGGGAAUGA GAAAGCCCGC CUUCCUGAGC GGCGAGCAGA

1751 AAAAGGCCAU CGUGGACCUG CUGUUCAAGA CCAACCGGAA AGUGACCGUG

1801 AAGCAGCUGA AAGAGGACUA CUUCAAGAAA AUCGAGUGCU UCGACUCCGU

1851 GGAAAUCUCC GGCGUGGAAG AUCGGUUCAA CGCCUCCCUG GGCACAUACC

1901 ACGAUCUGCU GAAAAUUAUC AAGGACAAGG ACUUCCUGGA CAAUGAGGAA

1951 AACGAGGACA UUCUGGAAGA UAUCGUGCUG ACCCUGACAC UGUUUGAGGA

2001 CAGAGAGAUG AUCGAGGAAC GGCUGAAAAC CUAUGCCCAC CUGUUCGACG

2051 ACAAAGUGAU GAAGCAGCUG AAGCGGCGGA GAUACACCGG CUGGGGCAGG

2101 CUGAGCCGGA AGCUGAUCAA CGGCAUCCGG GACAAGCAGU CCGGCAAGAC

2151 AAUCCUGGAU UUCCUGAAGU CCGACGGCUU CGCCAACAGA AACUUCAUGC

2201 AGCUGAUCCA CGACGACAGC CUGACCUUUA AAGAGGACAU CCAGAAAGCC

-continued

```
2251   CAGGUGUCCG GCCAGGGCGA UAGCCUGCAC GAGCACAUUG CCAAUCUGGC
2301   CGGCAGCCCC GCCAUUAAGA AGGGCAUCCU GCAGACAGUG AAGGUGGUGG
2351   ACGAGCUCGU GAAAGUGAUG GGCCGGCACA AGCCCGAGAA CAUCGUGAUC
2401   GAAAUGGCCA GAGAGAACCA GACCACCCAG AAGGGACAGA AGAACAGCCG
2451   CGAGAGAAUG AAGCGGAUCG AAGAGGGCAU CAAAGAGCUG GGCAGCCAGA
2501   UCCUGAAAGA ACACCCCGUG GAAAACACCC AGCUGCAGAA CGAGAAGCUG
2551   UACCUGUACU ACCUGCAGAA UGGGCGGGAU AUGUACGUGG ACCAGGAACU
2601   GGACAUCAAC CGGCUGUCCG ACUACGAUGU GGACgccAUC GUGCCUCAGA
2651   GCUUUCUGAA GGACGACUCC AUCGACAACA AGGUGCUGAC CAGAAGCGAC
2701   AAGAACCGGG GCAAGAGCGA CAACGUGCCC UCCGAAGAGG UCGUGAAGAA
2751   GAUGAAGAAC UACUGGCGGC AGCUGCUGAA CGCCAAGCUG AUUACCCAGA
2801   GAAAGUUCGA CAAUCUGACC AAGGCCGAGA GAGGCGGCCU GAGCGAACUG
2851   GAUAAGGCCG GCUUCAUCAA GAGACAGCUG GUGGAAACCC GGCAGAUCAC
2901   AAAGCACGUG GCACAGAUCC UGGACUCCCG GAUGAACACU AAGUACGACG
2951   AGAAUGACAA GCUGAUCCGG GAAGUGAAAG UGAUCACCCU GAAGUCCAAG
3001   CUGGUGUCCG AUUUCCGGAA GGAUUUCCAG UUUUACAAAG UGCGCGAGAU
3051   CAACAACUAC CACCACGCCC ACGACGCCUA CCUGAACGCC GUCGUGGGAA
3101   CCGCCCUGAU CAAAAAGUAC CCUAAGCUGG AAAGCGAGUU CGUGUACGGC
3151   GACUACAAGG UGUACGACGU GCGGAAGAUG AUCGCCAAGA GCGAGCAGGA
3201   AAUCGGCAAG GCUACCGCCA AGUACUUCUU CUACAGCAAC AUCAUGAACU
3251   UUUUCAAGAC CGAGAUUACC CUGGCCAACG GCGAGAUCCG GAAGCGGCCU
3301   CUGAUCGAGA CAAACGGCGA AACCGGGGAG AUCGUGUGGG AUAAGGGCCG
3351   GGAUUUUGCC ACCGUGCGGA AAGUGCUGAG CAUGCCCCAA GUGAAUAUCG
3401   UGAAAAAGAC CGAGGUGCAG ACAGGCGGCU UCAGCAAAGA GUCUAUCCUG
3451   CCCAAGAGGA ACAGCGAUAA GCUGAUCGCC AGAAAGAAGG ACUGGGACCC
3501   UAAGAAGUAC GGCGGCUUCG ACAGCCCCAC CGUGGCCUAU UCUGUGCUGG
3551   UGGUGGCCAA AGUGGAAAAG GGCAAGUCCA AGAAACUGAA GAGUGUGAAA
3601   GAGCUGCUGG GGAUCACCAU CAUGGAAAGA AGCAGCUUCG AGAAGAAUCC
3651   CAUCGACUUU CUGGAAGCCA AGGGCUACAA AGAAGUGAAA AAGGACCUGA
3701   UCAUCAAGCU GCCUAAGUAC UCCCUGUUCG AGCUGGAAAA CGGCCGGAAG
3751   AGAAUGCUGG CCUCUGCCGG CGAACUGCAG AAGGGAAACG AACUGGCCCU
3801   GCCCUCCAAA UAUGUGAACU UCCUGUACCU GGCCAGCCAC UAUGAGAAGC
3851   UGAAGGGCUC CCCCGAGGAU AAUGAGCAGA AACAGCUGUU UGUGGAACAG
3901   CACAAGCACU ACCUGGACGA GAUCAUCGAG CAGAUCAGCG AGUUCUCCAA
3951   GAGAGUGAUC CUGGCCGACG CUAAUCUGGA CAAAGUGCUG UCCGCCUACA
4001   ACAAGCACCG GGAUAAGCCC AUCAGAGAGC AGGCCGAGAA UAUCAUCCAC
4051   CUGUUUACCC UGACCAAUCU GGGAGCCCCU GCCGCCUUCA AGUACUUUGA
4101   CACCACCAUC GACCGGAAGA GGUACACCAG CACCAAAGAG GUGCUGGACG
4151   CCACCCUGAU CCACCAGAGC AUCACCGGCC UGUACGAGAC ACGGAUCGAC
4201   CUGUCUCAGC UGGGAGGCGA CAAAAGGCCG GCGGCCACGA AAAAGGCCGG
4251   CCAGGCAAAA AAGAAAAAGU AA
```

The following polyribonucleotide (e.g., RNA) sequence (SEQ ID NO: 64) corresponds to a 5' UTR derived from α-globin 5' UTR, referred to as HBA2.

```
                                          (SEQ ID NO: 64)
 1   cauaaacccu ggcgcgcucg cgggccggca cucuucuggu ccccacagac

51   ucagagagaa cccacc
```

The following polyribonucleotide (e.g., RNA) sequence (SEQ ID NO: 65) corresponds to a 5' UTR derived from α-globin 5' UTR, referred to as ETH.

```
                                 (SEQ ID NO: 65)
1     ucuucugguc cccacagacu cagagagaac
```

The following polynucleotide (e.g., DNA) sequence (SEQ ID NO: 66) corresponds to a NLS referred to as rpL23a.

```
                                            (SEQ ID NO: 66)
  1  gtgcacagcc acaagaagaa gaagatcaga accagcccca ccttcagaag

 51  acccaagacc ctgagactga gaagacagcc caagtacccc agaaagagcg

101  cccccagaag aaacaagctg gaccactac
```

The following polynucleotide (e.g., DNA) sequence (SEQ ID NO: 67) corresponds to a NLS referred to as TAT.

```
                                 (SEQ ID NO: 67)
1    ggcagaaaga agagaagaca gagaagaaga gccccc
```

The following polynucleotide (e.g., DNA) sequence (SEQ ID NO: 68) corresponds to a NLS referred to as IBB domain.

```
                                            (SEQ ID NO: 68)
  1  CACCGGATCA AGAGCTTCAA GAACAAGGGC CGGGACGTGG AAACCATGCG

 51  GCGGCACAGA AACGAAGTGA CCGTGGAACT GCGGAAGAAC AAGCGGGACG

101  AGCATCTGCT GAAGAAACGG AACGTGCCCC AGGAAGAGAG C
```

The following polynucleotide (e.g., DNA) sequence (SEQ ID NO: 69) corresponds to a NLS referred to as SwitchII-Ran.

```
                                 (SEQ ID NO: 69)
1 gacacagccg gccaggagaa attcggtgga ctgagagatg gc
```

The following polyribonucleotide (e.g., RNA) sequence (SEQ ID NO: 70) encodes a NLS referred to as rpL23a.

```
                                          (SEQ ID NO: 70)
  1  gugcacagcc acaagaagaa gaagaucaga accagcccca ccuucagaag

 51  acccaagacc cugagacuga gaagacagcc caaguacccc agaaagagcg

101  cccccagaag aaacaagcug gaccacuac
```

The following polyribonucleotide (e.g., RNA) sequence (SEQ ID NO: 71) encodes a NLS referred to as TAT.

```
                                 (SEQ ID NO: 71)
1    ggcagaaaga agagaagaca gagaagaaga gccccc
```

The following polyribonucleotide (e.g., RNA) sequence (SEQ ID NO: 72) encodes a NLS referred to as IBB domain.

```
                                              (SEQ ID NO: 72)
  1   CACCGGAUCA AGAGCUUCAA GAACAAGGGC CGGGACGUGG AAACCAUGCG

 51   GCGGCACAGA AACGAAGUGA CCGUGGAACU GCGGAAGAAC AAGCGGGACG

101   AGCAUCUGCU GAAGAAACGG AACGUGCCCC AGGAAGAGAG C
```

The following polyribonucleotide (e.g., RNA) sequence (SEQ ID NO: 73) encodes a NLS referred to as SwitchII-Ran.

```
                                    (SEQ ID NO: 73)
 1 gacacagccg gccaggagaa auucggugga cugagagaug gc
```

The following polyribonucleotide (e.g., RNA) sequence (SEQ ID NO: 74) corresponds to a tracer RNA (trRNA) sequence.

```
                                              (SEQ ID NO: 74)
 1    GUUUUAGAGC UAGAAAUAGC AAGUUAAAAU AAGGCUAGUC CGUUAUCAAC

51    UUGAAAAAGU GGCACCGAGU CGGUGCUUUU UU
```

The following polyribonucleotide (e.g., RNA) sequence (SEQ ID NO: 75) corresponds to a 5' UTR referred to as Minimal, without promoter sequence.

```
                                    (SEQ ID NO: 75)
            1             CGCCACC
```

The following polyribonucleotide (e.g., RNA) sequence (SEQ ID NO: 76) corresponds to a 5' UTR referred to as hAg, a 5' UTR derived from human alpha globin, without promoter sequence.

```
                                    (SEQ ID NO: 76)
    1    CUCUUCUGGUC CCCACAGACU CAGAGAGAAC GCCACC
```

The following polyribonucleotide (e.g., RNA) sequence (SEQ ID NO: 77) corresponds to a 5' UTR referred to as TISU, without promoter sequence.

```
                                    (SEQ ID NO: 77)
            1             CGCCAAG
```

The following polyribonucleotide (e.g., RNA) sequence (SEQ ID NO: 78) corresponds to a 5' UTR referred to as TISU+T, without promoter sequence.

```
                                    (SEQ ID NO: 78)
            1             CUGCCAAG
```

The following amino acid sequence (SEQ ID NO: 79) corresponds to a D10A H841A Cas9 (referred to as dCas9).

```
                                                  (SEQ ID NO: 79)
  1   MAPKKKRKVG IHGVPAADKK YSIGLAIGTN SVGWAVITDE YKVPSKKFKV

 51   LGNTDRHSIK KNLIGALLFD SGETAEATRL KRTARRRYTR RKNRICYLQE

101   IFSNEMAKVD DSFFHRLEES FLVEEDKKHE RHPIFGNIVD EVAYHEKYPT

151   IYHLRKKLVD STDKADLRLI YLALAHMIKF RGHFLIEGDL NPDNSDVDKL

201   FIQLVQTYNQ LFEENPINAS GVDAKAILSA RLSKSRRLEN LIAQLPGEKK

251   NGLFGNLIAL SLGLTPNFKS NFDLAEDAKL QLSKDTYDDD LDNLLAQIGD

301   QYADLFLAAK NLSDAILLSD ILRVNTEITK APLSASMIKR YDEHHQDLTL

351   LKALVRQQLP EKYKEIFFDQ SKNGYAGYID GGASQEEFYK FIKPILEKMD

401   GTEELLVKLN REDLLRKQRT FDNGSIPHQI HLGELHAILR RQEDFYPFLK

451   DNREKIEKIL TFRIPYYVGP LARGNSRFAW MTRKSEETIT PWNFEEVVDK

501   GASAQSFIER MTNFDKNLPN EKVLPKHSLL YEYFTVYNEL TKVKYVTEGM

551   RKPAFLSGEQ KKAIVDLLFK TNRKVTVKQL KEDYFKKIEC FDSVEISGVE

601   DRFNASLGTY HDLLKIIKDK DFLDNEENED ILEDIVLTLT LFEDREMIEE
```

-continued

```
 651  RLKTYAHLFD DKVMKQLKRR RYTGWGRLSR KLINGIRDKQ SGKTILDFLK

 701  SDGFANRNFM QLIHDDSLTF KEDIQKAQVS GQGDSLHEHI ANLAGSPAIK

 751  KGILQTVKVV DELVKVMGRH KPENIVIEMA RENQTTQKGQ KNSRERMKRI

 801  EEGIKELGSQ ILKEHPVENT QLQNEKLYLY YLQNGRDMYV DQELDINRLS

 851  DYDVDAIVPQ SFLKDDSIDN KVLTRSDKNR GKSDNVPSEE VVKKMKNYWR

 901  QLLNAKLITQ RKFDNLTKAE RGGLSELDKA GFIKRQLVET RQITKHVAQI

 951  LDSRMNTKYD ENDKLIREVK VITLKSKLVS DFRKDFQFYK VREINNYHHA

1001  HDAYLNAVVG TALIKKYPKL ESEFVYGDYK VYDVRKMIAK SEQEIGKATA

1051  KYFFYSNIMN FFKTEITLAN GEIRKRPLIE TNGETGEIVW DKGRDFATVR

1101  KVLSMPQVNI VKKTEVQTGG FSKESILPKR NSDKLIARKK DWDPKKYGGF

1151  DSPTVAYSVL VVAKVEKGKS KKLKSVKELL GITIMERSSF EKNPIDFLEA

1201  KGYKEVKKDL IIKLPKYSLF ELENGRKRML ASAGELQKGN ELALPSKYVN

1251  FLYLASHYEK LKGSPEDNEQ KQLFVEQHKH YLDEIIEQIS EFSKRVILAD

1301  ANLDKVLSAY NKHRDKPIRE QAENIIHLFT LTNLGAPAAF KYFDTTIDRK

1351  RYTSTKEVLD ATLIHQSITG LYETRIDLSQ LGGDKRPAAT KKAGQAKKKK
```

The following polyribonucleotide (e.g., RNA) sequence (SEQ ID NO: 80) corresponds to an alternative 5' UTR, without promoter sequence.

```
                                      (SEQ ID NO: 80)
1              UGCCAAG
```

The following polyribonucleotide (e.g., RNA) sequence (SEQ ID NO: 81) corresponds to a 5' UTR referred to as CYBA 5' UTR without promoter sequence.

```
                                      (SEQ ID NO: 81)
1 C CGCGCCUAGC AGUGUCCCAG CCGGGUUCGU GUCGCCGCCA CC
```

The following polyribonucleotide (e.g., RNA) sequence (SEQ ID NO: 82) corresponds to an alternative 5' UTR, without promoter sequence.

```
                                      (SEQ ID NO: 82)
1              GCCACC
```

The following polyribonucleotide (e.g., RNA) sequence (SEQ ID NO: 83 corresponds to an alternative 5' UTR, without promoter sequence.

```
                                      (SEQ ID NO: 83)
1   UCUUCUGGUC CCCACAGACU CAGAGAGAAC GCCACC
```

The following polyribonucleotide (e.g., RNA) sequence (SEQ ID NO: 84) corresponds to an alternative 5' UTR, without promoter sequence.

```
                                      (SEQ ID NO: 84)
1              GCCAAG
```

INCORPORATION BY REFERENCE

All publications and patents mentioned herein are hereby incorporated by reference in their entirety as if each individual publication or patent was specifically and individually indicated to be incorporated by reference.

While specific embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

We claim:

1. A modified polyribonucleotide comprising a sequence which encodes a Cas9 protein, wherein the modified polyribonucleotide contains a combination of unmodified and modified ribonucleotides, wherein 30-45% of the uridines are analogs of uridine and 5-10% of the cytidines are analogs of cytidine, and wherein the modified polyribonucleotide comprises a primary sequence as set forth in SEQ ID NO: 2.

2. The modified polyribonucleotide of claim 1, wherein the modified polyribonucleotide encodes a Cas9 polypeptide with altered activity relative to wildtype Cas9.

3. A composition comprising the modified polyribonucleotide of claim 1 and one or more sgRNAs (single guide RNAs) for targeting a gene of interest, the sgRNA comprising:

a. a first region comprising a guide sequence of 20-25 ribonucleotides, and b. a second region positioned at the 3' end of the first region.

4. The composition of claim 3, wherein the sgRNA targets PCSK9.

5. The composition of claim 4, wherein the sgRNA consists essentially of a sequence selected from the group consisting of SEQ ID NOs: 21-26.

6. The modified polyribonucleotide of claim 1, wherein the modified polyribonucleotide further comprises one or more copies of a nuclear localization sequence (NLS), wherein the NLS(s) are selected from the group consisting of SEQ ID NOs: 70-73.

7. The modified polyribonucleotide of claim 1, wherein the uridine analogs are selected from the group consisting of pseudouridine, 2-thiouridine, 5-iodouridine, and 5-methyluridine.

8. The modified polyribonucleotide of claim 1, wherein the cytidine analogs are selected from the group consisting of 5-methylcytidine, 2'-amino-2'-deoxycytidine, 2'-fluoro-2'-deoxycytidine, and 5-iodocytidine.

9. A method for cleaving, nicking, or binding to DNA, comprising administering to a subject or contacting cells with the composition of claim 3, wherein the sgRNA comprises a sequence complementary to a gene targeted for cleaving, nicking, or binding.

10. The method of claim 9, wherein the modified polyribonucleotide is capable of expressing a Cas9 protein for a time period in a cell comprising the modified polyribonucleotide, wherein the time period is up to 4 weeks, and wherein the expression is enhanced or substantially equivalent as compared to expression in a control cell that has been exposed to an unmodified polyribonucleotide encoding a Cas9 protein.

* * * * *